US011859010B2

(12) United States Patent
Boustany et al.

(10) Patent No.: US 11,859,010 B2
(45) Date of Patent: Jan. 2, 2024

(54) ANTIBODIES, ACTIVATABLE ANTIBODIES, BISPECIFIC ANTIBODIES, AND BISPECIFIC ACTIVATABLE ANTIBODIES AND METHODS OF USE THEREOF

(71) Applicant: CytomX Therapeutics, Inc., South San Francisco, CA (US)

(72) Inventors: Leila Marie Boustany, Redwood City, CA (US); Sherry L. La Porte, San Francisco, CA (US); Bryan A. Irving, Woodside, CA (US); Jeanne Grace Flandez, Oakland, CA (US)

(73) Assignee: CytomX Therapeutics, Inc., South San Francisco, CA (US)

(*) Notice: Subject to any disclaimer, the term of this patent is extended or adjusted under 35 U.S.C. 154(b) by 0 days.

(21) Appl. No.: 17/930,143

(22) Filed: Sep. 7, 2022

(65) Prior Publication Data

US 2023/0050083 A1 Feb. 16, 2023

Related U.S. Application Data

(62) Division of application No. 16/159,451, filed on Oct. 12, 2018, now Pat. No. 11,472,889.

(60) Provisional application No. 62/731,622, filed on Sep. 14, 2018, provisional application No. 62/666,065, filed on May 2, 2018, provisional application No. 62/613,358, filed on Jan. 3, 2018, provisional application No. 62/577,140, filed on Oct. 25, 2017, provisional application No. 62/572,468, filed on Oct. 14, 2017.

(51) Int. Cl.

| | |
|---|---|
| ***G01N 31/00*** | (2006.01) |
| ***G01N 33/53*** | (2006.01) |
| ***C07K 16/40*** | (2006.01) |
| ***C07K 16/28*** | (2006.01) |
| ***A61P 35/00*** | (2006.01) |
| ***C12N 15/62*** | (2006.01) |
| *A61K 39/00* | (2006.01) |

(52) U.S. Cl.

CPC .............. *C07K 16/40* (2013.01); *A61P 35/00* (2018.01); *C07K 16/2809* (2013.01); *C07K 16/2863* (2013.01); *C12N 15/62* (2013.01); *A61K 2039/505* (2013.01); *C07K 2317/24* (2013.01); *C07K 2317/31* (2013.01); *C07K 2317/52* (2013.01); *C07K 2317/622* (2013.01); *C07K 2317/64* (2013.01); *C07K 2317/71* (2013.01); *C07K 2317/73* (2013.01)

(58) Field of Classification Search

None

See application file for complete search history.

(56) References Cited

U.S. PATENT DOCUMENTS

| | | | | |
|---|---|---|---|---|
| 3,773,919 | A | 11/1973 | Boswell et al. | |
| 4,485,045 | A | 11/1984 | Regen | |
| 4,522,811 | A | 6/1985 | Eppstein et al. | |
| 4,544,545 | A | 10/1985 | Ryan et al. | |
| 5,013,556 | A | 5/1991 | Woodle et al. | |
| 5,030,719 | A | 7/1991 | Umemoto et al. | |
| 5,151,510 | A | 9/1992 | Stec et al. | |
| 5,624,821 | A | 4/1997 | Winter et al. | |
| 5,733,743 | A | 3/1998 | Jolmson et al. | |
| 6,538,124 | B1 | 3/2003 | Idusogie et al. | |
| 6,737,056 | B1 | 5/2004 | Presta | |
| 7,465,790 | B2 | 12/2008 | Waldmann et al. | |
| 7,563,441 | B2 | 7/2009 | Graus et al. | |
| 7,575,923 | B2 | 8/2009 | Dorken et al. | |
| 7,728,114 | B2 | 6/2010 | Mach et al. | |
| 7,951,918 | B2 | 5/2011 | Glaser et al. | |
| 8,513,390 | B2 | 8/2013 | Stagliano et al. | |
| 8,518,404 | B2 | 8/2013 | Daugherty et al. | |
| 8,529,898 | B2 | 9/2013 | Daugherty et al. | |
| 8,541,203 | B2 | 9/2013 | Daugherty et al. | |
| 8,563,269 | B2 | 10/2013 | Stagliano et al. | |
| 8,809,504 | B2 | 8/2014 | Lauermann | |
| 8,846,042 | B2 | 9/2014 | Zhou | |
| 8,969,526 | B2 | 3/2015 | Baehner et al. | |
| 9,079,965 | B2 * | 7/2015 | Zhou | C07K 16/32 |
| 9,120,853 | B2 | 9/2015 | Lowman et al. | |
| 9,169,321 | B2 | 10/2015 | Daugherty et al. | |
| 9,212,225 | B1 | 12/2015 | Ellwanger et al. | |
| 9,453,078 | B2 | 9/2016 | Stagliano et al. | |
| 9,540,440 | B2 | 1/2017 | Lowman et al. | |
| 9,545,442 | B2 | 1/2017 | Lowman et al. | |
| 9,562,073 | B2 | 2/2017 | Moore et al. | |
| 9,718,893 | B2 | 8/2017 | Jung et al. | |

(Continued)

FOREIGN PATENT DOCUMENTS

| | | |
|---|---|---|
| CN | 106255507 A | 12/2016 |
| EP | 1 523 503 B1 | 4/2009 |

(Continued)

OTHER PUBLICATIONS

Luo et al. (Moleuclar Pharmaceutics, 2014, vol. 11, pp. 1750-1761) (Year: 2014).*

(Continued)

*Primary Examiner* — Lisa V Cook

(74) *Attorney, Agent, or Firm* — Rothwell, Figg, Ernst & Manbeck, P.C.

(57) ABSTRACT

Provided herein antibodies, activatable antibodies (AAs), bispecific antibodies, and bispecific activatable antibodies (BAAs). Also provided herein are methods of making and methods of use of these antibodies, AAs, bispecific antibodies, and BAAs.

13 Claims, 27 Drawing Sheets

Specification includes a Sequence Listing.

(56) References Cited

U.S. PATENT DOCUMENTS

| | | | | |
|---|---|---|---|---|
| 9,889,211 | B2 | 2/2018 | Lowman et al. | |
| 10,059,762 | B2 | 8/2018 | Stagliano et al. | |
| 10,077,300 | B2 | 9/2018 | Daugherty et al. | |
| 10,118,961 | B2 | 11/2018 | Stagliano et al. | |
| 10,138,272 | B2 | 11/2018 | Moore et al. | |
| 10,179,817 | B2 | 1/2019 | Sagert et al. | |
| 10,533,053 | B2 | 1/2020 | Lowman et al. | |
| 10,669,337 | B2 * | 6/2020 | Irving | A61K 47/6845 |
| 10,709,799 | B2 | 7/2020 | Lowman et al. | |
| 10,875,913 | B2 | 12/2020 | Stagliano et al. | |
| 11,161,906 | B2 * | 11/2021 | Lowman | C07K 16/2896 |
| 11,472,889 | B2 * | 10/2022 | Boustany | C07K 16/40 |
| 2003/0150294 | A1 | 6/2003 | Gillies et al. | |
| 2004/0109855 | A1 | 6/2004 | Waldmann et al. | |
| 2005/0226876 | A1 | 10/2005 | Graus et al. | |
| 2009/0304719 | A1 | 12/2009 | Daugherty et al. | |
| 2010/0189651 | A1 | 6/2010 | Stagliano et al. | |
| 2010/0189727 | A1 | 7/2010 | Rodeck et al. | |
| 2011/0059078 | A1 | 3/2011 | Coyle et al. | |
| 2012/0149061 | A1 | 6/2012 | Stagliano et al. | |
| 2012/0207756 | A1 | 8/2012 | Stagliano et al. | |
| 2012/0237512 | A1 | 9/2012 | Daugherty et al. | |
| 2012/0237977 | A1 | 9/2012 | Daugherty et al. | |
| 2012/0244154 | A1 | 9/2012 | Daugherty et al. | |
| 2013/0060011 | A1 | 3/2013 | Bruenker et al. | |
| 2013/0129730 | A1 | 5/2013 | Kufer et al. | |
| 2013/0150558 | A1 | 6/2013 | Williams et al. | |
| 2013/0195881 | A1 | 8/2013 | Singh et al. | |
| 2013/0309230 | A1 | 11/2013 | Stagliano et al. | |
| 2013/0315906 | A1 | 11/2013 | Lowman et al. | |
| 2014/0010810 | A1 | 1/2014 | West et al. | |
| 2014/0024810 | A1 | 1/2014 | Stagliano et al. | |
| 2014/0045195 | A1 | 2/2014 | Daugherty et al. | |
| 2014/0154253 | A1 | 6/2014 | Ng et al. | |
| 2014/0212436 | A1 | 7/2014 | Moore et al. | |
| 2014/0255313 | A1 | 9/2014 | Vasiljeva et al. | |
| 2014/0288275 | A1 | 9/2014 | Moore et al. | |
| 2014/0302037 | A1 | 10/2014 | Borges et al. | |
| 2014/0308285 | A1 | 10/2014 | Yan et al. | |
| 2014/0363430 | A1 | 12/2014 | West et al. | |
| 2015/0005477 | A1 | 1/2015 | Lowman et al. | |
| 2015/0079088 | A1 | 3/2015 | Lowman et al. | |
| 2015/0118254 | A1 | 4/2015 | Lowman et al. | |
| 2015/0376271 | A1 | 12/2015 | Perlroth et al. | |
| 2016/0115241 | A1 | 4/2016 | Yan et al. | |
| 2016/0122425 | A1 | 5/2016 | Daugherty et al. | |
| 2016/0168263 | A1 | 6/2016 | Bigner et al. | |
| 2016/0193332 | A1 | 7/2016 | Lowman et al. | |
| 2016/0194399 | A1 | 7/2016 | Irving et al. | |
| 2016/0200826 | A1 | 7/2016 | West et al. | |
| 2016/0220537 | A1 | 8/2016 | Garner et al. | |
| 2016/0228546 | A1 | 8/2016 | Stagliano et al. | |
| 2016/0257748 | A1 | 9/2016 | Michaels et al. | |
| 2017/0081397 | A1 | 3/2017 | Stagliano et al. | |
| 2017/0096489 | A1 | 4/2017 | Lowman et al. | |
| 2017/0196996 | A1 | 7/2017 | Lowman et al. | |
| 2017/0218078 | A1 | 8/2017 | Raum et al. | |
| 2017/0247476 | A1 | 8/2017 | Yan et al. | |
| 2018/0333507 | A1 | 11/2018 | Lowman et al. | |
| 2019/0119370 | A1 | 4/2019 | Stagliano et al. | |
| 2019/0211089 | A1 | 7/2019 | Daugherty et al. | |
| 2020/0270350 | A1 | 8/2020 | Lowman et al. | |
| 2021/0023243 | A1 | 1/2021 | Lowman et al. | |
| 2021/0047406 | A1 | 2/2021 | Irving et al. | |

FOREIGN PATENT DOCUMENTS

| | | | |
|---|---|---|---|
| EP | 1 324 771 | B1 | 6/2011 |
| EP | 2155788 | B1 | 6/2012 |
| EP | 2155783 | B1 | 7/2013 |
| WO | WO 1994/11026 | A2 | 5/1994 |
| WO | WO 1995/16037 | A1 | 6/1995 |
| WO | 1999/043713 | | 9/1999 |
| WO | 2000/042072 | | 7/2000 |
| WO | 2001/058957 | | 8/2001 |
| WO | WO 2001/91798 | A2 | 12/2001 |
| WO | WO 2002/30460 | A2 | 4/2002 |
| WO | WO 2004/003019 | A2 | 1/2004 |
| WO | WO 2004/009638 | A1 | 1/2004 |
| WO | WO 2005/047461 | A2 | 5/2005 |
| WO | 2005/100402 | | 10/2005 |
| WO | 2005/118635 | | 12/2005 |
| WO | WO 2007/027935 | A2 | 3/2007 |
| WO | WO 2007/042261 | A2 | 4/2007 |
| WO | 2007/109254 | | 9/2007 |
| WO | WO 2007/105027 | A1 | 9/2007 |
| WO | 2007/147001 | | 12/2007 |
| WO | WO 2008/119566 | A2 | 10/2008 |
| WO | WO 2008/119567 | A2 | 10/2008 |
| WO | 2008/134046 | | 11/2008 |
| WO | WO 2009/014726 | A1 | 1/2009 |
| WO | WO 2009/018386 | A1 | 2/2009 |
| WO | WO 2009/025846 | A2 | 2/2009 |
| WO | 2009/100309 | | 8/2009 |
| WO | 2010/042904 | | 4/2010 |
| WO | WO 2010/037836 | A2 | 4/2010 |
| WO | WO 2010/037838 | A2 | 4/2010 |
| WO | 2010/077643 | A1 | 7/2010 |
| WO | WO 2010/081173 | A2 | 7/2010 |
| WO | WO 2010/096838 | A2 | 8/2010 |
| WO | WO 2010/129609 | A2 | 11/2010 |
| WO | WO 2011/109789 | A2 | 9/2011 |
| WO | WO 2012/025525 | A1 | 3/2012 |
| WO | 2012/088247 | | 6/2012 |
| WO | 2012/130831 | | 10/2012 |
| WO | WO 2012/158818 | A2 | 11/2012 |
| WO | WO 2012/162067 | A2 | 11/2012 |
| WO | 2013/026833 | A1 | 2/2013 |
| WO | 2013/026835 | | 2/2013 |
| WO | 2013/026837 | A1 | 2/2013 |
| WO | 2013/026839 | | 2/2013 |
| WO | 2013/092001 | | 6/2013 |
| WO | 2013/136078 | | 9/2013 |
| WO | WO 2013/128194 | A1 | 9/2013 |
| WO | WO 2013/163631 | A2 | 10/2013 |
| WO | WO 2013/192546 | A1 | 12/2013 |
| WO | WO 2013/192550 | A2 | 12/2013 |
| WO | 2014/022592 | | 2/2014 |
| WO | WO 2014/047231 | A1 | 3/2014 |
| WO | 2014/100139 | | 6/2014 |
| WO | 2014/108483 | | 7/2014 |
| WO | 2014/113510 | | 7/2014 |
| WO | WO 2014/107599 | A2 | 7/2014 |
| WO | 2014/186842 | | 11/2014 |
| WO | 2015/001085 | | 1/2015 |
| WO | WO 2015/013671 | A1 | 1/2015 |
| WO | 2015/104346 | A1 | 7/2015 |
| WO | WO 2016/014974 | A2 | 1/2016 |
| WO | 2016/071355 | | 5/2016 |
| WO | 2016/086189 | | 6/2016 |
| WO | 2016/116626 | | 7/2016 |
| WO | WO 2016/118629 | A1 | 7/2016 |
| WO | 2016164480 | A1 | 10/2016 |
| WO | 2017/162587 | | 9/2017 |
| WO | WO 2017/157305 | A1 | 9/2017 |
| WO | 2019/213444 | | 11/2019 |

OTHER PUBLICATIONS

Costa et al. (European Journal of Pharmaceutics and Biopharmaceutics 74 (2010) 127-138) | (Year: 2010).*

*Amgen, Inc. et al.* vs *Sanofz and Regeneron*. US Court of Appeals For the Federal Circuit, Case: 17-1480, Document 176, Filed: Feb. 6, 2018

Baeuerle, P.A. and Reinhardt, C. (Jun. 15, 2009)"Bispecific T-cell engaging antibodies for cancer therapy" *Cancer Res*, 69(12):4941-4944.

Bagshawe, K.D. (2006) "Antibody-directed enzyme prodrug therapy (ADEPT) for cancer" *Expert Rev Anticancer Ther*, 6(10):1421-1431.

Bahr, Robert W., Deputy Commissioner for Patent Examination Policy, U.S. Patent and Trademark Office Memorandum dated Feb. 22, 2018, 2 pages.

(56) References Cited

OTHER PUBLICATIONS

Bluemel, C. et al. (2010) "Epitope distance to the target cell membrane and antigen size determine the potency of T cell-mediated lysis by BiTE anibodies specific for a large melanoma surface antigen" *Cancer Immunol Immunother*, 59:1197-1209.
Boersma, Y.L. et al. (Dec. 2, 2011) "Bispecific Designed Ankyrin Repeat Proteins (DARPins) Targeting Epidermal Growth Factor Receptor Inhibit A431 Cell Proliferation and Receptor Recycling" *J. Biol. Chem.* 286(48):41273-41285.
Bostrom, J. et al. (Mar. 20, 2009) "Variants of the antibody herceptin that interact with HER2 and VEGF at the antigen binding" *Science*, 323:1610-1614.
Brorson, K. et al. (1999) "Mutational Analysis of Avidity and Fine Specificity of Anti-Levan Antibodies" *J Immunol*, vol. 163, p. 6694-6701.
Brummell et al. "Probing the combining site of an anti-carbohydrate antibody by saturation-mutagenesis: role of the heavy-chain CDR3 residues", *Biochemistry*, vol. 32, p. 1180-1187 (1993).
Burks, E.A. et al. (Jan. 1997) "In vitro scanning saturation mutagenesis of an antibody binding pocket" *Proc Natl Acad Sci USA*, vol. 94, p. 412-417.
Caron et al. "Engineered Humanized Dimeric Forms of IgG Are More Effective Antibodies" *J. Exp Med.*, vol. 176, p. 1191-1195 (1992).
Chan, A.C. and Carter, P.J. (2010) "Therapeutic antibodies for autoimmunity and inflammation" *Nature Reviews Immunol*, 10:301-316.
Chatenoud, L. (2005) "CD3-specific antibodies restore self-tolerance: mechanisms and clinical applications" *Curr Opin Immunol*, 17:632-637.
Chichili, G.R. et al. (May 27, 2015) "A CD3xCD123 bispecific DART for redirecting host T cells to myelogenous leukemia: Preclinical activity and safety in nonhuman primates" *Sci Transl Med*, 7(289):289ra82, 14 pages.
Cochlovius, B. et al. (2000) "Cure of Burkitt's lymphoma in severe combined immunodeficiency mice by T cells, tetravalent CD3 x CD19 tandem diabody, and CD28 costimulation" *Cancer Res*, 60:4336-4341.
Colman, P.M. (1994) "Effects of amino acid sequence changes on antibody -antigen interactions" *Research in Immunology*, vol. 145, p. 33-36.
Conrad, M.L. et al. (2007) "TCR and CD3 Antibody Cross-Reactivity in 44 Species" *Cytometry Part A*, 71A:925-933.
Deng, R. et al., "Subcutaneous bioavailability of therapeutic antibodies as a function of FcRn binding affinity in mice" *mAbs*. 4:101-109 (2012).
Desnoyers, L.R. et al. (2013) "Tumor-Specific Activation of an EGFR-Targeting Probody Enhances Therapeutic Index" *Science Translational Medicine*, 5(207):207ra144, 10 pages.
Dimasi, N. et al. (2009) "The Design and Characterization of Oligospecific Antibodies for Simultaneous Targeting of Multiple Disease Mediators" *J Mol Biol*, 393:672-692.
Donaldson, J. et al. (Nov. 2009) "Design and development of masked therapeutic antibodies to limit off-target effects: Application to anti-EGFR antibodies" Cancer Biol Ther, 8(22):2147-2152. NIH Public Access Author Manuscript; available in PMC Jan. 16, 2013, 12 pages.
Dong, J. et al. (2011) "A stable IgG-like bispecific antibody targeting the epidermal growth factor receptor and the type I insulin-like growth factor receptor demonstrates superior anti-tumor activity" *MAbs*, 3(3):273-288.
Epstein, D.A. et al. "Biological activity of liposome-encapsulated murine interferon gamma is mediated by a cell membrane receptor" *Proc. Natl. Acad. Sci. USA*, vol. 82, p. 3688-3692 (1985).
European Patent No. 2 155 783, Notice of Opposition by Affimed Therapeutics, Apr. 29, 2014, 10 pages.
European Patent No. 2 155 783, "D4" Submission filed with Notice of Oppositionby Affimed Therapeutics, Apr. 29, 2014, p. 1-5.
European Patent No. 2 155 783, Notice of Opposition by Chugai Seiyaku, Apr. 29, 2014, 19 pages.
European Patent No. 2 155 783, "D05" Submission filed with Notice of Opposition by Chugai Seiyaku, Apr. 29, 2014, 6 pages.
European Patent No. 2 155 788, Notice of Opposition by F. Hoffmann-La Roche Ag, Mar. 22. 2013, 39 pages.
European Patent No. 2 155 788, "D17" Summary: Methods used for the sequencing of SP34, filed dated Mar. 22, 2013, by F. Hoffmann-La Roche Ag, p. 1-4.
Fitzgerald, J. and A. Lugovsky (2011) "Rational engineering of antibody therapeutics targeting multiple oncogene pathways" *MAbs*, 3(3):299-309.
Grosschedl, R. and D. Baltimore (1985) "Cell-type specificity of immunoglobulin gene expression is regulated by at least three DNA sequence elements" *Cell*, 41:885-897.
Guilmeau, S. et al. (2010) "Heterogeneity of Jagged1 expression in human and mouse intestinal tumors: implications for targeting Notch signaling" *Oncogene*, 29:992-1002.
Ibragimova, G.T. et al. "Stability of the β-Sheet of the WW Domain: A Molecular Dynamics Simulation Study" *Biophysical Journal*, vol. 77, pp. 2191-2198 (1999).
Irving, B.A. (Feb. 2015) "Probodies Empower a New Generation of Antibody Immunotherapies," CytomX Therapeutics Inc. presentation at Key stone Symposia™ on Molecular and Cellular Biology, Feb. 8-13, 2015; 25 pages.
Jackman. J. et al. "Development of a two-part strategy to identify a therapeutic human bispecific antibody that inhibits IgE receptor signaling" *J. Biol. Chem.*, 285:20850-20859 (2010) Epub May 5, 2010.
Jang, Y-L. et al. "The structural basis for DNA binding by an anti-DNA Autoantibody", *Molecular Immunology*, vol. 35, p. 1207-1217 (1998).
Junttila, T.T. et al. (Oct. 2014) "Antitumor efficacy of a bispecific antibody that targets HER2 and activates T cells" *Cancer Res*, 74(19):5561-5571. Epub Sep. 16, 2014.
Kiewe, P. (2008) "Ertumaxomab: a trifunctional antibody for breast cancer treatment" *Expert Opinion on Investigational Drugs*, 17:1553-1558.
Kobayashi, H et al. (1999) "Tryptophan H33 plays an important role in pyrimidine (6-4) pyrimidine photoproduct binding by a high-affinity antibody" *Protein Engineering*, vol. 12, No. 10, p. 879-844.
Kroesen, B.J. et al. (1998) "Bispecific antibodies for treatment of cancer in experimental animal models and man" *Adv. Drug Delivery Rev*, 31:105-129.
Kumar, S. et al. "Molecular Cloning and Expression of the Fabs of Human Autoantibodies in *Escherichia coli", Journal of Biological Chemistry*, vol. 275, p. 35129-35136 (2000).
La Rocca, G. et al. "Zymographic detection and clinical correlations of MMP-2 and MMP-9 in breast cancer sera" *British Journal of Cancer*, vol. 90, p. 1414-1421 (2004).
Linke, R, et al. "Catumaxomab: clinical development and future directions" *mAbs*, 2:129-136 (2010).
Liu, M.A. et al. (1985) "Heteroantibody duplexes target cells for lysis by cytotoxic T lymphocytes" *Proc. Natl. Acad. Sci. USA*, 82:8648-8652.
Lund, J . et al. "Multiple binding sites on the CH2 domain of IgG for mouse FcgammaR11" *Mol. Immunol.* 29:53-39 (1992).
Lutterbuese, R. et al. (Jul. 13, 2010) "T cell-engaging BiTE antibodies specific for EGFR potently eliminate KRAS- and BRAF-mutated colorectal cancer cells" *Proc Natl Acad Sci USA*, 107(28):12605-12610. Epub Jun. 28, 2010.
Malcolm, S.L. et al. (2012) "A humanised mouse model of cytokine release: Comparison of CD3-specific antibody fragments" *J Immunol Meth*, 384:33-42.
Malmqvist, M. (Jan. 14, 1993) "Biospecific interaction analysis using biosensor technology" *Nature*, 361:186-187.
Marvin, J.S. and Z. Zhu "Recombinant approaches to IgG-like bispecific antibodies" *Acta Pharm. Sinica*, 26:649-658 (2005).
Nisonoff, A. and W.J. Mandy, "Quantitative estimation of the hybridization of rabbit antibodies" *Nature*, 194:355-359 (1962).
Okayama, H. and P. Berg, "A cDNA cloning vector that permits expression of cDNA inserts in mammalian cells" *Mol. Cell. Biol.*, 3:280-289 (1983).

(56) References Cited

OTHER PUBLICATIONS

Olafsen, T. "Fc engineering: serum half-life modulation through FcRn binding" in *Antibody Engineering: Methods and Protocols, SecondEdition.Methods Mol. Biol.*, vol. 907, pp. 537-556 (2012).
Orcutt, K.D. et al., "A modular IgG-scFv bispecific antibody topology" *Prot. Eng. Design Select*, 23 2221-228 (2010).
Pace, C.S. et al. (Aug. 13, 2013) "Bispecific antibodies directed to CD4 domain 2 and HIV envelope exhibit exceptional breadth and picomolar potency against HIV-1" *PNAS*, 110(33):13540-13545.
Petkova, S.B. et al., "Enhanced half-life of genetically engineered human IgG1 antibodies in a humanized FcRn mouse model: potential application in humorally mediated autoimmune disease" *Intl. Immunol.*, 18:1759-1769 (2006).
Polu, K.R. and H.B. Lowman (2014) "Probody therapeutics for targeting antibodies to diseased tissue" *Expert Opin Biol Ther*, 14(8): 1049-1053.
Reusch, U. et al. (Jan. 1, 20016) "Anti-CD3 x anti-epidermal growth factor receptor (EGFR) bispecific antibody redirects T-cell cytolytic activity to EGFR-positive cancers in vitro and in an animal model" *Clinical Cancer Research*, vol. 12, No. 1, p. 183-190.
Riethmuller, G. "Symmetry breaking: bispecific antibodies, the beginnings, and 50 years on" *Cancer Immunity*, 12:12-18 (2012).
Sebastian, M. et al. (2007) "Treatment of non-small cell lung cancer patients with the trifunctional monoclonal antibody catumaxomab (anti-EpCAM x anti-CD3): a phase I study" *Cancer Immunol. Immunother*, 56: 1637-1644.
Shopes, B. (1992) "A Genetically Engineered Human IgG Mutant with Enhanced Cytolytic Activity" *Journal of Immunology*, vol. 148, No. 1, p. 2918-2922.
Smith-Gill, S.J. et al. "Contributions of Immunoglobin Heavy and Light Chains to Antoibody Specificty for Lysozome and Two Haptens" *J Immunol*, vol. 139, p. 4135-4144 (1987).
Song, M-K. et al. "Light chain of. Natural Antibody Plays a Dominant Role in Protein Antigen Binding" *Biochemical and Biophysical Research Communications*, vol. 268, p. 390-394 (2000).
Stevenson, G.T. et al., "A chimeric antibody with dual Fc regions (bisFabFc) prepared by manipulations at the IgG hinge" *Anti-Cancer Drug Design*, vol. 3, p. 219-230 (1989).
Sun, L.L. et al. (May 13, 2015) "Anti-CD20/CD3 T cell-dependent bispecific antibody for the treatment of B cell malignancies" *Sci Transl Med.*, 7(287):287ra70, 11 pages.
Ward, E.S. et al. "Binding activities of a repertoire of single immunoglobin variable domains secreted from *Escherichia coli*" *Nature*, vol. 341, p. 544-546 (1989).
Watanabe, Y. et al. (2011) "In vitro and in viva antitumor effects of recombinant bispecific antibodies based on humanized anti-EGFR antibody", *Oncology Reports*, 26:949-955.
Wu, C. et al. (Nov. 2007) "Simultaneous targeting of multiple disease mediators by a dual-variable-domain immunoglobulin" *Nature Biotechnol.*, 25: 1290-1297.
Bedouelle et al., "Diversity and junction residues as hotspots of binding energy in an antibody neutralizing the dengue virus", FEBS J. (2006) 273(1):34-46.
Canfield and Morrison, "The Binding Affinity of Human Igg for its High Affinity Fc Receptor is Determined by Multiple Amino Acids in the CH2 Domain and is Modulated by the Hinge Region", J. Exp. Med. (1991) 173(6):1483-1491.
Chappel et al., "Identification of a secondary Fc gamma RI binding site within a genetically engineered human IgG antibody", J. Biol. Chem. (1993) 268(33):25124-25131.
Dong et al., "Stable IgG-like Bispecific Antibodies Directed toward the Type I Insulin-like Growth Factor Receptor Demonstrate Enhanced Ligand Blockade and Anti-tumor Activity", JBC (2011) 286(6):4703-4717. (Supplemental pp. 1-6).
Dufner et al., "Harnessing phage and ribosome display for antibody optimization", Trends Biotechnol. (2006) 24(11):523-529.
Erster et al., "Site-specific targeting of antibody activity in vivo mediated by disease-associated proteases", J. Control Release (2012) 161(3):804-812.
Geiger et al., "Protease-Activation Using Anti-Idiotypic Masks Enables Tumor Specificity of a Folate Receptor 1-T Cell Bispecific Antibody", Nat. Commun. (2020) 11:3196.
Han et al., "Masked Chimeric Antigen Receptor for Tumor-Specific Activation", Mol. Ther. (2017) 25(1):274-284.
Metz et al., "Bispecific Antibody Derivatives with Restricted Binding Functionalities that are Activated by Proteolytic Processing" Prot. Eng. Des. & Sel. (2012) 25(10): 571-580.
Vajdos et al., "Comprehensive Functional Maps of the Antigen-binding Site of an Anti-Erb82 Antibody Obtained with Shotgun Scanning Mutagenesis", J. Mol. Biol. (2002) 320(2):415-428.
Viricel et al., "Monodisperse Polysarcosine-Based Highly-Loaded Antibody-Drug Conjugates", Chem, Sci. (2019) 10(14):4048-4053.
Luo et al. (Molecular Pharmaceutics, 2014, vol. 11, pp. 1750-1761) (Year: 2014).
Japanese Office Action issued in Japanese Application No. 2020-520212 dated Sep. 27, 2022, with English Translation, 13 pages.
Kontermann, "Dual targeting strategies with bispecific antibodies", mAbs, vol. 4, Issue 2, pp. 182-197, (2012).
U.S. Appl. No. 61/858,402, filed Jul. 25, 2013, 156 pgs.

* cited by examiner (1A)

(1B)

FIGS. 3A-B
(3A)
(3B)
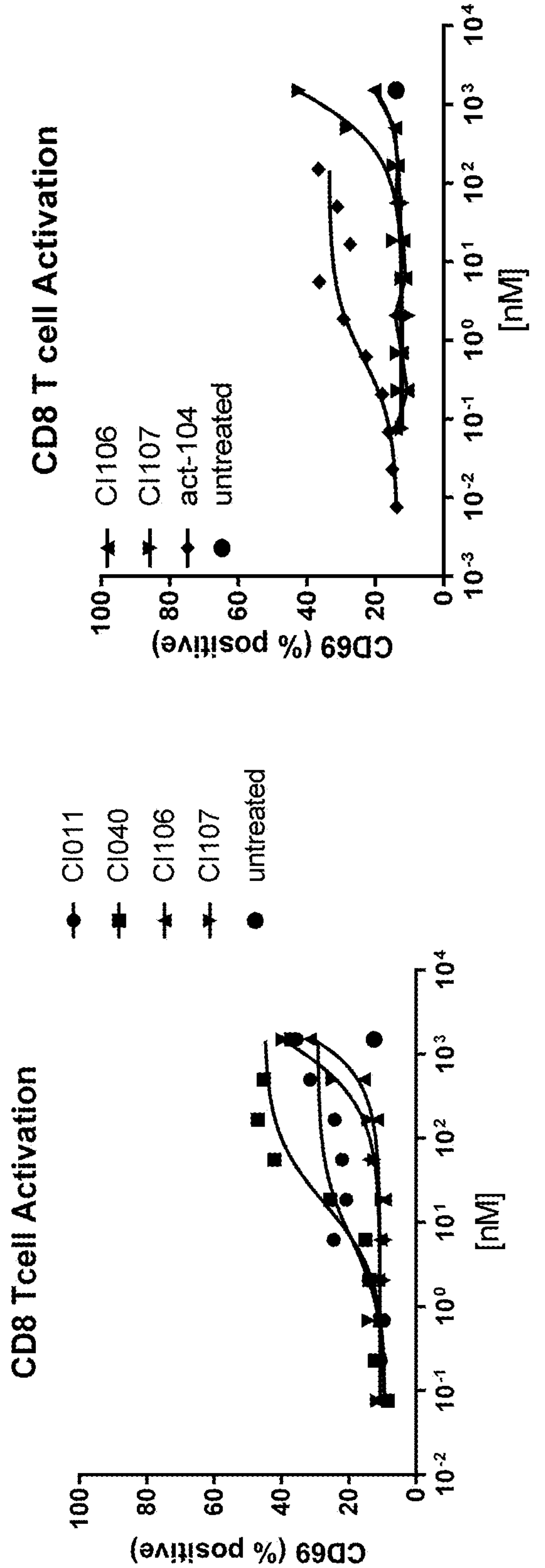

(6A)
Human
HT29-luc2 Cytotoxicity
% Cytotoxicity
[pM]
CI106
CI107
act-104
(6B)
Cyno
HT29-luc2 Cytotoxicity
Cytotoxicity (%)
[pM]
CI106
CI107
act-TCB
(6C)
Jurkat Binding
MFI (corrected)
[nM]
CI106
CI107
act-TCB
(6D)
Binding to Cyno Pan T cells
MFI (corrected)
[nM]
CI106
CI107
act-TCB FIGS. 10A-C
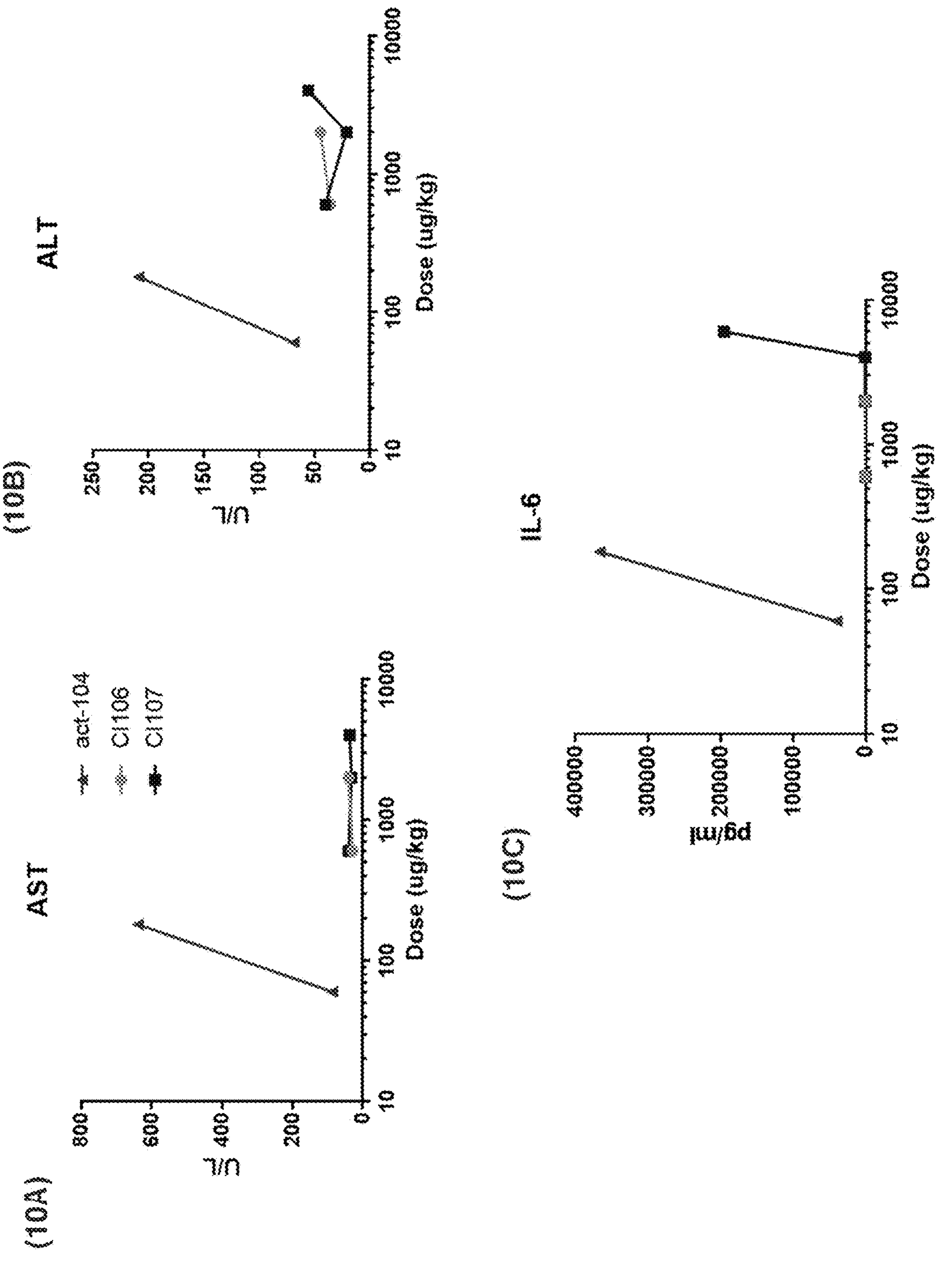

FIGS. 10D-E
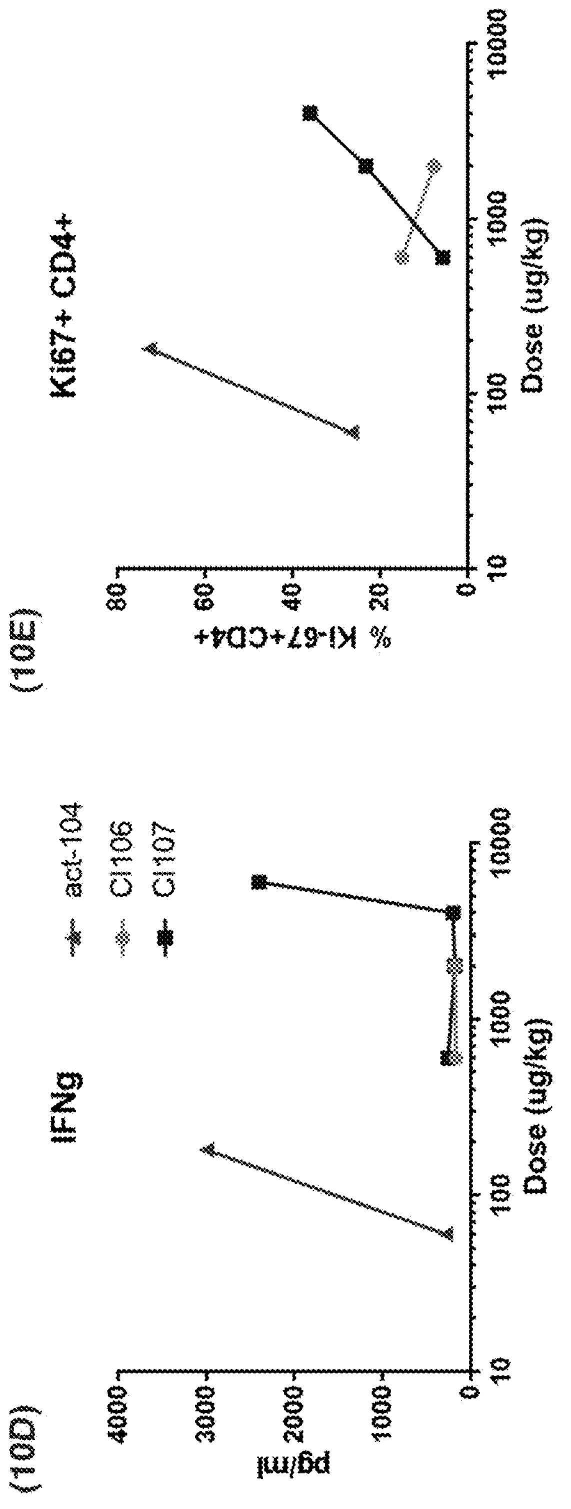

ANTIBODIES, ACTIVATABLE ANTIBODIES, BISPECIFIC ANTIBODIES, AND BISPECIFIC ACTIVATABLE ANTIBODIES AND METHODS OF USE THEREOF

CROSS-REFERENCE TO RELATED APPLICATIONS

This application is a divisional Ser. No. 16/159,451, filed Oct. 12, 2018, now U.S. Pat. No. 11,472,889 which claims the benefit of U.S. Provisional Application No. 62/572,468, filed Oct. 14, 2017; U.S. Provisional Application No. 62/577,140, filed Oct. 25, 2017; U.S. Provisional Application No. 62/613,358, filed Jan. 3, 2018; U.S. Provisional Application No. 62/666,065, filed May 2, 2018; and U.S. Provisional Application No. 62/731,622, filed Sep. 14, 2018, the contents of each of which are incorporated herein by reference in their entirety.

FIELD OF THE INVENTION

Provided herein antibodies, activatable antibodies (AAs), bispecific antibodies, and bispecific activatable antibodies (BAAs). Also provided herein are methods of making and methods of use of these antibodies, AAs, bispecific antibodies, and BAAs.

REFERENCE TO SEQUENCE LISTING

The "Sequence Listing" submitted electronically concurrently herewith pursuant 37 C.F.R. § 1.821 in computer readable form (CRF) via EFS-Web as file name CYTX045USDIV.XML is incorporated herein by reference. The electronic copy of the Sequence Listing was created on Sep. 6, 2022, and the size on disk is 393216 bytes.

BACKGROUND

Antibody-based therapies have proven effective treatments for several diseases but in some cases, toxicities due to broad target expression have limited their therapeutic effectiveness. In addition, antibody-based therapeutics have exhibited other limitations such as rapid clearance from the circulation following administration.

In the realm of small molecule therapeutics, strategies have been developed to provide prodrugs of an active chemical entity. Such prodrugs are administered in a relatively inactive (or significantly less active) form. Once administered, the prodrug is metabolized in vivo into the active compound. Such prodrug strategies can provide for increased selectivity of the drug for its intended target and for a reduction of adverse effects.

Accordingly, there is a continued need in the field of antibody-based therapeutics for antibodies that mimic the desirable characteristics of the small molecule prodrug.

SUMMARY OF THE INVENTION

Provided herein are antibodies, bispecific antibodies, activatable antibodies, and bispecific activatable antibodies, methods of making, and methods of use thereof. These find use in therapeutics and diagnostics. The activatable antibodies and bispecific activatable antibodies of the present disclosure may be used to reduce damage to healthy tissue generally caused by an antibody binding to its target on healthy tissue as well as on diseased tissue.

Accordingly in one aspect, provided herein are bispecific activatable antibodies (BAA), wherein said BAA, when activated, specifically binds to two targets and comprises the following structure:

a) an IgG antibody (AB1) that specifically binds to a first target wherein the AB1 comprises:
   a. two heavy chains (AB1 HCs) and two light chains (AB1 LCs); and
   b. a first masking moiety (MM1) linked to a first cleavable moiety (CM1) to form a MM1-CM1 construct, wherein the carboxyl terminus of a MM1-CM1 construct is linked to each amino terminus of each light chain of the AB1, wherein
   c. the MM1 inhibits the binding of the AB1 to its target; and
   d. the CM1 is a polypeptide that functions as a substrate for a first protease, b) two scFvs (AB2) that each specifically binds to a second target wherein each AB2 comprises:
   a. a light chain variable region linked to a heavy chain variable region, wherein the carboxyl terminus of each AB2 is linked to the amino terminus each of the AB1 heavy chains; and
   b. a second masking moiety (MM2) linked to a second cleavable moiety (CM2) to form a MM2-CM2 construct, wherein the carboxyl terminus of a MM2-CM2 construct is linked to the amino terminus of each AB2 wherein
   c. the MM2 inhibits the binding of the AB2 to its target; and
   d. the CM2 is a polypeptide that functions as a substrate for a second protease, c) and wherein the BAA has at least one of the following characteristics:
   a. MM2 comprises amino acid sequence SEQ ID NO: 12;
   b. MM1 comprises an amino acid sequence selected from the group consisting of sequences presented in Table 7;
   c. AB2 comprises a heavy chain variable domain as set forth in SEQ ID NO: 2 or SEQ ID NO: 3 or a light chain variable domain as set forth in SEQ ID NO: 1 or SEQ ID NO: 4; and
   d. AB1 comprises an Fc region comprising an amino acid substitution in at least one of amino acid positions L234, L235, N297, and P331, as numbered by the EU index as set forth in Kabat, such that the BAA has reduced effector function.

In some embodiments, the BAAs provided herein comprise:

A bispecific activatable antibody (BAA), wherein said BAA, when activated, specifically binds to two targets and comprises the following structure:
   a. an IgG antibody (AB1) that specifically binds to a first target wherein the AB1 comprises two heavy chains (AB1 HCs) and two light chains (AB1 LCs); and wherein the AB1 is linked to a first masking moiety (MM1) linked to a first cleavable moiety (CM1) to form a MM1-CM1 construct, wherein the carboxyl terminus of a MM1-CM1 construct is linked to each amino terminus of each light chain of the AB1, wherein
      the MM1 inhibits the binding of the AB1 to its target; and
      the CM1 is a polypeptide that functions as a substrate for a first protease, b. two scFvs (each an AB2) that each specifically binds to a second target wherein each AB2 comprises a light chain variable region linked to a heavy chain variable region, wherein the carboxyl terminus of each AB2 is linked to the amino terminus each of the AB1 heavy chains; and wherein each AB2 is linked to a second masking moiety (MM2) linked to a second cleavable moiety (CM2) to form a MM2-CM2 construct, wherein the carboxyl terminus of each MM2-CM2 construct is linked to the amino terminus of each AB2 wherein the MM2 inhibits the binding of the AB2 to its target; and the CM2 is a polypeptide that functions as a substrate for a second protease, and wherein the BAA has at least one of the following characteristics:

i. MM2 comprises amino acid sequence SEQ ID NO: 12;

ii. MM1 comprises an amino acid sequence selected from the group consisting of sequences presented in Table 7;

iii. AB2 comprises a heavy chain variable domain as set forth in SEQ ID NO: 2 or SEQ ID NO: 3 or a light chain variable domain as set forth in SEQ ID NO: 1 or SEQ ID NO: 4; and iv. AB1 comprises an Fc region comprising an amino acid substitution in at least one of amino acid positions L234, L235, N297, and P331, as numbered by the EU index as set forth in Kabat, such that the BAA has reduced effector function.

In some embodiments, the BAA comprises a heavy chain variable domain as set forth in SEQ ID NO: 2 or SEQ ID NO: 3 and a light chain variable domain as set forth in SEQ ID NO: 1 or SEQ ID NO: 4. In some embodiments, the AB1 binds a tumor target and the AB2 binds an immune effector target. In some embodiments, the BAA is a T cell-engaging bispecific (TCB) AA (TCBAA). In some embodiments, the AB1 binds EGFR and the AB2 binds CD3. In some embodiments, the MM1 comprises an amino acid sequence selected from the group consisting of sequences presented in Table 7. In some embodiments, the MM1 comprises an amino acid sequence selected from the group consisting of SEQ ID NO: 85 and SEQ ID NO: 78. In some embodiments, the MM1 comprises SEQ ID NO: 78. In some embodiments, the MM2 comprises the amino acid sequence SEQ ID NO: 12. In some embodiments, the CM comprises the amino acid sequence of SEQ ID NO: 14. In some embodiments, the CM comprises the amino acid sequence of SEQ ID NO: 17. In some embodiments, the CMs the CM comprises the amino acid sequence of SEQ ID NO: 16. In some embodiments, the CM1 comprises an amino acid sequence selected from the group comprising SEQ ID NO: 14 and SEQ ID NO: 16. In some embodiments, the CM2 comprises an amino acid sequence selected from the group comprising SEQ ID NO: 14 and SEQ ID NO: 17. In some embodiments, provided herein is BAA CI106, comprising the layout and sequence as provided in Table 11 and Example 1. In some embodiments, provided herein is BAA CI107, comprising the layout and sequence as provided in Table 11 and Example 1. In some embodiments, provided herein is BAA CI079, comprising the layout and sequence as provided in Table 11 and Example 1. In some embodiments, provided herein is BAA CI090, comprising the layout and sequence as provided in Table 11 and Example 1. In some embodiments, provided herein is BAA CI135, comprising the layout and sequence as provided in Table 11 and Example 1. In some embodiments, provided herein is BAA CI136, comprising the layout and sequence as provided in Table 11 and Example 1. In some embodiments, the AB1 comprises amino acid substitutions in at least two of amino acid positions L234, L235, and P331. In some embodiments, the AB1 comprises amino acid substitutions at amino acid positions L234, L235, and P331. In some embodiments, the AB1 comprises L234F, L235E, and P331S amino acid substitutions. In some embodiments, the AB1 comprises an Fc region comprising an amino acid substitution at N297. In some embodiments, the AB1 comprises L234F, L235E, P331S, and N297Q amino acid substitutions. In some embodiments, the heavy chain of the AB1 comprises any one of SEQ ID NO: 69, SEQ ID NO: 70, SEQ ID NO: 71, SEQ ID NO: 72, SEQ ID NO: 73, SEQ ID NO: 74, SEQ ID NO: 75 and SEQ ID NO: 76, as set forth in Table 6.

In another aspect, provided herein is a bispecific activatable antibody (BAA) comprising:

a) an IgG antibody (AB1) that specifically binds to a first target wherein the AB1 comprises:

i. two heavy chains (AB1 HCs) and two light chains (AB1 LCs); and ii. a first masking moiety (MM1) linked to a first cleavable moiety (CM1) to form a MM1-CM1 construct, wherein the carboxyl terminus of a MM1-CM1 construct is linked to each amino terminus of each light chain of the AB1, wherein the MM1 inhibits the binding of the AB1 to its target; and the CM1 is a polypeptide that functions as a substrate for a first protease, b) two scFvs (AB2) that each specifically binds to a second target wherein each AB2 comprises:

i. a heavy chain variable region linked to a light chain variable region, wherein the carboxyl terminus of each AB2 is linked to the amino terminus each of the AB1 heavy chains; and ii. a second masking moiety (MM2) linked to a second cleavable moiety (CM2) to form a MM2-CM2 construct, wherein the carboxyl terminus of a MM2-CM2 construct is linked to the amino terminus of each AB2 wherein the MM2 inhibits the binding of the AB2 to its target; and the CM2 is a polypeptide that functions as a substrate for a second protease, and wherein the AB1 comprises an Fc region comprises an amino acid substitution in at least one of amino acid positions L234, L235, N297, and P331, as numbered by the EU index as set forth in Kabat, such that the BAA has reduced effector function. In some embodiments, the Fc region comprises amino acid substitutions in at least amino acid positions L234, L235, N297 and P331, as numbered by the EU index as set forth in Kabat, such that the BAA has reduced effector function. In some embodiments, the Fc region comprises amino acid substitutions in at least amino acid positions L234, L235, and P331, as numbered by the EU index as set forth in Kabat, such that the BAA has reduced effector function. In some embodiments, the first target is selected from the group consisting of the targets presented in Table 9 and the second target is selected from the group consisting of the targets presented in Table 9.

In some embodiments, the BAAs provided herein comprise:

a) A bispecific activatable antibody (BAA) comprising:

i) an IgG antibody (AB1) that specifically binds to a first target wherein the AB1 comprises two heavy chains (AB1 HCs) and two light chains (AB1 LCs); and wherein the AB1 is linked to a first masking moiety (MM1) linked to a first cleavable moiety (CM1) to form a MM1-CM1 construct, wherein the carboxyl terminus of a MM1-CM1 construct is linked to each amino terminus of each light chain of the AB1, wherein the MM1 inhibits the binding of the AB1 to its target; and the CM1 is a polypeptide that functions as a substrate for a first protease, ii) two scFvs (each an AB2) that each specifically binds to a second target wherein each AB2 comprises a heavy chain variable region linked to a light chain variable region, wherein the carboxyl terminus of each AB2 is linked to the amino terminus each of the AB1 heavy chains; and wherein each AB2 is linked to a second masking moiety (MM2) linked to a second cleavable moiety (CM2) to form a MM2-CM2 construct, wherein the carboxyl terminus of each MM2-CM2 construct is linked to the amino terminus of each AB2 wherein the MM2 inhibits the binding of the AB2 to its target; and the CM2 is a polypeptide that functions as a substrate for a second protease, and wherein the AB1 comprises an Fc region comprises an amino acid substitution in at least one of amino acid positions L234, L235, N297, and P331, as numbered by the EU index as set forth in Kabat, such that the BAA has reduced effector function. In some embodiments, the Fc region comprises amino acid substitutions in at least amino acid positions L234, L235, N297 and P331, as numbered by the EU index as set forth in Kabat, such that the BAA has reduced effector function. In some embodiments, the Fc region comprises amino acid substitutions in at least amino acid positions L234, L235, and P331, as numbered by the EU index as set forth in Kabat, such that the BAA has reduced effector function. In some embodiments, the first target is selected from the group consisting of the targets presented in Table 9 and the second target is selected from the group consisting of the targets presented in Table 9.

In another aspect, provided herein is an activatable antibody (AA) comprising: (a) an antibody (AB) that specifically binds to Epidermal Growth Factor Receptor (EGFR), wherein the AB is an IgG1 antibody, and wherein the Fc region of the AB comprises an amino acid substitution in at least one of amino acid positions L234, L235, and P331, as numbered by the EU index as set forth in Kabat, such that the AA has reduced effector function; (b) a masking moiety (MM) coupled to the AB, wherein the MM reduces or inhibits the binding of the AB to the EGFR when the AA is in an uncleaved state; and (c) a cleavable moiety (CM) coupled to the AB, wherein the CM is a polypeptide that functions as a substrate for a protease. In some embodiments, the amino acid substitution is any one or more of L234F, L235E, and P331S. In some embodiments, the AB comprises amino acid substitutions in at least two of amino acid positions L234, L235, and P331. In some embodiments, the AB comprises amino acid substitutions at amino acid positions L234, L235, and P331. In some embodiments, the AB comprises L234F, L235E, and P331S amino acid substitutions. In some embodiments, the AB comprises an Fc region comprising an amino acid substitution at N297. In some embodiments, the Fc region comprises an N297Q mutation. In some embodiments, the AB comprises L234F, L235E, P331S, and N297Q amino acid substitutions. In some embodiments, the MM comprises an amino acid sequence selected from the group consisting of sequences presented in Table 7. In some embodiments, the MM comprises the amino acid sequence of SEQ ID NO: 78. In some embodiments, the MM comprises the amino acid sequence of SEQ ID NO: 85. In some embodiments, the CM comprises an amino acid sequence selected from the group consisting of sequences presented in Table 4. In some embodiments, the CM comprises the amino acid sequence of SEQ ID NO: 14. In some embodiments, the CM comprises the amino acid sequence of SEQ ID NO: 16. In some embodiments, the AA is part of a BAA.

In another aspect, provided herein is an activatable antibody (AA) comprising: (a) an antibody or an antigen binding fragment thereof (AB) that specifically binds to Epidermal Growth Factor Receptor (EGFR); (b) a masking moiety (MM) coupled to the AB, wherein the MM reduces or inhibits the binding of the AB to the EGFR when the AA is in an uncleaved state, and wherein the MM comprises an amino acid sequence selected from the group consisting of sequences presented in Table 7; and (c) a cleavable moiety (CM) coupled to the AB, wherein the CM is a polypeptide that functions as a substrate for a protease. In some embodiments, the MM comprises the amino acid sequence of SEQ ID NO: 78. In some embodiments, the CM comprises a substrate cleavable by a serine protease or an MMP. In some embodiments, the CM comprises an amino acid sequence selected from the group consisting of SEQ ID NO: 18-56. In some embodiments, the CM comprises the amino acid sequence of SEQ ID NO: 14. In some embodiments, the CM comprises the amino acid sequence of SEQ ID NO: 16. In some embodiments, the AA is part of a BAA.

In another aspect, provided herein is an activatable antibody (AA) comprising:

(a) an antibody or antigen binding fragment thereof (AB) that specifically binds to the epsilon chain of CD3, wherein the antibody comprises a heavy chain variable domain as set forth in SEQ ID NO: 2 or SEQ ID NO: 3 or comprises a light chain variable domain as set forth in SEQ ID NO: 1 or SEQ ID NO: 4; (b) a masking moiety (MM) coupled to the AB, wherein the MM reduces or inhibits the binding of the AB to the CD3 when the AA is in an uncleaved state; and (c) a cleavable moiety (CM) coupled to the AB, wherein the CM is a polypeptide that functions as a substrate for a protease. In some embodiments, the AB comprises a heavy chain variable domain as set forth in SEQ ID NO: 2. In some embodiments, the AB comprises a heavy chain variable domain as set forth in SEQ ID NO: 3. In some embodiments, the AB comprises a light chain variable domain as set forth in SEQ ID NO: 1. In some embodiments, the AB comprises a light chain variable domain as set forth in SEQ ID NO: 4. In some embodiments, the AB comprises a heavy chain variable domain as set forth in SEQ ID NO: 2 and a light chain variable domain as set forth in SEQ ID NO: 1. In some embodiments, the AB comprises a heavy chain variable domain as set forth in SEQ ID NO: 3 and a light chain variable domain as set forth in SEQ ID NO: 1. In some embodiments, the AB comprises a heavy chain variable domain as set forth in SEQ ID NO: 2 and a light chain variable domain as set forth in SEQ ID NO: 4. In some embodiments, the AB comprises a heavy chain variable domain as set forth in SEQ ID NO: 3 and a light chain variable domain as set forth in SEQ ID NO: 4. In some embodiments, the MM comprises any one of the sequences set forth in Table 3. In some embodiments, the CM comprises any one of the sequences set forth in Table 4. In some embodiments, the AA is part of a BAA.

In another aspect, provided herein is an activatable antibody (AA) comprising: (a) an antibody or antigen binding fragment thereof (AB) that specifically binds to the epsilon chain of CD3; (b) a masking moiety (MM) coupled to the AB, wherein the MM reduces or inhibits the binding of the AB to the CD3 when the AA is in an uncleaved state, wherein the MM comprises amino acid sequence SEQ ID NO: 12; and (b) a cleavable moiety (CM) coupled to the AB, wherein the CM is a polypeptide that functions as a substrate for a protease. In some embodiments, the CM comprises any one of the sequences set forth in Table 4. In some embodiments, the CM comprises a substrate cleavable by a serine protease or an MMP. In some embodiments, the CM comprises an amino acid sequence selected from the group consisting of SEQ ID NO: 18-56. In some embodiments, the protease is an MMP. In some embodiments, protease is a serine protease. In some embodiments, the AA is part of a BAA.

In another aspect, provided herein is an activatable antibody (AA) comprising: (a) an antibody (AB) that specifically binds a target, wherein the antibody is an IgG1 antibody, and wherein the Fc region of the antibody comprises an amino acid substitution in at least one of amino acid positions L234, L235, and P331, as numbered by the EU index as set forth in Kabat, such that the AA has reduced effector function; (b) a masking moiety (MM) coupled to the AB, wherein the MM reduces or inhibits the binding of the AB to the target when the AA is in an uncleaved state; and (c) a cleavable moiety (CM) coupled to the AB, wherein the CM is a polypeptide that functions as a substrate for a protease. In some embodiments, the Fc region comprises amino acid substitutions in at least amino acid positions L234, L235, N297 and P331, as numbered by the EU index as set forth in Kabat, such that the AA has reduced effector function. In some embodiments, the target is selected from the group consisting of the targets presented in Table 9. In some embodiments, the AA is part of a BAA.

In another aspect, provided herein is an antibody or antigen binding fragment thereof (AB) that specifically binds to the epsilon chain of CD3, wherein the antibody comprises a heavy chain variable domain as set forth in SEQ ID NO: 2 or SEQ ID NO: 3 or a light chain variable domain as set forth in SEQ ID NO: 1 or SEQ ID NO: 4. In some embodiments the antibody comprises a heavy chain variable domain as set forth in SEQ ID NO: 2 or SEQ ID NO: 3 and a light chain variable domain as set forth in SEQ ID NO: 1 or SEQ ID NO: 4. In some embodiments the AB comprises a heavy chain variable domain as set forth in SEQ ID NO: 2. In some embodiments the AB comprises a heavy chain variable domain as set forth in SEQ ID NO: 3. In some embodiments the AB comprises a light chain variable domain as set forth in SEQ ID NO: 1. In some embodiments the AB comprises a light chain variable domain as set forth in SEQ ID NO: 4. In some embodiments the AB comprises a heavy chain variable domain as set forth in SEQ ID NO: 2 and a light chain variable domain as set forth in SEQ ID NO: 1. In some embodiments the AB comprises a heavy chain variable domain as set forth in SEQ ID NO: 3 and a light chain variable domain as set forth in SEQ ID NO: 1. In some embodiments the AB comprises a heavy chain variable domain as set forth in SEQ ID NO: 3 and a light chain variable domain as set forth in SEQ ID NO: 4. In some embodiments the AB comprises a heavy chain variable domain as set forth in SEQ ID NO: 2 and a light chain variable domain as set forth in SEQ ID NO: 4. In some embodiments, the antibody is a bispecific AB. In some embodiments the antibody is a scFv. In some embodiments the antibody is an IgG1 antibody. In some embodiments, the antibody is part of an AA or is part of a BAA.

In another aspect, provided herein is an antibody that specifically binds to EGFR or CD3 (AB), wherein the antibody is an IgG1 antibody or a scFv linked to an Fc domain, wherein the antibody comprises an Fc region comprising an amino acid substitution in at least one of amino acid positions L234, L235, and P331, as numbered by the EU index as set forth in Kabat, such that the antibody has reduced effector function. In some embodiments, the amino acid substitution is any one or more of L234F, L235E, and P331S. In some embodiments, the antibody comprises amino acid substitutions in at least two of amino acid positions L234, L235, and P331. In some embodiments, the antibody comprises amino acid substitutions at amino acid positions L234, L235, and P331. In some embodiments, the antibody comprises L234F, L235E, and P331S amino acid substitutions. In some embodiments, the antibody comprises an Fc region comprising an amino acid substitution at N297. In some embodiments, the Fc region comprises an N297Q mutation. In some embodiments, the antibody comprises L234F, L235E, P331S, and N297Q amino acid substitutions. In some embodiments, the heavy chain of the antibody comprises any one of SEQ ID NO: 69, SEQ ID NO: 70, SEQ ID NO: 71, SEQ ID NO: 72, SEQ ID NO: 73, SEQ ID NO: 74, SEQ ID NO: 75 and SEQ ID NO: 76, as set forth in Table 6. In some embodiments, the heavy chain variable domain of the antibody comprises any one of SEQ ID NO: 2 or SEQ ID NO: 3 or wherein the light chain variable domain of the AB comprises any one of SEQ ID NO: 1 or SEQ ID NO: 4. In some embodiments, the antibody is part of an AA or is part of a BAA.

In another aspect, also provided herein are pharmaceutical composition comprising any one of the BAAs, AAs, and antibodies described above, and optionally a carrier. In another aspect, also provided herein are pharmaceutical composition comprising any one of the BAAs, AAs, and antibodies described above and a carrier. In some embodiments, the composition comprises an additional agent, for example the additional agent can be a therapeutic agent.

In another aspect, also provided herein are isolated nucleic acid molecules encoding any one of the BAAs, AAs, and antibodies described above. Also provided are vectors comprising the nucleic acid is provided. In some embodiments, the vector comprises the nucleic acid sequence of pLW289. In some embodiments, the vector comprises the nucleic acid sequence of pLW246. In some embodiments, the vector comprises the nucleic acid sequence of pLW307. In some embodiments, the vector comprises the nucleic acid sequence of pLW291. In some embodiments, the vector comprises the nucleic acid sequence of pLW352. In some embodiments, the vector comprises the nucleic acid sequence of pLW246. In some embodiments, the vector comprises the nucleic acid sequence of pLW353.

In another aspect, also provided herein is a cell comprising any one of the vectors described above. In some embodiments, provided herein is a cell comprising pLW289 and pLW246. In some embodiments, provided herein is a cell comprising pLW307 and pLW291. In some embodiments, provided herein is a cell comprising pLW352 and pLW246. In some embodiments, provided herein is a cell comprising pLW353 and pLW246.

In another aspect, provided herein are methods of producing the antibody, AA, or BAA provided above, by culturing a cell under conditions that lead to expression of the antibody, AA, or BAA, wherein the cell comprises the relevant nucleic acid molecule or vectors provided herein.

In another aspect, provided herein is a method of treating, alleviating a symptom of, or delaying the progression of a disorder or disease comprising administering a therapeutically effective amount of the antibodies/AAs/BAAs/pharmaceutical compositions described above to a subject in need thereof. In some embodiments, the disorder or disease comprises disease cells expressing EGFR. In some embodiments, the disorder or disease is cancer. In some embodiments, the cancer is anal cancer, basal cell carcinoma, brain cancer, bladder cancer, bone cancer, breast cancer, cervical cancer, cholangiocarcinoma, colorectal cancer, endometrial cancer, esophageal cancer, gall bladder cancer, gastric cancer, glioblastoma, head and neck cancer, liver cancer, lung cancer, ovarian cancer, pancreatic cancer, prostate cancer, renal cancer, sarcoma, small bowel carcinoma, skin cancer, testicular cancer, thyroid cancer or uterine cancer. In some embodiments, the disorder is lymphoma, e.g. Epstein-Barr virus associated lymphoma, B-cell lymphoma, T-cell lymphoma Hodgkins and non-Hodgkins lymphoma. In some embodiments, the cancer is a squamous cell cancer. In some embodiments, the cancer is a head and neck squamous cell cancer. In some embodiments, the cancer is a skin squamous cell carcinoma. In some embodiments, the cancer is an esophageal squamous cell carcinoma. In some embodiments, the cancer is a head and neck squamous cell carcinoma. In some embodiments, the cancer is a lung squamous cell carcinoma.

In another aspect, provided herein is a method of inhibiting angiogenesis in a subject comprising administering a therapeutically effective amount of the antibodies/AAs/BAAs/pharmaceutical compositions described above to a subject in need thereof. In some embodiments, the method comprises administering an additional agent. In some embodiments, the additional agent is a therapeutic agent.

In another aspect, provided herein is a method to reduce damage to healthy tissue caused by an antibody binding to its target on healthy tissue as well as on diseased tissue (e.g. cancerous tissue), the method comprising administering to a subject in need thereof an AA or BAA or a pharmaceutical composition comprising an AA or BAA, wherein said AA or BAA is an AA or BAA of any one of the embodiments provided herein.

In another aspect, provided herein is a method to improve tolerability of an antibody treatment comprising administering to a subject in need thereof (e.g. a subject suffering from cancer) an AA or BAA or a pharmaceutical composition comprising an AA or BAA, wherein said AA or BAA is an AA or BAA of any one of the embodiments provided herein.

In another aspect provided herein is a method to recruit T cells to tumor tissue comprising administering to a subject in need thereof an AA or BAA or a pharmaceutical composition comprising an AA or BAA, wherein said AA or BAA is an AA or BAA of any one of the embodiments provided herein.

In another aspect provided herein is an antibody, AA, BAA, or pharmaceutical composition, of any one of the embodiments provided herein, for use as a medicament. The medicament may be for use in a method of reducing damage to healthy tissue caused by an antibody binding to its target on healthy tissue as well as on diseased tissue. The medicament may be for use in improving the tolerability of an antibody treatment.

In another aspect provided herein is an antibody, AA, BAA, or pharmaceutical composition, of any one of the embodiments provided herein, for use in a method of treating, alleviating a symptom of, or delaying the progression of a disorder or disease, wherein the disorder or disease comprises disease cells expressing EGFR.

In another aspect provided herein is an antibody, AA, BAA, or pharmaceutical composition, of any one of the embodiments provided herein, for use in a method of treating cancer; optionally wherein the cancer is anal cancer, basal cell carcinoma, brain cancer, bladder cancer, breast cancer, bone cancer, cervical cancer, cholangiocarcinoma, colorectal cancer, endometrial cancer, esophageal cancer, gall bladder cancer, gastric cancer, glioblastoma, head and neck cancer, liver cancer, lung cancer, ovarian cancer, pancreatic cancer, prostate cancer, renal cancer, sarcoma, small bowel carcinoma, squamous cell cancer, skin cancer testicular cancer, thyroid cancer or uterine cancer. The use may comprise the recruitment of T cells to tumor tissue.

In another aspect provided herein is an antibody, AA, BAA, or pharmaceutical composition, of any one of the embodiments provided herein, for use in a method comprising inhibiting angiogenesis.

The antibody, AA, BAA, or pharmaceutical composition, of any one of the embodiments provided herein, may be for use in a method of treatment comprising administering an additional agent; optionally wherein the additional agent is a therapeutic agent.

BRIEF DESCRIPTION OF THE DRAWINGS

FIG. 2B also depicts a more than 300,000 fold EC50 shift of the dually masked antibodies (i.e., BAAs masked at both the EGFR and CD3 target binding domains) CI106 and CI107 relative to the protease activated bispecific antibody (i.e., BAA activated by protease treatment) act-104 (interchangeably referred to as CI104).

FIG. 3A demonstrates that activation of primary CD8+ T cells was attenuated by CI106 and CI107, relative to CI011 and CI040. FIG. 3B demonstrates that dually masked antibodies display a shifted dose response curve for T cell activation relative to protease activated bispecific antibody act-104 indicating that masking attenuates T cell activation.

FIGS. 6A-6B demonstrate that the EC50s of the tested dually masked and protease activated bispecific antibodies are similar when either human (6A) or cyno (6B) effector cells are used. FIGS. 6C-6D demonstrate that binding of the protease-activated and dually masked antibodies to human (6C) and cyno (6D) T cells is similar.

FIGS. 10A-E plot dose dependent increases in AST at 48 h post dose (10A), ALT at 48 h post dose (10B), IL-6 at 8 h post dose (10C), IFNg at 8 h post dose (10D), and Ki67 at 72 h post dose (10E) in cynomolgus monkeys treated with act-104, CI106 or CI107. The dose response curve for all parameters was shifted for the dually masked antibodies indicating improved tolerability and decreased pharmacodynamics effects relative to the protease activated bispecific antibody.

DETAILED DESCRIPTION OF THE INVENTION

Figures 1A, 1B:
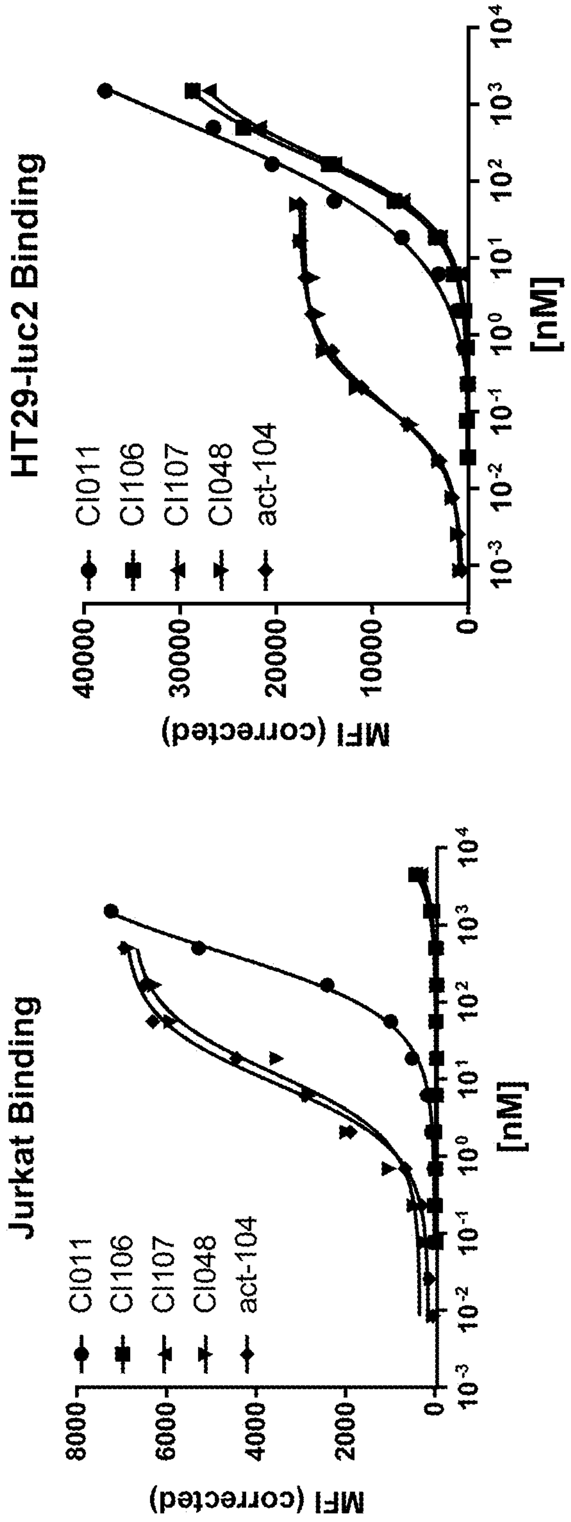
FIG. 1A demonstrates that incorporation of the h20GG CD3ε masking peptide into the EGFR masked BAAs CI106 and CI107 significantly reduced binding to Jurkat cells relative to CI011. A reduction in binding to EGFR+ HT29-luc2 cells was also evident for CI106 and CI107 relative to CI011 (FIG. 1B).

Provided herein are antibodies, activatable antibodies (AAs), bispecific antibodies, and bispecific activatable antibodies (BAAs).

In some embodiments, provided herein are humanized antibodies that specifically bind to the epsilon chain of CD3 (CD3ε; referred to herein interchangeably as CD3).

In some embodiments, provided herein are IgG1 antibodies that specifically bind to Epidermal Growth Factor Receptor (EGFR), wherein the antibodies comprise point mutations in the Fc region, such that the antibody has reduced effector function.

In some embodiments provided herein are AAs, for example AAs that specifically bind to EGFR or CD3. These AAs are optimized for affinity, effector function, masking, and cleavability.

In some embodiments, provided herein are BAAs, for example BAAs that bind to a target antigen (e.g. tumor antigen, such as a target presented in Table 9) and a second antigen (e.g. immune effector antigen on an immune effector cell). In some embodiments, the immune effector cell is a leukocyte cell. In some embodiments, the immune effector cell is a T cell. In some embodiments, the immune effector cell is a natural killer (NK) cell. In some embodiments, the immune effector cell is a macrophage. In some embodiments, the immune effector cell is a mononuclear cell, such as a myeloid mononuclear cell. In some embodiments, the BAAs are immune effector cell-engaging BAAs. In some embodiments, the BAAs are leukocyte cell-engaging BAAs. In some embodiments, the BAAs are T cell engaging bispecific (TCB) AAs, also referred to herein as TCBAAs. In some embodiments, the BAAs are NK cell-engaging BAAs. In some embodiments, the BAAs are macrophage cell-engaging BAAs. In some embodiments, the BAAs are mononuclear cell-engaging BAAs, such as myeloid mononuclear cell-engaging BAAs. In some embodiments, the bispecific antibodies bind EGFR and CD3. These BAAs are optimized for affinity, effector function, masking, and cleavability.

Also provided herein are methods of making and methods of use of these antibodies, AAs, and BAAs. AAs, including general production thereof and identification of masking moieties (MMs) and cleavable moieties (CMs) is described in International Publication Numbers WO 2009/025846 by Daugherty et al., published 26 Feb. 2009, and WO 2010/081173 by Stagliano et al., published 15 Jul. 2010, both of which are incorporated by reference in their entirety. BAAs, including general production thereof and identification of masking moieties (MMs) and cleavable moieties (CMs) is described in International Publication Numbers WO2015/013671 by Lowman et al., published 29 Jan. 2015 and WO2016/014974 by Irving et al., published 28 Jan. 2016, both of which are incorporated by reference in their entirety. Also incorporated by reference are International Publication WO2016/014974 by Irving et al., published 28 Jan. 2016, and International Publication WO2016/118629 by Moore et al., published 28 Jul. 2016 which provide AAs, general production, MMs, and CMs.

As used herein, unless specified otherwise, the term "antibody" includes an antibody or antigen-binding fragment thereof that specifically binds its target and is a monoclonal antibody, domain antibody, single chain, Fab fragment, a F(ab')2 fragment, a scFv, a scAb, a dAb, a single domain heavy chain antibody, and a single domain light chain antibody. In some embodiments, the antibody is an IgG antibody. In some embodiments, the antibody is an IgG1 antibody. In some embodiments, the antibody is an IgG4 antibody. In some embodiments, the antibody is a scFv antibody. In some embodiments, such an antibody or immunologically active fragment thereof that binds its target is a mouse, chimeric, humanized or fully human monoclonal antibody.

1. CD3 Antibodies

Provided herein is an antibody or antigen binding fragment thereof (AB) that specifically binds to the epsilon chain of CD3 (CD3ε, referred to herein throughout as CD3).

Exemplary amino acid sequences of CD3-binding antibodies of the disclosure (variable domains) are provided in Table 1. (Predicted CDR sequences are underlined). As provided below, L3 is a linker, linking the light and heavy chain variable domains, in the exemplary CD3-binding antibodies.

TABLE 1

Anti-CD3 variant v12

Light Chain Variable Domain LV12
QTVVTQEPSFSVSPGGTVTLTCRSSTGAVTTSNYANWVQQTPGQAPRGLIGGTNKRAPG
VPDRFSGSILGNKAALTITGAQADDESDYYCALWYSNLWVFGGGTKLTVL (SEQ ID NO:
1)

Heavy Chain Variable Domain HV12, wherein L3 is SEQ ID NO: 98
EVQLVESGGGLVQPGGSLRLSCAASGFTFSTYAMNWVRQAPGKGLEWVARIRSKYNNY
ATYYADSVKDRFTISRDDSKNSLYLQMNSLKTEDTAVYYCVRHGNFGNSYVSWFAYW
GQGTLVTVSS (SEQ ID NO: 2)

LV12-L3-HV12
QTVVTQEPSFSVSPGGTVTLTCRSSTGAVTTSNYANWVQQTPGQAPRGLIGGTNKRAPG
VPDRFSGSILGNKAALTITGAQADDESDYYCALWYSNLWVFGGGTKLTVL[GGGGSGGG
GSGGGGS]EVQLVESGGGLVQPGGSLRLSCAASGFTFSTYAMNWVRQAPGKGLEWVARI
RSKYNNYATYYADSVKDRFTISRDDSKNSLYLQMNSLKTEDTAVYYCVRHGNFGNSYV
SWFAYWGQGTLVTVSS (SEQ ID NO: 143)

Anti-CD3 variant v16

Light Chain Variable Domain LV12
Sequence provided above

Heavy Chain Variable Domain HV20
EVQLVESGGGLVQPGGSLKLSCAASGFTFSTYAMNWVRQASGKGLEWVGRIRSKYNNY
ATYYADSVKDRFTISRDDSKNTAYLQMNSLKTEDTAVYYCTRHGNFGNSYVSWFAYW
GQGTLVTVSS (SEQ ID NO: 3)

LV12-L3-HV20, wherein L3 is SEQ ID NO: 98
QTVVTQEPSFSVSPGGTVTLTCRSSTGAVTTSNYANWVQQTPGQAPRGLIGGTNKRAPG
VPDRFSGSILGNKAALTITGAQADDESDYYCALWYSNLWVFGGGTKLTVL[GGGGSGGG
GSGGGGS]EVQLVESGGGLVQPGGSLKLSCAASGFTFSTYAMNWVRQASGKGLEWVGR
IRSKYNNYATYYADSVKDRFTISRDDSKNTAYLQMNSLKTEDTAVYYCTRHGNFGNSY
VSWFAYWGQGTLVTVSS (SEQ ID NO: 144)

Anti-CD3 variant v19

Light Chain Variable Domain LV19
QAVVTQEPSLTVSPGGTVTLTCRSSTGAVTTSNYANWVQQKPGQAPRGLIGGTNKRAPG
TPARFSGSLIGGKAALTLSGAQPEDEAEYYCALWYSNLWVFGGGTKLTVL (SEQ ID NO:
4)

Heavy Chain Variable Domain HV20
Sequence provided above

LV19-L3-HV20, wherein L3 is SEQ ID NO: 98
QAVVTQEPSLTVSPGGTVTLTCRSSTGAVTTSNYANWVQQKPGQAPRGLIGGTNKRAPG
TPARFSGSLIGGKAALTLSGAQPEDEAEYYCALWYSNLWVFGGGTKLTVL[GGGGSGGG
GSGGGGS]EVQLVESGGGLVQPGGSLKLSCAASGFTFSTYAMNWVRQASGKGLEWVGR
IRSKYNNYATYYADSVKDRFTISRDDSKNTAYLQMNSLKTEDTAVYYCTRHGNFGNSY
VSWFAYWGQGTLVTVSS (SEQ ID NO: 145)

Anti-CD3 variant v26

Light Chain Variable Domain LV19
Sequence provided above

Heavy Chain Variable Domain HV12
Sequence provided above

LV19-L3-HV12, wherein L3 is SEQ ID NO: 98
QAVVTQEPSLTVSPGGTVTLTCRSSTGAVTTSNYANWVQQKPGQAPRGLIGGTNKRAPG
TPARFSGSLIGGKAALTLSGAQPEDEAEYYCALWYSNLWVFGGGTKLTVL[GGGGSGGG
GSGGGGS]EVQLVESGGGLVQPGGSLRLSCAASGFTFSTYAMNWVRQAPGKGLEWVARI
RSKYNNYATYYADSVKDRFTISRDDSKNSLYLQMNSLKTEDTAVYYCVRHGNFGNSYV
SWFAYWGQGTLVTVSS (SEQ ID NO: 150)

Exemplary scFv linkers (referred to herein as "L3" linking a VH and VL) are provided in Table 1-1.

TABLE 1-1

| SEQ ID NO: | Linker Amino Acid Sequence |
|---|---|
| 98 | GGGGSGGGGSGGGGS |

Exemplary CDR sequences of CD3-binding antibodies are provided in Table 2.

TABLE 2

| Name | CD3 Ab CDR Sequences | SEQ ID NO: |
|---|---|---|
| SP34L1 | RSSTGAVTTSNYAN | SEQ ID NO: 149 |
| SP34L2 | GTNKRAP | SEQ ID NO: 5 |
| SP34L3 | ALWYSNLWV | SEQ ID NO: 6 |
| SP34H1 | TYAMN | SEQ ID NO: 7 |
| SP34H2 | RIRSKYNNYATYYADSVKD | SEQ ID NO: 8 |
| SP34H3 | HGNFGNSYVSWFAY | SEQ ID NO: 9 |

As provided herein, the CD3 antibody comprises at least one of the CDR sequences provided in Table 2.

In some embodiments, the CD3 antibody comprises heavy chain variable domain as set forth in SEQ ID NO: 2.

In some embodiments, the CD3 antibody comprises a heavy chain variable domain as set forth in SEQ ID NO: 3.

In some embodiments, the CD3 antibody comprises a light chain variable domain as set forth in SEQ ID NO: 1.

In some embodiments, the CD3 antibody comprises a light chain variable domain as set forth in SEQ ID NO: 4.

In some embodiments, the CD3 antibody comprises a heavy chain variable domain as set forth in SEQ ID NO: 2 and a light chain variable domain as set forth in SEQ ID NO: 1.

In some embodiments, the CD3 antibody comprises a heavy chain variable domain as set forth in SEQ ID NO: 3 and a light chain variable domain as set forth in SEQ ID NO: 1.

In some embodiments, the CD3 antibody comprises a heavy chain variable domain as set forth in SEQ ID NO: 3 and a light chain variable domain as set forth in SEQ ID NO: 4.

In some embodiments, the CD3 antibody comprises a heavy chain variable domain as set forth in SEQ ID NO: 2 and a light chain variable domain as set forth in SEQ ID NO: 4.

In some embodiments, the CD3 antibody comprises a heavy chain variable domain as set forth in SEQ ID NO: 2 or SEQ ID NO: 3 or comprises a light chain variable domain as set forth in SEQ ID NO: 1 or SEQ ID NO: 4.

In some embodiments, the CD3 antibody comprises a heavy chain variable domain as set forth in SEQ ID NO: 2 or SEQ ID NO: 3 and comprises a light chain variable domain as set forth in SEQ ID NO: 1 or SEQ ID NO: 4.

In some embodiments, the CD3 antibody is a scFv antibody. In some embodiments, the variable domains comprise the following structure from N terminus to C terminus: LV-HV. In some embodiments, the variable domains comprise the following structure from N terminus to C terminus: HV-LV.

In some embodiments, the CD3 antibody is a scFv antibody comprising a heavy chain variable region (VH) linked to a light chain variable region (VL), wherein the VH is linked to the VL by a linker comprising amino acid sequence SEQ ID NO: 98. Exemplary sequences with such a linker are provided in Table 1.

In exemplary embodiments, provided herein is an antibody that specifically binds to CD3 (AB), wherein the antibody is an IgG1 antibody or a scFv linked to an Fc domain, wherein the antibody comprises an Fc region comprising an amino acid substitution in at least one of amino acid positions L234, L235, and P331, as numbered by the EU index as set forth in Kabat, such that the antibody has reduced effector function. In some embodiments, the amino acid substitution is any one or more of L234F, L235E, and P331S. In some embodiments, the antibody comprises amino acid substitutions in at least two of amino acid positions L234, L235, and P331. In some embodiments, the antibody comprises amino acid substitutions at amino acid positions L234, L235, and P331. In some embodiments, the antibody comprises L234F, L235E, and P331S amino acid substitutions. In some embodiments, the antibody comprises an Fc region comprising an amino acid substitution at N297. In some embodiments, the Fc region comprises an N297Q mutation. In some embodiments, the antibody comprises L234F, L235E, P331S, and N297Q amino acid substitutions. In some embodiments, the heavy chain variable domain of the antibody comprises any one of SEQ ID NO: 2 or SEQ ID NO: 3 or wherein the light chain variable domain of the AB comprises any one of SEQ ID NO: 1 or SEQ ID NO: 4.

2. Activatable CD3 Antibodies

In some embodiments, any one of the CD3 antibodies provided herein is in an activatable antibody (AA) format.

As generally provided herein, the AAs of the invention comprise MM-CM constructs, also referred to herein as a prodomain. Accordingly, as used herein, the term "prodomain" refers to a polypeptide comprising a masking moiety (MM) and a cleavable moiety (CM). In some embodiments, the MM and the CM are separated by a linker, referred to herein as L1. In some embodiments, the prodomain comprises a linker at the carboxyl terminus of the CM; this linker, referred to herein as L2, links the CM of the prodomain to the AB. In some embodiments, the prodomain comprises a linker between MM and CM and a linker after CM. In some embodiments, the MM and the CM are not separated by a linker. In certain embodiments a prodomain comprises one of the following formulae (where the formula below represents an amino acid sequence in either N- to C-terminal direction or C- to N-terminal direction): (MM)-L1-(CM), (MM)-(CM)-L2, (MM)-L1-(CM)-L2, or (MM)-(CM). In exemplary embodiments, a prodomain comprises an EGFR MM and a CM cleavable by a matriptase or MMP; or a CD3ε MM and a CM cleavable by a matriptase or MMP. In some embodiments, a prodomain comprises an EGFR MM and a CM that is cleavable by a matriptase and an MMP. In some embodiments, a prodomain comprises a CD3ε MM and a CM that is cleavable by a matriptase and an MMP. Provided herein are activatable antibodies (AAs) comprising a prodomain. Also provided herein are nucleotides encoding a prodomain of the invention.

Accordingly, provided herein is a CD3 AA comprising: (a) an antibody or antigen binding fragment thereof (AB) that specifically binds to the epsilon chain of CD3 (CD3ε), wherein the antibody comprises a heavy chain domain as set forth in SEQ ID NO: 2 or SEQ ID NO: 3 or comprises a light chain domain as set forth in SEQ ID NO: 1 or SEQ ID NO: 4; (b) a masking moiety (MM) coupled to the AB, wherein the MM reduces or inhibits the binding of the AB to the CD3ε when the AA is in an uncleaved state; and (c) a cleavable moiety (CM) coupled to the AB, wherein the CM is a polypeptide that functions as a substrate for a protease. As described above, (b) and (c) together are part of the prodomain.

In some embodiments, the AB of the CD3 AA is any one of the CD3 antibodies described in the preceding section.

In some embodiments, the AB of the CD3 AA comprises a heavy chain variable domain as set forth in SEQ ID NO: 2.

In some embodiments, the AB of the CD3 AA comprises a heavy chain variable domain as set forth in SEQ ID NO: 3.

In some embodiments, the AB of the CD3 AA comprises a light chain variable domain as set forth in SEQ ID NO: 1.

In some embodiments, the AB of the CD3 AA comprises a light chain variable domain as set forth in SEQ ID NO: 4.

In some embodiments, the AB of the CD3 AA comprises a heavy chain variable domain as set forth in SEQ ID NO: 2 and a light chain domain as set forth in SEQ ID NO: 1.

In some embodiments, the AB of the CD3 AA comprises a heavy chain variable domain as set forth in SEQ ID NO: 3 and a light chain domain as set forth in SEQ ID NO: 1.

In some embodiments, the AB of the CD3 AA comprises a heavy chain variable domain as set forth in SEQ ID NO: 3 and a light chain domain as set forth in SEQ ID NO: 4.

In some embodiments, the AB is a scFv comprising a heavy chain variable region (VH) linked to a light chain variable region (VL), wherein the VH is linked to the VL by a linker L3 comprising amino acid sequence SEQ ID NO: 98. Exemplary sequences with such a linker are provided in Table 1.

In some embodiments, the MM of the CD3 AA comprises any one of the sequences set forth in Table 3.

Exemplary CD3 masking moieties (MMs) of the invention are provided in Table 3.

In some embodiments, the MM of the CD3 AA comprises the sequence set forth in SEQ ID NO: 12. In some embodiments, the MM of the CD3 AA is the sequence set forth in SEQ ID NO: 10. In some embodiments, the MM of the CD3 AA is the sequence set forth in SEQ ID NO: 11.

TABLE 3

| MM | Name | AA sequence | SEQ ID NO: |
|---|---|---|---|
| CD3 MM | JF15865 | MMYCGGNEVLCGPRV | SEQ ID NO: 10 |
| CD3 MM | JF15003 | GYRWGCEWNCGGITT | SEQ ID NO: 11 |
| CD3 MM | h20GG | GYLWGCEWNCGGITT | SEQ ID NO: 12 |

In some embodiments, the CM of the CD3 AA comprises any one of the sequences set forth in Table 4. Exemplary cleavable moieties (CMs) of the invention are provided in Table 4.

In some embodiments, the CM of an AA of the disclosure comprises any one of the sequences set forth in Table 4-1.

TABLE 4

| CM Name | AA sequence | SEQ ID NO: |
|---|---|---|
| 0001 | LSGRSDNH | SEQ ID NO: 13 |
| 0011 | LSGRSDDH | SEQ ID NO: 14 |
| 2001 | ISSGLLSGRSDNH | SEQ ID NO: 15 |

TABLE 4-continued

| CM Name | AA sequence | SEQ ID NO: |
|---|---|---|
| 2008 | ISSGLLSGRSDQH | SEQ ID NO: 16 |
| 2006 | ISSGLLSGRSDDH | SEQ ID NO: 17 |

TABLE 4-1

| CM Name | AA sequence | SEQ ID NO: |
|---|---|---|
| 0001 | LSGRSDNH | SEQ ID NO: 18 |
| 0002 | LSGRSGNH | SEQ ID NO: 19 |
| 0003 | TSTSGRSANPRG | SEQ ID NO: 20 |
| 1001 | ISSGLLSS | SEQ ID NO: 21 |
| 1002 | QNQALRMA | SEQ ID NO: 22 |
| 1003 | VHMPLGFLGP | SEQ ID NO: 23 |
| 1004 | AVGLLAPP | SEQ ID NO: 24 |
| 0011 | LSGRSDDH | SEQ ID NO: 25 |
| 0021 | LSGRSDIH | SEQ ID NO: 26 |
| 0031 | LSGRSDQH | SEQ ID NO: 27 |
| 0041 | LSGRSDTH | SEQ ID NO: 28 |
| 0051 | LSGRSDYH | SEQ ID NO: 29 |
| 0061 | LSGRSDNP | SEQ ID NO: 30 |
| 0071 | LSGRSANP | SEQ ID NO: 31 |
| 0081 | LSGRSANI | SEQ ID NO: 32 |
| 0091 | LSGRSDNI | SEQ ID NO: 33 |
| 2001 | ISSGLLSGRSDNH | SEQ ID NO: 34 |
| 2002 | ISSGLLSGRSGNH | SEQ ID NO: 35 |
| 2003 | ISSGLLSGRSANPRG | SEQ ID NO: 36 |
| 2005 | AVGLLAPPSGRSANPRG | SEQ ID NO: 37 |
| 2006 | ISSGLLSGRSDDH | SEQ ID NO: 38 |
| 2007 | ISSGLLSGRSDIH | SEQ ID NO: 39 |
| 2008 | ISSGLLSGRSDQH | SEQ ID NO: 40 |
| 2009 | ISSGLLSGRSDTH | SEQ ID NO: 41 |
| 2010 | ISSGLLSGRSDYH | SEQ ID NO: 42 |
| 2011 | ISSGLLSGRSDNP | SEQ ID NO: 43 |
| 2012 | ISSGLLSGRSANP | SEQ ID NO: 44 |
| 2013 | ISSGLLSGRSANI | SEQ ID NO: 45 |
| 2014 | ISSGLLSGRSDNI | SEQ ID NO: 46 |
| 3001 | AVGLLAPPGGLSGRSDNH | SEQ ID NO: 47 |
| 3006 | AVGLLAPPGGLSGRSDDH | SEQ ID NO: 48 |
| 3007 | AVGLLAPPGGLSGRSDIH | SEQ ID NO: 49 |
| 3008 | AVGLLAPPGGLSGRSDQH | SEQ ID NO: 50 |

TABLE 4-1-continued

| CM Name | AA sequence | SEQ ID NO: |
|---|---|---|
| 3009 | AVGLLAPPGGLSGRSDTH | SEQ ID NO: 51 |
| 3010 | AVGLLAPPGGLSGRSDYH | SEQ ID NO: 52 |
| 3011 | AVGLLAPPGGLSGRSDNP | SEQ ID NO: 53 |
| 3012 | AVGLLAPPGGLSGRSANP | SEQ ID NO: 54 |
| 3013 | AVGLLAPPGGLSGRSANI | SEQ ID NO: 55 |
| 3014 | AVGLLAPPGGLSGRSDNI | SEQ ID NO: 56 |

3. Antibodies with Fc Mutations

Provided herein are IgG1 antibodies that that have Fc mutations or antibody fragments containing antigen-binding domains (e.g. scFv, Fab, F(ab')2) linked to a Fc domain, wherein the Fc exhibits reduced effector function (referred to herein as Fc variants). Any of the BAAs, AAs, and antibodies described herein may comprise any Fc variants disclosed herein.

The antibodies that comprise these Fc mutations result in reduced effector function, while maintaining target binding affinity. Accordingly, provided herein are antibodies that bind to a target of interest, wherein the antibody is an IgG1 antibody or an antibody fragment linked to an Fc, wherein the Fc region comprises an amino acid substitution in at least one of amino acid positions L234, L235, and P331, as numbered by the EU index as set forth in Kabat, such that the antibody has reduced effector function. In some embodiments, the amino acid substitution is any one or more of L234F, L235E, and P331S. In some embodiments, there is an additional mutation in N297. In some embodiments, the amino acid substitution is N297Q or N297A.

In some embodiments, the Fc is selected from the Fc sequences presented in Table 4-2. In some embodiments, the Fc is selected from SEQ ID NO: 154, SEQ ID NO:156, SEQ ID NO: SEQ ID NO:158, and SEQ ID NO:160, wherein the X is selected from the group consisting of any naturally occurring amino acid (e.g. alanine, arginine, asparagine, aspartic acid, cysteine, glutamine, glutamic acid, glycine, histidine, isoleucine, leucine, lysine, methionine, phenylalanine, proline, pyrrolysine, selenocysteine, serine, threonine, tryptophan, tyrosine, valine) or any non-naturally occurring amino acid (e.g. trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, tert-leucine, norvaline, 2-azaphenylalanine, 3-azaphenylalanine, 4-azaphenylalanine, and 4-fluorophenylalanine).

TABLE 4-2

| Name<br>SEQ ID NO: | AA Sequence |
|---|---|
| Fc-N297X<br>(SEQ ID NO:<br>154) | ASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKKVEP<br>KSCDKTHTCPPCPAPELLGGPSVFLFPPKPKDTLMISRTPEVTCVVVDVSH<br>EDPEVKFNWYVDGVEVHNAKTKPREEQYXSTYRVVSVLTVLHQDWLN<br>GKEYKCKVSNKALPAPIEKTISKAKGQPREPQVYTLPPSREEMTKNQVSL<br>TCLVKGFYPSDIAVEWESNGQPENNYKTTPPVLDSDGSFFLYSKLTVDKS<br>RWQQGNVFSCSVMHEALHNHYTQKSLSLSPGK |
| Fc-N297Q<br>(SEQ ID NO:<br>155) | ASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKKVEP<br>KSCDKTHTCPPCPAPELLGGPSVFLFPPKPKDTLMISRTPEVTCVVVDVSH<br>EDPEVKFNWYVDGVEVHNAKTKPREEQYQSTYRVVSVLTVLHQDWLN<br>GKEYKCKVSNKALPAPIEKTISKAKGQPREPQVYTLPPSREEMTKNQVSL<br>TCLVKGFYPSDIAVEWESNGQPENNYKTTPPVLDSDGSFFLYSKLTVDKS<br>RWQQGNVFSCSVMHEALHNHYTQKSLSLSPGK |
| Fc-L234X<br>(SEQ ID NO:<br>156) | ASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKKVEP<br>KSCDKTHTCPPCPAPEXLGGPSVFLFPPKPKDTLMISRTPEVTCVVVDVSH<br>EDPEVKFNWYVDGVEVHNAKTKPREEQYNSTYRVVSVLTVLHQDWLN<br>GKEYKCKVSNKALPAPIEKTISKAKGQPREPQVYTLPPSREEMTKNQVSL<br>TCLVKGFYPSDIAVEWESNGQPENNYKTTPPVLDSDGSFFLYSKLTVDKS<br>RWQQGNVFSCSVMHEALHNHYTQKSLSLSPGK |
| Fc-L234F<br>(SEQ ID NO:<br>157) | QVQLKQSGPGLVQPSQSLSITCTVSGFSLTNYGVHWVRQSPGKGLEWLG<br>VIWSGGNTDYNTPFTSRLSINKDNSKSQVFFKMNSLQSQDTAIYYCARAL<br>TYYDYEFAYWGQGTLVTVS(S/A)ASTKGPSVFPLAPSSKSTSGGTAALGC<br>LVKDYFPEPVTVSWNSGALTSGVHTFPAVLQSSGLYSLSSVVTVPSSSLG<br>TQTYICNVNHKPSNTKVDKKVEPKSCDKTHTCPPCPAPEFLGGPSVFLFPP<br>KPKDTLMISRTPEVTCVVVDVSHEDPEVKFNWYVDGVEVHNAKTKPRE<br>EQYNSTYRVVSVLTVLHQDWLNGKEYKCKVSNKALPAPIEKTISKAKGQ<br>PREPQVYTLPPSREEMTKNQVSLTCLVKGFYPSDIAVEWESNGQPENNY<br>KTTPPVLDSDGSFFLYSKLTVDKSRWQQGNVFSCSVMHEALHNHYTQKS<br>LSLSPGK |
| Fc-L235X<br>(SEQ ID NO:<br>158) | QVQLKQSGPGLVQPSQSLSITCTVSGFSLTNYGVHWVRQSPGKGLEWLG<br>VIWSGGNTDYNTPFTSRLSINKDNSKSQVFFKMNSLQSQDTAIYYCARAL<br>TYYDYEFAYWGQGTLVTVS(S/A)ASTKGPSVFPLAPSSKSTSGGTAALGC<br>LVKDYFPEPVTVSWNSGALTSGVHTFPAVLQSSGLYSLSSVVTVPSSSLG<br>TQTYICNVNHKPSNTKVDKKVEPKSCDKTHTCPPCPAPELXGGPSVFLFP<br>PKPKDTLMISRTPEVTCVVVDVSHEDPEVKFNWYVDGVEVHNAKTKPR<br>EEQYNSTYRVVSVLTVLHQDWLNGKEYKCKVSNKALPAPIEKTISKAKG<br>QPREPQVYTLPPSREEMTKNQVSLTCLVKGFYPSDIAVEWESNGQPENN |

TABLE 4-2-continued

| Name<br>SEQ ID NO: | AA Sequence |
|---|---|
| | YKTTPPVLDSDGSFFLYSKLTVDKSRWQQGNVFSCSVMHEALHNHYTQ<br>KSLSLSPGK |
| Fc-L235E<br>(SEQ ID NO:<br>159) | ASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKKVEP<br>KSCDKTHTCPPCPAPELEGGPSVFLFPPKPKDTLMISRTPEVTCVVVDVSH<br>EDPEVKFNWYVDGVEVHNAKTKPREEQYNSTYRVVSVLTVLHQDWLN<br>GKEYKCKVSNKALPAPIEKTISKAKGQPREPQVYTLPPSREEMTKNQVSL<br>TCLVKGFYPSDIAVEWESNGQPENNYKTTPPVLDSDGSFFLYSKLTVDKS<br>RWQQGNVFSCSVMHEALHNHYTQKSLSLSPGK |
| Fc-P331X<br>(SEQ ID NO:<br>160) | ASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKKVEP<br>KSCDKTHTCPPCPAPELLGGPSVFLFPPKPKDTLMISRTPEVTCVVVDVSH<br>EDPEVKFNWYVDGVEVHNAKTKPREEQYNSTYRVVSVLTVLHQDWLN<br>GKEYKCKVSNKALPAXIEKTISKAKGQPREPQVYTLPPSREEMTKNQVSL<br>TCLVKGFYPSDIAVEWESNGQPENNYKTTPPVLDSDGSFFLYSKLTVDKS<br>RWQQGNVFSCSVMHEALHNHYTQKSLSLSPGK |
| Fc-P331S<br>(SEQ ID NO:<br>161) | ASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKKVEP<br>KSCDKTHTCPPCPAPELLGGPSVFLFPPKPKDTLMISRTPEVTCVVVDVSH<br>EDPEVKFNWYVDGVEVHNAKTKPREEQYNSTYRVVSVLTVLHQDWLN<br>GKEYKCKVSNKALPASIEKTISKAKGQPREPQVYTLPPSREEMTKNQVSL<br>TCLVKGFYPSDIAVEWESNGQPENNYKTTPPVLDSDGSFFLYSKLTVDKS<br>RWQQGNVFSCSVMHEALHNHYTQKSLSLSPGK |
| Fc-Fcmt3<br>(SEQ ID NO:<br>162) | ASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKKVEP<br>KSCDKTHTCPPCPAPEFEGGPSVFLFPPKPKDTLMISRTPEVTCVVVDVSH<br>EDPEVKFNWYVDGVEVHNAKTKPREEQYNSTYRVVSVLTVLHQDWLN<br>GKEYKCKVSNKALPASIEKTISKAKGQPREPQVYTLPPSREEMTKNQVSL<br>TCLVKGFYPSDIAVEWESNGQPENNYKTTPPVLDSDGSFFLYSKLTVDKS<br>RWQQGNVFSCSVMHEALHNHYTQKSLSLSPGK |
| C225v5Fcmt4<br>HC<br>(SEQ ID NO:<br>163 | ASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKKVEP<br>KSCDKTHTCPPCPAPEFEGGPSVFLFPPKPKDTLMISRTPEVTCVVVDVSH<br>EDPEVKFNWYVDGVEVHNAKTKPREEQYQSTYRVVSVLTVLHQDWLN<br>GKEYKCKVSNKALPASIEKTISKAKGQPREPQVYTLPPSREEMTKNQVSL<br>TCLVKGFYPSDIAVEWESNGQPENNYKTTPPVLDSDGSFFLYSKLTVDKS<br>RWQQGNVFSCSVMHEALHNHYTQKSLSLSPGK |

Antibodies, AAs, bispecific antibodies, and BAAs comprising these Fc mutations are provided herein.

In some embodiments, such Fc variant-containing AAs and BAAs can bind an immune effector cell. In some embodiments, they can bind a target selectively located on an immune effector cell. In some embodiments, they can bind CD3. In some embodiments, they can bind any target listed in Table 9. In some embodiments, they can bind EGFR.

Accordingly, in some embodiments, provided herein is an activatable antibody (AA) comprising:

a) an antibody (AB) that specifically binds a target, wherein the antibody is an IgG1 antibody, and wherein the Fc region of the antibody comprises an amino acid substitution in at least one of amino acid positions L234, L235, and P331, as numbered by the EU index as set forth in Kabat, such that the AA has reduced effector function;

b) a masking moiety (MM) coupled to the AB, wherein the MM reduces or inhibits the binding of the AB to the target when the AA is in an uncleaved state; and c) a cleavable moiety (CM) coupled to the AB, wherein the CM is a polypeptide that functions as a substrate for a protease.

In some embodiments, the Fc region comprises amino acid substitutions in at least amino acid positions L234, L235, N297 and P331, as numbered by the EU index as set forth in Kabat, such that the AA has reduced effector function. In some embodiments, the target is selected from the group consisting of the targets presented in Table 9.

In some embodiments, provided herein is a bispecific activatable antibody (BAA) comprising:

a) an IgG antibody (AB1) that specifically binds to a first target wherein the AB1 comprises:

i. two heavy chains (AB1 HCs) and two light chains (AB1 LCs); and ii. a first masking moiety (MM1) linked to a first cleavable moiety (CM1) to form a MM1-CM1 construct, wherein the carboxyl terminus of a MM1-CM1 construct is linked to each amino terminus of each light chain of the AB1, wherein the MM1 inhibits the binding of the AB1 to its target; and the CM1 is a polypeptide that functions as a substrate for a first protease, b) two scFvs (AB2) that each specifically binds to a second target wherein each AB2 comprises:

i. a heavy chain variable region linked to a light chain variable region, wherein the carboxyl terminus of each AB2 is linked to the amino terminus each of the AB1 heavy chains; and ii. a second masking moiety (MM2) linked to a second cleavable moiety (CM2) to form a MM2-CM2 construct, wherein the carboxyl terminus of a MM2-CM2 construct is linked to the amino terminus of each AB2 wherein the MM2 inhibits the binding of the AB2 to its target; and the CM2 is a polypeptide that functions as a substrate for a second protease, and wherein the AB1 comprises an Fc region comprises an amino acid substitution in at least one of amino acid positions L234, L235, N297, and P331, as numbered by the EU index as set forth in Kabat, such that the BAA has reduced effector function.

In some embodiments provided herein, the BAAs provided herein comprise:

a) A bispecific activatable antibody (BAA) comprising:

i) an IgG antibody (AB1) that specifically binds to a first target wherein the AB1 comprises two heavy chains (AB1 HCs) and two light chains (AB1 LCs); and wherein the AB1 is linked to a first masking moiety (MM1) linked to a first cleavable moiety (CM1) to form a MM1-CM1 construct, wherein the carboxyl terminus of a MM1-CM1 construct is linked to each amino terminus of each light chain of the AB1, wherein the MM1 inhibits the binding of the AB1 to its target; and the CM1 is a polypeptide that functions as a substrate for a first protease, ii) two scFvs (each an AB2) that each specifically binds to a second target wherein each AB2 comprises a heavy chain variable region linked to a light chain variable region, wherein the carboxyl terminus of each AB2 is linked to the amino terminus each of the AB1 heavy chains; and wherein each AB2 is linked to a second masking moiety (MM2) linked to a second cleavable moiety (CM2) to form a MM2-CM2 construct, wherein the carboxyl terminus of each MM2-CM2 construct is linked to the amino terminus of each AB2 wherein the MM2 inhibits the binding of the AB2 to its target; and the CM2 is a polypeptide that functions as a substrate for a second protease, and wherein the AB1 comprises an Fc region comprises an amino acid substitution in at least one of amino acid positions L234, L235, N297, and P331, as numbered by the EU index as set forth in Kabat, such that the BAA has reduced effector function.

4. EGFR Antibodies

Provided herein are antibodies or antigen binding fragments thereof (AB) that specifically bind to EGFR. Exemplary CDR sequences of EGFR-binding antibodies are provided in Table 5.

Provided herein are EGFR antibodies, bispecific antibodies with one arm targeting EGFR, AAs capable of binding EGFR upon activation, and BAAs capable of binding EGFR upon activation. In some embodiments, the EGFR antibody comprises the CDRs of Table 5.

In some embodiments, e.g. in a BAA format, provided herein are IgG1 antibodies that specifically bind to the Epidermal Growth Factor Receptor (EGFR) and impart reduced effector function. The antibodies comprise Fc mutations that result in reduced effector function, while maintaining EGFR binding affinity. Accordingly, provided herein are antibodies that bind to EGFR, wherein the antibody is an IgG1 antibody, wherein the antibody comprises an Fc region comprising an amino acid substitution in at least one of amino acid positions L234, L235, and P331, as numbered by the EU index as set forth in Kabat, such that the antibody has reduced effector function. In some embodiments, the amino acid substitution is any one or more of L234F, L235E, and P331S.

In some embodiments, the antibody comprises amino acid substitutions in at least two of amino acid positions L234, L235, and P331.

In some embodiments, the antibody comprises amino acid substitutions at amino acid positions L234, L235, and P331.

In some embodiments, the antibody comprises L234F, L235E, and P331S amino acid substitutions.

In some embodiments, the antibody comprises an Fc region comprising an amino acid substitution at N297 along with an amino acid substitution in at least one of amino acid positions L234, L235, and/or P331. In some embodiments, the Fc region comprises an N297Q mutation. In some embodiments, the Fc region comprises an N297A mutation.

In some embodiments, the antibody comprises L234F, L235E, P331S and N297Q substitutions. In some embodiments, the antibody comprises L234F, L235E, P331S and N297A substitutions.

Exemplary CDR sequences of EGFR-binding antibodies are provided in Table 5, set forth in Kabat.

TABLE 5

| Name | Sequence | SEQ ID NO: |
|---|---|---|
| C225L1 | RASQSIGTNIH | SEQ ID NO: 57 |
| C225L2 | YASESIS | SEQ ID NO: 58 |
| C225L3 | QQNNNWPTT | SEQ ID NO: 59 |
| C225H1 | NYGVH | SEQ ID NO: 60 |
| C225H2 | VIWSGGNTDYNTPFTS | SEQ ID NO: 61 |
| C225H3 | ALTYYDYEFAY | SEQ ID NO: 62 |

Exemplary amino acid sequences of EGFR-binding antibodies are provided in Table 6. (VL and VH denote the variable light and variable heavy chains, respectively; LC and HC denote the light and heavy chains, respectively).

In some embodiments, the EGFR antibodies comprise any one of the sequences provided in Table 6.

In some embodiments, the heavy chain of the EGFR antibody comprises any one of the sequences set forth in SEQ ID NO: 67, SEQ ID NO: 69, SEQ ID NO: 70, SEQ ID NO: 71, SEQ ID NO: 72, SEQ ID NO: 73, SEQ ID NO: 74, SEQ ID NO: 75 and SEQ ID NO: 76, as set forth in Table 6. In some embodiments, the heavy chain EGFR antibody comprises any one of the sequences set forth in SEQ ID NO: 67, SEQ ID NO: 69, SEQ ID NO: 71, and SEQ ID NO: 73, wherein in X is selected from any naturally occurring amino acid (e.g. alanine, arginine, asparagine, aspartic acid, cysteine, glutamine, glutamic acid, glycine, histidine, isoleucine, leucine, lysine, methionine, phenylalanine, proline, pyrrolysine, selenocysteine, serine, threonine, tryptophan, tyrosine, valine) or any non-naturally occurring amino acid (e.g., trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, tert-leucine, norvaline, 2-azaphenylalanine, 3-azaphenylalanine, 4-azaphenylalanine, and 4-fluorophenylalanine). The notation Fcmt3 comprises a triple point mutation, wherein the Fc region of the heavy chain of the EGFR antibody comprises the following three point mutations: L234F, L235E, and P331S. Accordingly, in some embodiments, the EGFR antibody comprises a heavy chain with an amino acid sequence set forth in SEQ ID NO: C225v5Fcmt3 HC. In some embodiments, the Fc region of the heavy chain of the EGFR antibody comprises a fourth point mutation, N297Q. The notation Fcmt4 comprises the Fcmt3 triple point mutation and the fourth point mutation, N297Q. Accordingly, in such embodiments, the EGFR antibody comprises a heavy chain with an amino acid sequence set forth in SEQ ID NO: 76.

TABLE 6

| Name SEQ ID NO: | AA Sequence |
|---|---|
| C225v5-VL (SEQ ID NO: 63) | QILLTQSPVILSVSPGERVSFSCRASQSIGTNIHWYQQRTNGSPRLLIKYAS ESISGIPSRFSGSGSGTDFTLSINSVESEDIADYYCQQNNNWPTTFGAGTKL ELK |
| C225v5-VH (SEQ ID NO: 64) | QVQLKQSGPGLVQPSQSLSITCTVSGFSLTNYGVHWVRQSPGKGLEWLG VIWSGGNTDYNTPFTSRLSINKDNSKSQVFFKMNSLQSQDTAIYYCARAL TYYDYEFAYWGQGTLVTVS(S/A) |
| C225v5 LC (SEQ ID NO: 65) | QILLTQSPVILSVSPGERVSFSCRASQSIGTNIHWYQQRTNGSPRLLIKYAS ESISGIPSRFSGSGSGTDFTLSINSVESEDIADYYCQQNNNWPTTFGAGTKL ELKRTVAAPSVFIFPPSDEQLKSGTASVVCLLNNFYPREAKVQWKVDNA LQSGNSQESVTEQDSKDSTYSLSSTLTLSKADYEKHKVYACEVTHQGLSS PVTKSFNRGEC |
| C225v5 HC (SEQ ID NO: 66) | QVQLKQSGPGLVQPSQSLSITCTVSGFSLTNYGVHWVRQSPGKGLEWLG VIWSGGNTDYNTPFTSRLSINKDNSKSQVFFKMNSLQSQDTAIYYCARAL TYYDYEFAYWGQGTLVTVS(S/A)ASTKGPSVFPLAPSSKSTSGGTAALGC LVKDYFPEPVTVSWNSGALTSGVHTFPAVLQSSGLYSLSSVVTVPSSSLG TQTYICNVNHKPSNTKVDKKVEPKSCDKTHTCPPCPAPELLGGPSVFLFP PKPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAKG QPREPQVYTLPPSREEMTKNQVSLTCLVKGFYPSDIAVEWESNGQPENN YKTTPPVLDSDGSFFLYSKLTVDKSRWQQGNVFSCSVMHEALHNHYTQ KSLSLSPGK |
| C225v5N297X HC (SEQ ID NO: 67) | QVQLKQSGPGLVQPSQSLSITCTVSGFSLTNYGVHWVRQSPGKGLEWLG VIWSGGNTDYNTPFTSRLSINKDNSKSQVFFKMNSLQSQDTAIYYCARAL TYYDYEFAYWGQGTLVTVS(S/A)ASTKGPSVFPLAPSSKSTSGGTAALGC LVKDYFPEPVTVSWNSGALTSGVHTFPAVLQSSGLYSLSSVVTVPSSSLG TQTYICNVNHKPSNTKVDKKVEPKSCDKTHTCPPCPAPELLGGPSVFLFP PKPKDTLMISRTPEVTCVVVDVSHEDPEVKFNWYVDGVEVHNAKTKPR EEQYXSTYRVVSVLTVLHQDWLNGKEYKCKVSNKALPAPIEKTISKAKG QPREPQVYTLPPSREEMTKNQVSLTCLVKGFYPSDIAVEWESNGQPENN YKTTPPVLDSDGSFFLYSKLTVDKSRWQQGNVFSCSVMHEALHNHYTQ KSLSLSPGK |
| C225v5N297Q HC (SEQ ID NO: 68) | QVQLKQSGPGLVQPSQSLSITCTVSGFSLTNYGVHWVRQSPGKGLEWLG VIWSGGNTDYNTPFTSRLSINKDNSKSQVFFKMNSLQSQDTAIYYCARAL TYYDYEFAYWGQGTLVTVS(S/A)ASTKGPSVFPLAPSSKSTSGGTAALGC LVKDYFPEPVTVSWNSGALTSGVHTFPAVLQSSGLYSLSSVVTVPSSSLG TQTYICNVNHKPSNTKVDKKVEPKSCDKTHTCPPCPAPELLGGPSVFLFP PKPKDTLMISRTPEVTCVVVDVSHEDPEVKFNWYVDGVEVHNAKTKPR EEQYQSTYRVVSVLTVLHQDWLNGKEYKCKVSNKALPAPIEKTISKAKG QPREPQVYTLPPSREEMTKNQVSLTCLVKGFYPSDIAVEWESNGQPENN YKTTPPVLDSDGSFFLYSKLTVDKSRWQQGNVFSCSVMHEALHNHYTQ KSLSLSPGK |
| C225v5 L234X HC (SEQ ID NO: 69) | QVQLKQSGPGLVQPSQSLSITCTVSGFSLTNYGVHWVRQSPGKGLEWLG VIWSGGNTDYNTPFTSRLSINKDNSKSQVFFKMNSLQSQDTAIYYCARAL TYYDYEFAYWGQGTLVTVS(S/A)ASTKGPSVFPLAPSSKSTSGGTAALGC LVKDYFPEPVTVSWNSGALTSGVHTFPAVLQSSGLYSLSSVVTVPSSSLG TQTYICNVNHKPSNTKVDKKVEPKSCDKTHTCPPCPAPEXLGGPSVFLFP PKPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAKG QPREPQVYTLPPSREEMTKNQVSLTCLVKGFYPSDIAVEWESNGQPENN YKTTPPVLDSDGSFFLYSKLTVDKSRWQQGNVFSCSVMHEALHNHYTQ KSLSLSPGK |
| C225v5 L234F HC (SEQ ID NO: 70) | QVQLKQSGPGLVQPSQSLSITCTVSGFSLTNYGVHWVRQSPGKGLEWLG VIWSGGNTDYNTPFTSRLSINKDNSKSQVFFKMNSLQSQDTAIYYCARAL TYYDYEFAYWGQGTLVTVS(S/A)ASTKGPSVFPLAPSSKSTSGGTAALGC LVKDYFPEPVTVSWNSGALTSGVHTFPAVLQSSGLYSLSSVVTVPSSSLG TQTYICNVNHKPSNTKVDKKVEPKSCDKTHTCPPCPAPEFLGGPSVFLFPP KPKDTLMISRTPEVTCVVVDVSHEDPEVKFNWYVDGVEVHNAKTKPRE EQYNSTYRVVSVLTVLHQDWLNGKEYKCKVSNKALPAPIEKTISKAKGQ PREPQVYTLPPSREEMTKNQVSLTCLVKGFYPSDIAVEWESNGQPENNY KTTPPVLDSDGSFFLYSKLTVDKSRWQQGNVFSCSVMHEALHNHYTQKS LSLSPGK |

TABLE 6-continued

| Name<br>SEQ ID NO: | AA Sequence |
|---|---|
| C225v5<br>L235X HC<br>(SEQ ID NO:<br>71) | QVQLKQSGPGLVQPSQSLSITCTVSGFSLTNYGVHWVRQSPGKGLEWLG<br>VIWSGGNTDYNTPFTSRLSINKDNSKSQVFFKMNSLQSQDTAIYYCARAL<br>TYYDYEFAYWGQGTLVTVS(S/A)ASTKGPSVFPLAPSSKSTSGGTAALGC<br>LVKDYFPEPVTVSWNSGALTSGVHTFPAVLQSSGLYSLSSVVTVPSSSLG<br>TQTYICNVNHKPSNTKVDKKVEPKSCDKTHTCPPCPAPELXGGPSVFLFP<br>PKPKDTLMISRTPEVTCVVVDVSHEDPEVKFNWYVDGVEVHNAKTKPR<br>EEQYNSTYRVVSVLTVLHQDWLNGKEYKCKVSNKALPAPIEKTISKAKG<br>QPREPQVYTLPPSREEMTKNQVSLTCLVKGFYPSDIAVEWESNGQPENN<br>YKTTPPVLDSDGSFFLYSKLTVDKSRWQQGNVFSCSVMHEALHNHYTQ<br>KSLSLSPGK |
| C225v5<br>L235E HC<br>(SEQ ID NO:<br>72) | QVQLKQSGPGLVQPSQSLSITCTVSGFSLTNYGVHWVRQSPGKGLEWLG<br>VIWSGGNTDYNTPFTSRLSINKDNSKSQVFFKMNSLQSQDTAIYYCARAL<br>TYYDYEFAYWGQGTLVTVS(S/A)ASTKGPSVFPLAPSSKSTSGGTAALGC<br>LVKDYFPEPVTVSWNSGALTSGVHTFPAVLQSSGLYSLSSVVTVPSSSLG<br>TQTYICNVNHKPSNTKVDKKVEPKSCDKTHTCPPCPAPELEGGPSVFLFP<br>PKPKDTLMISRTPEVTCVVVDVSHEDPEVKFNWYVDGVEVHNAKTKPR<br>EEQYNSTYRVVSVLTVLHQDWLNGKEYKCKVSNKALPAPIEKTISKAKG<br>QPREPQVYTLPPSREEMTKNQVSLTCLVKGFYPSDIAVEWESNGQPENN<br>YKTTPPVLDSDGSFFLYSKLTVDKSRWQQGNVFSCSVMHEALHNHYTQ<br>KSLSLSPGK |
| C225v5<br>P331X HC<br>(SEQ ID NO:<br>73) | QVQLKQSGPGLVQPSQSLSITCTVSGFSLTNYGVHWVRQSPGKGLEWLG<br>VIWSGGNTDYNTPFTSRLSINKDNSKSQVFFKMNSLQSQDTAIYYCARAL<br>TYYDYEFAYWGQGTLVTVS(S/A)ASTKGPSVFPLAPSSKSTSGGTAALGC<br>LVKDYFPEPVTVSWNSGALTSGVHTFPAVLQSSGLYSLSSVVTVPSSSLG<br>TQTYICNVNHKPSNTKVDKKVEPKSCDKTHTCPPCPAPELLGGPSVFLFP<br>PKPKDTLMISRTPEVTCVVVDVSHEDPEVKFNWYVDGVEVHNAKTKPR<br>EEQYNSTYRVVSVLTVLHQDWLNGKEYKCKVSNKALPAXIEKTISKAKG<br>QPREPQVYTLPPSREEMTKNQVSLTCLVKGFYPSDIAVEWESNGQPENN<br>YKTTPPVLDSDGSFFLYSKLTVDKSRWQQGNVFSCSVMHEALHNHYTQ<br>KSLSLSPGK |
| C225v5<br>P331S HC<br>(SEQ ID NO:<br>74) | QVQLKQSGPGLVQPSQSLSITCTVSGFSLTNYGVHWVRQSPGKGLEWLG<br>VIWSGGNTDYNTPFTSRLSINKDNSKSQVFFKMNSLQSQDTAIYYCARAL<br>TYYDYEFAYWGQGTLVTVS(S/A)ASTKGPSVFPLAPSSKSTSGGTAALGC<br>LVKDYFPEPVTVSWNSGALTSGVHTFPAVLQSSGLYSLSSVVTVPSSSLG<br>TQTYICNVNHKPSNTKVDKKVEPKSCDKTHTCPPCPAPELLGGPSVFLFP<br>PKPKDTLMISRTPEVTCVVVDVSHEDPEVKFNWYVDGVEVHNAKTKPR<br>EEQYNSTYRVVSVLTVLHQDWLNGKEYKCKVSNKALPASIEKTISKAKG<br>QPREPQVYTLPPSREEMTKNQVSLTCLVKGFYPSDIAVEWESNGQPENN<br>YKTTPPVLDSDGSFFLYSKLTVDKSRWQQGNVFSCSVMHEALHNHYTQ<br>KSLSLSPGK |
| C225v5Fcmt3<br>HC<br>(SEQ ID NO:<br>75) | QVQLKQSGPGLVQPSQSLSITCTVSGFSLTNYGVHWVRQSPGKGLEWLG<br>VIWSGGNTDYNTPFTSRLSINKDNSKSQVFFKMNSLQSQDTAIYYCARAL<br>TYYDYEFAYWGQGTLVTVS(S/A)ASTKGPSVFPLAPSSKSTSGGTAALGC<br>LVKDYFPEPVTVSWNSGALTSGVHTFPAVLQSSGLYSLSSVVTVPSSSLG<br>TQTYICNVNHKPSNTKVDKKVEPKSCDKTHTCPPCPAPEFEGGPSVFLFPP<br>KPKDTLMISRTPEVTCVVVDVSHEDPEVKFNWYVDGVEVHNAKTKPRE<br>EQYNSTYRVVSVLTVLHQDWLNGKEYKCKVSNKALPASIEKTISKAKGQ<br>PREPQVYTLPPSREEMTKNQVSLTCLVKGFYPSDIAVEWESNGQPENNY<br>KTTPPVLDSDGSFFLYSKLTVDKSRWQQGNVFSCSVMHEALHNHYTQKS<br>LSLSPGK |
| C225v5Fcmt4<br>HC<br>(SEQ ID NO:<br>76) | QVQLKQSGPGLVQPSQSLSITCTVSGFSLTNYGVHWVRQSPGKGLEWLG<br>VIWSGGNTDYNTPFTSRLSINKDNSKSQVFFKMNSLQSQDTAIYYCARAL<br>TYYDYEFAYWGQGTLVTVS(S/A)ASTKGPSVFPLAPSSKSTSGGTAALGC<br>LVKDYFPEPVTVSWNSGALTSGVHTFPAVLQSSGLYSLSSVVTVPSSSLG<br>TQTYICNVNHKPSNTKVDKKVEPKSCDKTHTCPPCPAPEFEGGPSVFLFPP<br>KPKDTLMISRTPEVTCVVVDVSHEDPEVKFNWYVDGVEVHNAKTKPRE<br>EQYQSTYRVVSVLTVLHQDWLNGKEYKCKVSNKALPASIEKTISKAKGQ<br>PREPQVYTLPPSREEMTKNQVSLTCLVKGFYPSDIAVEWESNGQPENNY<br>KTTPPVLDSDGSFFLYSKLTVDKSRWQQGNVFSCSVMHEALHNHYTQKS<br>LSLSPGK |
| SynFcmt4<br>HC<br>(SEQ ID NO:<br>77) | QVTLRESGPALVKPTQTLTLTCTFSGFSLSTSGMSVGWIRQPPGKALEWL<br>ADIWWDDKKDYNPSLKSRLTISKDTSKNQVVLKVTNMDPADTATYYCA<br>RSMITNWYFDVWGAGTTVTVS(S/A)ASTKGPSVFPLAPSSKSTSGGTAAL<br>GCLVKDYFPEPVTVSWNSGALTSGVHTFPAVLQSSGLYSLSSVVTVPSSS<br>LGTQTYICNVNHKPSNTKVDKKVEPKSCDKTHTCPPCPAPEFEGGPSVFL<br>FPPKPKDTLMISRTPEVTCVVVDVSHEDPEVKFNWYVDGVEVHNAKTKP<br>REEQYQSTYRVVSVLTVLHQDWLNGKEYKCKVSNKALPASIEKTISKAK<br>GQPREPQVYTLPPSREEMTKNQVSLTCLVKGFYPSDIAVEWESNGQPEN<br>NYKTTPPVLDSDGSFFLYSKLTVDKSRWQQGNVFSCSVMHEALHNHYT<br>QKSLSLSPGK |

5. Activatable EGFR Antibodies

In some embodiments, any one of the EGFR antibodies provided herein are in an AA format (EGFR AAs). As described above for the CD3 AAs, the EGFR AAs also comprise a prodomain.

Accordingly provided herein are AAs comprising antibodies or antigen binding fragments thereof (AB) that specifically bind to EGFR. Exemplary CDR sequences of EGFR-binding antibodies are provided in Table 5.

In some embodiments, the AA comprises: (a) any antibody or an antigen binding fragment thereof (AB) that specifically binds to Epidermal Growth Factor Receptor (EGFR); (b) and a prodomain, wherein the prodomain comprises (i) a masking moiety (MM) coupled to the AB, wherein the MM reduces or inhibits the binding of the AB to the EGFR when the AA is in an uncleaved state, and wherein the MM comprises an amino acid sequence selected from the group consisting of sequences presented in Table 7; and (ii) a cleavable moiety (CM) coupled to the AB, wherein the CM is a polypeptide that functions as a substrate for a protease.

Exemplary EGFR masking moieties (MMs) of the invention are provided in Table 7 and Table 8.

TABLE 7

| MM | Name | AA sequence | SEQ ID NO: |
|---|---|---|---|
| EGFR MM | CF41 | LSCEGWAMNREQCRA | SEQ ID NO: 78 |
| EGFR MM | CF08 | PPLECNTKSMCSKHD | SEQ ID NO: 79 |
| EGFR MM | CF13 | DRDCRGRRARCQQEG | SEQ ID NO: 80 |
| EGFR MM | CF19 | FTCEGWAMNREQCRT | SEQ ID NO: 81 |
| EGFR MM | CF22 | GRCPPSRDIRFCTYM | SEQ ID NO: 82 |
| EGFR MM | CF46 | FSCEGWAMNRSQCRT | SEQ ID NO: 83 |
| EGFR MM | CF48 | FTCEGWAMNRDQCRT | SEQ ID NO: 84 |

TABLE 8

| MM | Name | AA sequence | SEQ ID NO: |
|---|---|---|---|
| EGFR MM | 3954 | CISPRGCPDGPYVMY | SEQ ID NO: 85 |
| EGFR MM | 3954a | CISPRGCPDGPYVM | SEQ ID NO: 86 |
| EGFR MM | 3960 | CISPRGC | SEQ ID NO: 87 |

In some embodiments, the MM of the EGFR AA comprises the amino acid sequence of SEQ ID NO: 78. In some embodiments, the MM of the EGFR AA comprises the amino acid sequence of SEQ ID NO: 85.

In some embodiments, the CM of the EGFR AA comprises an amino acid sequence selected from the group consisting of sequences presented in Table 4. In some embodiments, the CM comprises the amino acid sequence of SEQ ID NO: 14. In some embodiments, the CM comprises the amino acid sequence of SEQ ID NO: 16.

In some embodiments, provided herein is an activatable antibody (AA) comprising: (a) an antibody that specifically binds to Epidermal Growth Factor Receptor (EGFR), wherein the antibody is an IgG1 antibody, and wherein the Fc region of the antibody comprises an amino acid substitution in at least one of amino acid positions L234, L235, and P331, as numbered by the EU index as set forth in Kabat, such that the AA has reduced effector function; (b) a masking moiety (MM) coupled to the AB, wherein the MM reduces or inhibits the binding of the AB to the EGFR when the AA is in an uncleaved state; and (c) a cleavable moiety (CM) coupled to the AB, wherein the CM is a polypeptide that functions as a substrate for a protease. The EGFR IgG1 antibodies can be any of the IgG1 antibodies described in the immediately preceding section. In some embodiments, the MM comprises an amino acid sequence selected from the group consisting of sequences presented in Table 7.

In an exemplary embodiment, provided herein is an activatable antibody (AA) comprising: (a) an antibody (AB) that specifically binds to Epidermal Growth Factor Receptor (EGFR), wherein the AB is an IgG1 antibody, and wherein the Fc region of the AB comprises an amino acid substitution in at least one of amino acid positions L234, L235, and P331, as numbered by the EU index as set forth in Kabat, such that the AA has reduced effector function; (b) a masking moiety (MM) coupled to the AB, wherein the MM reduces or inhibits the binding of the AB to the EGFR when the AA is in an uncleaved state; and (c) a cleavable moiety (CM) coupled to the AB, wherein the CM is a polypeptide that functions as a substrate for a protease. In some embodiments, the amino acid substitution is any one or more of L234F, L235E, and P331S. In some embodiments, the AB comprises amino acid substitutions in at least two of amino acid positions L234, L235, and P331. In some embodiments, the AB comprises amino acid substitutions at amino acid positions L234, L235, and P331. In some embodiments, the AB comprises L234F, L235E, and P331S amino acid substitutions. In some embodiments, the AB comprises an Fc region comprising an amino acid substitution at N297. In some embodiments, the Fc region comprises an N297Q mutation. In some embodiments, the AB comprises L234F, L235E, P331S, and N297Q amino acid substitutions. In some embodiments, the MM comprises an amino acid sequence selected from the group consisting of sequences presented in Table 7 or Table 8. In some embodiments, the MM comprises the amino acid sequence of SEQ ID NO: 78. In some embodiments, the MM comprises the amino acid sequence of SEQ ID NO: 85. In some embodiments, the CM comprises an amino acid sequence selected from the group consisting of sequences presented in Table 4. In some embodiments, the CM comprises the amino acid sequence of SEQ ID NO: 14. In some embodiments, the CM comprises the amino acid sequence of SEQ ID NO: 16. In some embodiments, the AA is part of a BAA.

6. Bispecific Activatable Antibodies (BAAs)

Figure 17:
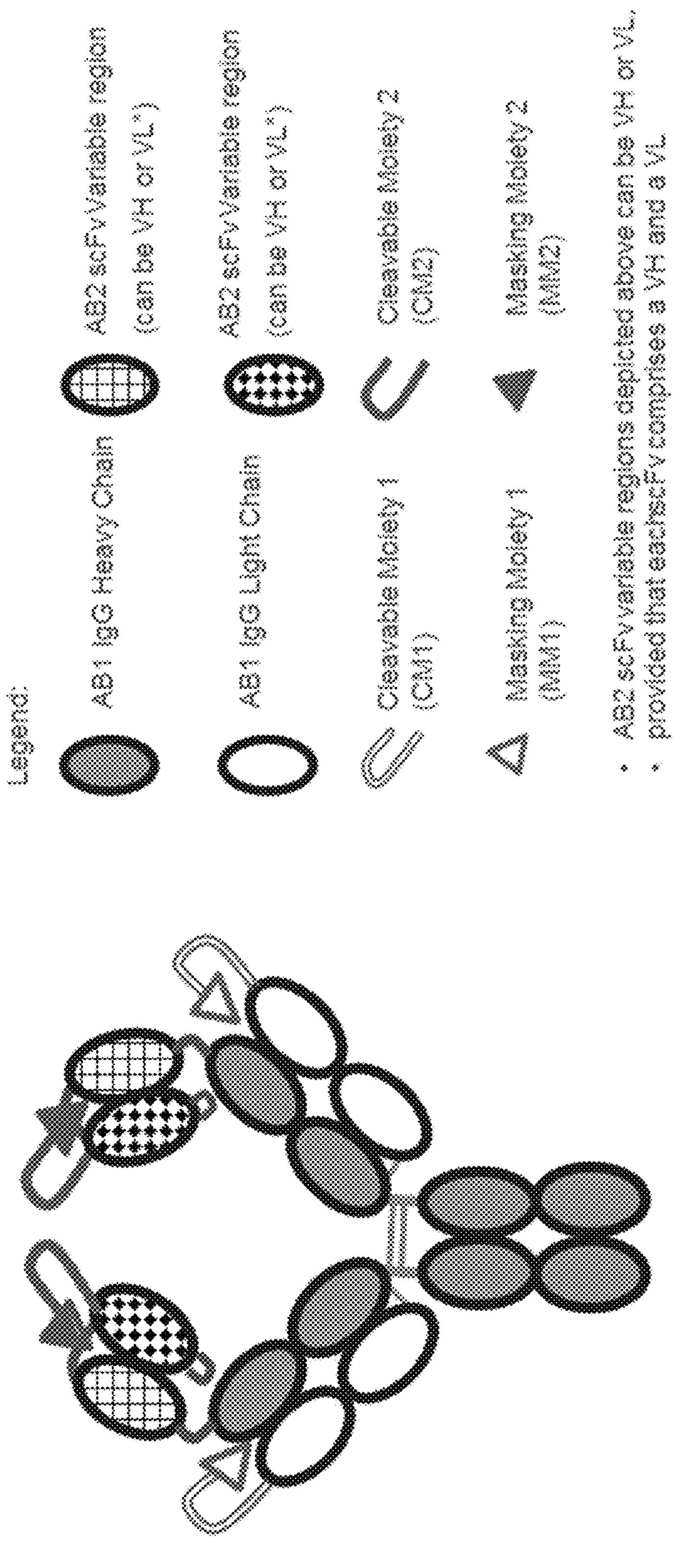
FIGS. 17-19 illustrate exemplary BAAs provided herein.
Figure 18:
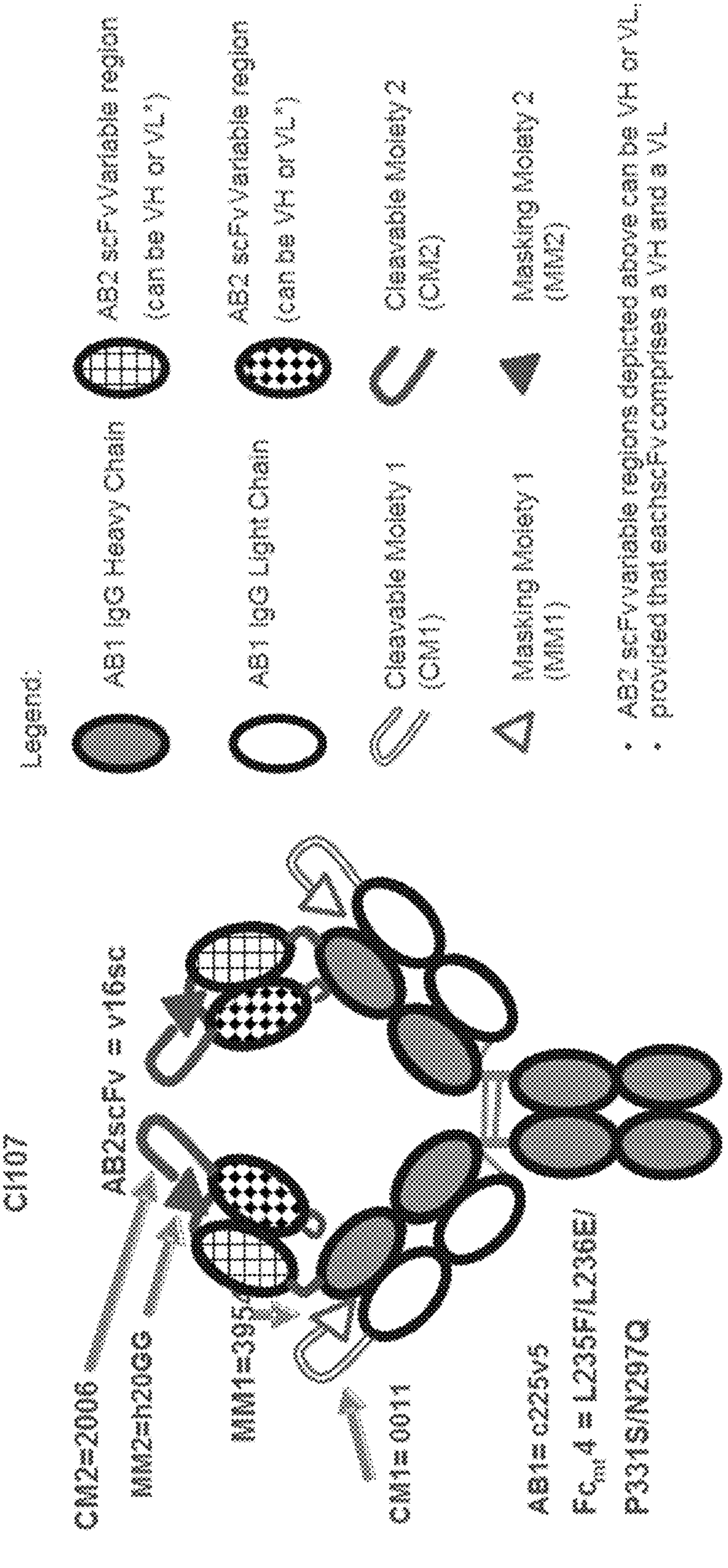
Figure 19:
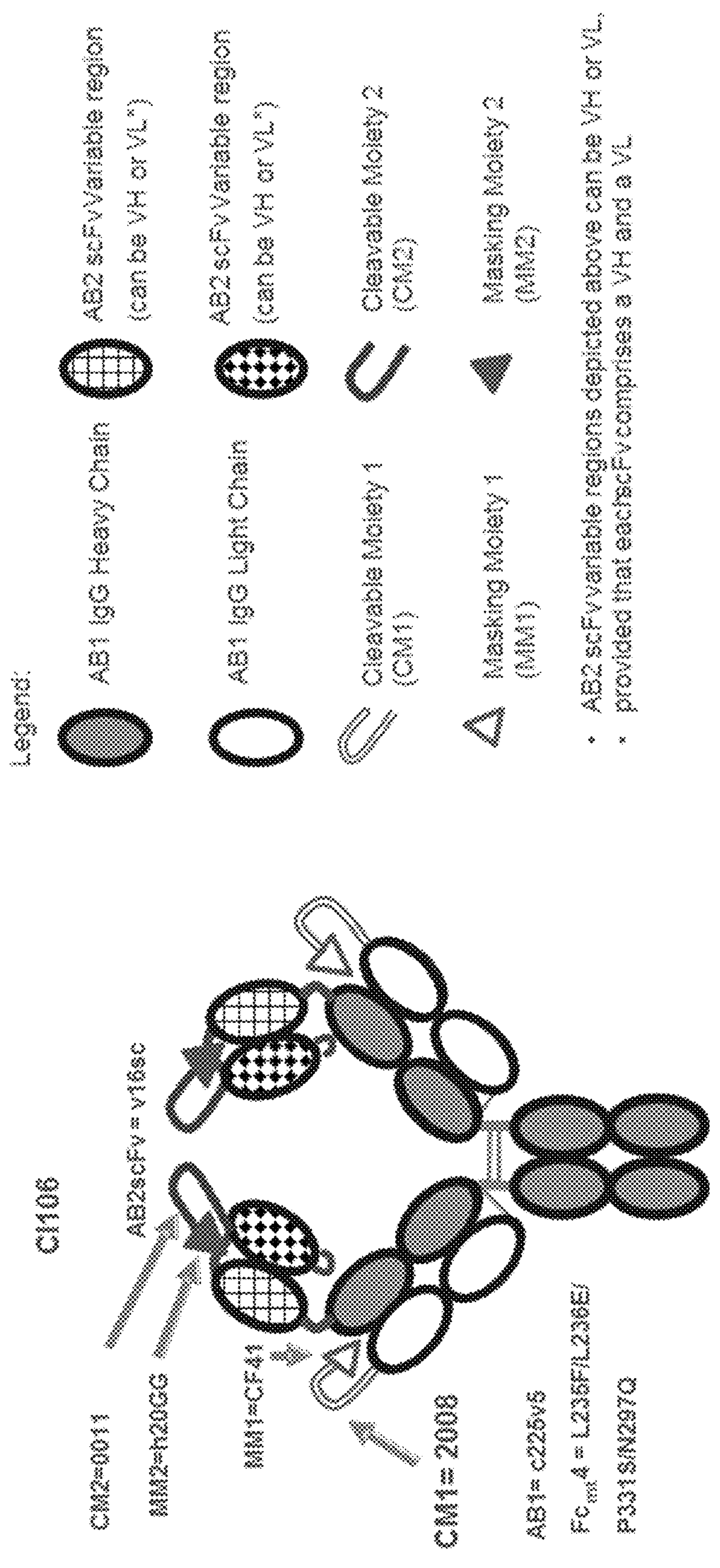

Provided herein are BAAs (bispecific AAs, BAAs), wherein said BAA, when activated, specifically binds to two targets (e.g. binds two different targets, or binds two different epitopes on the same target) and can comprise and can comprise one of the exemplary structures provided in FIGS. 17-19.

In some embodiments, the first target is selected from the group consisting of the targets presented in Table 9 and the second target is selected from the group consisting of the target presented in Table 9.

As generally provided herein, and as described above in the section describing AAs, the BAAs of the invention comprise MM-CM constructs, also referred to herein as a prodomain. Accordingly, as used herein, the term "prodomain" refers to a polypeptide comprising a masking moiety (MM) and a cleavable moiety (CM). In some embodiments, the MM and the CM are separated by a linker, referred to herein as L1. In some embodiments, the prodomain comprises a linker at the carboxyl terminus of the CM; this linker, referred to herein as L2, links the CM of the prodomain to the AB. In some embodiments, the prodomain comprises a linker between MM and CM and a linker after CM. In some embodiments, the MM and the CM are not separated by a linker. In certain embodiments a prodomain comprises one of the following formulae (where the formula below represents an amino acid sequence in either N- to C-terminal direction or C- to N-terminal direction): (MM)-L1-(CM), (MM)-(CM)-L2, (MM)-L1-(CM)-L2, or (MM)-(CM). In exemplary embodiments, a prodomain comprises an EGFR MM and a CM cleavable by a matriptase or MMP; or a CD3ε MM and a CM cleavable by a matriptase or MMP. In some embodiments, a prodomain comprises an EGFR MM and a CM that is cleavable by a matriptase and an MMP. In some embodiments, a prodomain comprises a CD3ε MM and a CM that is cleavable by a matriptase and an MMP. Provided herein are bispecific activatable antibodies (BAAs) comprising a prodomain. Also provided herein are nucleotides encoding a prodomain of the invention.

In some embodiments, provided herein is a BAA, wherein said BAA, when activated, specifically binds to two targets (e.g. two different targets; or two different epitopes on the same target), and wherein said BAA, when not activated, comprises the following structure:

a) an IgG antibody (AB1) that specifically binds to a first target wherein the AB1 comprises:
   i. two heavy chains (AB1 HCs) and two light chains (AB1 LCs); and
   ii. a first masking moiety (MM1) linked to a first cleavable moiety (CM1) to form a MM1-CM1 construct, wherein the carboxyl terminus of a MM1-CM1 construct is linked to each amino terminus of each light chain of the AB1, wherein
      1. the MM1 inhibits the binding of the AB1 to its target; and
      2. the CM1 is a polypeptide that functions as a substrate for a first protease,
b) two scFvs (AB2) that each specifically bind to a second target wherein each AB2 comprises:
   i. a heavy chain variable region linked to a light chain variable region, wherein the carboxyl terminus of each AB2 is linked to the amino terminus each of the AB1 heavy chains; and
   ii. a second masking moiety (MM2) linked to a second cleavable moiety (CM2) to form a MM2-CM2 construct, wherein the carboxyl terminus of a MM2-CM2 construct is linked to the amino terminus of each AB2 wherein
      the MM2 inhibits the binding of the AB2 to its target; and
      the CM2 is a polypeptide that functions as a substrate for a second protease,
   and wherein the BAA has at least one of the following characteristics:
i. MM2 comprises amino acid sequence SEQ ID NO: 12;
ii. MM1 comprises an amino acid sequence selected from the group consisting of sequences presented in Table 7;
iii. AB2 comprises a heavy chain variable domain as set forth in SEQ ID NO: 2 or SEQ ID NO: 3 or a light chain variable domain as set forth in SEQ ID NO: 1 or SEQ ID NO: 4; and
iv. AB1 comprises an Fc region comprising an amino acid substitution in at least one of amino acid positions L234, L235, N297, and P331 or L234, L235 and P331, as numbered by the EU index as set forth in Kabat, such that the BAA has reduced effector function.

In some embodiments, the BAAs provided herein comprise:

1. A bispecific activatable antibody (BAA), wherein said BAA, when activated, specifically binds to two targets and comprises the following structure:
   a. an IgG antibody (AB1) that specifically binds to a first target wherein the AB1 comprises two heavy chains (AB1 HCs) and two light chains (AB1 LCs); and wherein the AB1 is linked to a first masking moiety (MM1) linked to a first cleavable moiety (CM1) to form a MM1-CM1 construct, wherein the carboxyl terminus of a MM1-CM1 construct is linked to each amino terminus of each light chain of the AB1, wherein
      the MM1 inhibits the binding of the AB1 to its target; and
      the CM1 is a polypeptide that functions as a substrate for a first protease,
   b. two scFvs (each an AB2) that each specifically binds to a second target wherein each AB2 comprises a light chain variable region linked to a heavy chain variable region, wherein the carboxyl terminus of each AB2 is linked to the amino terminus each of the AB1 heavy chains; and wherein each AB2 is linked to a second masking moiety (MM2) linked to a second cleavable moiety (CM2) to form a MM2-CM2 construct, wherein the carboxyl terminus of each MM2-CM2 construct is linked to the amino terminus of each AB2 wherein
      the MM2 inhibits the binding of the AB2 to its target; and
      the CM2 is a polypeptide that functions as a substrate for a second protease,
   and wherein the BAA has at least one of the following characteristics:
   i. MM2 comprises amino acid sequence SEQ ID NO: 12;
   ii. MM1 comprises an amino acid sequence selected from the group consisting of sequences presented in Table 7;
   iii. AB2 comprises a heavy chain variable domain as set forth in SEQ ID NO: 2 or SEQ ID NO: 3 or a light chain variable domain as set forth in SEQ ID NO: 1 or SEQ ID NO: 4; and
   iv. AB1 comprises an Fc region comprising an amino acid substitution in at least one of amino acid positions L234, L235, N297, and P331, as numbered by the EU index as set forth in Kabat, such that the BAA has reduced effector function.

In some embodiments, the BAAs provided herein comprise:

a) an IgG antibody (AB1) that specifically binds to a first target wherein the AB1 comprises:
   a. two heavy chains (AB1 HCs) and two light chains (AB1 LCs); and
   b. a first masking moiety (MM1) linked to a first cleavable moiety (CM1) to form a MM1-CM1 construct, wherein the carboxyl terminus of a MM1-CM1 construct is linked to each amino terminus of each light chain of the AB1, wherein
      1. the MM1 inhibits the binding of the AB1 to its target; and
      2. the CM1 is a polypeptide that functions as a substrate for a first protease,
b) two scFvs (AB2) that each specifically binds to a second target wherein each AB2 comprises:

a. a heavy chain variable region linked to a light chain variable region, wherein the carboxyl terminus of each AB2 is linked to the amino terminus each of the AB1 heavy chains; and b. a second masking moiety (MM2) linked to a second cleavable moiety (CM2) to form a MM2-CM2 construct, wherein the carboxyl terminus of a MM2-CM2 construct is linked to the amino terminus of each AB2 wherein 1. the MM2 inhibits the binding of the AB2 to its target; and 2. the CM2 is a polypeptide that functions as a substrate for a second protease, and wherein the AB1 comprises an Fc region comprises an amino acid substitution in at least one of amino acid positions L234, L235, N297, and P331, as numbered by the EU index as set forth in Kabat, such that the BAA has reduced effector function. In some embodiments, the Fc region comprises amino acid substitutions in at least amino acid positions L234, L235, N297 and P331, as numbered by the EU index as set forth in Kabat, such that the BAA has reduced effector function.

In some embodiments, the BAAs provided herein comprise:

(1) A bispecific activatable antibody (BAA) comprising:

(a) an IgG antibody (AB1) that specifically binds to a first target wherein the AB1 comprises two heavy chains (AB1 HCs) and two light chains (AB1 LCs); and wherein the AB1 is linked to a first masking moiety (MM1) linked to a first cleavable moiety (CM1) to form a MM1-CM1 construct, wherein the carboxyl terminus of a MM1-CM1 construct is linked to each amino terminus of each light chain of the AB1, wherein the MM1 inhibits the binding of the AB1 to its target; and the CM1 is a polypeptide that functions as a substrate for a first protease, (b) two scFvs (each an AB2) that each specifically binds to a second target wherein each AB2 comprises a heavy chain variable region linked to a light chain variable region, wherein the carboxyl terminus of each AB2 is linked to the amino terminus each of the AB1 heavy chains; and wherein each AB2 is linked to a second masking moiety (MM2) linked to a second cleavable moiety (CM2) to form a MM2-CM2 construct, wherein the carboxyl terminus of each MM2-CM2 construct is linked to the amino terminus of each AB2 wherein the MM2 inhibits the binding of the AB2 to its target; and the CM2 is a polypeptide that functions as a substrate for a second protease, and wherein the AB1 comprises an Fc region comprises an amino acid substitution in at least one of amino acid positions L234, L235, N297, and P331, as numbered by the EU index as set forth in Kabat, such that the BAA has reduced effector function.

As provided above, the BAAs of the invention comprise two scFvs (AB2) that each specifically binds to a second target. The VL and VH of the scFvs can be in any order, either VL-VH or VH-VL.

In some embodiments, the Fc region of the AB1 comprises amino acid substitutions in at least amino acid positions L234, L235, and P331, as numbered by the EU index as set forth in Kabat, such that the BAA has reduced effector function. In some embodiments, the first target is selected from the group consisting of the targets presented in Table 9 and the second target is selected from the group consisting of the targets presented in Table 9.

In some embodiments, AB1 binds a target antigen, e.g. a tumor antigen, and the AB2 binds an immune effector target.

In some embodiments, AB2 binds a target antigen, e.g. a tumor antigen, and the AB1 binds an immune effector target.

In some embodiments, the AB1 binds EGFR and the AB2 binds CD3.

In some embodiments, the MM1 comprises SEQ ID NO: 78.

In some embodiments, the MM2 comprises the amino acid sequence SEQ ID NO: 12.

In some embodiments, the bispecific AA is CI106, as provided in Table 11, in Example 1.

In some embodiments, the BAA is CI107, as provided in Table 11, in Example 1.

In some embodiments, the BAA is CI011, as provided in Table 11, in Example 1.

In some embodiments, the BAA is CI020, as provided in Table 11, in Example 1.

In some embodiments, the BAA is CI040, as provided in Table 11, in Example 1.

In some embodiments, the BAA is CI079, as provided in Table 11, in Example 1.

In some embodiments, the BAA is CI090, as provided in Table 11, in Example 1.

In an exemplary embodiment, AB1 comprises the amino acid sequence of C225v5Fcmt3 HC or C225v5Fcmt4 HC.

In some embodiments, the first and second proteases are the same protease. In some embodiments, the first and second proteases are different proteases. In some embodiments, CM1 and CM2 comprise the same amino acid sequence. In some embodiments, CM1 and CM2 comprise different amino acid sequences. In some embodiments, CM1 and CM2 comprise different amino acid sequences that are cleavable by the same protease or proteases. In some embodiments, CM1 and CM2 are cleavable by more than one protease. In some embodiments, CM1 and/or CM2 is cleavable by a serine protease. In some embodiments, CM1 and/or CM2 is cleavable by a matrix metalloproteinase (MMP). In some embodiments, CM1 and/or CM2 is cleavable by a serine protease and an MMP.

Exemplary BAAs of the disclosure include, for example, those shown in the Examples provided herein, and variants thereof.

In some non-limiting embodiments, at least one of the AB in the BAA is specific for CD3 and at least one other AB is a binding partner for any target listed in Table 9.

In an exemplary embodiment, AB2 of the BAA is specific for CD3 and AB1 is a binding partner for any target listed in Table 9.

TABLE 9

| Exemplary Targets | | | | | |
|---|---|---|---|---|---|
| 1-92-LFA-3 | CD52 | DL44 | HVEM | LAG-3 | STEAP1 |
| Alpha-4 integrin | CD56 | DLK1 | Hyaluronidase | LIF-R | STEAP2 |

TABLE 9-continued

| Exemplary Targets | | | | | |
|---|---|---|---|---|---|
| Alpha-V integrin | CD64 | DLL4 | ICOS | Lewis X | TAG-72 |
| alpha4beta1 integrin | CD70 | DPP-4 | IFNalpha | LIGHT | TAPA1 |
| alpha4beta7 integrin | CD71 | DSG1 | IFNbeta | LRP4 | TGFbeta |
| AGR2 | CD74 | EGFR | IFNgamma | LRRC26 | TIGIT |
| Anti-Lewis-Y | | EGFRviii | IgE | MCSP | TIM-3 |
| Apelin J receptor | CD80 | Endothelin B receptor (ETBR) | IgE Receptor (FceRI) | Mesothelin | TLR2 |
| APRIL | CD81 | ENPP3 | IGF | MRP4 | TLR4 |
| B7-H4 | CD86 | EpCAM | IGF1R | MUC1 | TLR6 |
| BAFF | CD95 | EPHA2 | IL1B | Mucin-16 (MUC16, CA-125) | TLR7 |
| BTLA | CD117 | EPHB2 | IL1R | Na/K ATPase | TLR8 |
| C5 complement | CD125 | ERBB3 | IL2 | Neutrophil elastase | TLR9 |
| C-242 | CD132 (IL-2RG) | F protein of RSV | IL11 | NGF | TMEM31 |
| CA9 | CD133 | FAP | IL12 | Nicastrin | TNFalpha |
| CA19-9 (Lewis a) | CD137 | FGF-2 | IL12p40 | Notch Receptors | TNFR |
| Carbonic anhydrase 9 | CD138 | FGF8 | IL-12R, IL-12Rbeta1 | Notch 1 | TNFRS12A |
| CD2 | CD166 | FGFR1 | IL13 | Notch 2 | TRAIL-R1 |
| CD3 | CD172A | FGFR2 | IL13R | Notch 3 | TRAIL-R2 |
| CD6 | CD248 | FGFR3 | IL15 | Notch 4 | Transferrin |
| CD9 | CDH6 | FGFR4 | IL17 | NOV | Transferrin receptor |
| CD11a | CEACAM5 (CEA) | Folate receptor | IL18 | OSM-R | TRK-A |
| CD19 | CEACAM6 (NCA-90) | GAL3ST1 | IL21 | OX-40 | TRK-B |
| CD20 | CLAUDIN-3 | G-CSF | IL23 | PAR2 | uPAR |
| CD22 | CLAUDIN-4 | G-CSFR | IL23R | PDGF-AA | VAP1 |
| CD24 | cMet | GD2 | IL27/IL27R (wsx1) | PDGF-BB | VCAM-1 |
| CD25 | Collagen | GITR | IL29 | PDGFRalpha | VEGF |
| CD27 | Cripto | GLUT1 | IL-31R | PDGFRbeta | VEGF-A |
| CD28 | CSFR | GLUT4 | IL31/IL31R | PD-1 | VEGF-B |
| CD30 | CSFR-1 | GM-CSF | IL2R | PD-L1 | VEGF-C |
| CD33 | CTLA-4 | GM-CSFR | IL4 | PD-L2 | VEGF-D |
| CD38 | CTGF | GP IIb/IIIa receptors | IL4R | Phosphatidyl-serine | VEGFR1 |
| CD40 | CXCL10 | Gp130 | IL6, IL6R | P1GF | VEGFR2 |
| CD40L | CXCL13 | GPIIB/IIIA | Insulin Receptor | PSCA | VEGFR3 |
| CD41 | CXCR1 | GPNMB | Jagged Ligands | PSMA | VISTA |
| CD44 | CXCR2 | GRP78 | Jagged 1 | RAAG12 | WISP-1 |
| CD44v6 | | HER2/neu | Jagged 2 | RAGE | WISP-2 |
| CD47 | CXCR4 | HGF | | SLC44A4 | WISP-3 |
| CD51 | CYR61 | hGH | | Sphingosine 1 Phosphate | |

In some embodiments, the unmasked EGFR-CD3 bispecific antibody exhibits EGFR-dependent tumor cell killing, while the doubly-masked EGFR-CD3 BAA reduces target-dependent cytotoxicity by more than 100,000-fold. In established tumor models where tumor-resident proteases are expected to be active, it is shown that BAAs potently induce tumor regressions. In non-human primates, the maximum tolerated dose (MTD) of the EGFR-CD3 BAA is more than 60-fold higher than the MTD of the unmasked bispecific antibody, and the tolerated exposure (AUC) is more than 10,000-fold higher. Despite the 60-fold dose differential at the MTDs, transient serum cytokine and AST/ALT increases observed in non-human primates treated with the BAA are still lower than those induced by the bispecific antibody. By localizing activity to the tumor microenvironment, BAAs have the potential to expand clinical opportunities for T cell-engaging bispecific therapies that are limited by on target toxicities, especially in solid tumors. Moreover, an EGFR-CD3 BAA has the potential to address EGFR-expressing tumors that are poorly responsive to existing EGFR-directed therapies.

7. Cleavable Moieties (CM)

Both the monospecific AAs and the BAAs of the disclosure comprise at least one CM, when masked and not activated.

In some embodiments, the cleavable moiety (CM) of the AA or BAA includes an amino acid sequence that can serve as a substrate for at least one protease, usually an extracellular protease. In the case of a BAA, the CM may be selected based on a protease that is co-localized in tissue with the desired target of at least one AB of the BAA or AA. A CM can serve as a substrate for multiple proteases, e.g. a substrate for a serine protease and a second different protease, e.g. an MMP. In some embodiments, a CM can serve as a substrate for more than one serine protease, e.g., a matriptase and uPA. In some embodiments, a CM can serve as a substrate for more than one MMP, e.g., an MMP9 and an MMP14.

A variety of different conditions are known in which a target of interest is co-localized with a protease, where the substrate of the protease is known in the art. In the example of cancer, the target tissue can be a cancerous tissue, particularly cancerous tissue of a solid tumor. There are reports in the literature of increased levels of proteases in a number of cancers, e.g., liquid tumors or solid tumors. See, e.g., La Rocca et al, (2004) British J. of Cancer 90(7): 1414-1421. Non-limiting examples of disease include: all types of cancers, (such as, but not limited to breast, lung, colorectal, gastric, glioblastoma, ovarian, endometrial, renal, sarcoma, skin cancer, cervical, liver, bladder, cholangiocarcinoma, prostate, melanomas, head and neck cancer (e.g. head and neck squamous cell cancer, pancreatic, etc.), rheumatoid arthritis, Crohn's disease, SLE, cardiovascular damage, ischemia, etc. For example, indications would include leukemias, including T-cell acute lymphoblastic leukemia (T-ALL), lymphoblastic diseases including multiple myeloma, and solid tumors, including lung, colorectal, prostate, pancreatic and breast, including triple negative breast cancer. For example, indications include bone disease or metastasis in cancer, regardless of primary tumor origin; breast cancer, including by way of non-limiting example, ER/PR+ breast cancer, Her2+ breast cancer, triple-negative breast cancer; colorectal cancer; endometrial cancer; gastric cancer; glioblastoma; head and neck cancer, such as head and neck squamous cell cancer; esophageal cancer; lung cancer, such as by way of non-limiting example, non-small cell lung cancer; multiple myeloma ovarian cancer; pancreatic cancer; prostate cancer; sarcoma, such as osteosarcoma; renal cancer, such as by way of non-limiting example, renal cell carcinoma; and/or skin cancer, such as by way of non-limiting example, squamous cell cancer, basal cell carcinoma, or melanoma. In some embodiments, the cancer is a squamous cell cancer. In some embodiments, the cancer is a skin squamous cell carcinoma. In some embodiments, the cancer is an esophageal squamous cell carcinoma. In some embodiments, the cancer is a head and neck squamous cell carcinoma. In some embodiments, the cancer is a lung squamous cell carcinoma.

The CM is specifically cleaved by an enzyme at a rate of about 0.001-1500×$10^4$ $M^{-1}S^{-1}$ or at least 0.001, 0.005, 0.01, 0.05, 0.1, 0.5, 1, 2.5, 5, 7.5, 10, 15, 20, 25, 50, 75, 100, 125, 150, 200, 250, 500, 750, 1000, 1250, or 1500×$10^4$ $M^{-1}S^{-1}$.

For specific cleavage by an enzyme, contact between the enzyme and CM is made. When the AA or BAA comprises at least a first AB coupled to a MM and a CM, e.g., the AA comprises an AB coupled to a MM via a CM, is in the presence of target and sufficient enzyme activity, the CM can be cleaved. Sufficient enzyme activity can refer to the ability of the enzyme to make contact with the CM and effect cleavage. It can readily be envisioned that an enzyme may be in the vicinity of the CM but is unable to cleave because of other cellular factors or protein modification of the enzyme.

Exemplary CMs of the disclosure are provided in Table 4 above. In some embodiments, the CM has a length of up to 15 amino acids, a length of up to 20 amino acids, a length of up to 25 amino acids, a length of up to 30 amino acids, a length of up to 35 amino acids, a length of up to 40 amino acids, a length of up to 45 amino acids, a length of up to 50 amino acids, a length of up to 60 amino acids, a length in the range of 10-60 amino acids, a length in the range of 15-60 amino acids, a length in the range of 20-60 amino acids, a length in the range of 25-60 amino acids, a length in the range of 30-60 amino acids, a length in the range of 35-60 amino acids, a length in the range of 40-50 amino acids, a length in the range of 45-60 amino acids, a length in the range of 10-40 amino acids, a length in the range of 15-40 amino acids, a length in the range of 20-40 amino acids, a length in the range of 25-40 amino acids, a length in the range of 30-40 amino acids, a length in the range of 35-40 amino acids, a length in the range of 10-30 amino acids, a length in the range of 15-30 amino acids, a length in the range of 20-30 amino acids, a length in the range of 25-30 amino acids, a length in the range of 10-20 amino acids, or a length in the range of 10-15 amino acids.

8. Masking Moieties (MMs)

In both the activatable monospecific CD3 and EGFR AAs and the BAAs described above, the AAs/BAAs contain a MM. As described herein, the AAs and BAAs of the invention comprise a prodomain, which comprises a MM.

In some embodiments, the MM is selected for use with a specific antibody or antibody fragment.

In certain embodiments, the MM is not a natural binding partner of the AB. In some embodiments, the MM contains no or substantially no homology to any natural binding partner of the AB. In other embodiments the MM is no more than 5%, 10%, 15%, 20%, 25%, 30%, 35%, 40%, 45%, 50%, 55%, 60%, 65%, 70%, 75%, or 80% similar to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% identical to any natural binding partner of the AB. In some embodiments, the MM is no more than 50% identical to any natural binding partner of the AB. In some embodiments, the MM is no more than 25% identical to any natural binding partner of the AB. In some embodiments, the MM is no more than 20% identical to any natural binding partner of the AB. In some embodiments, the MM is no more than 10% identical to any natural binding partner of the AB.

Exemplary MMs of the disclosure can have a length of up to 15 amino acids, a length of up to 20 amino acids, a length of up to 25 amino acids, a length of up to 30 amino acids, a length of up to 35 amino acids, a length of up to 40 amino acids, a length of up to 45 amino acids, a length of up to 50 amino acids, a length of up to 60 amino acids, a length in the range of 10-60 amino acids, a length in the range of 15-60 amino acids, a length in the range of 20-60 amino acids, a length in the range of 25-60 amino acids, a length in the range of 30-60 amino acids, a length in the range of 35-60 amino acids, a length in the range of 40-50 amino acids, a length in the range of 45-60 amino acids, a length in the range of 10-40 amino acids, a length in the range of 15-40 amino acids, a length in the range of 20-40 amino acids, a length in the range of 25-40 amino acids, a length in the range of 30-40 amino acids, a length in the range of 35-40 amino acids, a length in the range of 10-30 amino acids, a length in the range of 15-30 amino acids, a length in the range of 20-30 amino acids, a length in the range of 25-30 amino acids, a length in the range of 10-20 amino acids, a length in the range of 10-15 amino acids, or a length of 10, 11, 12, 13, 14, 15, 16, 17, 18, 19, or 20 amino acids.

As provided herein, the MM inhibits the binding of the AB to the target. The MM binds the antigen binding domain of the AB and inhibits binding of the AB to the target. The MM can sterically inhibit the binding of the AB to the target. The MM can allosterically inhibit the binding of the AB to its target. In these embodiments when the AB is modified by or coupled to a MM and in the presence of target there is no binding or substantially no binding of the AB to the target, or no more than 0.001%, 0.01%, 0.1%, 1%, 2%, 3%, 4%, 5%, 6%, 7%, 8%, 9%, 10%, 15%, 20%, 25%, 30%, 35%, 40%, or 50% binding of the AB to the target, as compared to the binding of the AB not modified by or coupled to an MM, the parental AB, or the AB not coupled to an MM to the target, for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vivo or in an in vitro assay.

When an AB is coupled to or modified with a MM, the MM 'masks' or reduces or otherwise inhibits the specific binding of the AB to the target. When an AB is coupled to or modified by a MM, such coupling or modification can effect a structural change that reduces or inhibits the ability of the AB to specifically bind its target.

Exemplary MMs of the disclosure are provided in Tables 3, 7, and 8, above.

In any of the AAs and BAAs provided herein, the masked AB has a lower binding affinity than unmasked AB.

9. Linkers

In many embodiments, it may be desirable to insert one or more linkers, e.g., flexible linkers, into the AA/BAA constructs so as to provide for flexibility at one or more of the MM-CM junction, the CM-AB/CM-scFv junction, or both. For example, the AB, MM, and/or CM may not contain a sufficient number of residues (e.g., Gly, Ser, Asp, Asn, especially Gly and Ser) to provide the desired flexibility. As such, the ability of such BAA constructs to remain intact (not activated) or be activated as disclosed herein may benefit from introduction of one or more amino acids to provide for a flexible linker.

For example, in certain embodiments an AA comprises one of the following formulae (where the formula below represents an amino acid sequence in either N- to C-terminal direction or C- to N-terminal direction):

(MM1)-L1-(CM1)-(AB1)

(MM1)-(CM1)-L2-(AB1)

(MM1)-L1-(CM1)-L2-(AB1)

(MM2)-L1-(CM2)-(AB2)

(MM2)-(CM2)-L2-(AB2)

(MM2)-L1-(CM2)-L2-(AB2)

wherein MM, CM, and AB are as defined above; wherein L1 and L2 are each independently and optionally present or absent, are the same or different flexible linkers that include at least 1 flexible amino acid (e.g., Gly, Ser).

In some embodiments, the BAA comprises 2 heavy chains, each comprising the structural arrangement from N-terminus to C-terminus of MM2-CM2-AB2-AB1 HC and two light chains each comprising the structural arrangement from N-terminus to C-terminus of MM1-CM1-AB1 LC.

In some embodiments, the structure including with linkers is provided in FIG. 17.

In some embodiments, (MM2)-L1-(CM2)-L2-(AB2) is linked to the heavy chain of AB1 and AB2 is a scFv.

Linkers suitable for use in compositions described herein are generally ones that provide flexibility of the modified AB or the AAs to facilitate the inhibition of the binding of the AB to the target. Such linkers are generally referred to as flexible linkers. Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and can be 1, 2, 3, 4, 5, 6, 7, 8, 9, 10, 11, 12, 13, 14, 15, 16, 17, 18, 19, or 20 amino acids in length. In some embodiments, a suitable linker can be from 4 to 25 amino acids in length. In some embodiments, a suitable linker can be from 5 to 25 amino acids in length. In some embodiments, a suitable linker can be from 4 to 20 amino acids in length. In some embodiments, a suitable linker can be from 5 to 20 amino acids in length.

Exemplary linkers include glycine polymers (G)n, glycine-serine polymers (including, for example, (GS)n, (GSGGS)n (SEQ ID NO: 88) and (GGGS)n (SEQ ID NO: 89), where n is an integer of at least one), glycine-alanine polymers, alanine-serine polymers, and other flexible linkers known in the art. In some embodiments, n is from about 1 to about 10, or from about 1 to about 9, or from about 1 to about 8, or from about 1 to about 7, or from about 1 to about 6, or from about 1 to about 5, or from about 1 to about 4, or from about 1 to about 3, or from about 1 to about 2. Glycine and glycine-serine polymers are relatively unstructured, and therefore may be able to serve as a neutral tether between components. Glycine accesses significantly more phi-psi space than even alanine, and is much less restricted than residues with longer side chains (see Scheraga, Rev. Computational Chem. 11173-142 (1992)). Exemplary linkers are provided in Table 9-1.

TABLE 9-1

Exemplary L1 and L2 Linkers

| SEQ ID NO: | Linker Amino Acid Sequence |
|---|---|
| SEQ ID NO: 88 | GSGGS |
| SEQ ID NO: 89 | GGGS |
| SEQ ID NO: 90 | GGSG |
| SEQ ID NO: 91 | GGSGG |
| SEQ ID NO: 92 | GSGSG |
| SEQ ID NO: 93 | GSGGG |
| SEQ ID NO: 94 | GGGSG |
| SEQ ID NO: 95 | GSSSG |
| SEQ ID NO: 96 | GSSGGSGGSGG |
| SEQ ID NO: 97 | GGGS |
| SEQ ID NO: 99 | GGGGS |
| SEQ ID NO: 100 | GSSGGSGGSGGSG |
| SEQ ID NO: 101 | GSSGGSGGSGGGGGSGGGSGGGS |
| SEQ ID NO: 102 | GSSGGSGGSGGSGGGSGGGSGGS |
| SEQ ID NO: 103 | GSSGT |
| SEQ ID NO: 104 | GGGSSGGS |

The ordinarily skilled artisan will recognize that design of an AA can include linkers that are all or partially flexible, such that the linker can include a flexible linker as well as one or more portions that confer less flexible structure to provide for a desired AA structure.

10. Conjugation

In some embodiments, any of the antibodies, or ABs of the AAs, and BAAs disclosed herein may be conjugated to an agent. In some embodiments, the agent is a therapeutic agent. In some embodiments, the agent is a detectable moiety. In some embodiments, the agent is an antineoplastic agent. In some embodiments, the agent is a toxin or fragment thereof. In some embodiments, the agent is conjugated to the AB via a linker. In some embodiments, the linker is a non-cleavable linker. In some embodiments, the agent is a microtubule inhibitor. In some embodiments, the agent is a nucleic acid damaging agent, such as a DNA alkylator or DNA intercalator, or other DNA damaging agent. In some embodiments, the linker is a cleavable linker. In some embodiments, the agent is an agent selected from the group listed in Table 10.

TABLE 10

| Exemplary Pharmaceutical Agents for Conjugation |
|---|
| CYTOTOXIC AGENTS |
| Auristatins |
| Auristatin E |
| Monomethyl auristatin D (MMAD) |
| Monomethyl auristatin E (MMAE) |
| Desmethyl auristatin E (DMAE) |
| Auristatin F |
| Monomethyl auristatin F (MMAF) |
| Desmethyl auristatin F (DMAF) |
| Auristatin derivatives, e.g., amides thereof |
| Auristatin tyramine |
| Auristatin quinoline |
| Dolastatins |
| Dolastatin derivatives |
| Dolastatin 16 DmJ |
| Dolastatin 16 Dpv |
| Maytansinoids, e.g. DM-1; DM-4 |
| Maytansinoid derivatives |
| Duocarmycin |
| Duocarmycin derivatives |
| Alpha-amanitin |
| Anthracyclines |
| Doxorubicin |
| Daunorubicin |
| Bryostatins |
| Camptothecin |
| Camptothecin derivatives |
| 7-substituted Camptothecin |
| 10,11-Difluoromethylenedioxycamptothecin |
| Combretastatins |
| Debromoaplysiatoxin |
| Kahalalide-F |
| Discodermolide |
| Ecteinascidins |
| ANTIVIRALS |
| Acyclovir |
| Vira A |
| Symmetrel |
| ANTIFUNGALS |
| Nystatin |
| ADDITIONAL ANTI-NEOPLASTICS |
| Adriamycin |
| Cerubidine |
| Bleomycin |
| Alkeran |
| Velban |
| Oncovin |
| Fluorouracil |
| Methotrexate |
| Thiotepa |
| Bisantrene |
| Novantrone |
| Thioguanine |
| Procarabizine |
| Cytarabine |
| ANTI-BACTERIALS |
| Aminoglycosides |
| Streptomycin |
| Neomycin |
| Kanamycin |
| Amikacin |
| Gentamicin |
| Tobramycin |
| Streptomycin B |
| Spectinomycin |
| Ampicillin |
| Sulfanilamide |
| Polymyxin |
| Chloramphenicol |
| Turbostatin |
| Phenstatins |
| Hydroxyphenstatin |
| Spongistatin 5 |
| Spongistatin 7 |
| Halistatin 1 |
| Halistatin 2 |
| Halistatin 3 |
| Modified Bryostatins |
| Halocomstatins |
| Pyrrolobenzimidazoles |
| Cibrostatin6 |
| Doxaliform |
| Anthracyclins analogues |
| Cemadotin analogue (CemCH2-SH) |
| Pseudomonas toxin A (PE38) variant |
| Pseudomonas toxin A (ZZ-PE38) variant |
| ZJ-101 |
| OSW-1 |
| 4-Nitrobenzyloxycarbonyl Derivatives of O6-Benzylguanine |
| Topoisomerase inhibitors |
| Hemiasterlin |
| Cephalotaxine |
| Homoharringtonine |
| Pyrrolobenzodiazepine dimers (PBDs) |
| Functionalized pyrrolobenzodiazepenes |
| Calicheamicins |
| Podophyllotoxins |
| Taxanes |
| Vinca alkaloids |
| CONJUGATABLE DETECTABLE MOIETIES |
| Fluorescein and derivatives thereof |
| Fluorescein isothiocyanate (FITC) |
| RADIOPHARMACEUTICALS |
| $^{125}I$ |
| $^{131}I$ |
| $^{89}Zr$ |
| $^{111}In$ |
| $^{123}I$ |
| $^{131}I$ |
| $^{99}mTc$ |
| $^{201}Tl$ |
| $^{133}Xe$ |
| $^{11}C$ |
| $^{62}Cu$ |
| $^{18}F$ |
| $^{68}Ga$ |
| $^{13}N$ |
| $^{15}O$ |
| $^{38}K$ |
| $^{82}Rb$ |
| $^{99}mTc$ (Technetium) |
| HEAVY METALS |
| Barium |
| Gold |
| Platinum |

TABLE 10-continued

| Exemplary Pharmaceutical Agents for Conjugation |
|---|
| ANTI-MYCOPLASMALS |
| Tylosine |
| Spectinomycin |

Those of ordinary skill in the art will recognize that a large variety of possible moieties can be coupled to the resultant antibodies, AAs, and BAAs of the disclosure. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

In some embodiments, the antibody, AA or BAA comprises a detectable moiety. In some embodiments, the detectable moiety is a diagnostic agent.

In some embodiments, the antibody, AA or BAA contains one or more disulfide bonds. In some embodiments, the antibody, AA or BAA contains one or more lysines. In some embodiments, the antibody, AA or BAA can be engineered to include one or more disulfide bonds or can be otherwise engineered to enable site-specific conjugation.

11. Production

The disclosure also provides an isolated nucleic acid molecule encoding an antibody, AA or BAA described herein, as well as vectors that include these isolated nucleic acid sequences. The disclosure provides methods of producing an antibody, AA or BAA by culturing a cell under conditions that lead to expression of the antibody, AA or BAA, wherein the cell comprises such a nucleic acid molecule.

In some embodiments, the cell comprises such a vector. In some embodiments, the vector is pLW289. In some embodiments, the vector is pLW246. In some embodiments, the vector is pLW307. In some embodiments, the vector is pLW291. In some embodiments, the vector is pLW352. In some embodiments, the vector is pLW353. (these vectors and described and sequences provided below in Example 1)

12. Use of Antibodies, AAs, Bispecific Antibodies and BAAs

In some embodiments, the antibodies/bispecific antibodies/AAs/BAAs thereof may be used as therapeutic agents. Such agents will generally be employed to treat, alleviate, and/or prevent a disease or pathology in a subject. A therapeutic regimen is carried out by identifying a subject, e.g., a human patient or other mammal suffering from (or at risk of developing) a disorder using standard methods.

Administration of the antibodies/bispecific antibodies/AAs/BAAs thereof may abrogate or inhibit or interfere with the signaling function of one or more of the targets.

It will be appreciated that administration of therapeutic entities in accordance with the disclosure will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, PA (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present disclosure, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Generally, alleviation or treatment of a disease or disorder involves the lessening of one or more symptoms or medical problems associated with the disease or disorder. For example, in the case of cancer, the therapeutically effective amount of the drug can accomplish one or a combination of the following: reduce the number of cancer cells; reduce the tumor size; inhibit (i.e., to decrease to some extent and/or stop) cancer cell infiltration into peripheral organs; inhibit tumor metastasis; inhibit, to some extent, tumor growth; and/or relieve to some extent one or more of the symptoms associated with the cancer. In some embodiments, a composition of this disclosure can be used to prevent the onset or reoccurrence of the disease or disorder in a subject, e.g., a human or other mammal, such as a non-human primate, companion animal (e.g., cat, dog, horse), farm animal, work animal, or zoo animal. The terms subject and patient are used interchangeably herein.

A therapeutically effective amount of antibodies/bispecific antibodies/AAs/BAAs thereof of the disclosure relates generally to the amount needed to achieve a therapeutic objective.

Common ranges for therapeutically effective dosing of an antibodies/bispecific antibodies/AAs/BAAs thereof of the disclosure may be, by way of nonlimiting example, from about 0.1 mg/kg body weight to about 50 mg/kg body weight. Common dosing frequencies may range, for example, from twice daily to once a week.

Efficaciousness of treatment is determined in association with any known method for diagnosing or treating the particular disorder. Methods for the screening antibodies/bispecific antibodies/AAs/BAAs that possess the desired specificity include, but are not limited to, enzyme linked immunosorbent assay (ELISA) and other immunologically mediated techniques known within the art.

Other contemplated uses involve diagnostics, imaging, prognostics, and detection uses. In some embodiments, antibodies/bispecific antibodies/AAs/BAAs are used in methods known within the art relating to the localization and/or quantitation of the target (e.g., for use in measuring levels of one or more of the targets within appropriate physiological samples, for use in diagnostic methods, for use in imaging the protein, and the like).

In some embodiments, antibodies/bispecific antibodies/AAs/BAAs are used to isolate one or more of the targets by standard techniques, such as immunoaffinity, chromatography or immunoprecipitation. An antibody, an AA, a bispecific antibody or a BAA can be used diagnostically to monitor protein levels in tissue as part of a clinical testing procedure, e.g., to determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

In yet another embodiment, an antibody, bispecific antibody, AA, BAA directed two or more targets can be used as an agent for detecting the presence of one or more of the targets (or a fragment thereof) in a sample. In some embodiments, the antibody contains a detectable label. Antibodies are polyclonal, or in some embodiments, monoclonal. An intact antibody, or a fragment thereof (e.g., Fab, scFv, or $F(ab')_2$) is used. The term “labeled”, with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of an antibody with biotin such that it can be detected with fluorescently-labeled streptavidin. The term “biological sample” is intended to include tissues, cells and biological fluids isolated from a subject, as well as tissues, cells and fluids present within a subject. Included within the usage of the term “biological sample”, therefore, is blood and a fraction or component of blood including blood serum, blood plasma, or lymph. That is, the detection method of the disclosure can be used to detect a protein in a biological sample in vitro as well as in vivo. For example, in vitro techniques for detection of an analyte protein include enzyme linked immunosorbent assays (ELISAs), Western blots, immunoprecipitations, and immunofluorescence. Procedures for conducting immunoassays are described, for example in “ELISA: Theory and Practice: Methods in Molecular Biology”, Vol. 42, J. R. Crowther (Ed.) Human Press, Totowa, NJ, 1995; “Immunoassay”, E. Diamandis and T. Christopoulus, Academic Press, Inc., San Diego, CA, 1996; and “Practice and Theory of Enzyme Immunoassays”, P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

The antibodies, bispecific antibodies, AAs, and bispecific antibodies of the disclosure are also useful in a variety of diagnostic and prophylactic formulations. In one embodiment, an antibody, AA, bispecific antibody, BAA is administered to patients that are at risk of developing one or more of the aforementioned disorders. A patient’s or organ’s predisposition to one or more of the disorders can be determined using genotypic, serological or biochemical markers.

In another embodiment of the disclosure, an antibody, AA, bispecific antibody, BAA is administered to human individuals diagnosed with a clinical indication associated with one or more of the aforementioned disorders. Upon diagnosis, an antibody, AA, bispecific antibody, BAA is administered to mitigate or reverse the effects of the clinical indication.

Antibodies, bispecific antibodies, AAs, and bispecific antibodies are also useful in the detection of one or more targets in patient samples and accordingly are useful as diagnostics. For example, the antibodies, bispecific antibodies, AAs, and bispecific antibodies of the disclosure are used in in vitro assays, e.g., ELISA, to detect one or more target levels in a patient sample.

In one embodiment, an antibody, AA, bispecific antibody, BAA is immobilized on a solid support (e.g., the well(s) of a microtiter plate). The immobilized antibody and/or AA serves as a capture antibody for any target(s) that may be present in a test sample. Prior to contacting the immobilized antibody/AA with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of target antigen(s) in the test sample is determined by comparison with a standard curve developed from the standard samples.

It will be appreciated that based on the results obtained using the antibody, AA, bispecific antibody, BAA in an in vitro diagnostic assay, it is possible to stage a disease in a subject based on expression levels of the target antigen(s). For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

Antibodies, bispecific antibodies, AAs, and BAAs can also be used in diagnostic and/or imaging methods. In some embodiments, such methods are in vitro methods. In some embodiments, such methods are in vivo methods. In some embodiments, such methods are in situ methods. In some embodiments, such methods are ex vivo methods. For example, AAs, and bispecific antibodies having an enzymatically cleavable CM can be used to detect the presence or absence of an enzyme that is capable of cleaving the CM. Such AAs, and bispecific antibodies can be used in diagnostics, which can include in vivo detection (e.g., qualitative or quantitative) of enzyme activity (or, in some embodiments, an environment of increased reduction potential such as that which can provide for reduction of a disulfide bond) through measured accumulation of activated or bispecific activated antibodies (i.e., antibodies or bispecific antibodies resulting from cleavage of an AA or a BAA) in a given cell or tissue of a given host organism. Such accumulation of activated bispecific antibodies indicates not only that the tissue expresses enzymatic activity (or an increased reduction potential depending on the nature of the CM) but also that the tissue expresses at least one target to which the activated bispecific antibody binds.

For example, the CM can be selected to be a protease substrate for a protease found at the site of a tumor, at the site of a viral or bacterial infection at a biologically confined site (e.g., such as in an abscess, in an organ, and the like), and the like. At least one of the AB can be one that binds a target antigen. Using methods familiar to one skilled in the art, a detectable label (e.g., a fluorescent label or radioactive label or radiotracer) can be conjugated to an AB or other region of an antibody, AA, bispecific antibody, BAA. Suitable detectable labels are discussed in the context of the above screening methods and additional specific examples are provided below. Using at least one AB specific to a protein or peptide of the disease state, along with a protease whose activity is elevated in the disease tissue of interest, AAs will exhibit an increased rate of binding to disease tissue relative to tissues where the CM specific enzyme is not present at a detectable level or is present at a lower level than in disease tissue or is inactive (e.g., in zymogen form or in complex with an inhibitor). Since small proteins and peptides are rapidly cleared from the blood by the renal filtration system, and because the enzyme specific for the CM is not present at a detectable level (or is present at lower levels in non-disease tissues or is present in inactive conformation), accumulation of activated bispecific antibodies in the disease tissue is enhanced relative to non-disease tissues.

In another example, antibodies, antibodies/bispecific antibodies/AAs/BAAs of the present disclosure can be used to detect the presence or absence of a cleaving agent in a sample. For example, where the antibodies/bispecific antibodies/AAs/BAAs contain a CM susceptible to cleavage by an enzyme, the BAAs can be used to detect (either qualitatively or quantitatively) the presence of an enzyme in the sample. In another example, where the antibodies/bispecific antibodies/AAs/BAAs contain a CM susceptible to cleavage by reducing agent, the antibodies/bispecific antibodies/AAs/BAAs can be used to detect (either qualitatively or quantitatively) the presence of reducing conditions in a sample. To facilitate analysis in these methods, the antibodies/bispecific antibodies/AAs/BAAs can be detectably labeled, and can be bound to a support (e.g., a solid support, such as a slide or bead). The detectable label can be positioned on a portion of the antibodies/bispecific antibodies/AAs/BAAs that is not released following cleavage, for example, the detectable label can be a quenched fluorescent label or other label that is not detectable until cleavage has occurred. The assay can be conducted by, for example, contacting the immobilized, detectably labeled antibodies/bispecific antibodies/AAs/BAAs with a sample suspected of containing an enzyme and/or reducing agent for a time sufficient for cleavage to occur, then washing to remove excess sample and contaminants. The presence or absence of the cleaving agent (e.g., enzyme or reducing agent) in the sample is then assessed by a change in detectable signal of the antibodies/bispecific antibodies/AAs/BAAs prior to contacting with the sample e.g., the presence of and/or an increase in detectable signal due to cleavage of the antibodies/bispecific antibodies/AAs/BAAs by the cleaving agent in the sample.

Such detection methods can be adapted to also provide for detection of the presence or absence of a target that is capable of binding at least one AB of the antibodies/bispecific antibodies/AAs/BAAs of the present disclosure. Thus, the assays can be adapted to assess the presence or absence of a cleaving agent and the presence or absence of a target of interest. The presence or absence of the cleaving agent can be detected by the presence of and/or an increase in detectable label of the antibodies/bispecific antibodies/AAs/BAAs as described above, and the presence or absence of the target can be detected by detection of a target-AB complex e.g., by use of a detectably labeled anti-target antibody.

AAs/BAAs of the present disclosure are also useful in in situ imaging for the validation of AA activation, e.g., by protease cleavage, and binding to a particular target. In situ imaging is a technique that enables localization of proteolytic activity and target in biological samples such as cell cultures or tissue sections. Using this technique, it is possible to confirm both binding to a given target and proteolytic activity based on the presence of a detectable label (e.g., a fluorescent label).

These techniques are useful with any frozen cells or tissue derived from a disease site (e.g. tumor tissue) or healthy tissues. These techniques are also useful with fresh cell or tissue samples.

In these techniques, an AA/BAA is labeled with a detectable label. The detectable label may be a fluorescent dye, (e.g. a fluorophore, Fluorescein Isothiocyanate (FITC), Rhodamine Isothiocyanate (TRITC), an Alexa Fluor® label), a near infrared (NIR) dye (e.g., Qdot® nanocrystals), a colloidal metal, a hapten, a radioactive marker, biotin and an amplification reagent such as streptavidin, or an enzyme (e.g. horseradish peroxidase or alkaline phosphatase).

Detection of the label in a sample that has been incubated with the labeled, AA or BAA indicates that the sample contains the target and contains a protease that is specific for the CM of the AAs or BAAs of the present disclosure. In some embodiments, the presence of the protease can be confirmed using broad spectrum protease inhibitors such as those described herein, and/or by using an agent that is specific for the protease, for example, an antibody such as A11, which is specific for the protease matriptase (MT-SP1) and inhibits the proteolytic activity of MT-SP1; see e.g., International Publication Number WO 2010/129609, published 11 Nov. 2010. The same approach of using broad spectrum protease inhibitors such as those described herein, and/or by using a more selective inhibitory agent can be used to identify a protease or class of proteases specific for the CM of the AAs or BAAs of the present disclosure. In some embodiments, the presence of the target can be confirmed using an agent that is specific for the target or the detectable label can be competed with unlabeled target. In some embodiments, unlabeled AA could be used, with detection by a labeled secondary antibody or more complex detection system.

Similar techniques are also useful for in vivo imaging where detection of the fluorescent signal in a subject, e.g., a mammal, including a human, indicates that the disease site contains the target and contains a protease that is specific for the CM of the AAs or BAAs of the present disclosure.

These techniques are also useful in kits and/or as reagents for the detection, identification or characterization of protease activity in a variety of cells, tissues, and organisms based on the protease-specific CM in the AAs or BAAs of the present disclosure.

13. Therapeutic Administration

It will be appreciated that administration of therapeutic entities in accordance with the disclosure will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, PA (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present disclosure, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

In some embodiments, the antibodies, bispecific antibodies, AAs, or BAAs (or conjugated compositions thereof) are administered in conjunction with one or more additional agents, or with a combination of additional agents. Suitable additional agents include current pharmaceutical and/or surgical therapies for an intended application. For example, they can be used in conjunction with an additional chemotherapeutic or anti-neoplastic agent.

In some embodiments, the antibodies, bispecific antibodies, AAs, or BAAs (or conjugated compositions thereof) of the present disclosure are administered in conjunction with one or more additional agents selected from the group consisting of antibodies, conjugated antibodies, AAs, conjugated AAs, bispecific antibodies, conjugated bispecific antibodies, BAAs, or conjugated BAAs. In some embodiments, the antibody portion of any of the above-referenced additional agents is directed against a target such as one or more of the targets disclosed in Table 9. It is appreciated that in some embodiments the antibody portion of antibodies, bispecific antibodies, AAs, or BAAs (or conjugated compositions thereof) of the present disclosure and the antibody portion of the additional agent is directed against the same target (e.g. both may target EGFR). In some embodiments, they are directed against the same target, but target different epitopes. In some embodiments, they are directed against different targets entirely (e.g., an activatable antibody of the present disclosure that targets EGFR may be administered in conjunction with an AA targeting a different target; likewise e.g. a BAA of the present disclosure that targets EGFR and CD3 may be administered in conjunction with an AA targeting a different target.

In some embodiments, antibodies, bispecific antibodies, AAs or BAAs (or conjugated compositions thereof) of the disclosure are administered in conjunction with an immunotherapeutic agent. In some embodiments, antibodies, bispecific antibodies, AAs or BAAs (or conjugated compositions thereof) of the disclosure are administered in conjunction with a chemotherapeutic agent. In some embodiments, antibodies, bispecific antibodies, AAs or BAAs (or conjugated compositions thereof) of the disclosure are administered in conjunction with both an immunotherapeutic agent and a chemotherapeutic agent. In some embodiments, one or more additional agents is administered with any of these combination embodiments.

In some embodiments, they are formulated into a single therapeutic composition, and the antibodies/bispecific antibodies/AAs/BAAs thereof and the additional agent are administered simultaneously. Alternatively, the antibodies/bispecific antibodies/AAs/BAAs thereof are administered separate from each other, e.g., each is formulated into a separate therapeutic composition, and the antibodies/bispecific antibodies/AAs/BAAs thereof and the additional agent are administered simultaneously, or the antibodies/bispecific antibodies/AAs/BAAs thereof and the additional agent are administered at different times during a treatment regimen. The antibodies/bispecific antibodies/AAs/BAAs thereof and the additional agent can be administered in multiple doses.

The antibodies/bispecific antibodies/AAs/BAAs thereof can be incorporated into pharmaceutical compositions suitable for administration. Principles and considerations involved in preparing such compositions, as well as guidance in the choice of components are provided, for example, in Remington's Pharmaceutical Sciences: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Such compositions typically comprise the antibodies/bispecific antibodies/AAs/BAAs thereof and a pharmaceutically acceptable carrier.

As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Suitable examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated.

The formulations to be used for in vivo administration must be sterile. This is readily accomplished by filtration through sterile filtration membranes.

A pharmaceutical composition of the disclosure is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be suitable to include isotonic agents, for example, sugars, polyalcohols such as manitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as sustained/controlled release formulations, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

For example, the active ingredients can be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

The materials can also be obtained commercially from Alza Corporation and Nova Pharmaceuticals, Inc. Liposomal suspensions (including liposomes targeted to infected cells with monoclonal antibodies to viral antigens) and can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The formulation can also contain more than one active compound as necessary for the particular indication being treated, for example, those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

In one embodiment, the active compounds are administered in combination therapy, i.e., combined with other agents, e.g., therapeutic agents, that are useful for treating pathological conditions or disorders, such as autoimmune disorders and inflammatory diseases. The term "in combination" in this context means that the agents are given substantially contemporaneously, either simultaneously or sequentially. If given sequentially, at the onset of administration of the second compound, the first of the two compounds is still detectable at effective concentrations at the site of treatment.

For example, the combination therapy can include one or more antibodies/bispecific antibodies/AAs/BAAs thereof of the disclosure coformulated with, and/or coadministered with, one or more additional therapeutic agents, e.g., one or more cytokine and growth factor inhibitors, immunosuppressants, anti-inflammatory agents, metabolic inhibitors, enzyme inhibitors, and/or cytotoxic or cytostatic agents, as described in more detail below. Furthermore, one or more antibodies/bispecific antibodies/AAs/BAAs thereof described herein may be used in combination with two or more of the therapeutic agents described herein (e.g. one BAA administered with another BAA or AA of the disclosure, and the like). Such combination therapies may advantageously utilize lower dosages of the administered therapeutic agents, thus avoiding possible toxicities or complications associated with the various monotherapies.

In other embodiments, one or more antibodies of the disclosure can be coformulated with, and/or coadministered with, one or more anti-inflammatory drugs, immunosuppressants, or metabolic or enzymatic inhibitors. Nonlimiting examples of the drugs or inhibitors that can be used in combination with the antibodies described herein, include, but are not limited to, one or more of: nonsteroidal anti-inflammatory drug(s) (NSAIDs), e.g., ibuprofen, tenidap, naproxen, meloxicam, piroxicam, diclofenac, and indomethacin; sulfasalazine; corticosteroids such. as prednisolone; cytokine suppressive anti-inflammatory drug(s) (CSAIDs); inhibitors of nucleotide biosynthesis, e.g., inhibitors of purine biosynthesis, folate antagonists (e.g., methotrexate (N-[4-[[(2,4-diamino-6-pteridinyl)methyl] methylamino] benzoyl]L-glutamic acid); and inhibitors of pyrimidine biosynthesis, e.g., dihydroorotate dehydrogenase (DHODH) inhibitors. Suitable therapeutic agents for use in combination with the antibodies of the disclosure include NSAIDs, CSAIDs, (DHODH) inhibitors (e.g., leflunomide), and folate antagonists (e.g., methotrexate).

Examples of additional inhibitors include one or more of: corticosteroids (oral, inhaled and local injection); immunosuppressants, e.g., cyclosporin, tacrolimus (FK-506); and mTOR inhibitors, e.g., sirolimus (rapamycin—RAPAMUNE™ or rapamycin derivatives, e.g., soluble rapamycin derivatives (e.g., ester rapamycin derivatives, e.g., CCI-779); agents that interfere with signaling by proinflammatory cytokines such as TNFα or IL-1 (e.g. IRAK, NIK, IKK, p38 or MAP kinase inhibitors); COX2 inhibitors, e.g., celecoxib, rofecoxib, and variants thereof; phosphodiesterase inhibitors, e.g., R973401 (phosphodiesterase Type IV inhibitor); phospholipase inhibitors, e.g., inhibitors of cytosolic phospholipase 2 (cPLA2) (e.g., trifluoromethyl ketone analogs); inhibitors of vascular endothelial cell growth factor or growth factor receptor, e.g., VEGF inhibitor and/or VEGF-R inhibitor; and inhibitors of angiogenesis. Suitable therapeutic agents for use in combination with the antibodies of the disclosure are immunosuppressants, e.g., cyclosporin, tacrolimus (FK-506); mTOR inhibitors, e.g., sirolimus (rapamycin) or rapamycin derivatives, e.g., soluble rapamycin derivatives (e.g., ester rapamycin derivatives, e.g., CCI-779); COX2 inhibitors, e.g., celecoxib and variants thereof; and phospholipase inhibitors, e.g., inhibitors of cytosolic phospholipase 2 (cPLA2), e.g., trifluoromethyl ketone analogs.

Additional examples of therapeutic agents that can be combined with an antibody of the disclosure include one or more of: 6-mercaptopurines (6-MP); azathioprine sulphasalazine; mesalazine; olsalazine; chloroquine/hydroxychloroquine)(PLAQUENIL®); pencillamine; aurothiornalate (intramuscular and oral); azathioprine; coichicine; beta-2 adrenoreceptor agonists (salbutamol, terbutaline, salmeteral); xanthines (theophylline, aminophylline); cromoglycate; nedocromil; ketotifen; ipratropium and oxitropium; mycophenolate mofetil; adenosine agonists; antithrombotic agents; complement inhibitors; and adrenergic agents.

In some embodiments, antibodies/bispecific antibodies/AAs/BAAs thereof of the disclosure can be combined with one or more antibodies/bispecific antibodies/AAs/BAAs thereof.

14. Kits and Articles of Manufacture

Provided herein are kits and articles of manufacture comprising any one or more of the antibodies, AAs, bispecific antibodies, and BAAs provided herein The kits and articles of manufacture may comprise any one or more of the antibodies, AAs, bispecific antibodies, and BAAs provided herein in a format suitable for storage or shipping.

The kits and articles of manufacture may comprise at least a second component.

The kits and articles of manufacture may comprise a vessel, a diluent, a solvent, a second composition, or any component useful for converting a composition in a format for storage into a composition suitable for use in a method disclosed herein, if such a conversion is required. The method may be, for instance, a therapeutic method disclosed herein. The kit may comprise instructions for use.

The kits and articles of manufacture may comprise an agent as disclosed herein, for instance a cytotoxic agent or a detectable label, in a format suitable for conjugation to the antibodies, AAs, bispecific antibodies, and BAAs provided herein.

The following examples are included for illustrative purposes and are not intended to limit the scope of the invention.

ENUMERATED EMBODIMENTS

The invention may be defined by reference to the following enumerated, illustrative embodiments.

1. A bispecific activatable antibody (BAA), wherein said BAA, when activated, specifically binds to two targets and comprises the following structure:
   a. an IgG antibody (AB1) that specifically binds to a first target wherein the AB1 comprises two heavy chains (AB1 HCs) and two light chains (AB1 LCs); and wherein the AB1 is linked to a first masking moiety (MM1) linked to a first cleavable moiety (CM1) to form a MM1-CM1 construct, wherein the carboxyl terminus of a MM1-CM1 construct is linked to each amino terminus of each light chain of the AB1, wherein the MM1 inhibits the binding of the AB1 to its target; and
      the CM1 is a polypeptide that functions as a substrate for a first protease,
   b. two scFvs (each an AB2) that each specifically binds to a second target wherein each AB2 comprises a light chain variable region linked to a heavy chain variable region, wherein the carboxyl terminus of each AB2 is linked to the amino terminus each of the AB1 heavy chains; and wherein each AB2 is linked to a second masking moiety (MM2) linked to a second cleavable moiety (CM2) to form a MM2-CM2 construct, wherein the carboxyl terminus of each MM2-CM2 construct is linked to the amino terminus of each AB2 wherein
      the MM2 inhibits the binding of the AB2 to its target; and
      the CM2 is a polypeptide that functions as a substrate for a second protease,
      and wherein the BAA has at least one of the following characteristics:
      i. MM2 comprises amino acid sequence SEQ ID NO: 12;
      ii. MM1 comprises an amino acid sequence selected from the group consisting of sequences presented in Table 7;
      iii. AB2 comprises a heavy chain variable domain as set forth in SEQ ID NO: 2 or SEQ ID NO: 3 or a light chain variable domain as set forth in SEQ ID NO: 1 or SEQ ID NO: 4; and
      iv. AB1 comprises an Fc region comprising an amino acid substitution in at least one of amino acid positions L234, L235, N297, and P331, as numbered by the EU index as set forth in Kabat, such that the BAA has reduced effector function.

2. The BAA of embodiment 1, wherein AB2 comprises a heavy chain variable domain as set forth in SEQ ID NO: 2 or SEQ ID NO: 3 and a light chain variable domain as set forth in SEQ ID NO: 1 or SEQ ID NO: 4.

3. The BAA of embodiment 1, wherein the AB1 binds a tumor target and the AB2 binds an immune effector target.

4. The BAA of any one of embodiments 1 to 3, wherein the BAA is a T cell-engaging bispecific (TCB) AA (TCBAA).

5. The BAA of any one of embodiments 1 to 4, wherein the AB1 binds EGFR and the AB2 binds CD3E.

6. The BAA of any one of embodiments 1 to 5, wherein the MM1 comprises an amino acid sequence selected from the group consisting of sequences presented in Table 7.

7. The BAA of any one of embodiments 1 to 5, wherein the MM1 comprises an amino acid sequence selected from the group consisting of SEQ ID NO: 85 and SEQ ID NO: 78.

8. The BAA of any one of embodiments 1 to 5, wherein the MM1 comprises SEQ ID NO: 78.

9. The BAA of any one of embodiments 1 to 8, wherein the MM2 comprises the amino acid sequence SEQ ID NO: 12.

10. The BAA of any one of embodiments 1 to 9, wherein the CM comprises the amino acid sequence of SEQ ID NO: 14.

11. The BAA of any one of embodiments 1 to 9, wherein the CM comprises the amino acid sequence of SEQ ID NO: 17.

12. The BAA of any one of embodiments 1 to 9, wherein the CM the CM comprises the amino acid sequence of SEQ ID NO: 16.

13. The BAA of any one of embodiments 1 to 9, wherein CM1 comprises an amino acid sequence selected from the group comprising SEQ ID NO: 14 and SEQ ID NO: 16.

14. The BAA of any one of embodiments 1 to 9, wherein CM2 comprises an amino acid sequence selected from the group comprising SEQ ID NO: 14 and SEQ ID NO: 17.

15. The BAA of any one of embodiments 1 to 14, wherein AB1 comprises amino acid substitutions in at least two of amino acid positions L234, L235, and P331.

16. The BAA of embodiment 15, wherein AB1 comprises amino acid substitutions at amino acid positions L234, L235, and P331.

17. The BAA of embodiment 15, wherein AB1 comprises L234F, L235E, and P331S amino acid substitutions.

18. The BAA of embodiment 15, wherein the AB1 comprises an Fc region comprising an amino acid substitution at N297.

19. The BAA of any one of embodiments 1 to 14, wherein AB1 comprises amino acid substitutions at amino acid positions L234F, L235E, P331S, and N297Q.

20. The BAA of embodiment 1, wherein the heavy chain of the AB1 comprises any one of SEQ ID NO: 69, SEQ ID NO: 70, SEQ ID NO: 71, SEQ ID NO: 72, SEQ ID NO: 73, SEQ ID NO: 74, SEQ ID NO: 75 and SEQ ID NO: 76, as set forth in Table 6.

21. The BAA CI106, comprising the layout and sequence as provided in Table 11 and Example 1.

22. The BAA CI107, comprising the layout and sequence as provided in Table 11 and Example 1.

23. The BAA CI079, comprising the layout and sequence as provided in Table 11 and Example 1.

24. The BAA CI090, comprising the layout and sequence as provided in Table 11 and Example 1.

25. An activatable antibody (AA) comprising:
   a) an antibody or antigen binding fragment thereof (AB) that specifically binds to the epsilon chain of CD3 (CD3ε);
   b) a masking moiety (MM) coupled to the AB, wherein the MM reduces or inhibits the binding of the AB to the CD3ε when the AA is in an uncleaved state, wherein the MM comprises amino acid sequence SEQ ID NO: 12; and
   c) a cleavable moiety (CM) coupled to the AB, wherein the CM is a polypeptide that functions as a substrate for a protease.

26. The AA of embodiment 25, wherein the CM comprises any one of the sequences set forth in Table 4.

27. The AA of embodiment 25, wherein the CM comprises a substrate cleavable by a serine protease or an MMP.

28. The AA of embodiment 25, wherein the CM comprises an amino acid sequence selected from the group consisting of SEQ ID NO: 18-56.

29. The AA of embodiment 25, wherein the protease is an MMP.

30. The AA of embodiment 25, wherein the protease is a serine protease.

31. The AA of embodiment 25, wherein the AB that specifically binds to CD3 is the antibody of any one of embodiments 38-47.

32. An activatable antibody (AA) comprising:

a. an antibody or an antigen binding fragment thereof (AB) that specifically binds to Epidermal Growth Factor Receptor (EGFR);

b. a masking moiety (MM) coupled to the AB, wherein the MM reduces or inhibits the binding of the AB to the EGFR when the AA is in an uncleaved state, and wherein the MM comprises an amino acid sequence selected from the group consisting of sequences presented in Table 7; and c. a cleavable moiety (CM) coupled to the AB, wherein the CM is a polypeptide that functions as a substrate for a protease.

33. The AA of embodiment 32, wherein the MM comprises the amino acid sequence of SEQ ID NO: 78.

34. The AA of any one of embodiments 32 to 33, wherein the CM comprises a substrate cleavable by a serine protease or an MMP.

35. The AA of any one of embodiments 32 to 33, wherein the CM comprises an amino acid sequence selected from the group consisting of SEQ ID NO: 18-56.

36. The AA of embodiment 32, wherein the CM comprises the amino acid sequence of SEQ ID NO: 14.

37. The AA of embodiment 32, wherein the CM comprises the amino acid sequence of SEQ ID NO: 16.

38. An antibody or antigen binding fragment thereof (AB) that specifically binds to the epsilon chain of CD3 (CD3ε), wherein the antibody comprises a heavy chain variable domain as set forth in SEQ ID NO: 2 or SEQ ID NO: 3 or a light chain variable domain as set forth in SEQ ID NO: 1 or SEQ ID NO: 4.

39. The AB of embodiment 38, wherein, the antibody comprises a heavy chain variable domain as set forth in SEQ ID NO: 2 or SEQ ID NO: 3 and a light chain variable domain as set forth in SEQ ID NO: 1 or SEQ ID NO: 4.

40. The AB of embodiment 38, comprising a heavy chain variable domain as set forth in SEQ ID NO: 2.

41. The AB of embodiment 38, comprising a heavy chain variable domain as set forth in SEQ ID NO: 3.

42. The AB of embodiment 38, wherein the antibody comprises a light chain variable domain as set forth in SEQ ID NO: 1.

43. The AB of embodiment 38, comprising a light chain variable domain as set forth in SEQ ID NO: 4.

44. The AB of embodiment 38, comprising a heavy chain variable domain as set forth in SEQ ID NO: 2 and a light chain variable domain as set forth in SEQ ID NO: 1.

45. The AB of embodiment 38, comprising a heavy chain variable domain as set forth in SEQ ID NO: 3 and a light chain variable domain as set forth in SEQ ID NO: 1.

46. The AB of embodiment 38, comprising a heavy chain variable domain as set forth in SEQ ID NO: 3 and a light chain variable domain as set forth in SEQ ID NO: 4.

47. The AB of embodiment 38, comprising a heavy chain variable domain as set forth in SEQ ID NO: 2 and a light chain variable domain as set forth in SEQ ID NO: 4.

48. The AB of any one of embodiments 32 to 47, wherein the AB is a bispecific AB.

49. The AA of any one of embodiments 32 to 47, wherein the antibody is a scFv.

50. The AA of any one of embodiments 32 to 47, wherein the antibody is an IgG1 antibody.

51. An activatable antibody (AA) comprising:

a) an antibody or antigen binding fragment thereof (AB) that specifically binds to the epsilon chain of CD3 (CD3ε), wherein the antibody comprises a heavy chain variable domain as set forth in SEQ ID NO: 2 or SEQ ID NO: 3 or comprises a light chain variable domain as set forth in SEQ ID NO: 1 or SEQ ID NO: 4;

b) a masking moiety (MM) coupled to the AB, wherein the MM reduces or inhibits the binding of the AB to the CD3ε when the AA is in an uncleaved state; and c) a cleavable moiety (CM) coupled to the AB, wherein the CM is a polypeptide that functions as a substrate for a protease.

52. The AA of embodiment 51, wherein the AB comprises a heavy chain variable domain as set forth in SEQ ID NO: 2.

53. The AA of embodiment 51, wherein the AB comprises a heavy chain variable domain as set forth in SEQ ID NO: 3.

54. The AA of embodiment 51, wherein the AB comprises a light chain variable domain as set forth in SEQ ID NO: 1.

55. The AA of embodiment 51, wherein the AB comprises a light chain variable domain as set forth in SEQ ID NO: 4.

56. The AA of embodiment 51, wherein the AB comprises a heavy chain variable domain as set forth in SEQ ID NO: 2 and a light chain variable domain as set forth in SEQ ID NO: 1.

57. The AA of embodiment 51, wherein the AB comprises a heavy chain variable domain as set forth in SEQ ID NO: 3 and a light chain variable domain as set forth in SEQ ID NO: 1.

58. The AA of embodiment 51, wherein the AB comprises a heavy chain variable domain as set forth in SEQ ID NO: 2 and a light chain variable domain as set forth in SEQ ID NO: 4.

59. The AA of embodiment 51, wherein the AB comprises a heavy chain variable domain as set forth in SEQ ID NO: 3 and a light chain variable domain as set forth in SEQ ID NO: 4.

60. The AA of any one of embodiments 51 to 59, wherein the MM comprises any one of the sequences set forth in Table 3.

61. The AA of any one of embodiments 51 to 59, wherein the CM comprises any one of the sequences set forth in Table 4.

62. A bispecific activatable antibody (BAA) comprising any one of the AAs of embodiments 51 to 61.

63. An activatable antibody (AA) comprising:

a. an antibody (AB) that specifically binds a target, wherein the antibody is an IgG1 antibody, and wherein the Fc region of the antibody comprises an amino acid substitution in amino acid positions L234, L235, and P331, as numbered by the EU index as set forth in Kabat, such that the AA has reduced effector function;

b. a masking moiety (MM) coupled to the AB, wherein the MM reduces or inhibits the binding of the AB to the target when the AA is in an uncleaved state; and c. a cleavable moiety (CM) coupled to the AB, wherein the CM is a polypeptide that functions as a substrate for a protease.

64. The AA of embodiment 63, wherein the Fc region comprises amino acid substitutions in at least amino acid positions L234, L235, N297 and P331, as numbered by the EU index as set forth in Kabat, such that the AA has reduced effector function.

65. The AA of embodiment 63 or 64, wherein the target is selected from the group consisting of the targets presented in Table 9.

66. A bispecific activatable antibody (BAA) comprising:

a. an IgG antibody (AB1) that specifically binds to a first target wherein the AB1 comprises two heavy chains (AB1 HCs) and two light chains (AB1 LCs); and wherein the AB1 is linked to a first masking moiety (MM1) linked to a first cleavable moiety (CM1) to form a MM1-CM1 construct, wherein the carboxyl terminus of a MM1-CM1 construct is linked to each amino terminus of each light chain of the AB1, wherein the MM1 inhibits the binding of the AB1 to its target; and the CM1 is a polypeptide that functions as a substrate for a first protease, b. two scFvs (each an AB2) that each specifically binds to a second target wherein each AB2 comprises a heavy chain variable region linked to a light chain variable region, wherein the carboxyl terminus of each AB2 is linked to the amino terminus each of the AB1 heavy chains; and wherein each AB2 is linked to a second masking moiety (MM2) linked to a second cleavable moiety (CM2) to form a MM2-CM2 construct, wherein the carboxyl terminus of each MM2-CM2 construct is linked to the amino terminus of each AB2 wherein the MM2 inhibits the binding of the AB2 to its target; and the CM2 is a polypeptide that functions as a substrate for a second protease, and wherein the AB1 comprises an Fc region comprises an amino acid substitution in at least one of amino acid positions L234, L235, N297, and P331, as numbered by the EU index as set forth in Kabat, such that the BAA has reduced effector function.

67. The BAA of embodiment 66, wherein the Fc region comprises amino acid substitutions in at least amino acid positions L234, L235, N297 and P331, as numbered by the EU index as set forth in Kabat, such that the BAA has reduced effector function.

68. The BAA of embodiment 66, wherein the Fc region comprises amino acid substitutions in at least amino acid positions L234, L235, and P331, as numbered by the EU index as set forth in Kabat, such that the BAA has reduced effector function.

69. The BAA of any one of embodiments 66 to 68, wherein the first target is selected from the group consisting of the targets presented in Table 9 and the second target is selected from the group consisting of the targets presented in Table 9.

70. The AA or BAA of any one of the above embodiments, wherein the antigen binding fragment thereof is selected from the group consisting of a Fab fragment, a F(ab')2 fragment, a scFv, a scAb, a dAb, a single domain heavy chain antibody, and a single domain light chain antibody.

71. The AA or BAA of any one of the above embodiments wherein the antibody is a rodent antibody, a chimeric antibody, a humanized antibody, or a fully human monoclonal antibody.

72. The AA of any one of embodiments 32-37 and 51-71, wherein the AA is a BAA.

73. A pharmaceutical composition comprising the antibody, AA, or BAA of any one of embodiments 1-72 and optionally a carrier.

74. The pharmaceutical composition of embodiment 73 comprising an additional agent.

75. The pharmaceutical composition of embodiment 74, wherein the additional agent is a therapeutic agent.

76. An isolated nucleic acid molecule encoding the antibody, AA, or BAA of any one of embodiments 1-72.

77. A vector comprising the isolated nucleic acid molecule of embodiment 76.

78. A vector comprising the nucleic acid sequence of pLW289.

79. A vector comprising the nucleic acid sequence of pLW246.

80. A vector comprising the nucleic acid sequence of pLW307.

81. A vector comprising the nucleic acid sequence of pLW291.

82. A cell comprising any one of the vectors of embodiments 77-81.

83. A cell comprising pLW289 and pLW246.

84. A cell comprising pLW307 and pLW291.

85. A method of producing the antibody, AA, or BAA of any one of embodiments 1-72 by culturing a cell under conditions that lead to expression of the antibody, AA, or BAA, wherein the cell comprises the nucleic acid molecule of embodiment 76 or the vector of any one of embodiments 78-81.

86. A method of treating, alleviating a symptom of, or delaying the progression of a disorder or disease comprising administering a therapeutically effective amount of the antibody, AA, or BAA of any one of embodiments 1-72, or the pharmaceutical composition of any one of embodiments 73-75 to a subject in need thereof.

87. The method of embodiment 86, wherein the disorder or disease comprises disease cells expressing EGFR.

88. The method of embodiments 86 or 87, wherein the disorder or disease is cancer.

89. The method of embodiment 88, wherein the cancer is anal cancer, basal cell carcinoma, brain cancer, bladder cancer, breast cancer, bone cancer, cervical cancer, cholangiocarcinoma, colorectal cancer, endometrial cancer, esophageal cancer, gall bladder cancer, gastric cancer, glioblastoma, head and neck cancer, liver cancer, lung cancer, ovarian cancer, pancreatic cancer, prostate cancer, renal cancer, sarcoma, small bowel carcinoma, squamous cell cancer, skin cancer testicular cancer, thyroid cancer or uterine cancer.

90. A method of inhibiting angiogenesis in a subject comprising administering a therapeutically effective amount of the antibody, AA, or BAA of any one of embodiments 1-72, or the pharmaceutical composition of any one of embodiments 73-75 to a subject in need thereof.

91. The method of any one of embodiments 86-90, wherein the method comprises administering an additional agent.

92. The method of embodiment 91 wherein the additional agent is a therapeutic agent.

93. A method of reducing damage to healthy tissue caused by an antibody binding to its target on healthy tissue as well as on diseased tissue, the method comprising administering to a subject in need thereof an AA or BAA or a pharmaceutical composition comprising an AA or BAA, wherein said AA or BAA is an AA or BAA of any one of the embodiments provided herein.

94. A method to improve tolerability of an antibody treatment comprising administering to a subject in need thereof an AA or BAA or a pharmaceutical composition comprising an AA or BAA, wherein said AA or BAA is an AA or BAA of any one of the embodiments provided herein.

95. A method to recruit T cells to tumor tissue comprising administering to a subject in need thereof an AA or BAA or a pharmaceutical composition comprising an AA or BAA, wherein said AA or BAA is an AA or BAA of any one of the embodiments provided herein.

96. An antibody, AA, or BAA of any one of embodiments 1-72, or the pharmaceutical composition of any one of embodiments 73-75, for use as a medicament.

97. An antibody, AA, or BAA of any one of embodiments 1-72, or the pharmaceutical composition of any one of embodiments 73-75, for use in a method of treating, alleviating a symptom of, or delaying the progression of a disorder or disease, wherein the disorder or disease comprises disease cells expressing EGFR.

98. An antibody, AA, or BAA of any one of embodiments 1-72, or the pharmaceutical composition of any one of embodiments 73-75, for use in a method of treating cancer; optionally wherein the cancer is anal cancer, basal cell carcinoma, brain cancer, bladder cancer, breast cancer, bone cancer, cervical cancer, cholangiocarcinoma, colorectal cancer, endometrial cancer, esophageal cancer, gall bladder cancer, gastric cancer, glioblastoma, head and neck cancer, liver cancer, lung cancer, ovarian cancer, pancreatic cancer, prostate cancer, renal cancer, sarcoma, small bowel carcinoma, squamous cell cancer, skin cancer testicular cancer, thyroid cancer or uterine cancer.

99. An antibody, AA, or BAA of any one of embodiments 1-72, or the pharmaceutical composition of any one of embodiments 73-75, for use in a method of treatment, wherein the method comprises inhibiting angiogenesis.

100. The antibody, AA, or BAA, or the pharmaceutical composition, for use according to any of embodiments 96 to 99, wherein the use comprises administering an additional agent, optionally wherein the additional agent is a therapeutic agent.

EXAMPLES

Example 1. Sequences, Vector Construction and Expression of Antibodies, BAAs and Activated BAAs Antibodies of Interest The molecules as provided in Table 11 below were constructed and tested. As indicated, activated molecules were produced as masked and proteolytically cleaved to produce the activated forms.

TABLE 11

| Molecule Name | Molecule Component Parts | Heavy Chain Vector | Light Chain Vector |
|---|---|---|---|
| CI011 | 3954-0001-C225v5N297Q-JF15865-0001-CD3LvHv-H-N | pLW023 | OPP022 |
| CI020 | 3954-Nsub-C225v5N297Q-JF15865-Nsub-hSP34LvHv-H-N | pLW073 | pLW071 |
| CI040 | 3954-2001-C225v5N297Q-JF15865-2001-hSP34LvHv-H-N | pLW101 | CTX122 |
| CI048 | Activated CI011: 3954-0001-C225v5N297Q-JF15865-0001-CD3LvHv-H-N | pLW023 | OPP022 |
| CI079 | 3954-0001-C225v5Fcmt3-h20GG-0001-v16sc-H-N | pLW225 | OPP022 |
| CI090 | 3954-0001-C225v5Fcmt4-h20GG-0001-v16sc-H-N | pLW233 | OPP022 |
| Activated CI090 | Activated 3954-0001-C225v5Fcmt4-h20GG-0001-v16sc-H-N | pLW233 | OPP022 |
| Activated CI104 | Activated 3954-0011-C225v5Fcmt4-h20GG-0011-v16sc-H-N | pLW289 | pLW291 |
| CI106 | CF41-2008-C225v5Fcmt4-h20GG-0011-v16sc-H-N | pLW289 | pLW246 |
| CI107 | 3954-0011-C225v5Fcmt4-h20GG-2006-v16sc-H-N | pLW307 | pLW291 |
| CI127 | SynFcmt4-h20GG-0011-v16sc-H-N | pLW334 | pLW139 |
| CI128 | SynFcmt4-h20GG-2006-v16sc-H-N | pLW335 | pLW139 |
| CI135 | CF41-2008-C225v5Fcmt4-h20GG-0011-v12sc-H-N | pLW352 | pLW246 |
| CI136 | CF41-2008-C225v5Fcmt4-h20GG-0011-v19sc-H-N | pLW353 | pLW246 |
| CI091 | 3954-1490DQH-C225v5Fcmt4-h20GG-2008-v16sc-H-N | pLW242 | CX320 |
| CI064 | SynN297Q-JF15865-0001-hSP34LvHv-H-N | pLW138 | pLW139 |
| v12 | Anti-CD3 variant | HV12 | LV12 |
| v16 | Anti-CD3 variant | HV20 | LV12 |
| v19 | Anti-CD3 variant | HV20 | LV19 |
| v26 | Anti-CD3 variant | HV12 | LV19 |

The sequences of the molecules and vectors are provided below. Brackets denote some of the component parts of the molecules presented. In some sequences, linkers are provided. Underlined amino acids denote predicted CDR sequences.

| CI011:3954-0001-C225v5N297Q-JF15865-0001-CD3LvHv-H-N |
|---|

```
pLW023: HC JF15865-0001-CD3LvHv-C225v5N297Q (H-N)
Nucleotide Sequence
[spacer SEQ ID NO: 176][pLW023 without spacer SEQ ID NO: 177]
CAAGGCCAGTCTGGCCAAATGATGTATTGCGGTGGGAATGAGGTGTTGTGCGGGCCGC
GGGTTGGCTCGAGCGGTGGCAGCGGTGGCTCTGGTGGTCTGAGCGGCCGTTCCGATAA
TCATGGCGGCGGTTCTCAGACCGTGGTCACACAGGAGCCCTCACTGACAGTGAGCCCT
GGCGGGACCGTCACACTGACTTGTCGCAGTTCAACTGGCGCCGTGACTACCAGCAATT
ACGCTAACTGGGTCCAGCAGAAACCAGGACAGGCACCACGAGGACTGATCGGAGGAA
CTAATAAGAGAGCACCAGGAACCCCTGCAAGGTTCTCCGGATCTCTGCTGGGGGGAAA
```

-continued

AGCCGCTCTGACACTGAGCGGCGTGCAGCCTGAGGACGAAGCTGAGTACTATTGCGCA
CTGTGGTACTCCAACCTGTGGGTGTTTGGCGGGGAACTAAGCTGACCGTCCTGGGAG
GAGGAGGAAGCGGAGGAGGAGGGAGCGGAGGAGGAGGATCCGAAGTGCAGCTGGTC
GAGAGCGGAGGAGGACTGGTGCAGCCAGGAGGATCCCTGAAGCTGTCTTGTGCAGCCA
GTGGCTTCACCTTCAACACTTACGCAATGAACTGGGTGCGGCAGGCACCTGGGAAGGG
ACTGGAATGGGTCGCCCGGATCAGATCTAAATACAATAACTATGCCACCTACTATGCTG
ACAGTGTGAAGGATAGGTTCACCATTTCACGCGACGATAGCAAAAACACAGCTTATCT
GCAGATGAATAACCTGAAGACCGAGGATACAGCAGTGTACTATTGCGTCAGACACGGC
AATTTCGGGAACTCTTACGTGAGTTGGTTTGCCTATTGGGGACAGGGGACACTGGTCAC
CGTCTCCTCAGGAGGTGGTGGATCCCAGGTGCAGCTGAAACAGAGCGGCCCGGGCCTG
GTGCAGCCGAGCCAGAGCCTGAGCATTACCTGCACCGTGAGCGGCTTTAGCCTGACCA
ACTATGGCGTGCATTGGGTGCGCCAGAGCCCGGGCAAAGGCCTGGAATGGCTGGGCGT
GATTTGGAGCGGCGGCAACACCGATTATAACACCCCGTTTACCAGCCGCCTGAGCATT
AACAAAGATAACAGCAAAAGCCAGGTGTTTTTTAAAATGAACAGCCTGCAAAGCCAGG
ATACCGCGATTTATTATTGCGCGCGCGCTGACCTATTATGATTATGAATTTGCGTATT
GGGGCCAGGGCACCCTGGTGACCGTGAGCGCGGCTAGCACCAAGGGCCCATCGGTCTT
CCCCCTGGCACCCTCCTCCAAGAGCACCTCTGGGGGCACAGCGGCCCTGGGCTGCCTG
GTCAAGGACTACTTCCCCGAACCGGTGACGGTGTCGTGGAACTCAGGCGCCCTGACCA
GCGGCGTGCACACCTTCCCGGCTGTCCTACAGTCCTCAGGACTCTACTCCCTCAGCAGC
GTGGTGACCGTGCCCTCCAGCAGCTTGGGCACCCAGACCTACATCTGCAACGTGAATC
ACAAGCCCAGCAACACCAAGGTGGACAAGAAAGTTGAGCCCAAATCTTGTGACAAAA
CTCACACATGCCCACCGTGCCCAGCACCTGAACTCCTGGGGGGACCGTCAGTCTTCCTC
TTCCCCCCAAAACCCAAGGACACCCTCATGATCTCCCGGACCCCTGAGGTCACATGCGT
GGTGGTGGACGTGAGCCACGAAGACCCTGAGGTCAAGTTCAACTGGTACGTGGACGGC
GTGGAGGTGCATAATGCCAAGACAAAGCCGCGGGAGGAGCAGTACCAGAGCACGTAC
CGTGTGGTCAGCGTCCTCACCGTCCTGCACCAGGACTGGCTGAATGGCAAGGAGTACA
AGTGCAAGGTCTCCAACAAAGCCCTCCCAGCCCCCATCGAGAAAACCATCTCCAAAGC
CAAAGGGCAGCCCCGAGAACCACAGGTGTACACCCTGCCCCCATCCCGGGAGGAGATG
ACCAAGAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCG
TGCTGGACTCCGACGGCTCCTTCTTCCTCTACAGCAAGCTCACCGTGGACAAGAGCAGG
TGGCAGCAGGGGAACGTCTTCTCATGCTCCGTGATGCATGAGGCTCTGCACAACCACTA
CACGCAGAAGAGCCTCTCCCTGTCTCCGGGTAAA (SEQ ID NO: 105)

Amino Acid Sequence
[spacer SEQ ID NO: 178][pLW023 without spacer SEQ ID NO: 179]
QGQSGQ[MMYCGGNEVLCGPRV][GSSGGSGGSGG][LSGRSDNH][GGGS]QTVVTQEPSLT
VSPGGTVTLTCRSSTGAVTTSNYANWVQQKPGQAPRGLIGGTNKRAPGTPARFSGSLLGG
KAALTLSGVQPEDEAEYYCALWYSNLWVFGGGTKLTVL[GGGGSGGGGSGGGGS]EVQLV
ESGGGLVQPGGSLKLSCAASGFTFNTYAMNWVRQAPGKGLEWVARIRSKYNNYATYYAD
SVKDRFTISRDDSKNTAYLQMNNLKTEDTAVYYCVRHGNFGNSYVSWFAYWGQGTLVTV
SS[GGGGS]QVQLKQSGPGLVQPSQSLSITCTVSGFSLTNYGVHWVRQSPGKGLEWLGVIWS
GGNTDYNTPFTSRLSINKDNSKSQVFFKMNSLQSQDTAIYYCARALTYYDYEFAYWGQGT
LVTVSAASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCPPCPAPEL
LGGPSVFLFPPKPKDTLMISRTPEVTCVVVDVSHEDPEVKFNWYVDGVEVHNAKTKPREE
QYQSTYRVVSVLTVLHQDWLNGKEYKCKVSNKALPAPIEKTISKAKGQPREPQVYTLPPSR
EEMTKNQVSLTCLVKGFYPSDIAVEWESNGQPENNYKTTPPVLDSDGSFFLYSKLTVDKSR
WQQGNVFSCSVMHEALHNHYTQKSLSLSPGK (SEQ ID NO: 106)

OPP022: LC 3954-0001-C225v5
Nucleotide Sequence
[spacer SEQ ID NO: 180][OPP022 without spacer SEQ ID NO: 181]
TCCGATAATCATGGCAGTAGCGGTACCCAGATCTTGCTGACCCAGAGCCCGGTGATTCT
GAGCGTGAGCCCGGGCGAACGTGTGAGCTTTAGCTGCCGCGCGAGCCAGAGCATTGGC
ACCAACATTCATTGGTATCAGCAGCGCACCAACGGCAGCCCGCGCCTGCTGATTAAAT
ATGCGAGCGAAAGCATTAGCGGCATTCCGAGCCGCTTTAGCGGCAGCGGCAGCGGCAC
CGATTTTACCCTGAGCATTAACAGCGTGGAAAGCGAAGATATTGCGGATTATTATTGCC
AGCAGAACAACAACTGGCCGACCACCTTTGGCGCGGGCACCAAACTGGAACTGAAACG
TACGGTGGCTGCACCATCTGTCTTCATCTTCCCGCCATCTGATGAGCAGTTGAAATCTG
GAACTGCCTCTGTTGTGTGCCTGCTGAATAACTTCTATCCCAGAGAGGCCAAAGTACAG
TGGAAGGTGGATAACGCCCTCCAATCGGGTAACTCCCAGGAGAGTGTCACAGAGCAGG
ACAGCAAGGACAGCACCTACAGCCTCAGCAGCACCCTGACGCTGAGCAAAGCAGACTA
CGAGAAACACAAAGTCTACGCCTGCGAAGTCACCCATCAGGGCCTGAGCTCGCCCGTC
ACAAAGAGCTTCAACAGGGGAGAGTGT (SEQ ID NO: 107)

Amino Acid Sequence
[spacer SEQ ID NO: 178][OPP022 without spacer SEQ ID NO: 182]
[SDNH][GSSGT][QILLTQSPVILSVSPGERVSFSCRASQSIGTNIHWYQQRTNGSPRLLIKYAS
ESISGIPSRFSGSGSGTDFTLSINSVESEDIADYYCQQNNNWPTTFGAGTKLELKRTVAAPSV
FIFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC (SEQ ID NO: 108)

-continued

CI020: 3954-Nsub-C225v5N297O-JF15865-Nsub-hSP34LvHv-H-N pLW073: HC C225v5N297Q-JF15865-Nsub-hSP34LvHv (H-N)
Nucleotide Sequence
[spacer SEQ ID NO: 176][pLW073 without spacer SEQ ID NO: 183]
CAAGGCCAGTCTGGCCAAATGATGTATTGCGGTGGGAATGAGGTGTTGTGCGGGCCGC
GGGTTGGCTCGAGCGGTGGCAGCGGTGGCTCTGGTGGTGGTGGAGGCTCGGGCGGTGG
GAGCGGCGGCGGTTCTCAGACCGTGGTCACACAGGAGCCCTCACTGACAGTGAGCCCT
GGCGGGACCGTCACACTGACTTGTCGCAGTTCAACTGGCGCCGTGACTACCAGCAATT
ACGCTAACTGGGTCCAGCAGAAACCAGGACAGGCACCACGAGGACTGATCGGAGGAA
CTAATAAGAGAGCACCAGGAACCCCTGCAAGGTTCTCCGGATCTCTGCTGGGGGGAAA
AGCCGCTCTGACACTGAGCGGCGTGCAGCCTGAGGACGAAGCTGAGTACTATTGCGCA
CTGTGGTACTCCAACCTGTGGGTGTTTGGCGGGGGAACTAAGCTGACCGTCCTGGGAG
GAGGAGGAAGCGGAGGAGGAGGGAGCGGAGGAGGAGGATCCGAAGTGCAGCTGGTC
GAGAGCGGAGGAGGACTGGTGCAGCCAGGAGGATCCCTGAAGCTGTCTTGTGCAGCCA
GTGGCTTCACCTTCAACACTTACGCAATGAACTGGGTGCGGCAGGCACCTGGGAAGGG
ACTGGAATGGGTCGCCCGGATCAGATCTAAATACAATAACTATGCCACCTACTATGCTG
ACAGTGTGAAGGATAGGTTCACCATTTCACGCGACGATAGCAAAAACACAGCTTATCT
GCAGATGAATAACCTGAAGACCGAGGATACAGCAGTGTACTATTGCGTCAGACACGGC
AATTTCGGGAACTCTTACGTGAGTTGGTTTGCCTATTGGGGACAGGGGACACTGGTCAC
CGTCTCCTCAGGAGGTGGTGGATCCCAGGTGCAGCTGAAACAGAGCGGCCCGGGCCTG
GTGCAGCCGAGCCAGAGCCTGAGCATTACCTGCACCGTGAGCGGCTTTAGCCTGACCA
ACTATGGCGTGCATTGGGTGCGCCAGAGCCCGGGCAAAGGCCTGGAATGGCTGGGCGT
GATTTGGAGCGGCGGCAACACCGATTATAACACCCCGTTTACCAGCCGCCTGAGCATT
AACAAAGATAACAGCAAAAGCCAGGTGTTTTTTAAAATGAACAGCCTGCAAAGCCAGG
ATACCGCGATTTATTATTGCGCGCGCGCGCTGACCTATTATGATTATGAATTTGCGTATT
GGGGCCAGGGCACCCTGGTGACCGTGAGCGCGGCTAGCACCAAGGGCCCATCGGTCTT
CCCCCTGGCACCCTCCTCCAAGAGCACCTCTGGGGGCACAGCGGCCCTGGGCTGCCTG
GTCAAGGACTACTTCCCCGAACCGGTGACGGTGTCGTGGAACTCAGGCGCCCTGACCA
GCGGCGTGCACACCTTCCCGGCTGTCCTACAGTCCTCAGGACTCTACTCCCTCAGCAGC
GTGGTGACCGTGCCCTCCAGCAGCTTGGGCACCCAGACCTACATCTGCAACGTGAATC
ACAAGCCCAGCAACACCAAGGTGGACAAGAAAGTTGAGCCCAAATCTTGTGACAAAA
CTCACACATGCCCACCGTGCCCAGCACCTGAACTCCTGGGGGGACCGTCAGTCTTCCTC
TTCCCCCCAAAACCCAAGGACACCCTCATGATCTCCCGGACCCCTGAGGTCACATGCGT
GGTGGTGGACGTGAGCCACGAAGACCCTGAGGTCAAGTTCAACTGGTACGTGGACGGC
GTGGAGGTGCATAATGCCAAGACAAAGCCGCGGGAGGAGCAGTACCAGAGCACGTAC
CGTGTGGTCAGCGTCCTCACCGTCCTGCACCAGGACTGGCTGAATGGCAAGGAGTACA
AGTGCAAGGTCTCCAACAAAGCCCTCCCAGCCCCCATCGAGAAAACCATCTCCAAAGC
CAAAGGGCAGCCCCGAGAACCACAGGTGTACACCCTGCCCCCATCCCGGGAGGAGATG
ACCAAGAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCG
TGCTGGACTCCGACGGCTCCTTCTTCCTCTACAGCAAGCTCACCGTGGACAAGAGCAGG
TGGCAGCAGGGGAACGTCTTCTCATGCTCCGTGATGCATGAGGCTCTGCACAACCACTA
CACGCAGAAGAGCCTCTCCCTGTCTCCGGGTAAA (SEQ ID NO: 109)

Amino Acid Sequence
[spacer SEQ ID NO: 178][pLW073 without spacer SEQ ID NO: 184]
QGQSGQ[MMYCGGNEVLCGPRV][GSSGGSGGSGGGGSGGGSGGGS]QTVVTQEPSLTVS
PGGTVTLTCRSSTGAVTTSNYANWVQQKPGQAPRGLIGGTNKRAPGTPARFSGSLLGGKA
ALTLSGVQPEDEAEYYCALWYSNLWVFGGGTKLTVL[GGGGSGGGGSGGGGS]EVQLVES
GGGLVQPGGSLKLSCAASGFTFNTYAMNWVRQAPGKGLEWVARIRSKYNNYATYYADSV
KDRFTISRDDSKNTAYLQMNNLKTEDTAVYYCVRHGNFGNSYVSWFAYWGQGTLVTVSS
[GGGGS]QVQLKQSGPGLVQPSQSLSITCTVSGFSLTNYGVHWVRQSPGKGLEWLGVIWSG
GNTDYNTPFTSRLSINKDNSKSQVFFKMNSLQSQDTAIYYCARALTYYDYEFAYWGQGTL
VTVSAASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSCDKTHTCPPCPAPELL
GGPSVFLFPPKPKDTLMISRTPEVTCVVVDVSHEDPEVKFNWYVDGVEVHNAKTKPREEQ
YQSTYRVVSVLTVLHQDWLNGKEYKCKVSNKALPAPIEKTISKAKGQPREPQVYTLPPSRE
EMTKNQVSLTCLVKGFYPSDIAVEWESNGQPENNYKTTPPVLDSDGSFFLYSKLTVDKSR
WQQGNVFSCSVMHEALHNHYTQKSLSLSPGK (SEQ ID NO: 110)

pLW071: LC 3954-Nsub-C225v5
Nucleotide Sequence
[spacer SEQ ID NO: 180][pLW071 without spacer SEQ ID NO: 185]
CAAGGCCAGTCTGGCCAGTGCATCTCACCTCGTGGTTGTCCGGACGGCCCATACGTCAT
GTACGGCTCGAGCGGTGGCAGCGGTGGCTCTGGTGGCTCAGGTGGAGGCTCGGGCGGT
GGGAGCGGCGGTTCTGATATCTTGCTGACCCAGAGCCCGGTGATTCTGAGCGTGAGCC
CGGGCGAACGTGTGAGCTTTAGCTGCCGCGCGAGCCAGAGCATTGGCACCAACATTCA
TTGGTATCAGCAGCGCACCAACGGCAGCCCGCGCCTGCTGATTAAATATGCGAGCGAA
AGCATTAGCGGCATTCCGAGCCGCTTTAGCGGCAGCGGCAGCGGCACCGATTTTACCCT
GAGCATTAACAGCGTGGAAAGCGAAGATATTGCGGATTATTATTGCCAGCAGAACAAC
AACTGGCCGACCACCTTTGGCGCGGGCACCAAACTGGAACTGAAACGTACGGTGGCTG
CACCATCTGTCTTCATCTTCCCGCCATCTGATGAGCAGTTGAAATCTGGAACTGCCTCT
GTTGTGTGCCTGCTGAATAACTTCTATCCCAGAGAGGCCAAAGTACAGTGGAAGGTGG
ATAACGCCCTCCAATCGGGTAACTCCCAGGAGAGTGTCACAGAGCAGGACAGCAAGGA
CAGCACCTACAGCCTCAGCAGCACCCTGACGCTGAGCAAAGCAGACTACGAGAAACAC
AAAGTCTACGCCTGCGAAGTCACCCATCAGGGCCTGAGCTCGCCCGTCACAAAGAGCT
TCAACAGGGGAGAGTGT (SEQ ID NO: 111)

-continued

Amino Acid Sequence
[spacer SEQ ID NO: 178][pLW071 without spacer SEQ ID NO: 186]
QGQSGQ[CISPRGCPDGPYVMY][GSSGGSGGSGGSGGGSGGGSGGS]DILLTQSPVILSVSPG
ERVSFSCRASQSIGTNIHWYQQRTNGSPRLLIKYASESISGIPSRFSGSGSGTDFTLSINSVESE
DIADYYCQQNNNWPTTFGAGTKLELKRTVAAPSVFIFPPSDEQLKSGTASVVCLLNNFYPR
EAKVQWKVDNALQSGNSQESVTEQDSKDSTYSLSSTLTLSKADYEKHKVYACEVTHQGLS
SPVTKSFNRGEC (SEQ ID NO: 112)

CI040: 3954-2001-C225v5N297Q-JF15865-2001-hSP34LvHv-H-N pLW101: HC JF15865-2001-CD3LvHv-C225v5N297Q (H-N)
Nucleotide Sequence
[spacer SEQ ID NO: 176][pLW101 without spacer SEQ ID NO: 187]
CAAGGCCAGTCTGGCCAAATGATGTATTGCGGTGGGAATGAGGTGTTGTGCGGGCCGC
GGGTTGGCTCGAGCGGTGGCAGCGGTGGCTCTGGTGGTATCTCTTCCGGACTGCTGTCC
GGCAGATCCGACAATCACGGCGGCGGTTCTCAGACCGTGGTCACACAGGAGCCCTCAC
TGACAGTGAGCCCTGGCGGGACCGTCACACTGACTTGTCGCAGTTCAACTGGCGCCGT
GACTACCAGCAATTACGCTAACTGGGTCCAGCAGAAACCAGGACAGGCACCACGAGG
ACTGATCGGAGGAACTAATAAGAGAGCACCAGGAACCCCTGCAAGGTTCTCCGGATCT
CTGCTGGGGGGAAAAGCCGCTCTGACACTGAGCGGCGTGCAGCCTGAGGACGAAGCTG
AGTACTATTGCGCACTGTGGTACTCCAACCTGTGGGTGTTTGGCGGGGGAACTAAGCTG
ACCGTCCTGGGAGGAGGAGGAAGCGGAGGAGGAGGGAGCGGAGGAGGAGGATCCGA
AGTGCAGCTGGTCGAGAGCGGAGGAGGACTGGTGCAGCCAGGAGGATCCCTGAAGCT
GTCTTGTGCAGCCAGTGGCTTCACCTTCAACACTTACGCAATGAACTGGGTGCGGCAGG
CACCTGGGAAGGGACTGGAATGGGTCGCCCGGATCAGATCTAAATACAATAACTATGC
CACCTACTATGCTGACAGTGTGAAGGATAGGTTCACCATTTCACGCGACGATAGCAAA
AACACAGCTTATCTGCAGATGAATAACCTGAAGACCGAGGATACAGCAGTGTACTATT
GCGTCAGACACGGCAATTTCGGGAACTCTTACGTGAGTTGGTTTGCCTATTGGGGACAG
GGGACACTGGTCACCGTCTCCTCAGGAGGTGGTGGATCCCAGGTGCAGCTGAAACAGA
GCGGCCCGGGCCTGGTGCAGCCGAGCCAGAGCCTGAGCATTACCTGCACCGTGAGCGG
CTTTAGCCTGACCAACTATGGCGTGCATTGGGTGCGCCAGAGCCCGGGCAAAGGCCTG
GAATGGCTGGGCGTGATTTGGAGCGGCGGCAACACCGATTATAACACCCCGTTTACCA
GCCGCCTGAGCATTAACAAAGATAACAGCAAAAGCCAGGTGTTTTTTAAAATGAACAG
CCTGCAAAGCCAGGATACCGCGATTTATTATTGCGCGCGCGCGCTGACCTATTATGATT
ATGAATTTGCGTATTGGGGCCAGGGCACCCTGGTGACCGTGAGCGCGGCTAGCACCAA
GGGCCCATCGGTCTTCCCCCTGGCACCCTCCTCCAAGAGCACCTCTGGGGGCACAGCGG
CCCTGGGCTGCCTGGTCAAGGACTACTTCCCCGAACCGGTGACGGTGTCGTGGAACTCA
GGCGCCCTGACCAGCGGCGTGCACACCTTCCCGGCTGTCCTACAGTCCTCAGGACTCTA
CTCCCTCAGCAGCGTGGTGACCGTGCCCTCCAGCAGCTTGGGCACCCAGACCTACATCT
GCAACGTGAATCACAAGCCCAGCAACACCAAGGTGGACAAGAAAGTTGAGCCCAAAT
CTTGTGACAAAACTCACACATGCCCACCGTGCCCAGCACCTGAACTCCTGGGGGGACC
GTCAGTCTTCCTCTTCCCCCCAAAACCCAAGGACACCCTCATGATCTCCCGGACCCCTG
AGGTCACATGCGTGGTGGTGGACGTGAGCCACGAAGACCCTGAGGTCAAGTTCAACTG
GTACGTGGACGGCGTGGAGGTGCATAATGCCAAGACAAAGCCGCGGGAGGAGCAGTA
CCAGAGCACGTACCGTGTGGTCAGCGTCCTCACCGTCCTGCACCAGGACTGGCTGAAT
GGCAAGGAGTACAAGTGCAAGGTCTCCAACAAAGCCCTCCCAGCCCCCATCGAGAAAA
CCATCTCCAAAGCCAAAGGGCAGCCCCGAGAACCACAGGTGTACACCCTGCCCCCATC
CCGGGAGGAGATGACCAAGAACCAGGTCAGCCTGACCTGCCTGGTCAAAGGCTTCTAT
CCCAGCGACATCGCCGTGGAGTGGGAGAGCAATGGGCAGCCGGAGAACAACTACAAG
ACCACGCCTCCCGTGCTGGACTCCGACGGCTCCTTCTTCCTCTACAGCAAGCTCACCGT
GGACAAGAGCAGGTGGCAGCAGGGGAACGTCTTCTCATGCTCCGTGATGCATGAGGCT
CTGCACAACCACTACACGCAGAAGAGCCTCTCCCTGTCTCCGGGTAAA (SEQ ID NO:
113)

Amino Acid Sequence
[spacer SEQ ID NO: 178][pLW101 without spacer SEQ ID NO: 188]
QGQSGQ[MMYCGGNEVLCGPRV][GSSGGSGGSGG][ISSGLLSGRSDNH][GGGS]QTVVTQE
PSLTVSPGGTVTLTCRSSTGAVTTSNYANWVQQKPGQAPRGLIGGTNKRAPGTPARFSGSL
LGGKAALTLSGVQPEDEAEYYCALWYSNLWVFGGGTKLTVL[GGGGSGGGGSGGGGS]EV
QLVESGGGLVQPGGSLKLSCAASGFTFNTYAMNWVRQAPGKGLEWVARIRSKYNNYATY
YADSVKDRFTISRDDSKNTAYLQMNNLKTEDTAVYYCVRHGNFGNSYVSWFAYWGQGT
LVTVSS[GGGGS]QVQLKQSGPGLVQPSQSLSITCTVSGFSLTNYGVHWVRQSPGKGLEWL
GVIWSGGNTDYNTPFTSRLSINKDNSKSQVFFKMNSLQSQDTAIYYCARALTYYDYEFAY
WGQGTLVTVSAASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEPKSCDKTHTCPPC
PAPELLGGPSVFLFPPKPKDTLMISRTPEVTCVVVDVSHEDPEVKFNWYVDGVEVHNAKTK
PREEQYQSTYRVVSVLTVLHQDWLNGKEYKCKVSNKALPAPIEKTISKAKGQPREPQVYTL
PPSREEMTKNQVSLTCLVKGFYPSDIAVEWESNGQPENNYKTTPPVLDSDGSFFLYSKLTV
DKSRWQQGNVFSCSVMHEALHNHYTQKSLSLSPGK (SEQ ID NO: 114)

CTX122: LC 3954-2001-C225v5
Nucleotide Sequence
[spacer SEQ ID NO: 180][CTX122 without spacer SEQ ID NO: 189]
CAAGGCCAGTCTGGCCAGTGCATCTCACCTCGTGGTTGTCCGGACGGCCCATACGTCAT
GTACGGCTCGAGCGGTGGCAGCGGTGGCTCTGGTGGATCCGGTATTAGCAGTGGTCTG
TTAAGCGGTCGTAGCGATAATCATGGCAGTAGCGGTACCCAGATCTTGCTGACCCAGA
GCCCGGTGATTCTGAGCGTGAGCCCGGGCGAACGTGTGAGCTTTAGCTGCCGCGCGAG
CCAGAGCATTGGCACCAACATTCATTGGTATCAGCAGCGCACCAACGGCAGCCCGCGC -continued CTGCTGATTAAATATGCGAGCGAAAGCATTAGCGGCATTCCGAGCCGCTTTAGCGGCA
GCGGCAGCGGCACCGATTTTACCCTGAGCATTAACAGCGTGGAAAGCGAAGATATTGC
GGATTATTATTGCCAGCAGAACAACAACTGGCCGACCACCTTTGGCGCGGGCACCAAA
CTGGAACTGAAACGTACGGTGGCTGCACCATCTGTCTTCATCTTCCCGCCATCTGATGA
GCAGTTGAAATCTGGAACTGCCTCTGTTGTGTGCCTGCTGAATAACTTCTATCCCAGAG
AGGCCAAAGTACAGTGGAAGGTGGATAACGCCCTCCAATCGGGTAACTCCCAGGAGAG
TGTCACAGAGCAGGACAGCAAGGACAGCACCTACAGCCTCAGCAGCACCCTGACGCTG
AGCAAAGCAGACTACGAGAAACACAAAGTCTACGCCTGCGAAGTCACCCATCAGGGCC
TGAGCTCGCCCGTCACAAAGAGCTTCAACAGGGGAGAGTGT (SEQ ID NO: 115)

Amino Acid Sequence
[spacer SEQ ID NO: 178][CTX122 without spacer SEQ ID NO: 190]
QGQSGQ[CISPRGCPDGPYVMY][GSSGGSGGSGGSG][ISSGLLSGRSDNH][GSSGT]QILLTQ
SPVILSVSPGERVSFSCRASQSIGTNIHWYQQRTNGSPRLLIKYASESISGIPSRFSGSGSGTDF
TLSINSVESEDIADYYCQQNNNWPTTFGAGTKLELKRTVAAPSVFIFPPSDEQLKSGTASVV
CLLNNFYPREAKVQWKVDNALQSGNSQESVTEQDSKDSTYSLSSTLTLSKADYEKHKVYA
CEVTHQGLSSPVTKSFNRGEC (SEQ ID NO: 116)

CI048: Activated CI011: 3954-0001-C225v5N2970-JF15865-0001-CD3LvHv-H-N pLW023 and OPP022 sequences encoding corresponding masked antibody components are provided herein as “pLW023” and “OPP022, respectively and are summarized in Table 11. Activated pLW023: HC JF15865-0001-CD3LvHv-C225v5N297Q (H-N)

Nucleotide Sequence
TCCGATAATCATGGCGGCGGTTCTCAGACCGTGGTCACACAGGAGCCCTCACT
GACAGTGAGCCCTGGCGGGACCGTCACACTGACTTGTCGCAGTTCAACTGGCGCCGTG
ACTACCAGCAATTACGCTAACTGGGTCCAGCAGAAACCAGGACAGGCACCACGAGGAC
TGATCGGAGGAACTAATAAGAGAGCACCAGGAACCCCTGCAAGGTTCTCCGGATCTCT
GCTGGGGGGAAAAGCCGCTCTGACACTGAGCGGCGTGCAGCCTGAGGACGAAGCTGA
GTACTATTGCGCACTGTGGTACTCCAACCTGTGGGTGTTTGGCGGGGGAACTAAGCTGA
CCGTCCTGGGAGGAGGAGGAAGCGGAGGAGGAGGGAGCGGAGGAGGAGGATCCGAA
GTGCAGCTGGTCGAGAGCGGAGGAGGACTGGTGCAGCCAGGAGGATCCCTGAAGCTGT
CTTGTGCAGCCAGTGGCTTCACCTTCAACACTTACGCAATGAACTGGGTGCGGCAGGCA
CCTGGGAAGGGACTGGAATGGGTCGCCCGGATCAGATCTAAATACAATAACTATGCCA
CCTACTATGCTGACAGTGTGAAGGATAGGTTCACCATTTCACGCGACGATAGCAAAAA
CACAGCTTATCTGCAGATGAATAACCTGAAGACCGAGGATACAGCAGTGTACTATTGC
GTCAGACACGGCAATTTCGGGAACTCTTACGTGAGTTGGTTTGCCTATTGGGGACAGGG
GACACTGGTCACCGTCTCCTCAGGAGGTGGTGGATCCCAGGTGCAGCTGAAACAGAGC
GGCCCGGGCCTGGTGCAGCCGAGCCAGAGCCTGAGCATTACCTGCACCGTGAGCGGCT
TTAGCCTGACCAACTATGGCGTGCATTGGGTGCGCCAGAGCCCGGGCAAAGGCCTGGA
ATGGCTGGGCGTGATTTGGAGCGGCGGCAACACCGATTATAACACCCCGTTTACCAGC
CGCCTGAGCATTAACAAAGATAACAGCAAAAGCCAGGTGTTTTTTAAAATGAACAGCC
TGCAAAGCCAGGATACCGCGATTTATTATTGCGCGCGCGCGCTGACCTATTATGATTAT
GAATTTGCGTATTGGGGCCAGGGCACCCTGGTGACCGTGAGCGCGGCTAGCACCAAGG
GCCCATCGGTCTTCCCCCTGGCACCCTCCTCCAAGAGCACCTCTGGGGGCACAGCGGCC
CTGGGCTGCCTGGTCAAGGACTACTTCCCCGAACCGGTGACGGTGTCGTGGAACTCAG
GCGCCCTGACCAGCGGCGTGCACACCTTCCCGGCTGTCCTACAGTCCTCAGGACTCTAC
TCCCTCAGCAGCGTGGTGACCGTGCCCTCCAGCAGCTTGGGCACCCAGACCTACATCTG
CAACGTGAATCACAAGCCCAGCAACACCAAGGTGGACAAGAAAGTTGAGCCCAAATCT
TGTGACAAAACTCACACATGCCCACCGTGCCCAGCACCTGAACTCCTGGGGGGACCGT
CAGTCTTCCTCTTCCCCCCAAAACCCAAGGACACCCTCATGATCTCCCGGACCCCTGAG
GTCACATGCGTGGTGGTGGACGTGAGCCACGAAGACCCTGAGGTCAAGTTCAACTGGT
ACGTGGACGGCGTGGAGGTGCATAATGCCAAGACAAAGCCGCGGGAGGAGCAGTACC
AGAGCACGTACCGTGTGGTCAGCGTCCTCACCGTCCTGCACCAGGACTGGCTGAATGG
CAAGGAGTACAAGTGCAAGGTCTCCAACAAAGCCCTCCCAGCCCCCATCGAGAAAACC
ATCTCCAAAGCCAAAGGGCAGCCCCGAGAACCACAGGTGTACACCCTGCCCCCATCCC
GGGAGGAGATGACCAAGAACCAGGTCAGCCTGACCTGCCTGGTCAAAGGCTTCTATCC
CAGCGACATCGCCGTGGAGTGGGAGAGCAATGGGCAGCCGGAGAACAACTACAAGAC
CACGCCTCCCGTGCTGGACTCCGACGGCTCCTTCTTCCTCTACAGCAAGCTCACCGTGG
ACAAGAGCAGGTGGCAGCAGGGGAACGTCTTCTCATGCTCCGTGATGCATGAGGCTCT
GCACAACCACTACACGCAGAAGAGCCTCTCCCTGTCTCCGGGTAAA (SEQ ID NO: 117)

Amino Acid Sequence
[SDNH][GGGS]QTVVTQEPSLTVSPGGTVTLTCRSSTGAVTTSNYANWVQQKPGQAPRGLI
GGTNKRAPGTPARFSGSLLGGKAALTLSGVQPEDEAEYYCALWYSNLWVFGGGTKLTVL[
GGGGSGGGGSGGGGS]EVQLVESGGGLVQPGGSLKLSCAASGFTFNTYAMNWVRQAPGK
GLEWVARIRSKYNNYATYYADSVKDRFTISRDDSKNTAYLQMNNLKTEDTAVYYCVRHG
NFGNSYVSWFAYWGQGTLVTVSS[GGGGS]QVQLKQSGPGLVQPSQSLSITCTVSGFSLTNY
GVHWVRQSPGKGLEWLGVIWSGGNTDYNTPFTSRLSINKDNSKSQVFFKMNSLQSQDTAI
YYCARALTYYDYEFAYWGQGTLVTVSAASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVD
KKVEPKSCDKTHTCPPCPAPELLGGPSVFLFPPKPKDTLMISRTPEVTCVVVDVSHEDPEVK
FNWYVDGVEVHNAKTKPREEQYQSTYRVVSVLTVLHQDWLNGKEYKCKVSNKALPAPIE
KTISKAKGQPREPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLSPGK (SEQ ID NO: 118)

-continued

Activated OPP022: LC 3954-0001-C225v5
Nucleotide Sequence
TCCGATAATCATGGCAGTAGCGGTACCCAGATCTTGCTGACCCAGAGCCCGGT
GATTCTGAGCGTGAGCCCGGGCGAACGTGTGAGCTTTAGCTGCCGCGCGAGCCAGAGC
ATTGGCACCAACATTCATTGGTATCAGCAGCGCACCAACGGCAGCCCGCGCCTGCTGA
TTAAATATGCGAGCGAAAGCATTAGCGGCATTCCGAGCCGCTTTAGCGGCAGCGGCAG
CGGCACCGATTTTACCCTGAGCATTAACAGCGTGGAAAGCGAAGATATTGCGGATTAT
TATTGCCAGCAGAACAACAACTGGCCGACCACCTTTGGCGCGGGCACCAAACTGGAAC
TGAAACGTACGGTGGCTGCACCATCTGTCTTCATCTTCCCGCCATCTGATGAGCAGTTG
AAATCTGGAACTGCCTCTGTTGTGTGCCTGCTGAATAACTTCTATCCCAGAGAGGCCAA
AGTACAGTGGAAGGTGGATAACGCCCTCCAATCGGGTAACTCCCAGGAGAGTGTCACA
GAGCAGGACAGCAAGGACAGCACCTACAGCCTCAGCAGCACCCTGACGCTGAGCAAA
GCAGACTACGAGAAACACAAAGTCTACGCCTGCGAAGTCACCCATCAGGGCCTGAGCT
CGCCCGTCACAAAGAGCTTCAACAGGGGAGAGTGT (SEQ ID NO: 119)

Amino Acid Sequence
[SDNH][GSSGT]QILLTQSPVILSVSPGERVSFSCRASQSIGTNIHWYQQRTNGSPRLLIKYASE
SISGIPSRFSGSGSGTDFTLSINSVESEDIADYYCQQNNNWPTTFGAGTKLELKRTVAAPSVFI
FPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC (SEQ ID NO: 120)

CI079: 3954-0001-C225v5Fcmt3-h20GG-0001-v16sc-H-N pLW225: HC h20GG-0001-v16sc-C225v5Fcmt3 (H-N)
Nucleotide Sequence
[spacer SEQ ID NO: 191][pLW225_without spacer SEQ ID NO: 192]
CAAGGCCAGTCTGGATCCGGTTATCTGTGGGGTTGCGAGTGGAATTGCGGAGGGATCA
CTACAGGCTCGAGCGGTGGCAGCGGTGGCTCTGGTGGTCTGAGCGGCCGTTCCGATAA
TCATGGCGGCGGTTCTCAAACTGTAGTAACTCAAGAACCAAGCTTCTCCGTCTCCCCTG
GGGGAACAGTCACACTTACCTGCCGAAGTAGTACAGGTGCTGTTACGACCAGTAACTA
TGCCAATTGGGTACAACAAACGCCTGGTCAGGCTCCGCGCGGATTGATAGGAGGCACG
AATAAACGGGCACCCGGTGTCCCGGACAGATTCAGCGGAAGCATACTCGGTAATAAGG
CAGCTCTTACTATCACTGGGGCCCAAGCTGATGATGAAAGTGATTATTATTGTGCGCTC
TGGTACAGCAACCTCTGGGTGTTTGGGGGTGGCACGAAACTTACTGTCTTGGGCGGCG
GCGGATCAGGGGGAGGTGGCTCTGGAGGAGGAGGCTCAGAAGTCCAACTGGTCGAAT
CCGGGGGAGGGCTCGTACAGCCGGGTGGGTCCCTCAAACTCTCTTGTGCGGCCTCAGG
GTTTACCTTCAGTACATACGCGATGAATTGGGTCCGGCAGGCCAGTGGGAAAGGGCTC
GAATGGGTAGGACGAATCCGATCAAAATACAACAACTACGCTACTTATTACGCTGATT
CCGTGAAGGACAGATTCACAATATCCCGCGACGATAGCAAGAATACGGCATATCTTCA
GATGAATTCTCTTAAAACTGAGGATACCGCTGTGTATTACTGCACAAGACATGGTAATT
TTGGAAACTCATATGTCTCTTGGTTCGCTTATTGGGGACAGGGCACGTTGGTTACCGTG
TCTAGCGGAGGTGGTGGATCCCAGGTGCAGCTGAAACAGAGCGGCCCGGGCCTGGTGC
AGCCGAGCCAGAGCCTGAGCATTACCTGCACCGTGAGCGGCTTTAGCCTGACCAACTA
TGGCGTGCATTGGGTGCGCCAGAGCCCGGGCAAAGGCCTGGAATGGCTGGGCGTGATT
TGGAGCGGCGGCAACACCGATTATAACACCCCGTTTACCAGCCGCCTGAGCATTAACA
AAGATAACAGCAAAAGCCAGGTGTTTTTTAAAATGAACAGCCTGCAAAGCCAGGATAC
CGCGATTTATTATTGCGCGCGCGCGCTGACCTATTATGATTATGAATTTGCGTATTGGG
GCCAGGGCACCCTGGTGACCGTGAGCGCGGCTAGCACCAAGGGCCCATCGGTCTTCCC
CCTGGCACCCTCCTCCAAGAGCACCTCTGGGGGCACAGCGGCCCTGGGCTGCCTGGTC
AAGGACTACTTCCCCGAACCGGTGACGGTGTCGTGGAACTCAGGCGCCCTGACCAGCG
GCGTGCACACCTTCCCGGCTGTCCTACAGTCCTCAGGACTCTACTCCCTCAGCAGCGTG
GTGACCGTGCCCTCCAGCAGCTTGGGCACCCAGACCTACATCTGCAACGTGAATCACA
AGCCCAGCAACACCAAGGTGGACAAGAAAGTTGAGCCCAAATCTTGTGACAAAACTCA
CACATGCCCACCGTGCCCAGCACCTGAATTTGAAGGGGGACCGTCAGTCTTCCTCTTCC
CCCCAAAACCCAAGGACACCCTCATGATCTCCCGGACCCCTGAGGTCACATGCGTGGT
GGTGGACGTGAGCCACGAAGACCCTGAGGTCAAGTTCAACTGGTACGTGGACGGCGTG
GAGGTGCATAATGCCAAGACAAAGCCGCGGGAGGAGCAGTACAATAGCACGTACCGT
GTGGTCAGCGTCCTCACCGTCCTGCACCAGGACTGGCTGAATGGCAAGGAGTACAAGT
GCAAGGTCTCCAACAAAGCCCTCCCAGCCTCAATCGAGAAAACCATCTCCAAAGCCAA
AGGGCAGCCCCGAGAACCACAGGTGTACACCCTGCCCCCATCCCGGGAGGAGATGACC
AAGAACCAGGTCAGCCTGACCTGCCTGGTCAAAGGCTTCTATCCCAGCGACATCGCCG
TGGAGTGGGAGAGCAATGGGCAGCCGGAGAACAACTACAAGACCACGCCTCCCGTGCT
GGACTCCGACGGCTCCTTCTTCCTCTACAGCAAGCTCACCGTGGACAAGAGCAGGTGG
CAGCAGGGGAACGTCTTCTCATGCTCCGTGATGCATGAGGCTCTGCACAACCACTACAC
GCAGAAGAGCCTCTCCCTGTCTCCGGGTAAATGA (SEQ ID NO: 121)

Amino Acid Sequence
[spacer SEQ ID NO: 178][pLW225 without spacer SEQ ID NO: 193]
QGQSGS[GYLWGCEWNCGGITT][GSSGGSGGSGG][LSGRSDNH][GGGS]QTVVTQEPSFSV
SPGGTVTLTCRSSTGAVTTSNYANWVQQTPGQAPRGLIGGTNKRAPGVPDRFSGSILGNKA
ALTITGAQADDESDYYCALWYSNLWVFGGGTKLTVL[GGGGSGGGGSGGGGS]EVQLVES
GGGLVQPGGSLKLSCAASGFTFSTYAMNWVRQASGKGLEWVGRIRSKYNNYATYYADSV
KDRFTISRDDSKNTAYLQMNSLKTEDTAVYYCTRHGNFGNSYVSWFAYWGQGTLVTVSS
[GGGGS]QVQLKQSGPGLVQPSQSLSITCTVSGFSLTNYGVHWVRQSPGKGLEWLGVIWSGG
NTDYNTPFTSRLSINKDNSKSQVFFKMNSLQSQDTAIYYCARALTYYDYEFAYWGQGTLV
TVSAASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPPCPAPEFEG
GPSVFLFPPKPKDTLMISRTPEVTCVVVDVSHEDPEVKFNWYVDGVEVHNAKTKPREEQY -continued NSTYRVVSVLTVLHQDWLNGKEYKCKVSNKALPASIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGK (SEQ ID NO: 122)

OPP022: LC 3954-0001-C225v5
Sequences provided above

CI090: 3954-0001-C225v5Fcmt4-h20GG-0001-v16sc-H-N pLW233: HC h20GG-0001-v16sc-C225v5Fcmt4 (H-N)
Nucleotide Sequence
[spacer SEQ ID NO: 191][pLW233_without spacer SEQ ID NO: 194]
CAAGGCCAGTCTGGATCCGGTTATCTGTGGGGTTGCGAGTGGAATTGCGGAGGGATCA
CTACAGGCTCGAGCGGTGGCAGCGGTGGCTCTGGTGGTCTGAGCGGCCGTTCCGATAA
TCATGGCGGCGGTTCTCAAACTGTAGTAACTCAAGAACCAAGCTTCTCCGTCTCCCCTG
GGGGAACAGTCACACTTACCTGCCGAAGTAGTACAGGTGCTGTTACGACCAGTAACTA
TGCCAATTGGGTACAACAAACGCCTGGTCAGGCTCCGCGCGGATTGATAGGAGGCACG
AATAAACGGGCACCCGGTGTCCCGGACAGATTCAGCGGAAGCATACTCGGTAATAAGG
CAGCTCTTACTATCACTGGGGCCCAAGCTGATGATGAAAGTGATTATTATTGTGCGCTC
TGGTACAGCAACCTCTGGGTGTTTGGGGGTGGCACGAAACTTACTGTCTTGGGCGGCG
GCGGATCAGGGGGAGGTGGCTCTGGAGGAGGAGGCTCAGAAGTCCAACTGGTCGAAT
CCGGGGGAGGGCTCGTACAGCCGGGTGGGTCCCTCAAACTCTCTTGTGCGGCCTCAGG
GTTTACCTTCAGTACATACGCGATGAATTGGGTCCGGCAGGCCAGTGGGAAAGGGCTC
GAATGGGTAGGACGAATCCGATCAAAATACAACAACTACGCTACTTATTACGCTGATT
CCGTGAAGGACAGATTCACAATATCCCGCGACGATAGCAAGAATACGGCATATCTTCA
GATGAATTCTCTTAAAACTGAGGATACCGCTGTGTATTACTGCACAAGACATGGTAATT
TTGGAAACTCATATGTCTCTTGGTTCGCTTATTGGGGACAGGGCACGTTGGTTACCGTG
TCTAGCGGAGGTGGTGGATCCCAGGTGCAGCTGAAACAGAGCGGCCCGGGCCTGGTGC
AGCCGAGCCAGAGCCTGAGCATTACCTGCACCGTGAGCGGCTTTAGCCTGACCAACTA
TGGCGTGCATTGGGTGCGCCAGAGCCCGGGCAAAGGCCTGGAATGGCTGGGCGTGATT
TGGAGCGGCGGCAACACCGATTATAACACCCCGTTTACCAGCCGCCTGAGCATTAACA
AAGATAACAGCAAAAGCCAGGTGTTTTTTAAAATGAACAGCCTGCAAAGCCAGGATAC
CGCGATTTATTATTGCGCGCGCGCGCTGACCTATTATGATTATGAATTTGCGTATTGGG
GCCAGGGCACCCTGGTGACCGTGAGCGCGGCTAGCACCAAGGGCCCATCGGTCTTCCC
CCTGGCACCCTCCTCCAAGAGCACCTCTGGGGGCACAGCGGCCCTGGGCTGCCTGGTC
AAGGACTACTTCCCCGAACCGGTGACGGTGTCGTGGAACTCAGGCGCCCTGACCAGCG
GCGTGCACACCTTCCCGGCTGTCCTACAGTCCTCAGGACTCTACTCCCTCAGCAGCGTG
GTGACCGTGCCCTCCAGCAGCTTGGGCACCCAGACCTACATCTGCAACGTGAATCACA
AGCCCAGCAACACCAAGGTGGACAAGAAAGTTGAGCCCAAATCTTGTGACAAAACTCA
CACATGCCCACCGTGCCCAGCACCTGAATTTGAAGGGGGACCGTCAGTCTTCCTCTTCC
CCCCAAAACCCAAGGACACCCTCATGATCTCCCGGACCCCTGAGGTCACATGCGTGGT
GGTGGACGTGAGCCACGAAGACCCTGAGGTCAAGTTCAACTGGTACGTGGACGGCGTG
GAGGTGCATAATGCCAAGACAAAGCCGCGGGAGGAGCAGTACCAGAGCACGTACCGT
GTGGTCAGCGTCCTCACCGTCCTGCACCAGGACTGGCTGAATGGCAAGGAGTACAAGT
GCAAGGTCTCCAACAAAGCCCTCCCAGCCTCAATCGAGAAAACCATCTCCAAAGCCAA
AGGGCAGCCCCGAGAACCACAGGTGTACACCCTGCCCCCATCCCGGGAGGAGATGACC
AAGAACCAGGTCAGCCTGACCTGCCTGGTCAAAGGCTTCTATCCCAGCGACATCGCCG
TGGAGTGGGAGAGCAATGGGCAGCCGGAGAACAACTACAAGACCACGCCTCCCGTGCT
GGACTCCGACGGCTCCTTCTTCCTCTACAGCAAGCTCACCGTGGACAAGAGCAGGTGG
CAGCAGGGGAACGTCTTCTCATGCTCCGTGATGCATGAGGCTCTGCACAACCACTACAC
GCAGAAGAGCCTCTCCCTGTCTCCGGGTAAATGA (SEQ ID NO: 123)

Amino Acid Sequence
[spacer SEQ ID NO: 178][pLW233 without spacer SEQ ID NO: 195]
QGQSGS[GYLWGCEWNCGGITT][GSSGGSGGSGG][LSGRSDNH][GGGS]QTVVTQEPSFSV
SPGGTVTLTCRSSTGAVTTSNYANWVQQTPGQAPRGLIGGTNKRAPGVPDRFSGSILGNKA
ALTITGAQADDESDYYCALWYSNLWVFGGGTKLTVL[GGGGSGGGGSGGGGS]EVQLVES
GGGLVQPGGSLKLSCAASGFTFSTYAMNWVRQASGKGLEWVGRIRSKYNNYATYYADSV
KDRFTISRDDSKNTAYLQMNSLKTEDTAVYYCTRHGNFGNSYVSWFAYWGQGTLVTVSS
[GGGGS]QVQLKQSGPGLVQPSQSLSITCTVSGFSLTNYGVHWVRQSPGKGLEWLGVIWSGG
NTDYNTPFTSRLSINKDNSKSQVFFKMNSLQSQDTAIYYCARALTYYDYEFAYWGQGTLV
TVSAASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPPCPAPEFEG
GPSVFLFPPKPKDTLMISRTPEVTCVVVDVSHEDPEVKFNWYVDGVEVHNAKTKPREEQY
QSTYRVVSVLTVLHQDWLNGKEYKCKVSNKALPASIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGK (SEQ ID NO: 124)

OPP022: LC 3954-0001-C225v5
Sequences provided above

Activated CI090: Activated-3954-0001-C225v5Fcmt4-h20GG-0001-v16sc-H-N

Activated pLW233: HC C225v5Fcmt4-h20GG-0001-v16sc (H-N)
Nucleic Acid Sequence
TCCGATAATCATGGCGGCGGTTCTCAAACTGTAGTAACTCAAGAACCAAGCTTCTCCGT
CTCCCCTGGGGGAACAGTCACACTTACCTGCCGAAGTAGTACAGGTGCTGTTACGACC
AGTAACTATGCCAATTGGGTACAACAAACGCCTGGTCAGGCTCCGCGCGGATTGATAG
GAGGCACGAATAAACGGGCACCCGGTGTCCCGGACAGATTCAGCGGAAGCATACTCGG -continued TAATAAGGCAGCTCTTACTATCACTGGGGCCCAAGCTGATGATGAAAGTGATTATTATT
GTGCGCTCTGGTACAGCAACCTCTGGGTGTTTGGGGGTGGCACGAAACTTACTGTCTTG
GGCGGCGGCGGATCAGGGGGAGGTGGCTCTGGAGGAGGAGGCTCAGAAGTCCAACTG
GTCGAATCCGGGGGAGGGCTCGTACAGCCGGGTGGGTCCCTCAAACTCTCTTGTGCGG
CCTCAGGGTTTACCTTCAGTACATACGCGATGAATTGGGTCCGGCAGGCCAGTGGGAA
AGGGCTCGAATGGGTAGGACGAATCCGATCAAAATACAACAACTACGCTACTTATTAC
GCTGATTCCGTGAAGGACAGATTCACAATATCCCGCGACGATAGCAAGAATACGGCAT
ATCTTCAGATGAATTCTCTTAAAACTGAGGATACCGCTGTGTATTACTGCACAAGACAT
GGTAATTTTGGAAACTCATATGTCTCTTGGTTCGCTTATTGGGGACAGGGCACGTTGGT
TACCGTGTCTAGCGGAGGTGGTGGATCCCAGGTGCAGCTGAAACAGAGCGGCCCGGGC
CTGGTGCAGCCGAGCCAGAGCCTGAGCATTACCTGCACCGTGAGCGGCTTTAGCCTGA
CCAACTATGGCGTGCATTGGGTGCGCCAGAGCCCGGGCAAAGGCCTGGAATGGCTGGG
CGTGATTTGGAGCGGCGGCAACACCGATTATAACACCCCGTTTACCAGCCGCCTGAGC
ATTAACAAAGATAACAGCAAAAGCCAGGTGTTTTTTAAAATGAACAGCCTGCAAAGCC
AGGATACCGCGATTTATTATTGCGCGCGCGCGCTGACCTATTATGATTATGAATTTGCG
TATTGGGGCCAGGGCACCCTGGTGACCGTGAGCGCGGCTAGCACCAAGGGCCCATCGG
TCTTCCCCCTGGCACCCTCCTCCAAGAGCACCTCTGGGGGCACAGCGGCCCTGGGCTGC
CTGGTCAAGGACTACTTCCCCGAACCGGTGACGGTGTCGTGGAACTCAGGCGCCCTGA
CCAGCGGCGTGCACACCTTCCCGGCTGTCCTACAGTCCTCAGGACTCTACTCCCTCAGC
AGCGTGGTGACCGTGCCCTCCAGCAGCTTGGGCACCCAGACCTACATCTGCAACGTGA
ATCACAAGCCCAGCAACACCAAGGTGGACAAGAAAGTTGAGCCCAAATCTTGTGACAA
AACTCACACATGCCCACCGTGCCCAGCACCTGAATTTGAAGGGGGACCGTCAGTCTTCC
TCTTCCCCCCAAAACCCAAGGACACCCTCATGATCTCCCGGACCCCTGAGGTCACATGC
GTGGTGGTGGACGTGAGCCACGAAGACCCTGAGGTCAAGTTCAACTGGTACGTGGACG
GCGTGGAGGTGCATAATGCCAAGACAAAGCCGCGGGAGGAGCAGTACCAGAGCACGT
ACCGTGTGGTCAGCGTCCTCACCGTCCTGCACCAGGACTGGCTGAATGGCAAGGAGTA
CAAGTGCAAGGTCTCCAACAAAGCCCTCCCAGCCTCAATCGAGAAAACCATCTCCAAA
GCCAAAGGGCAGCCCCGAGAACCACAGGTGTACACCCTGCCCCCATCCCGGGAGGAGA
TGACCAAGAACCAGGTCAGCCTGACCTGCCTGGTCAAAGGCTTCTATCCCAGCGACAT
CGCCGTGGAGTGGGAGAGCAATGGGCAGCCGGAGAACAACTACAAGACCACGCCTCC
CGTGCTGGACTCCGACGGCTCCTTCTTCCTCTACAGCAAGCTCACCGTGGACAAGAGCA
GGTGGCAGCAGGGGAACGTCTTCTCATGCTCCGTGATGCATGAGGCTCTGCACAACCA
CTACACGCAGAAGAGCCTCTCCCTGTCTCCGGGTAAA (SEQ ID NO: 164

Amino Acid Sequence
[SDNH]GGGSQTVVTQEPSFSVSPGGTVTLTCRSSTGAVTTSNYANWVQQTPGQAPRGLIGG
TNKRAPGVPDRFSGSILGNKAALTITGAQADDESDYYCALWYSNLWVFGGGTKLTVLGGG
GSGGGGSGGGGSEVQLVESGGGLVQPGGSLKLSCAASGFTFSTYAMNWVRQASGKGLEW
VGRIRSKYNNYATYYADSVKDRFTISRDDSKNTAYLQMNSLKTEDTAVYYCTRHGNFGNS
YVSWFAYWGQGTLVTVSSGGGGSQVQLKQSGPGLVQPSQSLSITCTVSGFSLTNYGVHWV
RQSPGKGLEWLGVIWSGGNTDYNTPFTSRLSINKDNSKSQVFFKMNSLQSQDTAIYYCARA
LTYYDYEFAYWGQGTLVTVSAASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKVDKKVEPK
SCDKTHTCPPCPAPEFEGGPSVFLFPPKPKDTLMISRTPEVTCVVVDVSHEDPEVKFNWYVD
GVEVHNAKTKPREEQYQSTYRVVSVLTVLHQDWLNGKEYKCKVSNKALPASIEKTISKAK
GQPREPQVYTLPPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPGK (SEQ ID NO: 165)

Activated OPP022: 3954-0001-C225v5
Nucleic Acid Sequence
TCCGATAATCATGGCAGTAGCGGTACCCAGATCTTGCTGACCCAGAGCCCGGTGATTCT
GAGCGTGAGCCCGGGCGAACGTGTGAGCTTTAGCTGCCGCGCGAGCCAGAGCATTGGC
ACCAACATTCATTGGTATCAGCAGCGCACCAACGGCAGCCCGCGCCTGCTGATTAAAT
ATGCGAGCGAAAGCATTAGCGGCATTCCGAGCCGCTTTAGCGGCAGCGGCAGCGGCAC
CGATTTTACCCTGAGCATTAACAGCGTGGAAAGCGAAGATATTGCGGATTATTATTGCC
AGCAGAACAACAACTGGCCGACCACCTTTGGCGCGGGCACCAAACTGGAACTGAAACG
TACGGTGGCTGCACCATCTGTCTTCATCTTCCCGCCATCTGATGAGCAGTTGAAATCTG
GAACTGCCTCTGTTGTGTGCCTGCTGAATAACTTCTATCCCAGAGAGGCCAAAGTACAG
TGGAAGGTGGATAACGCCCTCCAATCGGGTAACTCCCAGGAGAGTGTCACAGAGCAGG
ACAGCAAGGACAGCACCTACAGCCTCAGCAGCACCCTGACGCTGAGCAAAGCAGACTA
CGAGAAACACAAAGTCTACGCCTGCGAAGTCACCCATCAGGGCCTGAGCTCGCCCGTC
ACAAAGAGCTTCAACAGGGGAGAGTGT (SEQ ID NO: 166)

Amino Acid Sequence
[SDNH]GSSGTQILLTQSPVILSVSPGERVSFSCRASQSIGTNIHWYQQRTNGSPRLLIKYASES
ISGIPSRFSGSGSGTDFTLSINSVESEDIADYYCQQNNNWPTTFGAGTKLELKRTVAAPSVFIF
PPSDEQLKSGTASVVCLLNNFYPREAKVQWKVDNALQSGNSQESVTEQDSKDSTYSLSSTL
TLSKADYEKHKVYACEVTHQGLSSPVTKSFNRGEC (SEQ ID NO: 167)

CI104: 3954-0011-C225v5Fcmt4-h20GG-0011-v16sc-H-N pLW289 and pLW291 sequences encoding corresponding masked antibody components are provided herein as "pLW289" and "pLW291", respectively and are summarized in Table 11.

-continued

| Activated CI104: 3954-0011-C225v5Fcmt4-h20GG-0011-v16sc-H-N |
|---|

Activated pLW289: HC h20GG-0011-v16sc-C225v5Fcmt4 (H-N)
Nucleotide Sequence
TCCGATGATCATGGCGGCGGTTCTCAAACTGTAGTAACTCAAGAACCAAGCTTCTCCGT
CTCCCCTGGGGGAACAGTCACACTTACCTGCCGAAGTAGTACAGGTGCTGTTACGACC
AGTAACTATGCCAATTGGGTACAACAAACGCCTGGTCAGGCTCCGCGCGGATTGATAG
GAGGCACGAATAAACGGGCACCCGGTGTCCCGGACAGATTCAGCGGAAGCATACTCGG
TAATAAGGCAGCTCTTACTATCACTGGGGCCCAAGCTGATGATGAAAGTGATTATTATT
GTGCGCTCTGGTACAGCAACCTCTGGGTGTTTGGGGGTGGCACGAAACTTACTGTCTTG
GGCGGCGGCGGATCAGGGGGAGGTGGCTCTGGAGGAGGAGGCTCAGAAGTCCAACTG
GTCGAATCCGGGGGAGGGCTCGTACAGCCGGGTGGGTCCCTCAAACTCTCTTGTGCGG
CCTCAGGGTTTACCTTCAGTACATACGCGATGAATTGGGTCCGGCAGGCCAGTGGGAA
AGGGCTCGAATGGGTAGGACGAATCCGATCAAAATACAACAACTACGCTACTTATTAC
GCTGATTCCGTGAAGGACAGATTCACAATATCCCGCGACGATAGCAAGAATACGGCAT
ATCTTCAGATGAATTCTCTTAAAACTGAGGATACCGCTGTGTATTACTGCACAAGACAT
GGTAATTTTGGAAACTCATATGTCTCTTGGTTCGCTTATTGGGGACAGGGCACGTTGGT
TACCGTGTCTAGCGGAGGTGGTGGATCCCAGGTGCAGCTGAAACAGAGCGGCCCGGGC
CTGGTGCAGCCGAGCCAGAGCCTGAGCATTACCTGCACCGTGAGCGGCTTTAGCCTGA
CCAACTATGGCGTGCATTGGGTGCGCCAGAGCCCGGGCAAAGGCCTGGAATGGCTGGG
CGTGATTTGGAGCGGCGGCAACACCGATTATAACACCCCGTTTACCAGCCGCCTGAGC
ATTAACAAAGATAACAGCAAAAGCCAGGTGTTTTTTAAAATGAACAGCCTGCAAAGCC
AGGATACCGCGATTTATTATTGCGCGCGCGCGCTGACCTATTATGATTATGAATTTGCG
TATTGGGGCCAGGGCACCCTGGTGACCGTGAGCGCGGCTAGCACCAAGGGCCCATCGG
TCTTCCCCCTGGCACCCTCCTCCAAGAGCACCTCTGGGGGCACAGCGGCCCTGGGCTGC
CTGGTCAAGGACTACTTCCCCGAACCGGTGACGGTGTCGTGGAACTCAGGCGCCCTGA
CCAGCGGCGTGCACACCTTCCCGGCTGTCCTACAGTCCTCAGGACTCTACTCCCTCAGC
AGCGTGGTGACCGTGCCCTCCAGCAGCTTGGGCACCCAGACCTACATCTGCAACGTGA
ATCACAAGCCCAGCAACACCAAGGTGGACAAGAAAGTTGAGCCCAAATCTTGTGACAA
AACTCACACATGCCCACCGTGCCCAGCACCTGAATTTGAAGGGGGACCGTCAGTCTTCC
TCTTCCCCCCAAAACCCAAGGACACCCTCATGATCTCCCGGACCCCTGAGGTCACATGC
GTGGTGGTGGACGTGAGCCACGAAGACCCTGAGGTCAAGTTCAACTGGTACGTGGACG
GCGTGGAGGTGCATAATGCCAAGACAAAGCCGCGGGAGGAGCAGTACCAGAGCACGT
ACCGTGTGGTCAGCGTCCTCACCGTCCTGCACCAGGACTGGCTGAATGGCAAGGAGTA
CAAGTGCAAGGTCTCCAACAAAGCCCTCCCAGCCTCAATCGAGAAAACCATCTCCAAA
GCCAAAGGGCAGCCCCGAGAACCACAGGTGTACACCCTGCCCCCATCCCGGGAGGAGA
TGACCAAGAACCAGGTCAGCCTGACCTGCCTGGTCAAAGGCTTCTATCCCAGCGACAT
CGCCGTGGAGTGGGAGAGCAATGGGCAGCCGGAGAACAACTACAAGACCACGCCTCC
CGTGCTGGACTCCGACGGCTCCTTCTTCCTCTACAGCAAGCTCACCGTGGACAAGAGCA
GGTGGCAGCAGGGGAACGTCTTCTCATGCTCCGTGATGCATGAGGCTCTGCACAACCA
CTACACGCAGAAGAGCCTCTCCCTGTCTCCGGGTAAA (SEQ ID NO: 125)

Amino Acid Sequence
[SDDH][GGGS]QTVVTQEPSFSVSPGGTVTLTCRSSTGAVTTSNYANWVQQTPGQAPRGLIG
GTNKRAPGVPDRFSGSILGNKAALTITGAQADDESDYYCALWYSNLWVFGGGTKLTVL]
[GGGGSGGGGSGGGGS]EVQLVESGGGLVQPGGSLKLSCAASGFTFSTYAMNWVRQASGKGL
EWVGRIRSKYNNYATYYADSVKDRFTISRDDSKNTAYLQMNSLKTEDTAVYYCTRHGNF
GNSYVSWFAYWGQGTLVTVSS[GGGGS]QVQLKQSGPGLVQPSQSLSITCTVSGFSLTNYG
VHWVRQSPGKGLEWLGVIWSGGNTDYNTPFTSRLSINKDNSKSQVFFKMNSLQSQDTAIY
YCARALTYYDYEFAYWGQGTLVTVSAASTKGPSVFPLAPSSKSTSGGTAALGCLVKDYFP
EPVTVSWNSGALTSGVHTFPAVLQSSGLYSLSSVVTVPSSSLGTQTYICNVNHKPSNTKVD
KKVEPKSCDKTHTCPPCPAPEFEGGPSVFLFPPKPKDTLMISRTPEVTCVVVDVSHEDPEVK
FNWYVDGVEVHNAKTKPREEQYQSTYRVVSVLTVLHQDWLNGKEYKCKVSNKALPASIE
KTISKAKGQPREPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLSPGK (SEQ ID
NO: 126)

Activated pLW291: LC 3954-0011-C225v5
Nucleotide Sequence
TCCGATGATCATGGCAGTAGCGGTACCCAGATCTTGCTGACCCAGAGCCCGGTGATTCT
GAGCGTGAGCCCGGGCGAACGTGTGAGCTTTAGCTGCCGCGCGAGCCAGAGCATTGGC
ACCAACATTCATTGGTATCAGCAGCGCACCAACGGCAGCCCGCGCCTGCTGATTAAAT
ATGCGAGCGAAAGCATTAGCGGCATTCCGAGCCGCTTTAGCGGCAGCGGCAGCGGCAC
CGATTTTACCCTGAGCATTAACAGCGTGGAAAGCGAAGATATTGCGGATTATTATTGCC
AGCAGAACAACAACTGGCCGACCACCTTTGGCGCGGGCACCAAACTGGAACTGAAACG
TACGGTGGCTGCACCATCTGTCTTCATCTTCCCGCCATCTGATGAGCAGTTGAAATCTG
GAACTGCCTCTGTTGTGTGCCTGCTGAATAACTTCTATCCCAGAGAGGCCAAAGTACAG
TGGAAGGTGGATAACGCCCTCCAATCGGGTAACTCCCAGGAGAGTGTCACAGAGCAGG
ACAGCAAGGACAGCACCTACAGCCTCAGCAGCACCCTGACGCTGAGCAAAGCAGACTA
CGAGAAACACAAAGTCTACGCCTGCGAAGTCACCCATCAGGGCCTGAGCTCGCCCGTC
ACAAAGAGCTTCAACAGGGGAGAGTGT (SEQ ID NO: 127)

Amino Acid Sequence
[SDDH][GSSGT]QILLTQSPVILSVSPGERVSFSCRASQSIGTNIHWYQQRTNGSPRLLIKYASE
SISGIPSRFSGSGSGTDFTLSINSVESEDIADYYCQQNNNWPTTFGAGTKLELKRTVAAPSVFI
FPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC (SEQ ID NO: 128)

-continued

| CI106: CF41-2008-C225v5Fcmt4-h20GG-0011-v16sc-H-N |
|---|

pLW289: HC h20GG-0011-v16sc-C225v5Fcmt4 (H-N)
Nucleotide Sequence
[spacer SEQ ID NO: 191][pLW289 without spacer SEQ ID NO: 196]
CAAGGCCAGTCTGGATCCGGTTATCTGTGGGGTTGCGAGTGGAATTGCGGAGGGATCA
CTACAGGCTCGAGCGGTGGCAGCGGTGGCTCTGGTGGTCTGAGCGGCCGTTCCGATGA
TCATGGCGGCGGTTCTCAAACTGTAGTAACTCAAGAACCAAGCTTCTCCGTCTCCCCTG
GGGGAACAGTCACACTTACCTGCCGAAGTAGTACAGGTGCTGTTACGACCAGTAACTA
TGCCAATTGGGTACAACAAACGCCTGGTCAGGCTCCGCGCGGATTGATAGGAGGCACG
AATAAACGGGCACCCGGTGTCCCGGACAGATTCAGCGGAAGCATACTCGGTAATAAGG
CAGCTCTTACTATCACTGGGGCCCAAGCTGATGATGAAAGTGATTATTATTGTGCGCTC
TGGTACAGCAACCTCTGGGTGTTTGGGGGTGGCACGAAACTTACTGTCTTGGGCGGCG
GCGGATCAGGGGGAGGTGGCTCTGGAGGAGGAGGCTCAGAAGTCCAACTGGTCGAAT
CCGGGGGAGGGCTCGTACAGCCGGGTGGGTCCCTCAAACTCTCTTGTGCGGCCTCAGG
GTTTACCTTCAGTACATACGCGATGAATTGGGTCCGGCAGGCCAGTGGGAAAGGGCTC
GAATGGGTAGGACGAATCCGATCAAAATACAACAACTACGCTACTTATTACGCTGATT
CCGTGAAGGACAGATTCACAATATCCCGCGACGATAGCAAGAATACGGCATATCTTCA
GATGAATTCTCTTAAAACTGAGGATACCGCTGTGTATTACTGCACAAGACATGGTAATT
TTGGAAACTCATATGTCTCTTGGTTCGCTTATTGGGGACAGGGCACGTTGGTTACCGTG
TCTAGCGGAGGTGGTGGATCCCAGGTGCAGCTGAAACAGAGCGGCCCGGGCCTGGTGC
AGCCGAGCCAGAGCCTGAGCATTACCTGCACCGTGAGCGGCTTTAGCCTGACCAACTA
TGGCGTGCATTGGGTGCGCCAGAGCCCGGGCAAAGGCCTGGAATGGCTGGGCGTGATT
TGGAGCGGCGGCAACACCGATTATAACACCCCGTTTACCAGCCGCCTGAGCATTAACA
AAGATAACAGCAAAAGCCAGGTGTTTTTTAAAATGAACAGCCTGCAAAGCCAGGATAC
CGCGATTTATTATTGCGCGCGCGCGCTGACCTATTATGATTATGAATTTGCGTATTGGG
GCCAGGGCACCCTGGTGACCGTGAGCGCGGCTAGCACCAAGGGCCCATCGGTCTTCCC
CCTGGCACCCTCCTCCAAGAGCACCTCTGGGGGCACAGCGGCCCTGGGCTGCCTGGTC
AAGGACTACTTCCCCGAACCGGTGACGGTGTCGTGGAACTCAGGCGCCCTGACCAGCG
GCGTGCACACCTTCCCGGCTGTCCTACAGTCCTCAGGACTCTACTCCCTCAGCAGCGTG
GTGACCGTGCCCTCCAGCAGCTTGGGCACCCAGACCTACATCTGCAACGTGAATCACA
AGCCCAGCAACACCAAGGTGGACAAGAAAGTTGAGCCCAAATCTTGTGACAAAACTCA
CACATGCCCACCGTGCCCAGCACCTGAATTTGAAGGGGGACCGTCAGTCTTCCTCTTCC
CCCCAAAACCCAAGGACACCCTCATGATCTCCCGGACCCCTGAGGTCACATGCGTGGT
GGTGGACGTGAGCCACGAAGACCCTGAGGTCAAGTTCAACTGGTACGTGGACGGCGTG
GAGGTGCATAATGCCAAGACAAAGCCGCGGGAGGAGCAGTACCAGAGCACGTACCGT
GTGGTCAGCGTCCTCACCGTCCTGCACCAGGACTGGCTGAATGGCAAGGAGTACAAGT
GCAAGGTCTCCAACAAAGCCCTCCCAGCCTCAATCGAGAAAACCATCTCCAAAGCCAA
AGGGCAGCCCCGAGAACCACAGGTGTACACCCTGCCCCCATCCCGGGAGGAGATGACC
AAGAACCAGGTCAGCCTGACCTGCCTGGTCAAAGGCTTCTATCCCAGCGACATCGCCG
TGGAGTGGGAGAGCAATGGGCAGCCGGAGAACAACTACAAGACCACGCCTCCCGTGCT
GGACTCCGACGGCTCCTTCTTCCTCTACAGCAAGCTCACCGTGGACAAGAGCAGGTGG
CAGCAGGGGAACGTCTTCTCATGCTCCGTGATGCATGAGGCTCTGCACAACCACTACAC
GCAGAAGAGCCTCTCCCTGTCTCCGGGTAAA (SEQ ID NO: 129)

Amino Acid Sequence
[spacer SEQ ID NO: 178][pLW289 without spacer SEQ ID NO: 197]
QGQSGS[GYLWGCEWNCGGITT][GSSGGSGGSGG][LSGRSDDH][GGGS]QTVVTQEPSFSV
SPGGTVTLTCRSSTGAVTTSNYANWVQQTPGQAPRGLIGGTNKRAPGVPDRFSGSILGNKA
ALTITGAQADDESDYYCALWYSNLWVFGGGTKLTVL[GGGGSGGGGSGGGGS]EVQLVES
GGGLVQPGGSLKLSCAASGFTFSTYAMNWVRQASGKGLEWVGRIRSKYNNYATYYADSV
KDRFTISRDDSKNTAYLQMNSLKTEDTAVYYCTRHGNFGNSYVSWFAYWGQGTLVTVSS
[GGGGS]QVQLKQSGPGLVQPSQSLSITCTVSGFSLTNYGVHWVRQSPGKGLEWLGVIWSGG
NTDYNTPFTSRLSINKDNSKSQVFFKMNSLQSQDTAIYYCARALTYYDYEFAYWGQGTLV
TVSAASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPPCPAPEFEG
GPSVFLFPPKPKDTLMISRTPEVTCVVVDVSHEDPEVKFNWYVDGVEVHNAKTKPREEQY
QSTYRVVSVLTVLHQDWLNGKEYKCKVSNKALPASIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGK (SEQ ID NO: 130)

pLW246: LC CF41-2008-C225v5
Nucleotide Sequence
[spacer SEQ ID NO: 176][pLW246 without spacer SEQ ID NO: 198]
CAAGGCCAGTCTGGCCAAGGTCTTAGTTGTGAAGGTTGGGCGATGAATAGAGAACAAT
GTCGAGCCGGAGGTGGCTCGAGCGGCGGCTCTATCTCTTCCGGACTGCTGTCCGGCAG
ATCCGACCAGCACGGCGGAGGATCCCAAATCCTGCTGACACAGTCTCCTGTCATACTG
AGTGTCTCCCCCGGCGAGAGAGTCTCTTTCTCATGTCGGGCCAGTCAGTCTATTGGGAC
TAACATACACTGGTACCAGCAACGCACCAACGGAAGCCCGCGCCTGCTGATTAAATAT
GCGAGCGAAAGCATTAGCGGCATTCCGAGCCGCTTTAGCGGCAGCGGCAGCGGCACCG
ATTTTACCCTGAGCATTAACAGCGTGGAAAGCGAAGATATTGCGGATTATTATTGCCAG
CAGAACAACAACTGGCCGACCACCTTTGGCGCGGGCACCAAACTGGAACTGAAACGTA
CGGTGGCTGCACCATCTGTCTTCATCTTCCCGCCATCTGATGAGCAGTTGAAATCTGGA
ACTGCCTCTGTTGTGTGCCTGCTGAATAACTTCTATCCCAGAGAGGCCAAAGTACAGTG
GAAGGTGGATAACGCCCTCCAATCGGGTAACTCCCAGGAGAGTGTCACAGAGCAGGAC
AGCAAGGACAGCACCTACAGCCTCAGCAGCACCCTGACGCTGAGCAAAGCAGACTACG
AGAAACACAAAGTCTACGCCTGCGAAGTCACCCATCAGGGCCTGAGCTCGCCCGTCAC
AAAGAGCTTCAACAGGGGAGAGTGT (SEQ ID NO: 131)

-continued

Amino Acid Sequence
[spacer SEQ ID NO: 178][pLW246 without spacer SEQ ID NO: 199]
QGQSGQG[LSCEGWAMNREQCRA][GGGSSGGS][ISSGLLSGRSDQH][GGGS]QILLTQSPVI
LSVSPGERVSFSCRASQSIGTNIHWYQQRTNGSPRLLIKYASESISGIPSRFSGSGSGTDFTLSI
NSVESEDIADYYCQQNNNWPTTFGAGTKLELKRTVAAPSVFIFPPSDEQLKSGTASVVCLL
NNFYPREAKVQWKVDNALQSGNSQESVTEQDSKDSTYSLSSTLTLSKADYEKHKVYACEV
THQGLSSPVTKSFNRGEC (SEQ ID NO: 132)

CI107: 3954-0011-C225v5Fcmt4-h20GG-2006-v16sc-H-N pLW307: HC h20GG-2006-v16sc-C225v5Fcmt4 (H-N)
Nucleotide Sequence
[spacer SEQ ID NO: 191][pLW307 without spacer SEQ ID NO: 200]
CAAGGCCAGTCTGGATCCGGTTATCTGTGGGGTTGCGAGTGGAATTGCGGAGGGATCA
CTACAGGCTCGAGCGGTGGCAGCGGTGGCTCTGGTGGTATATCGAGTGGATTGCTGTCT
GGCAGATCTGACGATCACGGCGGCGGTTCTCAAACTGTAGTAACTCAAGAACCAAGCT
TCTCCGTCTCCCCTGGGGGAACAGTCACACTTACCTGCCGAAGTAGTACAGGTGCTGTT
ACGACCAGTAACTATGCCAATTGGGTACAACAAACGCCTGGTCAGGCTCCGCGCGGAT
TGATAGGAGGCACGAATAAACGGGCACCCGGTGTCCCGGACAGATTCAGCGGAAGCAT
ACTCGGTAATAAGGCAGCTCTTACTATCACTGGGGCCCAAGCTGATGATGAAAGTGAT
TATTATTGTGCGCTCTGGTACAGCAACCTCTGGGTGTTTGGGGGTGGCACGAAACTTAC
TGTCTTGGGCGGCGGCGGATCAGGGGGAGGTGGCTCTGGAGGAGGAGGCTCAGAAGTC
CAACTGGTCGAATCCGGGGGAGGGCTCGTACAGCCGGGTGGGTCCCTCAAACTCTCTT
GTGCGGCCTCAGGGTTTACCTTCAGTACATACGCGATGAATTGGGTCCGGCAGGCCAGT
GGGAAAGGGCTCGAATGGGTAGGACGAATCCGATCAAAATACAACAACTACGCTACTT
ATTACGCTGATTCCGTGAAGGACAGATTCACAATATCCCGCGACGATAGCAAGAATAC
GGCATATCTTCAGATGAATTCTCTTAAAACTGAGGATACCGCTGTGTATTACTGCACAA
GACATGGTAATTTTGGAAACTCATATGTCTCTTGGTTCGCTTATTGGGGACAGGGCACG
TTGGTTACCGTGTCTAGCGGAGGTGGTGGATCCCAGGTGCAGCTGAAACAGAGCGGCC
CGGGCCTGGTGCAGCCGAGCCAGAGCCTGAGCATTACCTGCACCGTGAGCGGCTTTAG
CCTGACCAACTATGGCGTGCATTGGGTGCGCCAGAGCCCGGGCAAAGGCCTGGAATGG
CTGGGCGTGATTTGGAGCGGCGGCAACACCGATTATAACACCCCGTTTACCAGCCGCCT
GAGCATTAACAAAGATAACAGCAAAAGCCAGGTGTTTTTTAAAATGAACAGCCTGCAA
AGCCAGGATACCGCGATTTATTATTGCGCGCGCGCGCTGACCTATTATGATTATGAATT
TGCGTATTGGGGCCAGGGCACCCTGGTGACCGTGAGCGCGGCTAGCACCAAGGGCCCA
TCGGTCTTCCCCCTGGCACCCTCCTCCAAGAGCACCTCTGGGGGCACAGCGGCCCTGGG
CTGCCTGGTCAAGGACTACTTCCCCGAACCGGTGACGGTGTCGTGGAACTCAGGCGCC
CTGACCAGCGGCGTGCACACCTTCCCGGCTGTCCTACAGTCCTCAGGACTCTACTCCCT
CAGCAGCGTGGTGACCGTGCCCTCCAGCAGCTTGGGCACCCAGACCTACATCTGCAAC
GTGAATCACAAGCCCAGCAACACCAAGGTGGACAAGAAAGTTGAGCCCAAATCTTGTG
ACAAAACTCACACATGCCCACCGTGCCCAGCACCTGAATTTGAAGGGGGACCGTCAGT
CTTCCTCTTCCCCCCAAAACCCAAGGACACCCTCATGATCTCCCGGACCCCTGAGGTCA
CATGCGTGGTGGTGGACGTGAGCCACGAAGACCCTGAGGTCAAGTTCAACTGGTACGT
GGACGGCGTGGAGGTGCATAATGCCAAGACAAAGCCGCGGGAGGAGCAGTACCAGAG
CACGTACCGTGTGGTCAGCGTCCTCACCGTCCTGCACCAGGACTGGCTGAATGGCAAG
GAGTACAAGTGCAAGGTCTCCAACAAAGCCCTCCCAGCCTCAATCGAGAAAACCATCT
CCAAAGCCAAAGGGCAGCCCCGAGAACCACAGGTGTACACCCTGCCCCCATCCCGGGA
GGAGATGACCAAGAACCAGGTCAGCCTGACCTGCCTGGTCAAAGGCTTCTATCCCAGC
GACATCGCCGTGGAGTGGGAGAGCAATGGGCAGCCGGAGAACAACTACAAGACCACG
CCTCCCGTGCTGGACTCCGACGGCTCCTTCTTCCTCTACAGCAAGCTCACCGTGGACAA
GAGCAGGTGGCAGCAGGGGAACGTCTTCTCATGCTCCGTGATGCATGAGGCTCTGCAC
AACCACTACACGCAGAAGAGCCTCTCCCTGTCTCCGGGTAAA (SEQ ID NO: 133)

Amino Acid Sequence
[spacer SEQ ID NO: 178][pLW307 without spacer SEQ ID NO: 201]
QGQSGS[GYLWGCEWNCGGITT][GSSGGSGGSGG][ISSGLLSGRSDDH][GGGS]QTVVTQE
PSFSVSPGGTVTLTCRSSTGAVTTSNYANWVQQTPGQAPRGLIGGTNKRAPGVPDRFSGSIL
GNKAALTITGAQADDESDYYCALWYSNLWVFGGGTKLTVL[GGGGSGGGGSGGGGS]EV
QLVESGGGLVQPGGSLKLSCAASGFTFSTYAMNWVRQASGKGLEWVGRIRSKYNNYATY
YADSVKDRFTISRDDSKNTAYLQMNSLKTEDTAVYYCTRHGNFGNSYVSWFAYWGQGTL
VTVSS[GGGGS]QVQLKQSGPGLVQPSQSLSITCTVSGFSLTNYGVHWVRQSPGKGLEWLG
VIWSGGNTDYNTPFTSRLSINKDNSKSQVFFKMNSLQSQDTAIYYCARALTYYDYEFAYW
GQGTLVTVSAASTKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPKSCDKTHTCPPCP
APEFEGGPSVFLFPPKPKDTLMISRTPEVTCVVVDVSHEDPEVKFNWYVDGVEVHNAKTKP
REEQYQSTYRVVSVLTVLHQDWLNGKEYKCKVSNKALPASIEKTISKAKGQPREPQVYTLP
PSREEMTKNQVSLTCLVKGFYPSDIAVEWESNGQPENNYKTTPPVLDSDGSFFLYSKLTVD
KSRWQQGNVFSCSVMHEALHNHYTQKSLSLSPGK (SEQ ID NO: 134)

pLW291: LC 3954-0011-C225v5
Nucleotide Sequence
[spacer SEQ ID NO: 180][pLW291 without spacer SEQ ID NO: 202]
CAAGGCCAGTCTGGCCAGTGCATCTCACCTCGTGGTTGTCCGGACGGCCCATACGTCAT
GTACGGCTCGAGCGGTGGCAGCGGTGGCTCTGGTGGATCCGGTCTGAGCGGCCGTTCC
GATGATCATGGCAGTAGCGGTACCCAGATCTTGCTGACCCAGAGCCCGGTGATTCTGA
GCGTGAGCCCGGGCGAACGTGTGAGCTTTAGCTGCCGCGCGAGCCAGAGCATTGGCAC
CAACATTCATTGGTATCAGCAGCGCACCAACGGCAGCCCGCGCCTGCTGATTAAATAT
GCGAGCGAAAGCATTAGCGGCATTCCGAGCCGCTTTAGCGGCAGCGGCAGCGGCACCG
ATTTTACCCTGAGCATTAACAGCGTGGAAAGCGAAGATATTGCGGATTATTATTGCCAG -continued CAGAACAACAACTGGCCGACCACCTTTGGCGCGGGCACCAAACTGGAACTGAAACGTA
CGGTGGCTGCACCATCTGTCTTCATCTTCCCGCCATCTGATGAGCAGTTGAAATCTGGA
ACTGCCTCTGTTGTGTGCCTGCTGAATAACTTCTATCCCAGAGAGGCCAAAGTACAGTG
GAAGGTGGATAACGCCCTCCAATCGGGTAACTCCCAGGAGAGTGTCACAGAGCAGGAC
AGCAAGGACAGCACCTACAGCCTCAGCAGCACCCTGACGCTGAGCAAAGCAGACTACG
AGAAACACAAAGTCTACGCCTGCGAAGTCACCCATCAGGGCCTGAGCTCGCCCGTCAC
AAAGAGCTTCAACAGGGGAGAGTGT (SEQ ID NO: 135)

Amino Acid Sequence
[spacer SEQ ID NO: 178][pLW291 without spacer SEQ ID NO: 203]
QGQSGQ[CISPRGCPDGPYVMY][GSSGGSGGSGGSG][LSGRSDDH][GSSGT]QILLTQSPVIL
SVSPGERVSFSCRASQSIGTNIHWYQQRTNGSPRLLIKYASESISGIPSRFSGSGSGTDFTLSIN
SVESEDIADYYCQQNNNWPTTFGAGTKLELKRTVAAPSVFIFPPSDEQLKSGTASVVCLLN
NFYPREAKVQWKVDNALQSGNSQESVTEQDSKDSTYSLSSTLTLSKADYEKHKVYACEVT
HQGLSSPVTKSFNRGEC (SEQ ID NO: 136)

CI127: SynFcmt4-h20GG-0011-v16sc-H-N pLW334: HC h20GG-0011-v16sc-Synagis ®Fcmt4 (H-N)
Nucleotide Sequence
[spacer SEQ ID NO: 191][pLW334 without spacer SEQ ID NO: 204]
CAAGGCCAGTCTGGATCCGGTTATCTGTGGGGTTGCGAGTGGAATTGCGGAGGGATCA
CTACAGGCTCGAGCGGTGGCAGCGGTGGCTCTGGTGGTCTGAGCGGCCGTTCCGATGA
TCATGGCGGCGGTTCTCAAACTGTAGTAACTCAAGAACCAAGCTTCTCCGTCTCCCCTG
GGGGAACAGTCACACTTACCTGCCGAAGTAGTACAGGTGCTGTTACGACCAGTAACTA
TGCCAATTGGGTACAACAAACGCCTGGTCAGGCTCCGCGCGGATTGATAGGAGGCACG
AATAAACGGGCACCCGGTGTCCCGGACAGATTCAGCGGAAGCATACTCGGTAATAAGG
CAGCTCTTACTATCACTGGGGCCCAAGCTGATGATGAAAGTGATTATTATTGTGCGCTC
TGGTACAGCAACCTCTGGGTGTTTGGGGGTGGCACGAAACTTACTGTCTTGGGCGGCG
GCGGATCAGGGGGAGGTGGCTCTGGAGGAGGAGGCTCAGAAGTCCAACTGGTCGAAT
CCGGGGGAGGGCTCGTACAGCCGGGTGGGTCCCTCAAACTCTCTTGTGCGGCCTCAGG
GTTTACCTTCAGTACATACGCGATGAATTGGGTCCGGCAGGCCAGTGGGAAAGGGCTC
GAATGGGTAGGACGAATCCGATCAAAATACAACAACTACGCTACTTATTACGCTGATT
CCGTGAAGGACAGATTCACAATATCCCGCGACGATAGCAAGAATACGGCATATCTTCA
GATGAATTCTCTTAAAACTGAGGATACCGCTGTGTATTACTGCACAAGACATGGTAATT
TTGGAAACTCATATGTCTCTTGGTTCGCTTATTGGGGACAGGGCACGTTGGTTACCGTG
TCTAGCGGAGGTGGTGGATCCCAAGTGACCCTGAGAGAGTCTGGCCCTGCCCTCGTGA
AGCCTACCCAGACCCTGACACTGACCTGCACCTTCAGCGGCTTCAGCCTGAGCACCAGC
GGCATGTCTGTGGGCTGGATCAGACAGCCTCCTGGCAAGGCCCTGGAATGGCTGGCCG
ACATTTGGTGGGACGACAAGAAGGACTACAACCCCAGCCTGAAGTCCCGGCTGACCAT
CAGCAAGGACACCAGCAAGAACCAGGTGGTGCTGAAAGTGACCAACATGGACCCCGC
CGACACCGCCACCTACTACTGCGCCAGATCCATGATCACCAACTGGTACTTCGACGTGT
GGGGAGCCGGCACCACCGTGACAGTGTCATCTGCTAGCACCAAGGGCCCATCGGTCTT
CCCCCTGGCACCCTCCTCCAAGAGCACCTCTGGGGGCACAGCGGCCCTGGGCTGCCTG
GTCAAGGACTACTTCCCCGAACCGGTGACGGTGTCGTGGAACTCAGGCGCCCTGACCA
GCGGCGTGCACACCTTCCCGGCTGTCCTACAGTCCTCAGGACTCTACTCCCTCAGCAGC
GTGGTGACCGTGCCCTCCAGCAGCTTGGGCACCCAGACCTACATCTGCAACGTGAATC
ACAAGCCCAGCAACACCAAGGTGGACAAGAAAGTTGAGCCCAAATCTTGTGACAAAA
CTCACACATGCCCACCGTGCCCAGCACCTGAATTTGAAGGGGGACCGTCAGTCTTCCTC
TTCCCCCCAAAACCCAAGGACACCCTCATGATCTCCCGGACCCCTGAGGTCACATGCGT
GGTGGTGGACGTGAGCCACGAAGACCCTGAGGTCAAGTTCAACTGGTACGTGGACGGC
GTGGAGGTGCATAATGCCAAGACAAAGCCGCGGGAGGAGCAGTACCAGAGCACGTAC
CGTGTGGTCAGCGTCCTCACCGTCCTGCACCAGGACTGGCTGAATGGCAAGGAGTACA
AGTGCAAGGTCTCCAACAAAGCCCTCCCAGCCTCAATCGAGAAAACCATCTCCAAAGC
CAAAGGGCAGCCCCGAGAACCACAGGTGTACACCCTGCCCCCATCCCGGGAGGAGATG
ACCAAGAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCG
TGCTGGACTCCGACGGCTCCTTCTTCCTCTACAGCAAGCTCACCGTGGACAAGAGCAGG
TGGCAGCAGGGGAACGTCTTCTCATGCTCCGTGATGCATGAGGCTCTGCACAACCACTA
CACGCAGAAGAGCCTCTCCCTGTCTCCGGGTAAA (SEQ ID NO: 137)

Amino Acid Sequence
[spacer SEQ ID NO: 178][pLW334 without spacer SEQ ID NO: 205]
QGQSGS[GYLWGCEWNCGGITT][GSSGGSGGSGG][LSGRSDDH][GGGS]QTVVTQEPSFSV
SPGGTVTLTCRSSTGAVTTSNYANWVQQTPGQAPRGLIGGTNKRAPGVPDRFSGSILGNKA
ALTITGAQADDESDYYCALWYSNLWVFGGGTKLTVL[GGGGSGGGGSGGGGS]EVQLVES
GGGLVQPGGSLKLSCAASGFTFSTYAMNWVRQASGKGLEWVGRIRSKYNNYATYYADSV
KDRFTISRDDSKNTAYLQMNSLKTEDTAVYYCTRHGNFGNSYVSWFAYWGQGTLVTVSS
[GGGGS]QVTLRESGPALVKPTQTLTLTCTFSGFSLSTSGMSVGWIRQPPGKALEWLADIWW
DDKKDYNPSLKSRLTISKDTSKNQVVLKVTNMDPADTATYYCARSMITNWYFDVWGAGT
TVTVSSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSCDKTHTCPPCPAPEFE
GGPSVFLFPPKPKDTLMISRTPEVTCVVVDVSHEDPEVKFNWYVDGVEVHNAKTKPREEQ
YQSTYRVVSVLTVLHQDWLNGKEYKCKVSNKALPASIEKTISKAKGQPREPQVYTLPPSRE
EMTKNQVSLTCLVKGFYPSDIAVEWESNGQPENNYKTTPPVLDSDGSFFLYSKLTVDKSR
WQQGNVFSCSVMHEALHNHYTQKSLSLSPGK (SEQ ID NO: 138)

-continued pLW139: LC Synagis ®
Nucleotide Sequence
GACATCCAGATGACCCAGAGCCCCAGCACACTGAGCGCCAGCGTGGGCGACAGAGTG
ACCATCACATGCAAGTGCCAGCTGAGCGTGGGCTACATGCACTGGTATCAGCAGAAGC
CCGGCAAGGCCCCCAAGCTGCTGATCTACGACACCAGCAAGCTGGCCTCCGGCGTGCC
CAGCAGATTTTCTGGCAGCGGCTCCGGCACCGAGTTCACCCTGACAATCAGCAGCCTGC
AGCCCGACGACTTCGCCACCTACTACTGTTTTCAAGGCTCCGGCTACCCCTTCACCTTC
GGCGGAGGCACCAAGCTGGAAATCAAGCGGACGGTGGCTGCACCATCTGTCTTCATCT
TCCCGCCATCTGATGAGCAGTTGAAATCTGGAACTGCCTCTGTTGTGTGCCTGCTGAAT
AACTTCTATCCCAGAGAGGCCAAAGTACAGTGGAAGGTGGATAACGCCCTCCAATCGG
GTAACTCCCAGGAGAGTGTCACAGAGCAGGACAGCAAGGACAGCACCTACAGCCTCA
GCAGCACCCTGACGCTGAGCAAAGCAGACTACGAGAAACACAAAGTCTACGCCTGCGA
AGTCACCCATCAGGGCCTGAGCTCGCCCGTCACAAAGAGCTTCAACAGGGGAGAGTGT
(SEQ ID NO: 139)

Amino Acid
SequenceDIQMTQSPSTLSASVGDRVTITCKCQLSVGYMHWYQQKPGKAPKLLIYDTSKLAS
GVPSRFSGSGSGTEFTLTISSLQPDDFATYYCFQGSGYPFTFGGGTKLEIKRTVAAPSVFIFPP
SDEQLKSGTASVVCLLNNFYPREAKVQWKVDNALQSGNSQESVTEQDSKDSTYSLSSTLTL
SKADYEKHKVYACEVTHQGLSSPVTKSFNRGEC (SEQ ID NO: 140)

CI128: SynFcmt4-h20GG-2006-v16sc-H-N pLW335: HC h20GG-2006-v16sc-Synagis ®Fcmt4 (H-N)
Nucleotide Sequence
[spacer SEQ ID NO: 191][pLW335 without spacer SEQ ID NO: 206]
CAAGGCCAGTCTGGATCCGGTTATCTGTGGGGTTGCGAGTGGAATTGCGGAGGGATCA
CTACAGGCTCGAGCGGTGGCAGCGGTGGCTCTGGTGGTATATCGAGTGGATTGCTGTCT
GGCAGATCTGACGATCACGGCGGCGGTTCTCAAACTGTAGTAACTCAAGAACCAAGCT
TCTCCGTCTCCCCTGGGGGAACAGTCACACTTACCTGCCGAAGTAGTACAGGTGCTGTT
ACGACCAGTAACTATGCCAATTGGGTACAACAAACGCCTGGTCAGGCTCCGCGCGGAT
TGATAGGAGGCACGAATAAACGGGCACCCGGTGTCCCGGACAGATTCAGCGGAAGCAT
ACTCGGTAATAAGGCAGCTCTTACTATCACTGGGGCCCAAGCTGATGATGAAAGTGAT
TATTATTGTGCGCTCTGGTACAGCAACCTCTGGGTGTTTGGGGGTGGCACGAAACTTAC
TGTCTTGGGCGGCGGCGGATCAGGGGGAGGTGGCTCTGGAGGAGGAGGCTCAGAAGTC
CAACTGGTCGAATCCGGGGGAGGGCTCGTACAGCCGGGTGGGTCCCTCAAACTCTCTT
GTGCGGCCTCAGGGTTTACCTTCAGTACATACGCGATGAATTGGGTCCGGCAGGCCAGT
GGGAAAGGGCTCGAATGGGTAGGACGAATCCGATCAAAATACAACAACTACGCTACTT
ATTACGCTGATTCCGTGAAGGACAGATTCACAATATCCCGCGACGATAGCAAGAATAC
GGCATATCTTCAGATGAATTCTCTTAAAACTGAGGATACCGCTGTGTATTACTGCACAA
GACATGGTAATTTTGGAAACTCATATGTCTCTTGGTTCGCTTATTGGGGACAGGGCACG
TTGGTTACCGTGTCTAGCGGAGGTGGTGGATCCCAAGTGACCCTGAGAGAGTCTGGCC
CTGCCCTCGTGAAGCCTACCCAGACCCTGACACTGACCTGCACCTTCAGCGGCTTCAGC
CTGAGCACCAGCGGCATGTCTGTGGGCTGGATCAGACAGCCTCCTGGCAAGGCCCTGG
AATGGCTGGCCGACATTTGGTGGGACGACAAGAAGGACTACAACCCCAGCCTGAAGTC
CCGGCTGACCATCAGCAAGGACACCAGCAAGAACCAGGTGGTGCTGAAAGTGACCAA
CATGGACCCCGCCGACACCGCCACCTACTACTGCGCCAGATCCATGATCACCAACTGGT
ACTTCGACGTGTGGGGAGCCGGCACCACCGTGACAGTGTCATCTGCTAGCACCAAGGG
CCCATCGGTCTTCCCCCTGGCACCCTCCTCCAAGAGCACCTCTGGGGGCACAGCGGCCC
TGGGCTGCCTGGTCAAGGACTACTTCCCCGAACCGGTGACGGTGTCGTGGAACTCAGG
CGCCCTGACCAGCGGCGTGCACACCTTCCCGGCTGTCCTACAGTCCTCAGGACTCTACT
CCCTCAGCAGCGTGGTGACCGTGCCCTCCAGCAGCTTGGGCACCCAGACCTACATCTGC
AACGTGAATCACAAGCCCAGCAACACCAAGGTGGACAAGAAAGTTGAGCCCAAATCTT
GTGACAAAACTCACACATGCCCACCGTGCCCAGCACCTGAATTTGAAGGGGGACCGTC
AGTCTTCCTCTTCCCCCCAAAACCCAAGGACACCCTCATGATCTCCCGGACCCCTGAGG
TCACATGCGTGGTGGTGGACGTGAGCCACGAAGACCCTGAGGTCAAGTTCAACTGGTA
CGTGGACGGCGTGGAGGTGCATAATGCCAAGACAAAGCCGCGGGAGGAGCAGTACCA
GAGCACGTACCGTGTGGTCAGCGTCCTCACCGTCCTGCACCAGGACTGGCTGAATGGC
AAGGAGTACAAGTGCAAGGTCTCCAACAAAGCCCTCCCAGCCTCAATCGAGAAAACCA
TCTCCAAAGCCAAAGGGCAGCCCCGAGAACCACAGGTGTACACCCTGCCCCCATCCCG
GGAGGAGATGACCAAGAACCAGGTCAGCCTGACCTGCCTGGTCAAAGGCTTCTATCCC
AGCGACATCGCCGTGGAGTGGGAGAGCAATGGGCAGCCGGAGAACAACTACAAGACC
ACGCCTCCCGTGCTGGACTCCGACGGCTCCTTCTTCCTCTACAGCAAGCTCACCGTGGA
CAAGAGCAGGTGGCAGCAGGGGAACGTCTTCTCATGCTCCGTGATGCATGAGGCTCTG
CACAACCACTACACGCAGAAGAGCCTCTCCCTGTCTCCGGGTAAA (SEQ ID NO: 141)

Amino Acid Sequence
[spacer SEQ ID NO: 178][pLW335 without spacer SEQ ID NO: 207]
QGQSGS[GYLWGCEWNCGGITT][GSSGGSGGSGG][ISSGLLSGRSDDH][GGGS]QTVVTQE
PSFSVSPGGTVTLTCRSSTGAVTTSNYANWVQQTPGQAPRGLIGGTNKRAPGVPDRFSGSIL
GNKAALTITGAQADDESDYYCALWYSNLWVFGGGTKLTVL[GGGGSGGGGSGGGGS]EV
QLVESGGGLVQPGGSLKLSCAASGFTFSTYAMNWVRQASGKGLEWVGRIRSKYNNYATY
YADSVKDRFTISRDDSKNTAYLQMNSLKTEDTAVYYCTRHGNFGNSYVSWFAYWGQGTL
VTVSS[GGGGS]QVTLRESGPALVKPTQTLTLTCTFSGFSLSTSGMSVGWIRQPPGKALEWL
ADIWWDDKKDYNPSLKSRLTISKDTSKNQVVLKVTNMDPADTATYYCARSMITNWYFDV
WGAGTTVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEPKSCDKTHTCPPC
PAPEFEGGPSVFLFPPKPKDTLMISRTPEVTCVVVDVSHEDPEVKFNWYVDGVEVHNAKTK -continued PREEQYQSTYRVVSVLTVLHQDWLNGKEYKCKVSNKALPASIEKTISKAKGQPREPQVYTL
PPSREEMTKNQVSLTCLVKGFYPSDIAVEWESNGQPENNYKTTPPVLDSDGSFFLYSKLTV
DKSRWQQGNVFSCSVMHEALHNHYTQKSLSLSPGK (SEQ ID NO: 142)

pLW139: LC Synagis ®
Sequences provided above

CI135: CF41-2008-C225v5Fcmt4-h20GG-0011-v12sc-H-N pLW352: HC h20GG-0011-v12sc-C225v5Fcmt4 (H-N)
Nucleotide Sequence
[spacer SEQ ID NO: 208][pLW352 without spacer SEQ ID NO: 209]
CAAGGCCAGTCTGGTTCTGGTTATCTGTGGGGTTGCGAGTGGAATTGCGGAGGGATCA
CTACAGGCTCGAGCGGTGGCAGCGGTGGCTCTGGTGGTCTGAGCGGCCGTTCCGATGA
TCATGGCGGCGGATCCCAGACGGTAGTGACTCAGGAGCCATCATTTTCTGTCTCTCCTG
GAGGTACTGTGACACTCACATGTAGAAGCTCAACTGGTGCAGTCACCACTTCAAATTAC
GCGAATTGGGTCCAGCAGACCCCTGGGCAGGCTCCGAGAGGGTTGATTGGAGGTACTA
ACAAACGGGCACCGGGAGTGCCTGATAGGTTTTCCGGTTCTATTCTCGGAAACAAGGC
GGCTCTCACGATCACGGGTGCGCAGGCCGACGATGAATCAGACTATTACTGCGCTTTGT
GGTACTCAAACCTGTGGGTATTCGGAGGGGGCACCAAGCTGACGGTGTTGGGTGGGGG
GGGCTCTGGGGGAGGGGGAAGCGGAGGTGGGGGCAGCGAGGTTCAGCTTGTTGAAAG
TGGTGGCGGACTCGTACAACCGGGTGGAAGTCTTAGACTCTCATGTGCAGCATCTGGAT
TTACTTTTTCTACTTATGCTATGAACTGGGTAAGACAGGCACCGGGGAAAGGGCTGGA
ATGGGTTGCACGCATTCGATCTAAATACAATAACTATGCTACATACTACGCCGATAGTG
TTAAGGATCGATTCACTATATCTCGGGACGACAGTAAGAACTCACTTTACCTGCAGATG
AATTCCTTGAAAACTGAGGACACGGCCGTTTATTATTGTGTACGGCACGGGAATTTCGG
CAATTCTTACGTTTCCTGGTTCGCCTATTGGGGGCAAGGTACGCTGGTCACGGTGTCTA
GCGGAGGTGGTGGATCCCAGGTGCAGCTGAAACAGAGCGGCCCGGGCCTGGTGCAGCC
GAGCCAGAGCCTGAGCATTACCTGCACCGTGAGCGGCTTTAGCCTGACCAACTATGGC
GTGCATTGGGTGCGCCAGAGCCCGGGCAAAGGCCTGGAATGGCTGGGCGTGATTTGGA
GCGGCGGCAACACCGATTATAACACCCCGTTTACCAGCCGCCTGAGCATTAACAAAGA
TAACAGCAAAAGCCAGGTGTTTTTTAAAATGAACAGCCTGCAAAGCCAGGATACCGCG
ATTTATTATTGCGCGCGCGCGCTGACCTATTATGATTATGAATTTGCGTATTGGGGCCA
GGGCACCCTGGTGACCGTGAGCGCGGCTAGCACCAAGGGCCCATCGGTCTTCCCCCTG
GCACCCTCCTCCAAGAGCACCTCTGGGGGCACAGCGGCCCTGGGCTGCCTGGTCAAGG
ACTACTTCCCCGAACCGGTGACGGTGTCGTGGAACTCAGGCGCCCTGACCAGCGGCGT
GCACACCTTCCCGGCTGTCCTACAGTCCTCAGGACTCTACTCCCTCAGCAGCGTGGTGA
CCGTGCCCTCCAGCAGCTTGGGCACCCAGACCTACATCTGCAACGTGAATCACAAGCC
CAGCAACACCAAGGTGGACAAGAAAGTTGAGCCCAAATCTTGTGACAAAACTCACACA
TGCCCACCGTGCCCAGCACCTGAATTTGAAGGGGGACCGTCAGTCTTCCTCTTCCCCCC
AAAACCCAAGGACACCCTCATGATCTCCCGGACCCCTGAGGTCACATGCGTGGTGGTG
GACGTGAGCCACGAAGACCCTGAGGTCAAGTTCAACTGGTACGTGGACGGCGTGGAGG
TGCATAATGCCAAGACAAAGCCGCGGGAGGAGCAGTACCAGAGCACGTACCGTGTGGT
CAGCGTCCTCACCGTCCTGCACCAGGACTGGCTGAATGGCAAGGAGTACAAGTGCAAG
GTCTCCAACAAAGCCCTCCCAGCCTCAATCGAGAAAACCATCTCCAAAGCCAAAGGGC
AGCCCCGAGAACCACAGGTGTACACCCTGCCCCCATCCCGGGAGGAGATGACCAAGAA
CCAGGTCAGCCTGACCTGCCTGGTCAAAGGCTTCTATCCCAGCGACATCGCCGTGGAGT
GGGAGAGCAATGGGCAGCCGGAGAACAACTACAAGACCACGCCTCCCGTGCTGGACTC
CGACGGCTCCTTCTTCCTCTACAGCAAGCTCACCGTGGACAAGAGCAGGTGGCAGCAG
GGGAACGTCTTCTCATGCTCCGTGATGCATGAGGCTCTGCACAACCACTACACGCAGA
AGAGCCTCTCCCTGTCTCCGGGTAAA (SEQ ID NO: 151)

Amino Acid Sequence
[spacer SEQ ID NO: 176][pLW352 without spacer SEQ ID NO: 210]
QGQSGS[GYLWGCEWNCGGITT][GSSGGSGGSGG][LSGRSDDH][GGGS]QTVVTQEPSFSV
SPGGTVTLTCRSSTGAVTTSNYANWVQQTPGQAPRGLIGGTNKRAPGVPDRFSGSILGNKA
ALTITGAQADDESDYYCALWYSNLWVFGGGTKLTVL[GGGGSGGGGSGGGGS]EVQLVES
GGGLVQPGGSLRLSCAASGFTFSTYAMNWVRQAPGKGLEWVARIRSKYNNYATYYADSV
KDRFTISRDDSKNSLYLQMNSLKTEDTAVYYCVRHGNFGNSYVSWFAYWGQGTLVTVSS
[GGGGS]QVQLKQSGPGLVQPSQSLSITCTVSGFSLTNYGVHWVRQSPGKGLEWLGVIWSGG
NTDYNTPFTSRLSINKDNSKSQVFFKMNSLQSQDTAIYYCARALTYYDYEFAYWGQGTLV
TVSAASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPPCPAPEFEG
GPSVFLFPPKPKDTLMISRTPEVTCVVVDVSHEDPEVKFNWYVDGVEVHNAKTKPREEQY
QSTYRVVSVLTVLHQDWLNGKEYKCKVSNKALPASIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGK (SEQ ID NO: 146)

pLW246: LC CF41-2008-C225v5
Nucleotide Sequence
Sequences provided above

Amino Acid Sequence
Sequences provided above

-continued

CI136: CF41-2008-C225v5Fcmt4-h20GG-0011-v19sc-H-N pLW353: HC h20GG-0011-v19sc-C225v5Fcmt4 (H-N)
Nucleotide Sequence
[spacer SEQ ID NO: 191][pLW353 without spacer SEQ ID NO: 211]
CAAGGCCAGTCTGGATCCGGTTATCTGTGGGGTTGCGAGTGGAATTGCGGAGGGATCA
CTACAGGCTCGAGCGGTGGCAGCGGTGGCTCTGGTGGTCTGAGCGGCCGTTCCGATGA
TCATGGCGGCGGTTCTCAGGCCGTTGTTACACAAGAGCCTTCACTTACTGTGTCTCCAG
GAGGCACTGTGACACTTACGTGCCGATCCTCTACGGGTGCCGTGACCACAAGCAACTA
TGCCAACTGGGTCCAGCAGAAGCCAGGTCAAGCGCCTCGAGGTCTGATCGGGGGCACG
AATAAACGAGCTCCTGGAACTCCGGCCAGATTTTCTGGGAGTCTTATTGGTGGCAAGGC
GGCGTTGACCCTGAGTGGAGCCCAACCGGAAGACGAGGCCGAGTACTACTGCGCCTTG
TGGTATTCCAATTTGTGGGTCTTCGGAGGCGGAACAAAGCTCACAGTACTGGGAGGTG
GAGGTAGCGGGGGCGGAGGCTCCGGGGGAGGTGGTTCCGAAGTCCAGCTTGTTGAATC
AGGTGGGGGCTTGGTACAACCAGGTGGTTCACTGAAGTTGTCCTGTGCAGCGTCCGGA
TTTACATTTAGTACGTATGCTATGAACTGGGTCAGGCAGGCCAGTGGTAAAGGTCTCGA
ATGGGTTGGCCGGATAAGGTCAAAGTACAATAATTACGCAACCTACTACGCGGATTCC
GTGAAAGACAGGTTCACTATTTCACGAGATGATAGCAAAAATACTGCGTATCTCCAAA
TGAATAGTCTTAAAACTGAAGACACTGCCGTATATTATTGCACTAGGCACGGCAACTTT
GGTAACTCTTATGTTTCTTGGTTCGCATACTGGGGACAAGGAACTTTGGTCACTGTCTC
ATCTGGAGGTGGTGGATCCCAGGTGCAGCTGAAACAGAGCGGCCCGGGCCTGGTGCAG
CCGAGCCAGAGCCTGAGCATTACCTGCACCGTGAGCGGCTTTAGCCTGACCAACTATG
GCGTGCATTGGGTGCGCCAGAGCCCGGGCAAAGGCCTGGAATGGCTGGGCGTGATTTG
GAGCGGCGGCAACACCGATTATAACACCCCGTTTACCAGCCGCCTGAGCATTAACAAA
GATAACAGCAAAAGCCAGGTGTTTTTTAAAATGAACAGCCTGCAAAGCCAGGATACCG
CGATTTATTATTGCGCGCGCGCGCTGACCTATTATGATTATGAATTTGCGTATTGGGGC
CAGGGCACCCTGGTGACCGTGAGCGCGGCTAGCACCAAGGGCCCATCGGTCTTCCCCC
TGGCACCCTCCTCCAAGAGCACCTCTGGGGGCACAGCGGCCCTGGGCTGCCTGGTCAA
GGACTACTTCCCCGAACCGGTGACGGTGTCGTGGAACTCAGGCGCCCTGACCAGCGGC
GTGCACACCTTCCCGGCTGTCCTACAGTCCTCAGGACTCTACTCCCTCAGCAGCGTGGT
GACCGTGCCCTCCAGCAGCTTGGGCACCCAGACCTACATCTGCAACGTGAATCACAAG
CCCAGCAACACCAAGGTGGACAAGAAAGTTGAGCCCAAATCTTGTGACAAAACTCACA
CATGCCCACCGTGCCCAGCACCTGAATTTGAAGGGGGACCGTCAGTCTTCCTCTTCCCC
CCAAAACCCAAGGACACCCTCATGATCTCCCGGACCCCTGAGGTCACATGCGTGGTGG
TGGACGTGAGCCACGAAGACCCTGAGGTCAAGTTCAACTGGTACGTGGACGGCGTGGA
GGTGCATAATGCCAAGACAAAGCCGCGGGAGGAGCAGTACCAGAGCACGTACCGTGT
GGTCAGCGTCCTCACCGTCCTGCACCAGGACTGGCTGAATGGCAAGGAGTACAAGTGC
AAGGTCTCCAACAAAGCCCTCCCAGCCTCAATCGAGAAAACCATCTCCAAAGCCAAAG
GGCAGCCCCGAGAACCACAGGTGTACACCCTGCCCCCATCCCGGGAGGAGATGACCAA
GAACCAGGTCAGCCTGACCTGCCTGGTCAAAGGCTTCTATCCCAGCGACATCGCCGTG
GAGTGGGAGAGCAATGGGCAGCCGGAGAACAACTACAAGACCACGCCTCCCGTGCTG
GACTCCGACGGCTCCTTCTTCCTCTACAGCAAGCTCACCGTGGACAAGAGCAGGTGGC
AGCAGGGGAACGTCTTCTCATGCTCCGTGATGCATGAGGCTCTGCACAACCACTACAC
GCAGAAGAGCCTCTCCCTGTCTCCGGGTAAA (SEQ ID NO: 152)

Amino Acid Sequence
[spacer SEQ ID NO: 178][pLW353 without spacer SEQ ID NO: 212]
QGQSGS[GYLWGCEWNCGGITT][GSSGGSGGSGG][LSGRSDDH][GGGS]QAVVTQEPSLTV
SPGGTVTLTCRSSTGAVTTSNYANWVQQKPGQAPRGLIGGTNKRAPGTPARFSGSLIGGKA
ALTLSGAQPEDEAEYYCALWYSNLWVFGGGTKLTVL[GGGGSGGGGSGGGGS]EVQLVES
GGGLVQPGGSLKLSCAASGFTFSTYAMNWVRQASGKGLEWVGRIRSKYNNYATYYADSV
KDRFTISRDDSKNTAYLQMNSLKTEDTAVYYCTRHGNFGNSYVSWFAYWGQGTLVTVSS
[GGGGS]QVQLKQSGPGLVQPSQSLSITCTVSGFSLTNYGVHWVRQSPGKGLEWLGVIWSGG
NTDYNTPFTSRLSINKDNSKSQVFFKMNSLQSQDTAIYYCARALTYYDYEFAYWGQGTLV
TVSAASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPPCPAPEFEG
GPSVFLFPPKPKDTLMISRTPEVTCVVVDVSHEDPEVKFNWYVDGVEVHNAKTKPREEQY
QSTYRVVSVLTVLHQDWLNGKEYKCKVSNKALPASIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGK (SEQ ID NO: 148)

pLW246: LC CF41-2008-C225v5
Sequences provided above

CI091: 3954-1490DQH-C225v5Fcmt4-h20GG-2008-v16sc-H-N pLW242: HC C225v5Fcmt4-h20GG-2008-v16sc (H-N)
Nucleic Acid Sequence
[spacer SEQ ID NO: 191][pLW242 without spacer SEQ ID NO: 213]
CAAGGCCAGTCTGGATCCGGTTATCTGTGGGGTTGCGAGTGGAATTGCGGAGGGATCA
CTACAGGCTCGAGCGGTGGCAGCGGTGGCTCTGGTGGTATATCGAGTGGATTGCTGTCT
GGCAGATCTGACCAACACGGCGGCGGTTCTCAAACTGTAGTAACTCAAGAACCAAGCT
TCTCCGTCTCCCCTGGGGGAACAGTCACACTTACCTGCCGAAGTAGTACAGGTGCTGTT
ACGACCAGTAACTATGCCAATTGGGTACAACAAACGCCTGGTCAGGCTCCGCGCGGAT
TGATAGGAGGCACGAATAAACGGGCACCCGGTGTCCCGGACAGATTCAGCGGAAGCAT
ACTCGGTAATAAGGCAGCTCTTACTATCACTGGGGCCCAAGCTGATGATGAAAGTGAT
TATTATTGTGCGCTCTGGTACAGCAACCTCTGGGTGTTTGGGGGTGGCACGAAACTTAC
TGTCTTGGGCGGCGGCGGATCAGGGGGAGGTGGCTCTGGAGGAGGAGGCTCAGAAGTC -continued CAACTGGTCGAATCCGGGGGAGGGCTCGTACAGCCGGGTGGGTCCCTCAAACTCTCTT
GTGCGGCCTCAGGGTTTACCTTCAGTACATACGCGATGAATTGGGTCCGGCAGGCCAGT
GGGAAAGGGCTCGAATGGGTAGGACGAATCCGATCAAAATACAACAACTACGCTACTT
ATTACGCTGATTCCGTGAAGGACAGATTCACAATATCCCGCGACGATAGCAAGAATAC
GGCATATCTTCAGATGAATTCTCTTAAAACTGAGGATACCGCTGTGTATTACTGCACAA
GACATGGTAATTTTGGAAACTCATATGTCTCTTGGTTCGCTTATTGGGGACAGGGCACG
TTGGTTACCGTGTCTAGCGGAGGTGGTGGATCCCAGGTGCAGCTGAAACAGAGCGGCC
CGGGCCTGGTGCAGCCGAGCCAGAGCCTGAGCATTACCTGCACCGTGAGCGGCTTTAG
CCTGACCAACTATGGCGTGCATTGGGTGCGCCAGAGCCCGGGCAAAGGCCTGGAATGG
CTGGGCGTGATTTGGAGCGGCGGCAACACCGATTATAACACCCCGTTTACCAGCCGCCT
GAGCATTAACAAAGATAACAGCAAAAGCCAGGTGTTTTTTAAAATGAACAGCCTGCAA
AGCCAGGATACCGCGATTTATTATTGCGCGCGCGCGCTGACCTATTATGATTATGAATT
TGCGTATTGGGGCCAGGGCACCCTGGTGACCGTGAGCGCGGCTAGCACCAAGGGCCCA
TCGGTCTTCCCCCTGGCACCCTCCTCCAAGAGCACCTCTGGGGGCACAGCGGCCCTGGG
CTGCCTGGTCAAGGACTACTTCCCCGAACCGGTGACGGTGTCGTGGAACTCAGGCGCC
CTGACCAGCGGCGTGCACACCTTCCCGGCTGTCCTACAGTCCTCAGGACTCTACTCCCT
CAGCAGCGTGGTGACCGTGCCCTCCAGCAGCTTGGGCACCCAGACCTACATCTGCAAC
GTGAATCACAAGCCCAGCAACACCAAGGTGGACAAGAAAGTTGAGCCCAAATCTTGTG
ACAAAACTCACACATGCCCACCGTGCCCAGCACCTGAATTTGAAGGGGGACCGTCAGT
CTTCCTCTTCCCCCCAAAACCCAAGGACACCCTCATGATCTCCCGGACCCCTGAGGTCA
CATGCGTGGTGGTGGACGTGAGCCACGAAGACCCTGAGGTCAAGTTCAACTGGTACGT
GGACGGCGTGGAGGTGCATAATGCCAAGACAAAGCCGCGGGAGGAGCAGTACCAGAG
CACGTACCGTGTGGTCAGCGTCCTCACCGTCCTGCACCAGGACTGGCTGAATGGCAAG
GAGTACAAGTGCAAGGTCTCCAACAAAGCCCTCCCAGCCTCAATCGAGAAAACCATCT
CCAAAGCCAAAGGGCAGCCCCGAGAACCACAGGTGTACACCCTGCCCCCATCCCGGGA
GGAGATGACCAAGAACCAGGTCAGCCTGACCTGCCTGGTCAAAGGCTTCTATCCCAGC
GACATCGCCGTGGAGTGGGAGAGCAATGGGCAGCCGGAGAACAACTACAAGACCACG
CCTCCCGTGCTGGACTCCGACGGCTCCTTCTTCCTCTACAGCAAGCTCACCGTGGACAA
GAGCAGGTGGCAGCAGGGGAACGTCTTCTCATGCTCCGTGATGCATGAGGCTCTGCAC
AACCACTACACGCAGAAGAGCCTCTCCCTGTCTCCGGGTAAA (SEQ ID NO: 168)

Amino Acid Sequence
[spacer SEQ ID NO: 178][pLW242 without spacer SEQ ID NO: 214]
QGQSGS[GYLWGCEWNCGGITT]GSSGGSGGSGG[ISSGLLSGRSDQH]GGGSQTVVTQEPSF
SVSPGGTVTLTCRSSTGAVTTSNYANWVQQTPGQAPRGLIGGTNKRAPGVPDRFSGSILGN
KAALTITGAQADDESDYYCALWYSNLWVFGGGTKLTVLGGGGSGGGGSGGGGSEVQLVE
SGGGLVQPGGSLKLSCAASGFTFSTYAMNWVRQASGKGLEWVGRIRSKYNNYATYYADS
VKDRFTISRDDSKNTAYLQMNSLKTEDTAVYYCTRHGNFGNSYVSWFAYWGQGTLVTVS
SGGGGSQVQLKQSGPGLVQPSQSLSITCTVSGFSLTNYGVHWVRQSPGKGLEWLGVIWSG
GNTDYNTPFTSRLSINKDNSKSQVFFKMNSLQSQDTAIYYCARALTYYDYEFAYWGQGTL
VTVSAASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSCDKTHTCPPCPAPEFE
GGPSVFLFPPKPKDTLMISRTPEVTCVVVDVSHEDPEVKFNWYVDGVEVHNAKTKPREEQ
YQSTYRVVSVLTVLHQDWLNGKEYKCKVSNKALPASIEKTISKAKGQPREPQVYTLPPSRE
EMTKNQVSLTCLVKGFYPSDIAVEWESNGQPENNYKTTPPVLDSDGSFFLYSKLTVDKSR
WQQGNVFSCSVMHEALHNHYTQKSLSLSPGK (SEQ ID NO: 169)

CX320: 3954-C225v5-2008
Nucleic Acid Sequence
[spacer SEQ ID NO: 180][CX320 without spacer SEQ ID NO: 215]
CAAGGCCAGTCTGGCCAGTGCATCTCACCTCGTGGTTGTCCGGACGGCCCATACGTCAT
GTACGGCTCGAGCGGTGGCAGCGGTGGCTCTGGTGGATCCGGTATATCGAGTGGATTG
CTGTCTGGCAGATCTGACCAACACGGCAGTAGCGGTACCCAGATCTTGCTGACCCAGA
GCCCGGTGATTCTGAGCGTGAGCCCGGGCGAACGTGTGAGCTTTAGCTGCCGCGCGAG
CCAGAGCATTGGCACCAACATTCATTGGTATCAGCAGCGCACCAACGGCAGCCCGCGC
CTGCTGATTAAATATGCGAGCGAAAGCATTAGCGGCATTCCGAGCCGCTTTAGCGGCA
GCGGCAGCGGCACCGATTTTACCCTGAGCATTAACAGCGTGGAAAGCGAAGATATTGC
GGATTATTATTGCCAGCAGAACAACAACTGGCCGACCACCTTTGGCGCGGGCACCAAA
CTGGAACTGAAACGTACGGTGGCTGCACCATCTGTCTTCATCTTCCCGCCATCTGATGA
GCAGTTGAAATCTGGAACTGCCTCTGTTGTGTGCCTGCTGAATAACTTCTATCCCAGAG
AGGCCAAAGTACAGTGGAAGGTGGATAACGCCCTCCAATCGGGTAACTCCCAGGAGAG
TGTCACAGAGCAGGACAGCAAGGACAGCACCTACAGCCTCAGCAGCACCCTGACGCTG
AGCAAAGCAGACTACGAGAAACACAAAGTCTACGCCTGCGAAGTCACCCATCAGGGCC
TGAGCTCGCCCGTCACAAAGAGCTTCAACAGGGGAGAGTGT (SEQ ID NO: 170)

Amino Acid Sequence
[spacer SEQ ID NO: 178][CX320 without spacer SEQ ID NO: 216]
QGQSGQ[CISPRGCPDGPYVMY]GSSGGSGGSGGSG[ISSGLLSGRSDQH]GSSGTQILLTQSP
VILSVSPGERVSFSCRASQSIGTNIHWYQQRTNGSPRLLIKYASESISGIPSRFSGSGSGTDFTL
SINSVESEDIADYYCQQNNNWPTTFGAGTKLELKRTVAAPSVFIFPPSDEQLKSGTASVVCL
LNNFYPREAKVQWKVDNALQSGNSQESVTEQDSKDSTYSLSSTLTLSKADYEKHKVYACE
VTHQGLSSPVTKSFNRGEC (SEQ ID NO: 171)

-continued

CI064: SynN2970-JF15865-0001-hSP34LvHv-H-N pLW138: HC SynN297Q-JF15865-0001-hSP34LvHv-H-N
Nucleic Acid Sequence
[spacer SEQ ID NO: 176][pLW138 without spacer SEQ ID NO: 147]
CAAGGCCAGTCTGGCCAAATGATGTATTGCGGTGGGAATGAGGTGTTGTGCGGGCCGC
GGGTTGGCTCGAGCGGTGGCAGCGGTGGCTCTGGTGGTCTGAGCGGCCGTTCCGATAA
TCATGGCGGCGGTTCTCAGACCGTGGTCACACAGGAGCCCTCACTGACAGTGAGCCCT
GGCGGGACCGTCACACTGACTTGTCGCAGTTCAACTGGCGCCGTGACTACCAGCAATT
ACGCTAACTGGGTCCAGCAGAAACCAGGACAGGCACCACGAGGACTGATCGGAGGAA
CTAATAAGAGAGCACCAGGAACCCCTGCAAGGTTCTCCGGATCTCTGCTGGGGGGAAA
AGCCGCTCTGACACTGAGCGGCGTGCAGCCTGAGGACGAAGCTGAGTACTATTGCGCA
CTGTGGTACTCCAACCTGTGGGTGTTTGGCGGGGAACTAAGCTGACCGTCCTGGGAG
GAGGAGGAAGCGGAGGAGGAGGGAGCGGAGGAGGAGGATCCGAAGTGCAGCTGGTC
GAGAGCGGAGGAGGACTGGTGCAGCCAGGAGGATCCCTGAAGCTGTCTTGTGCAGCCA
GTGGCTTCACCTTCAACACTTACGCAATGAACTGGGTGCGGCAGGCACCTGGGAAGGG
ACTGGAATGGGTCGCCCGGATCAGATCTAAATACAATAACTATGCCACCTACTATGCTG
ACAGTGTGAAGGATAGGTTCACCATTTCACGCGACGATAGCAAAAACACAGCTTATCT
GCAGATGAATAACCTGAAGACCGAGGATACAGCAGTGTACTATTGCGTCAGACACGGC
AATTTCGGGAACTCTTACGTGAGTTGGTTTGCCTATTGGGGACAGGGGACACTGGTCAC
CGTCTCCTCAGGAGGTGGTGGATCCCAAGTGACCCTGAGAGAGTCTGGCCCTGCCCTCG
TGAAGCCTACCCAGACCCTGACACTGACCTGCACCTTCAGCGGCTTCAGCCTGAGCACC
AGCGGCATGTCTGTGGGCTGGATCAGACAGCCTCCTGGCAAGGCCCTGGAATGGCTGG
CCGACATTTGGTGGGACGACAAGAAGGACTACAACCCCAGCCTGAAGTCCCGGCTGAC
CATCAGCAAGGACACCAGCAAGAACCAGGTGGTGCTGAAAGTGACCAACATGGACCC
CGCCGACACCGCCACCTACTACTGCGCCAGATCCATGATCACCAACTGGTACTTCGACG
TGTGGGGAGCCGGCACCACCGTGACAGTGTCATCTGCTAGCACCAAGGGCCCATCGGT
CTTCCCCCTGGCACCCTCCTCCAAGAGCACCTCTGGGGGCACAGCGGCCCTGGGCTGCC
TGGTCAAGGACTACTTCCCCGAACCGGTGACGGTGTCGTGGAACTCAGGCGCCCTGAC
CAGCGGCGTGCACACCTTCCCGGCTGTCCTACAGTCCTCAGGACTCTACTCCCTCAGCA
GCGTGGTGACCGTGCCCTCCAGCAGCTTGGGCACCCAGACCTACATCTGCAACGTGAA
TCACAAGCCCAGCAACACCAAGGTGGACAAGAAAGTTGAGCCCAAATCTTGTGACAAA
ACTCACACATGCCCACCGTGCCCAGCACCTGAACTCCTGGGGGGACCGTCAGTCTTCCT
CTTCCCCCCAAAACCCAAGGACACCCTCATGATCTCCCGGACCCCTGAGGTCACATGCG
TGGTGGTGGACGTGAGCCACGAAGACCCTGAGGTCAAGTTCAACTGGTACGTGGACGG
CGTGGAGGTGCATAATGCCAAGACAAAGCCGCGGGAGGAGCAGTACCAGAGCACGTA
CCGTGTGGTCAGCGTCCTCACCGTCCTGCACCAGGACTGGCTGAATGGCAAGGAGTAC
AAGTGCAAGGTCTCCAACAAAGCCCTCCCAGCCCCCATCGAGAAAACCATCTCCAAAG
CCAAAGGGCAGCCCCGAGAACCACAGGTGTACACCCTGCCCCCATCCCGGGAGGAGAT
GACCAAGAACCAGGTCAGCCTGACCTGCCTGGTCAAAGGCTTCTATCCCAGCGACATC
GCCGTGGAGTGGGAGAGCAATGGGCAGCCGGAGAACAACTACAAGACCACGCCTCCC
GTGCTGGACTCCGACGGCTCCTTCTTCCTCTACAGCAAGCTCACCGTGGACAAGAGCAG
GTGGCAGCAGGGGAACGTCTTCTCATGCTCCGTGATGCATGAGGCTCTGCACAACCACT
ACACGCAGAAGAGCCTCTCCCTGTCTCCGGGTAAA (SEQ ID NO: 172)

Amino Acid Sequence
[spacer SEQ ID NO: 178][pLW138 without spacer SEQ ID NO: 153]
QGQSGQ[MMYCGGNEVLCGPRV]GSSGGSGGSGG[LSGRSDNH]GGGSQTVVTQEPSLTVS
PGGTVTLTCRSSTGAVTTSNYANWVQQKPGQAPRGLIGGTNKRAPGTPARFSGSLLGGKA
ALTLSGVQPEDEAEYYCALWYSNLWVFGGGTKLTVLGGGGSGGGGSGGGGSEVQLVESG
GGLVQPGGSLKLSCAASGFTFNTYAMNWVRQAPGKGLEWVARIRSKYNNYATYYADSVK
DRFTISRDDSKNTAYLQMNNLKTEDTAVYYCVRHGNFGNSYVSWFAYWGQGTLVTVSSG
GGGSQVTLRESGPALVKPTQTLTLTCTFSGFSLSTSGMSVGWIRQPPGKALEWLADIWWDD
KKDYNPSLKSRLTISKDTSKNQVVLKVTNMDPADTATYYCARSMITNWYFDVWGAGTTV
TVSSASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAKTKPREEQYQS
TYRVVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQ
GNVFSCSVMHEALHNHYTQKSLSLSPGK (SEQ ID NO: 173)

pLW139: LC Syn kappa
Nucleic Acid Sequence
GACATCCAGATGACCCAGAGCCCCAGCACACTGAGCGCCAGCGTGGGCGACAGAGTG
ACCATCACATGCAAGTGCCAGCTGAGCGTGGGCTACATGCACTGGTATCAGCAGAAGC
CCGGCAAGGCCCCCAAGCTGCTGATCTACGACACCAGCAAGCTGGCCTCCGGCGTGCC
CAGCAGATTTTCTGGCAGCGGCTCCGGCACCGAGTTCACCCTGACAATCAGCAGCCTGC
AGCCCGACGACTTCGCCACCTACTACTGTTTTCAAGGCTCCGGCTACCCCTTCACCTTC
GGCGGAGGCACCAAGCTGGAAATCAAGCGGACGGTGGCTGCACCATCTGTCTTCATCT
TCCCGCCATCTGATGAGCAGTTGAAATCTGGAACTGCCTCTGTTGTGTGCCTGCTGAAT
AACTTCTATCCCAGAGAGGCCAAAGTACAGTGGAAGGTGGATAACGCCCTCCAATCGG
GTAACTCCCAGGAGAGTGTCACAGAGCAGGACAGCAAGGACAGCACCTACAGCCTCA
GCAGCACCCTGACGCTGAGCAAAGCAGACTACGAGAAACACAAAGTCTACGCCTGCGA
AGTCACCCATCAGGGCCTGAGCTCGCCCGTCACAAAGAGCTTCAACAGGGGAGAGTGT
(SEQ ID NO: 174)

-continued

```
Amino Acid Sequence
DIQMTQSPSTLSASVGDRVTITCKCQLSVGYMHWYQQKPGKAPKLLIYDTSKLASGVPSRF
SGSGSGTEFTLTISSLQPDDFATYYCFQGSGYPFTFGGGTKLEIKRTVAAPSVFIFPPSDEQLK
SGTASVVCLLNNFYPREAKVQWKVDNALQSGNSQESVTEQDSKDSTYSLSSTLTLSKADY
EKHKVYACEVTHQGLSSPVTKSFNRGEC (SEQ ID NO: 175)

Anti-CD3 scFv variant v12
Light chain LV12
Heavy chain HV12
Sequences provided above

Anti-CD3 scFv variant v16
Light chain LV12
Heavy chain HV20
Sequences provided above

Anti-CD3 scFv variant v19
Light chain LV19
Heavy chain HV20
Sequences provided above

Anti-CD3 scFv variant v26
Light chain LV 19
Heavy chain HV 12
Sequences provided above
```

Vector Construction

The heavy and light chains were cloned separately into a mammalian expression vector using standard molecular biology techniques. Briefly, DNA fragments encoding the region of interest were amplified with primers binding to the terminal ends. Overlapping fragments were combined and amplified with flanking primers as needed to build the entire desired region. DNA fragments were subsequently cloned into the expression vector using a commercially available homologous recombination kit (MCLabs, South San Francisco, CA). The mammalian expression vector is a modified version of cDNA™3.1 (+) from Invitrogen with selection marker of G418 or hygromycin. Mutations were introduced using the QuikChange Kit (Agilent, Santa Clara, CA).

Expression of AAs and Dually Masked BAAs (BAAs)

AAs and BAAs were expressed in mammalian cells using a standard transfection kit (Life Technologies, Grand Island, NY). Briefly, 293 cells were transfected with nucleic acids using a lipid-based system, following the manufacturer's recommended protocol. AAs and dually masked BAAs were purified from cell-free supernatant using Protein A beads (GE, Piscataway, NJ) and concentrated using standard buffer exchange columns (Millipore, Temecula, CA).

Example 2. Binding of Dually Masked, Bispecific, AAs to EGFR+ HT-29 Cells and CD3ε+ Jurkat Cells To determine if the described EGFR and CD3ε masking peptides and protease substrates could inhibit binding in the context of a dually masked, bispecific, AA, a flow cytometry-based binding assay was performed.

HT-29-luc2 (Caliper) and Jurkat (Clone E6-1, ATCC, TIB-152) cells were cultured in RPMI-1640+glutamax (Life Technologies, Catalog 72400-047), 10% Heat Inactivated-Fetal Bovine Serum (HI-FBS, Life Technologies, Catalog 10438-026), 100 U/ml penicillin, and 100 μg/ml streptomycin (Life Technologies, Catalog 15140-122) according to manufacturer guidelines. The following bispecific, activated antibodies CI048 and CI104 (act-104), and dually masked, bispecific, AAs CI011, CI106, and CI107 were tested. Two versions of SP34 scFv were utilized, namely the scFv in CI011 and CI048 versus the scFv in CI104, CI106, and CI107. Two versions of the EGFR mask were utilized, namely the EGFR mask in CI011 and CI107 versus the EGFR mask in CI106. Two versions of the CD3 mask were utilized, namely the CD3 mask in CI011 versus the CD3 mask in CI106 and CI107.

HT29-luc2 cells were detached with Versene™ (Life Technologies, Catalog 15040-066), washed, plated in 96 well plates at 150,000 cells/well, and re-suspended in 50 μL of primary antibody. Titrations started at the concentrations indicated in FIGS. 1A-1B followed by 3-fold serial dilutions in FACS Stain Buffer+2% FBS (BD Pharmingen, Catalog 554656). Cells were incubated at 4° C. with shaking for about 1 hour, harvested, and washed with 2×200 μL of FACS Stain Buffer. Cells were resuspended in 50 μL of Alexa Fluor 647 conjugated anti-Human IgG Fc (10 μg/ml, Jackson ImmunoResearch, Product 109-606-008) and incubated at 4° C. with shaking for about 1 hour. HT29-luc2 were harvested, washed, and resuspended in a final volume of 60 μL of FACS Stain Buffer containing 2.5 μg/ml 7-AAD (BD Biosciences, Catalog 559925). Cells stained with secondary antibody alone were used as a negative control. Data was acquired on a MACSQuant® Analyzer 10 (Miltenyi) and the median fluorescence intensity (MFI) of viable cells was calculated using FlowJo® V10 (Treestar). Background subtracted MFI data was graphed in GraphPad Prism 6 using curve fit analysis.

Jurkats growing in suspension were harvested, washed, plated in 96 well plates at 150000 cells/well and resuspended in 50 μl of primary antibody. Staining and data acquisition were carried out as described for HT29-luc2 cells above.

FIG. 1A demonstrates that incorporation of the h20GG CD3ε masking peptide into the EGFR masked BAAs CI106 and CI107 significantly reduced binding to Jurkat cells relative to CI011. In some embodiments, the reduction in binding to Jurkat cells was more than 5,000-fold. In some embodiments, an scFv of the disclosure also led to reduced binding. A reduction in binding to EGFR+ HT29-luc2 cells was also evident for CI106 and CI107 relative to CI011

(FIG. 1B). In some embodiments, the reduction in binding to EGFR+HT29-luc2 cells was more than 1,000-fold. In FIG. 1A and FIG. 1B, the dually masked, BAAs exhibit reduced binding relative to the activated bispecific antibodies.

Example 3. EGFR-Dependent Cytotoxicity of Dually Masked BAAs

To determine if the CD3ε and EGFR masks and the protease substrates in CI106 and CI107 could further attenuate cell killing relative to CI011 and CI040, a cytotoxicity assay was performed. Human PBMCs were purchased in frozen aliquots (HemaCare) and co-cultured with EGFR expressing HT29-luc2 cells at a ratio of 10:1 in RPMI-1640+glutamax supplemented with 5% heat inactivated human serum (Sigma, Catalog H3667). Titrations of the following bispecific, activated antibodies and dually masked BAAs were tested: CI011, CI040, activated CI104, CI106, and CI107. In addition, non-EGFR binding, masked bispecific, AAs CI127 and CI128 were used to demonstrate the EGFR dependence of cytotoxicity. After 48 hours, cytotoxicity was evaluated using the ONE-Glo™ Luciferase Assay System (Promega, Catalog E6130). Luminescence was measured on the Infinite M200 Pro (Tecan). Percent cytotoxicity was calculated and plotted in GraphPad PRISM with curve fit analysis. EGFR receptor number on a panel of cell lines was quantified by flow cytometry using QIFIKIT (Dako).

Figures 2A, 2B, 2C:
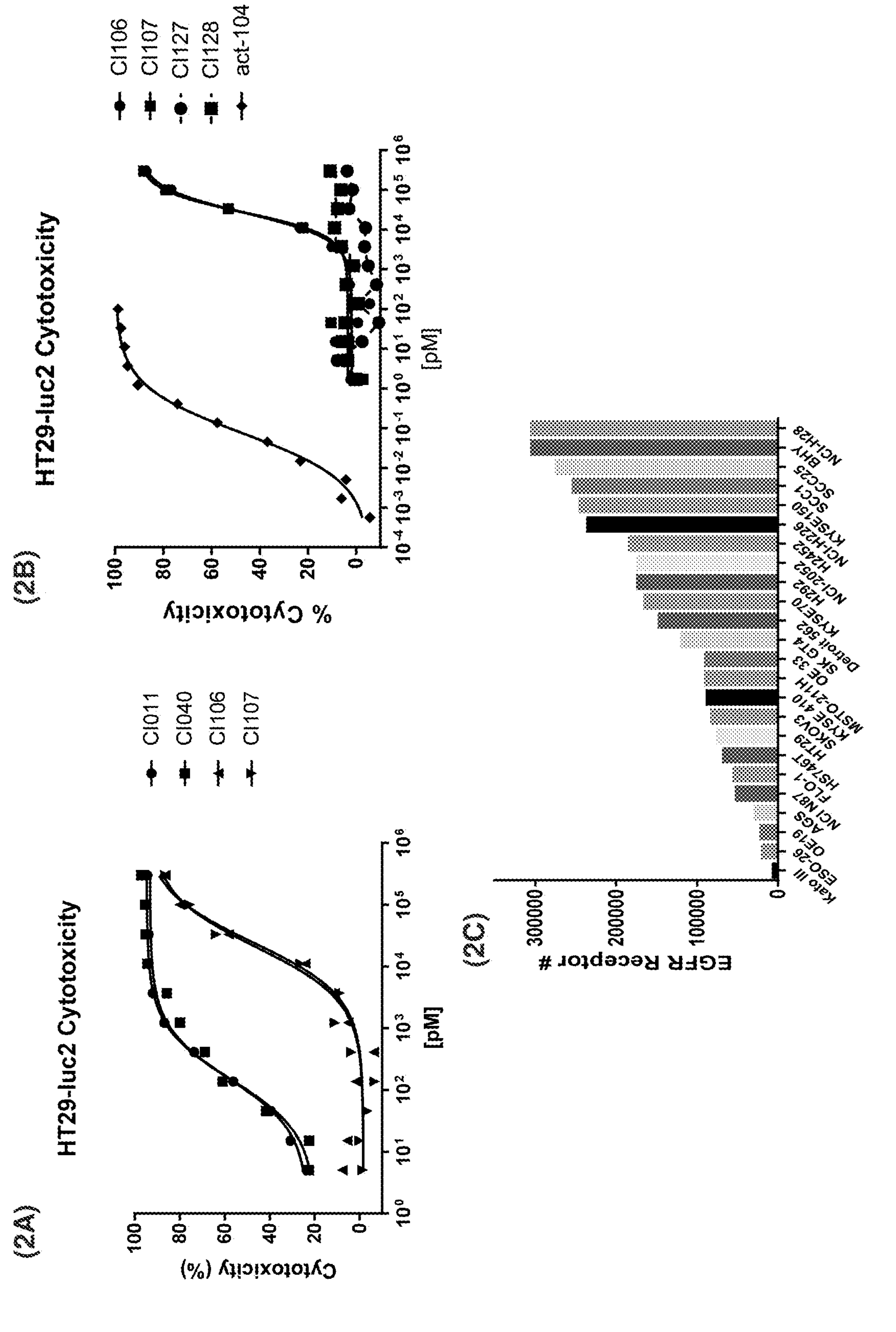
FIG. 2A demonstrates that killing of EGFR+ HT29-luc2 cells was further attenuated by CI106 and CI107 relative to CI011 and CI040.
FIG. 2B shows that no detectable cytotoxicity was observed when cells were treated with CI127 and CI128 demonstrating the dependence of EGFR targeting for cell killing.
FIG. 2C depicts the EGFR receptor number on a panel of cell lines that includes HT29. The approximate EGFR receptor number on HT29 cells was 75,000, indicating that high antigen density was not required for potent cytotoxicity of the tested BAAs.

FIG. 2A demonstrates that killing of EGFR+HT29-luc2 cells was further attenuated by CI106 and CI106 relative to CI011 and CI040. FIG. 2B shows that no cytotoxicity was observed when cells were treated with CI127 and CI128 demonstrating the dependence of EGFR targeting for cell killing. Additionally, FIG. 2B depicts a more than 300,000 fold EC50 shift of the dually masked bispecific antibodies CI106 and CI107 relative to the protease activated bispecific antibody act-104. FIG. 2C depicts the EGFR receptor number on a panel of cell lines that includes HT29. The approximate EGFR receptor number on HT29 cells was 75,000, indicating that high antigen density was not required for potent cytotoxicity of the tested antibodies.

Example 4. Primary T Cell Activation by Dually Masked BAAs

To determine if the CD3ε and EGFR masks in CI106 and CI107 could attenuate primary T cell activation relative to CI011 and CI040, a flow cytometry assay was performed. Human PBMCs and U266 cells were co-cultured according to the conditions described in Example 3. After a 48 hour incubation, cells were pelleted, media was removed, and cells were resuspended in 50 μl of a cocktail containing anti-CD45 VioBlue® (Miltenyi, Catalog 130-002-880), anti-CD8 APC-Vio770 (Miltenyi, Catalog 130-096-561) and anti-CD69 PE (BD Pharmingen, Catalog 555531) in FACS Stain Buffer+2% FBS. Cells were stained for 1 h at 4° C. with shaking, harvested, washed, and re-suspended in a final volume of 60 μL FACS Buffer. Data was acquired on a MACSQuant® Analyzer 10 (Miltenyi) and activation was quantified in FlowJo® V10 (Treestar) as the percentage of CD8+ T cells with expression of CD69 above the PE isotype control. Data was plotted in GraphPad PRISM 6 with curve fit analysis.

FIG. 3A demonstrates that activation of primary CD8+ T cells was attenuated by CI106 and CI107, relative to CI011 and CI040. FIG. 3B demonstrates that dually masked antibodies display a shifted dose response curve for T cell activation relative to protease activated bispecific antibody act-104 indicating that masking attenuates T cell activation.

Example 5. Dually Masked, Bispecific, AAs of the Embodiments Induced Regression of Established HT29-Luc2 Tumors in Mice In this example, dually masked BAAs CI106 and CI107 targeting EGFR and CD3ε were analyzed for the ability to induce regression or reduce growth of established HT-29-Luc2 xenograft tumors in human T-cell engrafted NSG mice.

The human colon cancer cell line HT29-luc2 was obtained from Perkin Elmer, Inc., Waltham, MA (formerly Caliper Life Sciences, Inc.) and cultured according to established procedures. Purified, frozen human PBMCs were obtained from Hemacare, Inc., Van Nuys, CA NSG™ (NOD.Cg-Prkdcscid Il2rg$^{tm1\,Wjl}$/SzJ) mice were obtained from The Jackson Laboratories, Bar Harbor, ME On day 0, each mouse was inoculated subcutaneously at the right flank with 2×10$^6$ HT29-luc2 cells in 100 μL RPMI+Glutamax, serum-free medium. Previously frozen PBMCs from a single donor were administered (i.p.) on day 3 at a CD3+ T cell to tumor cell ratio of 1:1. When tumor volumes reached 200 mm$^3$ (approximately day 12), mice were randomized, assigned to treatment groups and dosed i.v. according to Table 12. Tumor volume and body weights were measured twice weekly.

TABLE 12

Groups and doses for HT2-9luc2 xenograft study.

| Group | Count | Treatment | Dose (mg/kg) |
|---|---|---|---|
| 1 | 7 | PBS | N/A |
| 2 | 7 | CI106 | 0.5 |
| 3 | 7 | CI106 | 1.5 |
| 4 | 7 | CI107 | 0.5 |
| 5 | 7 | CI107 | 1.5 |

Figure 4:
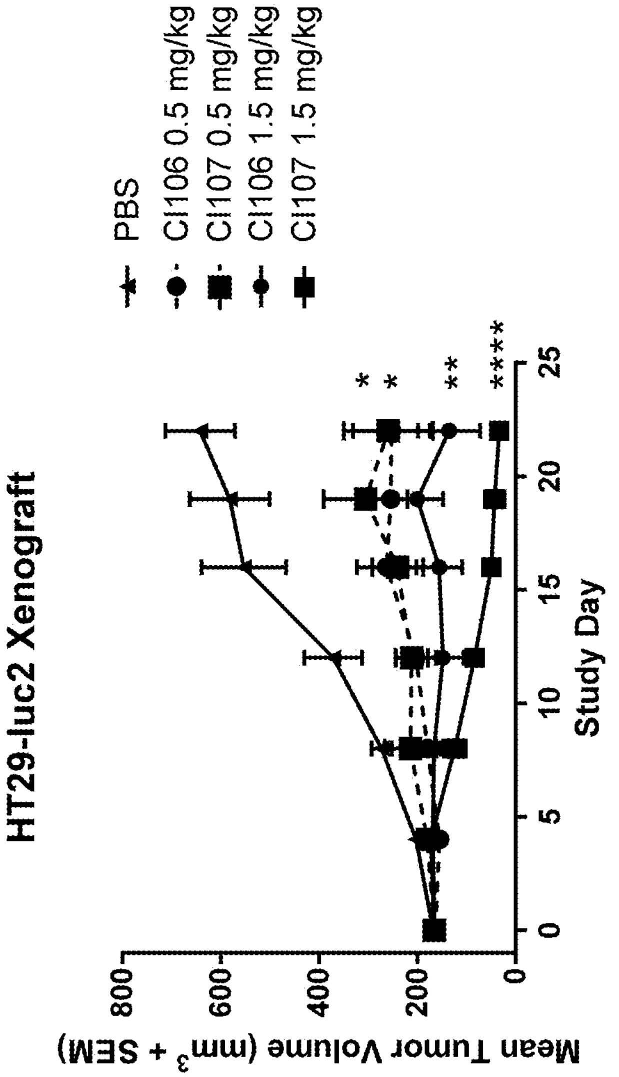
FIG. 4, which plots tumor volume versus days post initial treatment dose, demonstrates a dose-dependent effect of CI106 and CI107 dually masked, bispecific, AAs on the growth of HT29-luc2 xenograft tumors.

FIG. 4, which plots tumor volume versus days post initial treatment dose, demonstrates a dose-dependent effect of CI106 and CI107 dually masked, bispecific, AAs on the growth of HT29-luc2 xenograft tumors. The most efficacious dose tested was 1.5 mg/kg, resulting in tumor regression. Statistical analysis (RMANOVA with Dunnett's vs. PBS control) was carried out in GraphPad PRISM. *=p<0.05, =p<0.01, **=p<0.0001.

Example 6. Dually Masked, Bispecific, AAs and Bispecific Antibodies of the Embodiments Reduce Growth of Established HCT116 Tumors in Mice In this example, bispecific antibody, activated CI104, and dually masked BAAs CI106 and CI107 targeting EGFR and CD3ε were analyzed for the ability to induce regression or reduce growth of established HCT116 xenograft tumors in human T-cell engrafted NSG mice. The human colon cancer cell line HCT116 was obtained from ATCC and was cultured in RPMI+Glutamax+10% FBS according to established procedures. The tumor model was carried out as described in Example 5. Mice were dosed according to Table 13.

TABLE 13

| Groups and doses for HCT116 xenograft study. | | | |
|---|---|---|---|
| Group | Count | Treatment | Dose (mg/kg) |
| 1 | 8 | PBS | N/A |
| 2 | 8 | CI106 | 0.3 |
| 3 | 8 | CI106 | 1.0 |
| 4 | 8 | CI107 | 0.3 |
| 5 | 8 | CI107 | 1.0 |
| 6 | 8 | act-104 | 0.3 |

Figure 5:
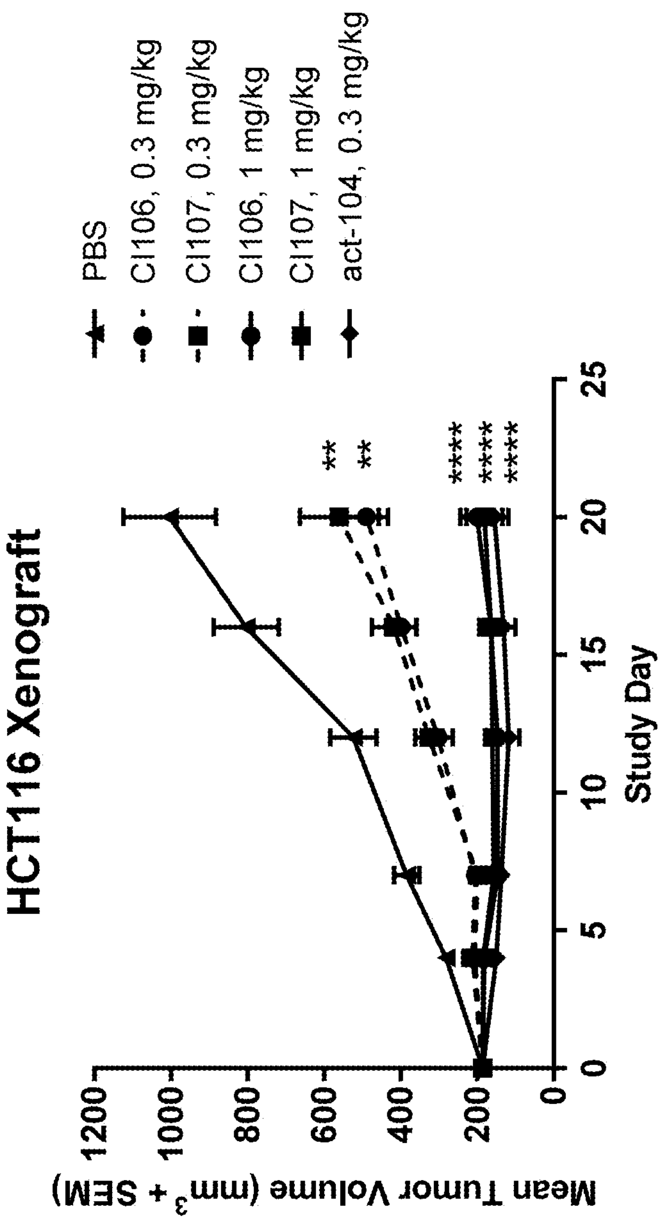
FIG. 5, which plots tumor volume versus days post initial treatment dose, demonstrated a dose-dependent effect of CI106 and CI107 dually masked, bispecific, AAs on the growth of HCT116 xenograft tumors.

FIG. 5 which plots tumor volume versus days post initial treatment dose, demonstrated a dose-dependent effect of CI106 and CI107 dually masked bispecific, AAs on the growth of HCT116 xenograft tumors. The most efficacious dose tested was 1.0 mg/kg, resulting in tumor stasis. Act-104 dosed at 0.3 mg/kg also resulted in tumor stasis, demonstrating a 3 fold difference in efficacy between dually masked and protease activated bispecific antibodies. Statistical analysis (RMANOVA with Dunnett's vs. PBS control) was carried out in GraphPad PRISM. *=p<0.05, =p<0.01, **=p<0.0001.

Example 7. Cross Reactivity of Dually Masked Bispecific, AAs to Cynomolgus Monkey T Cells To confirm that Cynomolgus monkey is a relevant toxicity species, protease activated CI104, CI106 and CI107 were used in a flow cytometry based cell binding assay and a HT29-luc2 cytotoxicity assay using Cynomolgus pan T cells (BioreclamationIVT) and the potency was compared to human PBMCs. Protocol was as described in Examples 2 and 3.

Figures 6A, 6B, 6C, 6D:
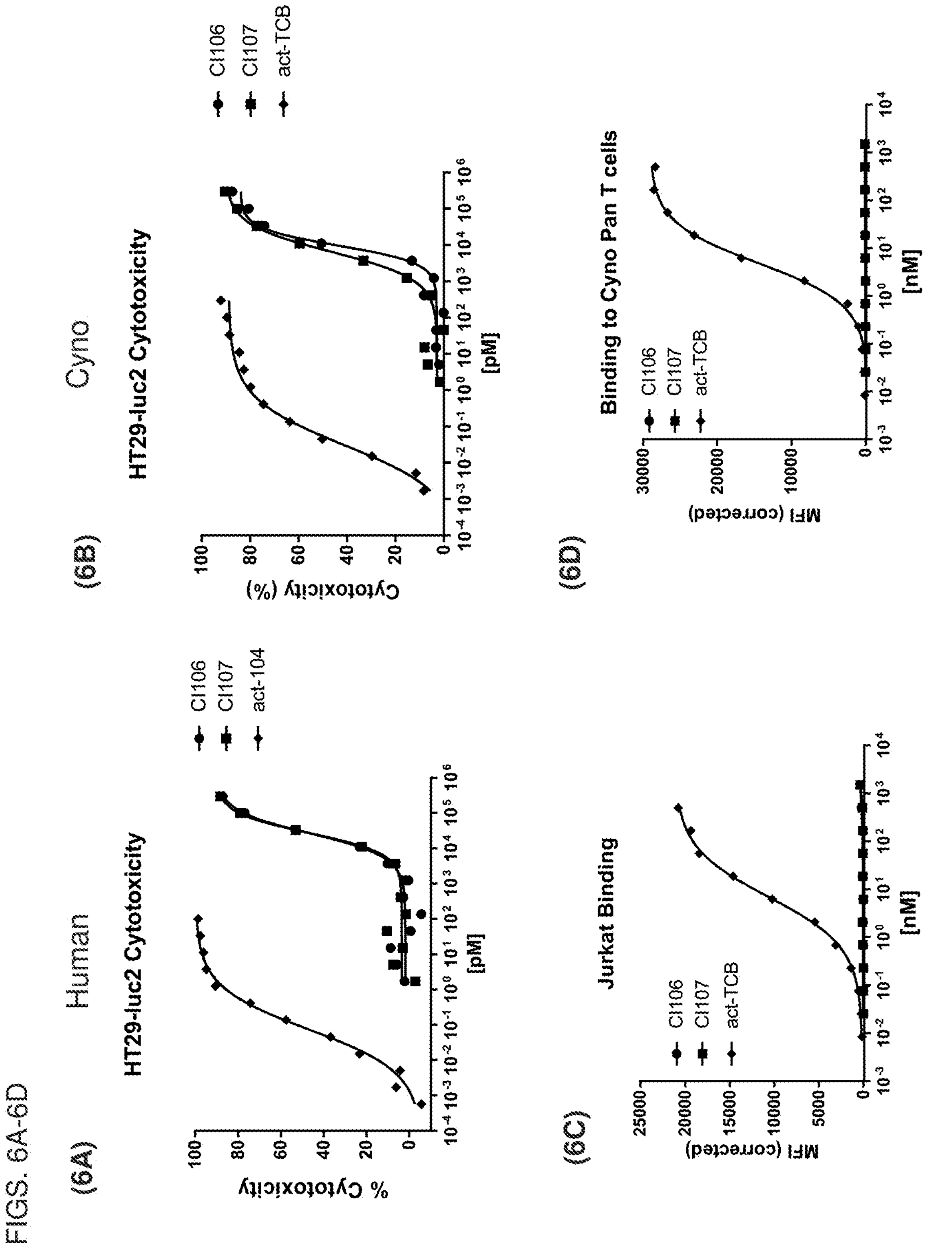

FIG. 6A and FIG. 6B demonstrate that the EC50s of the tested dually masked and protease activated bispecific antibodies in a cytotoxicity assay are similar when either human (6A) or cyno (6B) effector cells are used. FIG. 6C and FIG. 6D demonstrate that binding of the protease-activated and dually masked antibodies to human (6C) and cyno (6D) T cells is similar.

Therefore, cynomolgus monkey was determined to be a relevant species for tolerability studies.

Example 8. Mutations in the Fc Region Affect Tolerability of Dually Masked, Bispecific, AAs in Cynomolgus Monkeys In this example, CI079 and CI090 were dosed at 600, µg/kg in naïve cynomolgus monkeys (n=1) to assess tolerability. The starting dose of 600 µg/kg was chosen based on the MTD of CI011 as previously established. The monkeys were of Chinese origin and ranged in weight from 2.5 to 4 kg. Each study animal was monitored for a minimum of 7 days. Tolerability was evaluated based on clinical signs, body weight, and food consumption. This study was conducted in compliance with standard operating procedures at SNBL USA, Ltd. (Everett, WA).

Table 14 describes clinical observations following dosing of CI079 and CI090 dually masked, bispecific, AAs (BAAs) that differ only in their Fc regions (Table 15). CI079 contains Fc mutations L234F, L235E, and P331S. CI090 contains those Fc mutations and N297Q mutation. No clinical observations were noted following dosing of CI090 at 600 µg/kg, whereas, emesis was noted in the first 24 hours following dosing of CI079, demonstrating that mutations in the Fc region contribute to tolerability of these molecules.

TABLE 14

| BAA | Dose (µpk) | Observations |
|---|---|---|
| CI079 | 600 | emesis during $1^{st}$ 24 hours |
| CI090 | 600 | no clinical observations |

TABLE 15

| BAA | EGFR Mask & Substrate | CD3 Mask &Substrate | Fc |
|---|---|---|---|
| CI079 | 3954 0001 | h20GG 0001 | Fcmt3 |
| CI090 | 3954 0001 | h20GG 0001 | Fcmt4 |

Example 9. Tolerability of Dually Masked BAAs in Cynomolgus Monkeys

In this example, CI106 and CI107 were dosed at 600, 2000, 4000 µg/kg (CI107 only), or 6000 µg/kg (CI107 only) to establish the maximum tolerated dose (MTD) following a single IV bolus administration to naïve cynomolgus monkeys (n=1). The starting dose of 600 µg/kg was chosen based on the MTD of CI011 as previously established. The monkeys were of Chinese origin and ranged in weight from 2.5 to 4 kg. Each study animal was monitored for a minimum of 7 days. Tolerability was evaluated based on clinical signs, body weight, food consumption and laboratory analyses that included serum chemistry, hematology, cytokine analysis, and flow cytometry to evaluate T cell activation. Blood was collected for standard serum chemistry and hematology analysis once during acclimation and at pre-dose, 48 h, 72 h (hematology only), and 7 days post dose. Blood was collected for cytokine analysis pre-dose and at 1 h, 4 h, 8 h, and 24 h post dose. Flow cytometry was performed on peripheral blood pre-dose, 72 h, and 7 days post dose. This study was conducted in compliance with standard operating procedures at SNBL USA, Ltd. (Everett, WA).

CI107 dosed at 6000 µg/kg was fatal within 24 hours post dose. In the other groups, abnormal clinical signs including emesis and reduced food intake were observed in cynos treated with CI106 and CI107 at doses of 2000 µg/kg and above. These findings, when present, were transient and generally confined to the 48 h post-dose period. Serum chemistry findings at these doses included mild elevations of alanine transaminase (ALT) and aspartate aminotransferase (AST) at 48 h that did not exceed normal ranges. In CI107 treated animals at 2000 and 4000 µg/kg, total bilirubin increased outside of normal range at 48 hours and was fully reversed by day 8. In both CI106 and CI107 treated animals, transient increases in serum cytokines IL-2, IL-6, and IFNg were observed after dosing and were resolved by 24 h post dose. An increase in the percentage of T cells expressing CD69, Ki67, and PD-1 was observed at 72 h post-dose and, generally, the percentage of positive cells was greater for CI107 treated animals.

Figures 7A, 7B, 7C:
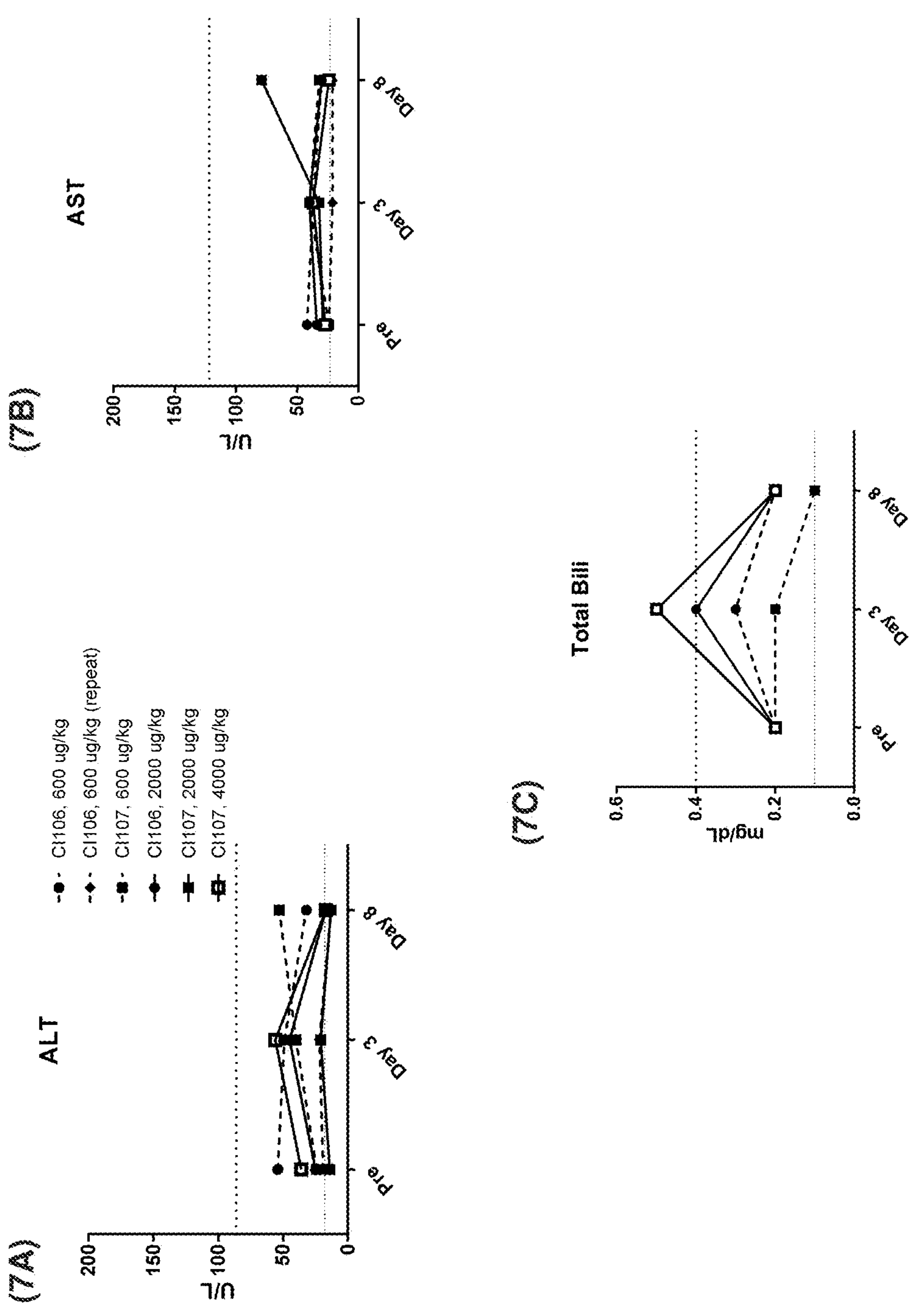
FIGS. 7A-7C depict pre-dose, 48 h, and 7 days post-dose serum concentrations of ALT (7A), AST (7B), and total bilirubin (7C) in cynomolgus monkeys treated with CI106 or CI107.

FIGS. 7A-7C depict pre-dose, 48 h, and 7 days post-dose serum concentration of ALT (7A), AST (7B), and total bilirubin (7C). With the exception of total bilirubin at 2000 and 4000 µg/kg, all values are within established normal ranges for cynomolgus monkeys. Only pre-dose data was available for CI107 at 6000 µg/kg, and was not included.

Figures 8A, 8B, 8C:
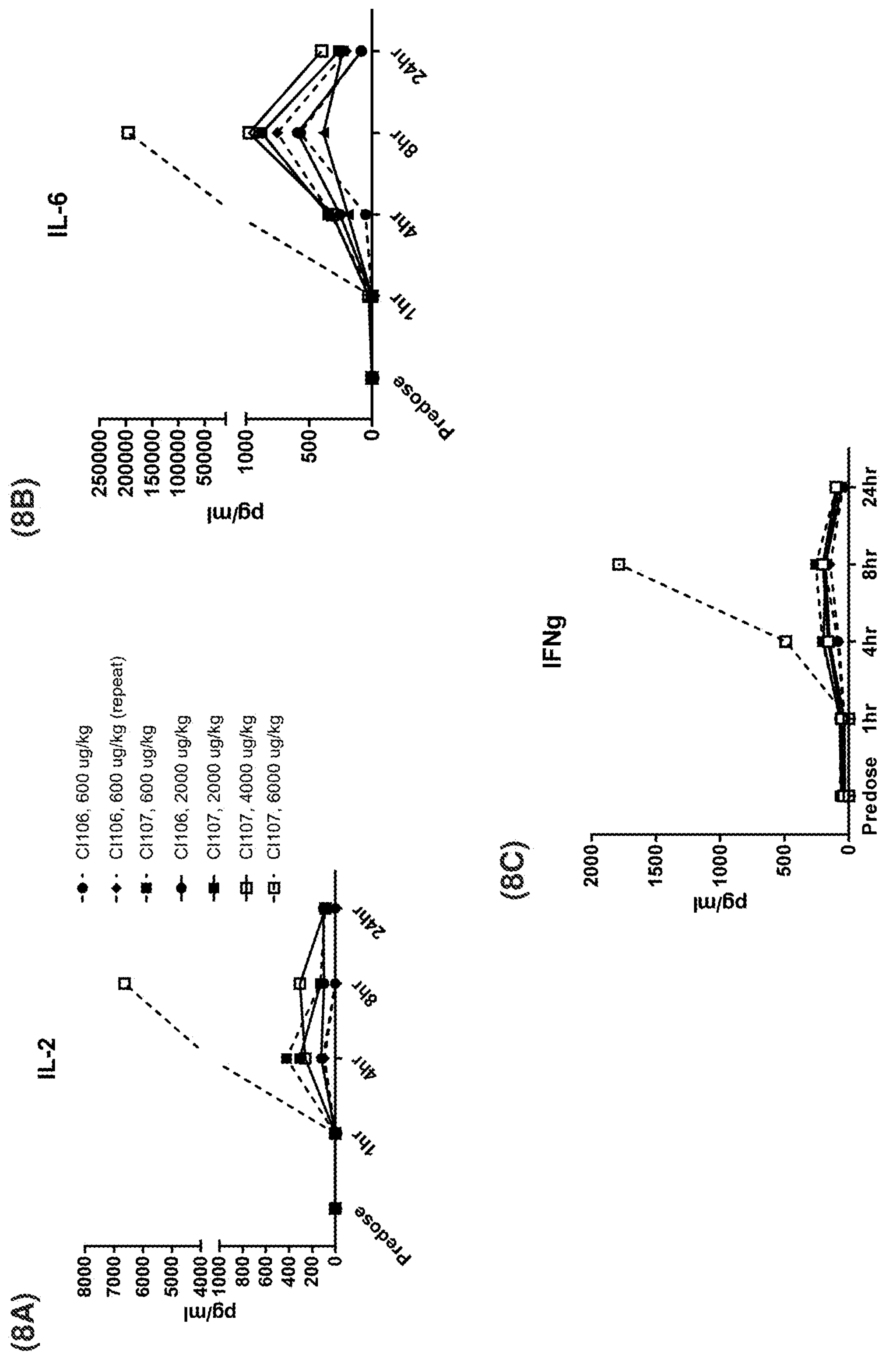
FIGS. 8A-8C plot the increase in serum cytokine levels for IL-2 (8A), IL-6 (8B), and IFNg (8C) in cynomolgus monkeys treated with CI106 or CI107.

FIGS. 8A-8C plot the increase in serum cytokine levels for IL-2 (8A), IL-6 (8B), and IFNg (8C).

Figures 9A, 9B, 9C:
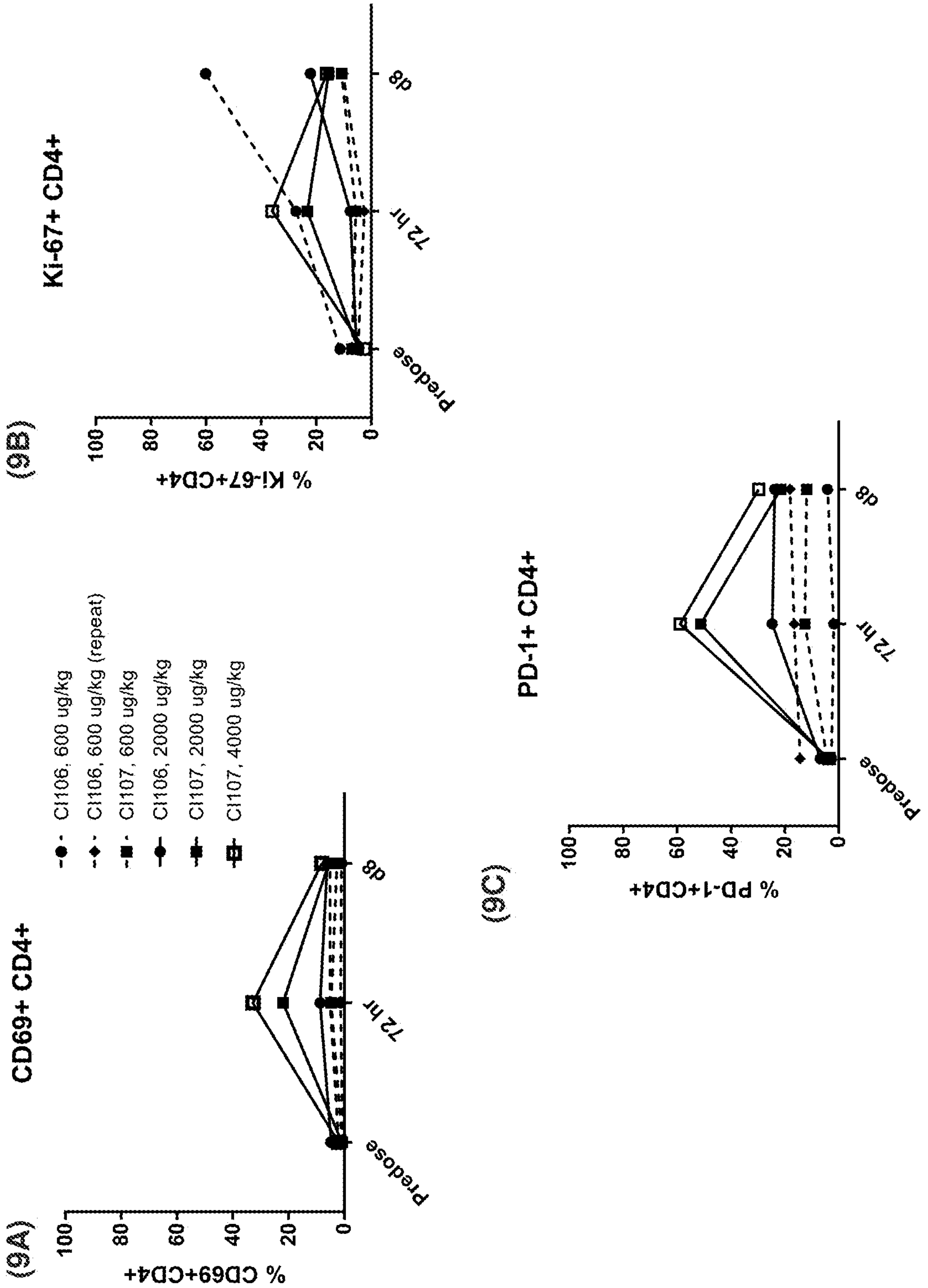
FIGS. 9A-9C depict T cell activation as measured by CD69 (9A), Ki67 (9B), and PD-1 (9B) expression on CD4+ T cells in cynomolgus monkeys treated with CI106 or CI107.

FIGS. 9A-9C depict T cell activation as measured by CD69 (9A), Ki67 (9B), and PD-1 (9B) expression on CD4+ T cells.

Example 10. Dually Masked, Bispecific, AAs are Safer in Cynomolgus Monkeys than Activated Bispecific Antibodies In this example, protease activated CI104 and dually masked CI106 and CI107 were dosed in cynomolgus monkeys (n=1) at 60, 180 (activated CI104 only), 600, 2000, 4000 μg/kg (CI107 only), or 6000 μg/kg (CI107 only) to compare the tolerability of masked and unmasked antibodies following a single IV bolus. Tolerability evaluation and blood collections were as described in Example 9. Dually masked, BAAs CI106 and CI107 were tolerated at 30-60 fold higher dose level than the protease activated, bispecific antibody.

FIGS. 10A-E plot dose dependent increases in AST at 48 h post dose (10A), ALT at 48 h post dose (10B), IL-6 at 8 h post dose (10C), IFNg at 8 h post dose (10D), and Ki67 at 72 h post dose (10E). The dose response curve for all parameters was shifted for the dually masked antibodies indicating improved tolerability and decreased pharmacodynamics effects relative to the protease activated bispecific antibody. In some embodiments, the IL-6 dose response curve was shifted by more than 60-fold.

Example 11. Tolerability of EGFR Binding, Dually Masked, Bispecific, AAs is Dependent on EGFR In this example, dually masked bispecific antibody, CI107, targeting EGFR and CD3ε and CI128, targeting RSV and CD3ε were dosed at 2000 μg/kg in cynomolgus monkeys (n=1). Tolerability evaluation and blood collections were as described in Example 9 above. There was no effect of CI128 on measures of acute organ toxicity (total bilirubin) and T cell activation (IL-6, PD-1) demonstrating that the toxicity observed in cyno was dependent on EGFR binding. These data also demonstrate that CD3ε binding alone was not sufficient to induce toxicity.

Figures 11A, 11B, 11C:
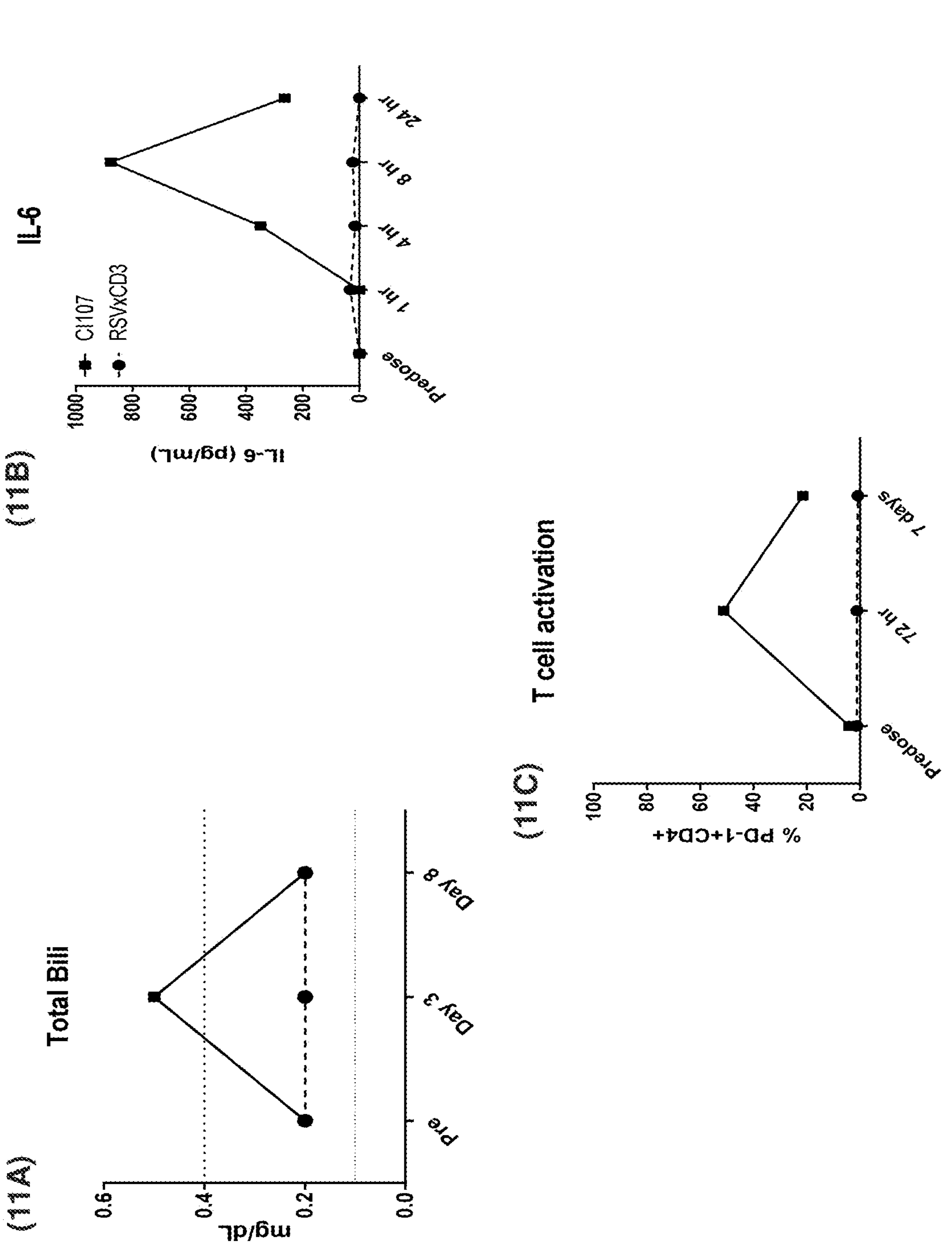
FIGS. 11A-11C compare the effects of EGFR-binding CI107 and non-EGFR-binding CI128 (RSVxCD3) on increases in total bilirubin (11A), IL-6 (11B), and PD-1 expressing CD4+ T cells (11C) in cynomolgus monkeys treated with CI107 or CI128.

FIGS. 11A-11C compares the effects of EGFR binding CI107 and non EGFR binding CI128 on increases in total bilirubin (11A), IL-6 (11B), and PD-1 expressing CD4+ T cells (11C).

Example 12. Humanization of Anti-CD3 Variants v12, v16, and v19 which have Different Affinities and Potencies This example describes anti-CD3 antibody variants v12, v16, and v19. These three variants were derived from the parent antibody hSP34

Humanization of the anti-human CD3 single-chain variable fragment (scFv) was performed by selectively mutating the framework. Briefly, CDRs were grafted into a series of light chain (LC) and heavy chain (HC) human IgG scaffolds and a number of amino acids in the variable region framework was selectively mutated. Immunoglobulins were expressed in all possible combinations of LC and HC, and then evaluated for expression level, percent monomer, and CD3 affinity using ELISA and on-cell binding to Jurkat cells. The variable regions of desirable combinations were expressed as scFv in the bispecific antibody (TCB) format and then evaluated for expression levels, percent monomer, CD3 affinity and function in cell cytotoxicity assays.

The affinity of v12, v16, and v19 variant was measured using surface plasmon resonance (SPR). Surfaces were HC200m, carboxylated hydrogel based on a linear, synthetic polycarboxylate. Surface channels were activated with a standard EDC/NHS amine coupling protocols. Channels 1 and 2 were blank, Channels 3 and 4 were various anti-human CD3 antibodies. Surfaces were generated by diluting v12, v16, v19 and MM194 antibodies to 5 μg/ml in 1.0 mL 10 mM Sodium Acetate pH 4.5.

Kinetic analysis was performed in PBST (10 mM Sodium Phosphates, pH 7.4, 150 mM Sodium Chloride, 0.05% TWEEN®-20) at 20° C. Regeneration was a series of three injections; a single 5 μl injection of 20 mM Sodium Hydroxide followed by two 5 μL injection of 10 mM Sodium Hydroxide freshly-made.

The configuration was run with an inverse 3-fold serial dilution alternating with buffer blanks. Human CD3egFc was from Sino Biological Inc., (Beijing, China, Catalog #CT041-H0305H) reconstituted with sterile water from a lyophilized formulation based on PBS and stabilizers. Serial dilutions with the analyte in solution from concentrations starting at 300 nM or 100 nM human CD3. Processing was done with Scrubber software.

These variants were also engineered using described methods into dually masked, bispecific, AAs targeting EGFR and CD3 and used in an in vitro cytotoxicity assay as described in example 3.

Figure 12A:
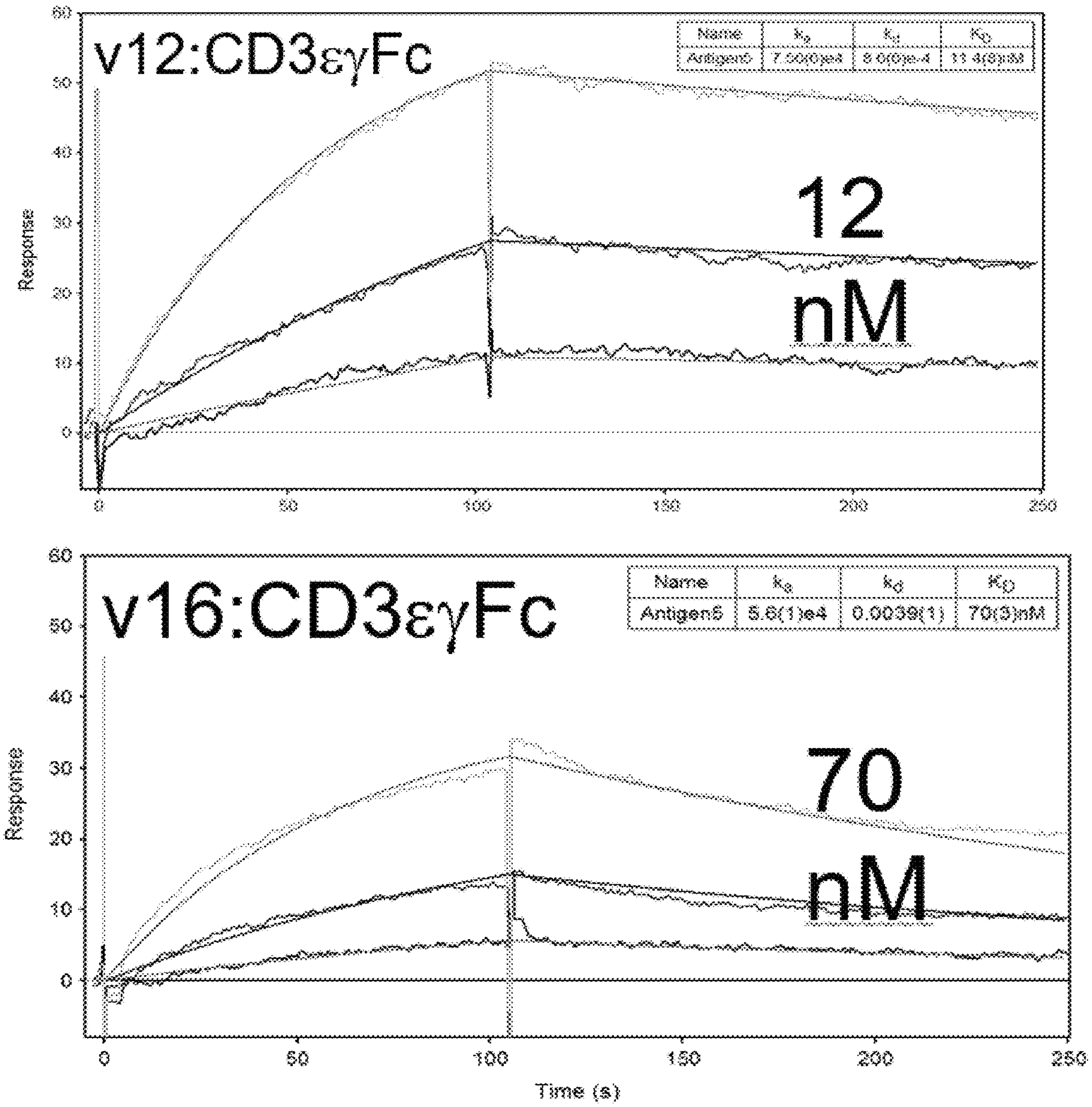
FIG. 12A depicts the affinity measurements of v12, v16, and v19 CD3 antibodies relative to hSP34.
Figure 12A:
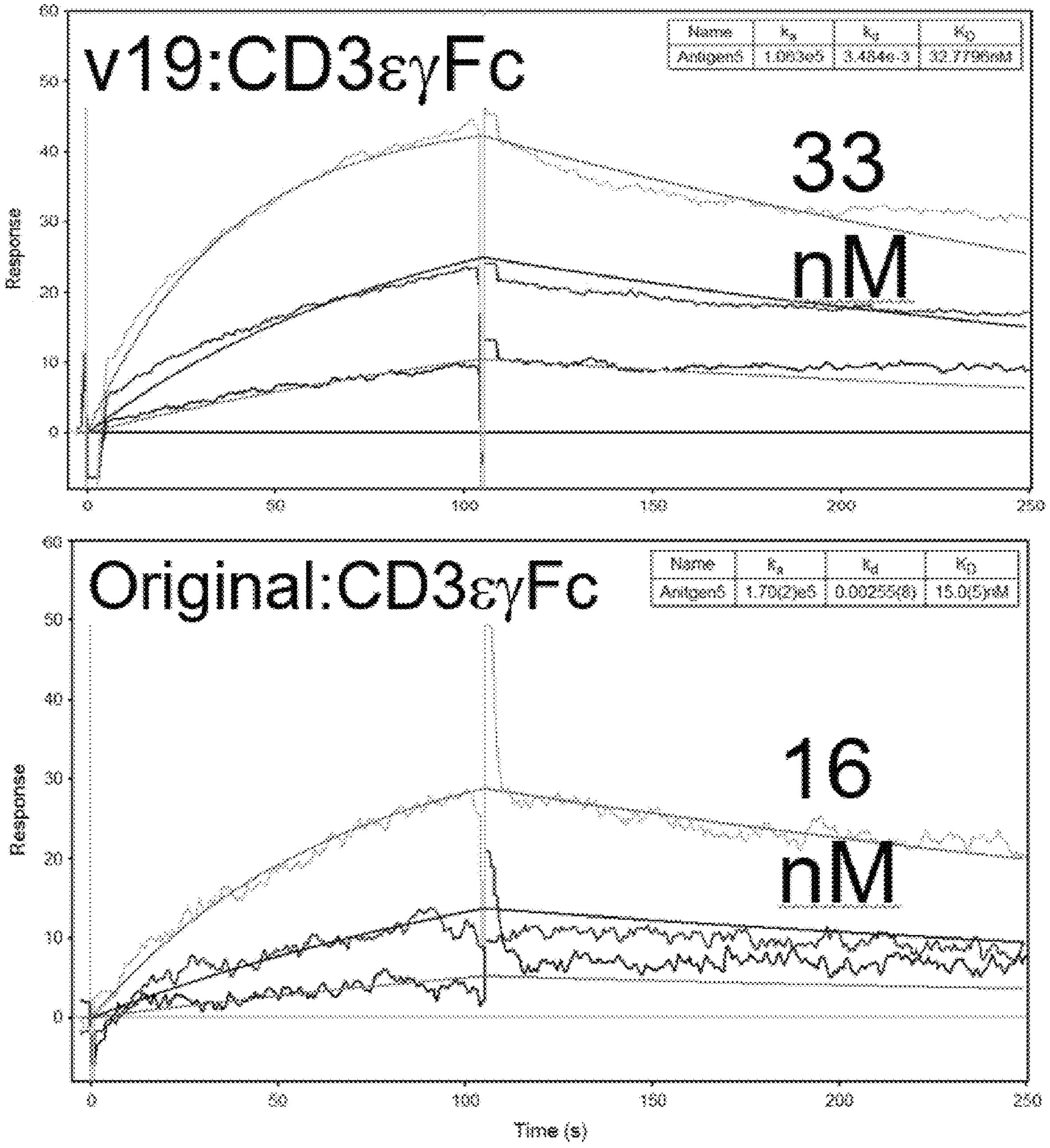

FIG. 12A depicts the affinity measurements of v12, v16, and v19 relative to hSP34. V12 was the highest affinity at 12 nM while v16 was the lowest affinity at 70 nM.

Figure 12B:
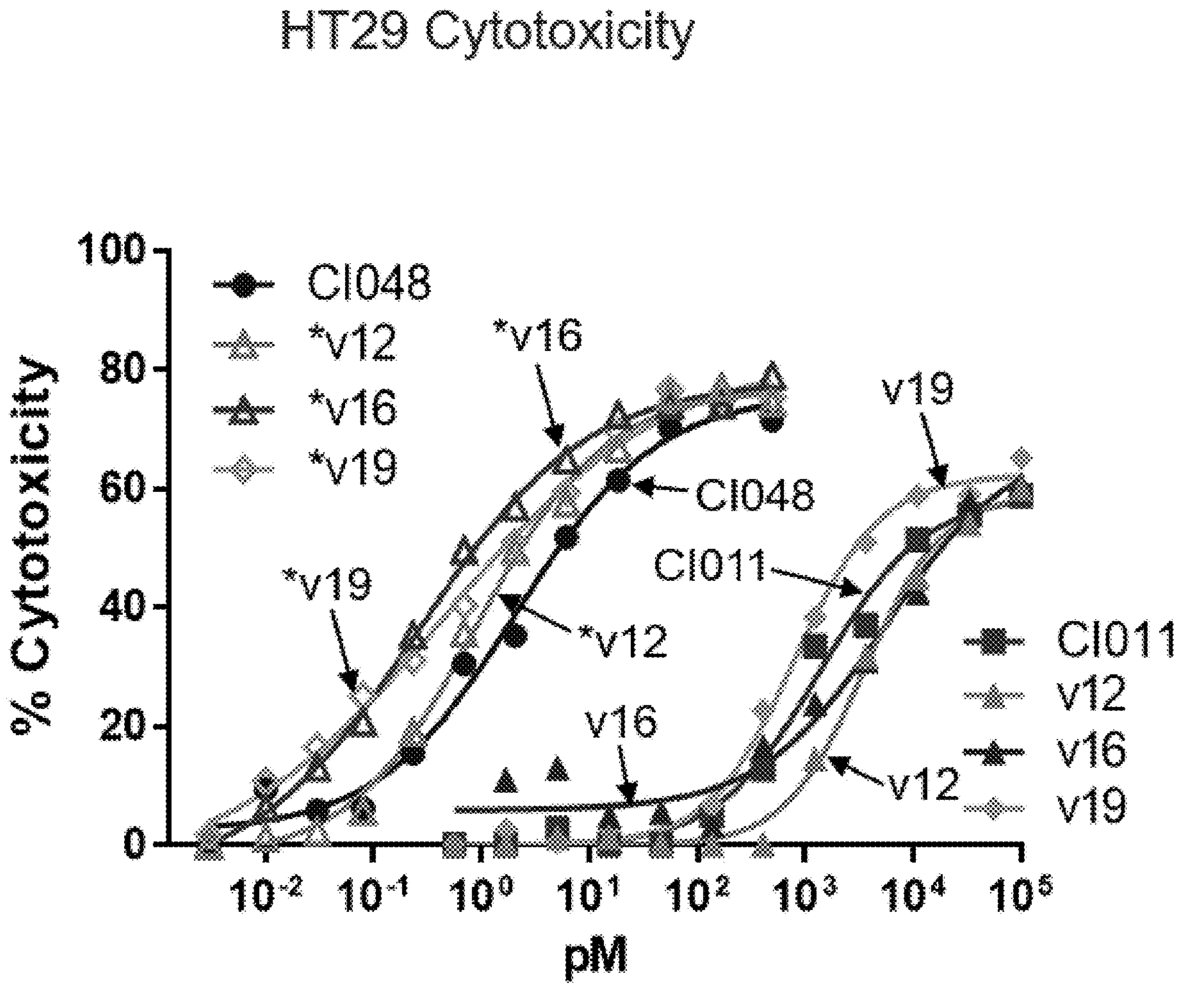
FIG. 12B depicts the cytotoxicity of activated or dually masked, bispecific antibodies on HT29-luc2 cells.

FIG. 12B depicts the cytotoxicity of activated or dually masked, bispecific antibodies on HT29-luc2 cells. There were slight differences in the potency of cell killing of the activated molecules with v16 being the most potent. There are also slight differences in protection against cell killing for the dually masked molecules.

Example 13. Dually Masked BAAs Enable Extended PK in Cynomolgus Monkeys

In this example, protease activated, bispecific antibody act-104 and dually masked, bispecific antibody CI107 were dosed at 60 μg/kg, 180 μg/kg (act-104) or 2000 μg/kg (CI107) in cynomolgus monkey. Plasma samples were collected at 5 min (act-104 only), 30 min, 4 h (act-104 only), 24 h, 48 h (act-104 only), 96 h, and 168 h. Plasma concentration was measured by ELISA using an anti-idiotype antibody to capture, a horseradish peroxidase (HRP) labeled anti-human IgG (Fc) for detection, and visualized using 3,3',5,5'-tetramethylbenzidine (TMB). Plasma concentration values were interpolated from a standard curve and plotted using GraphPad PRISM. Area under the curve (AUC) analysis was also performed.

Figure 13:
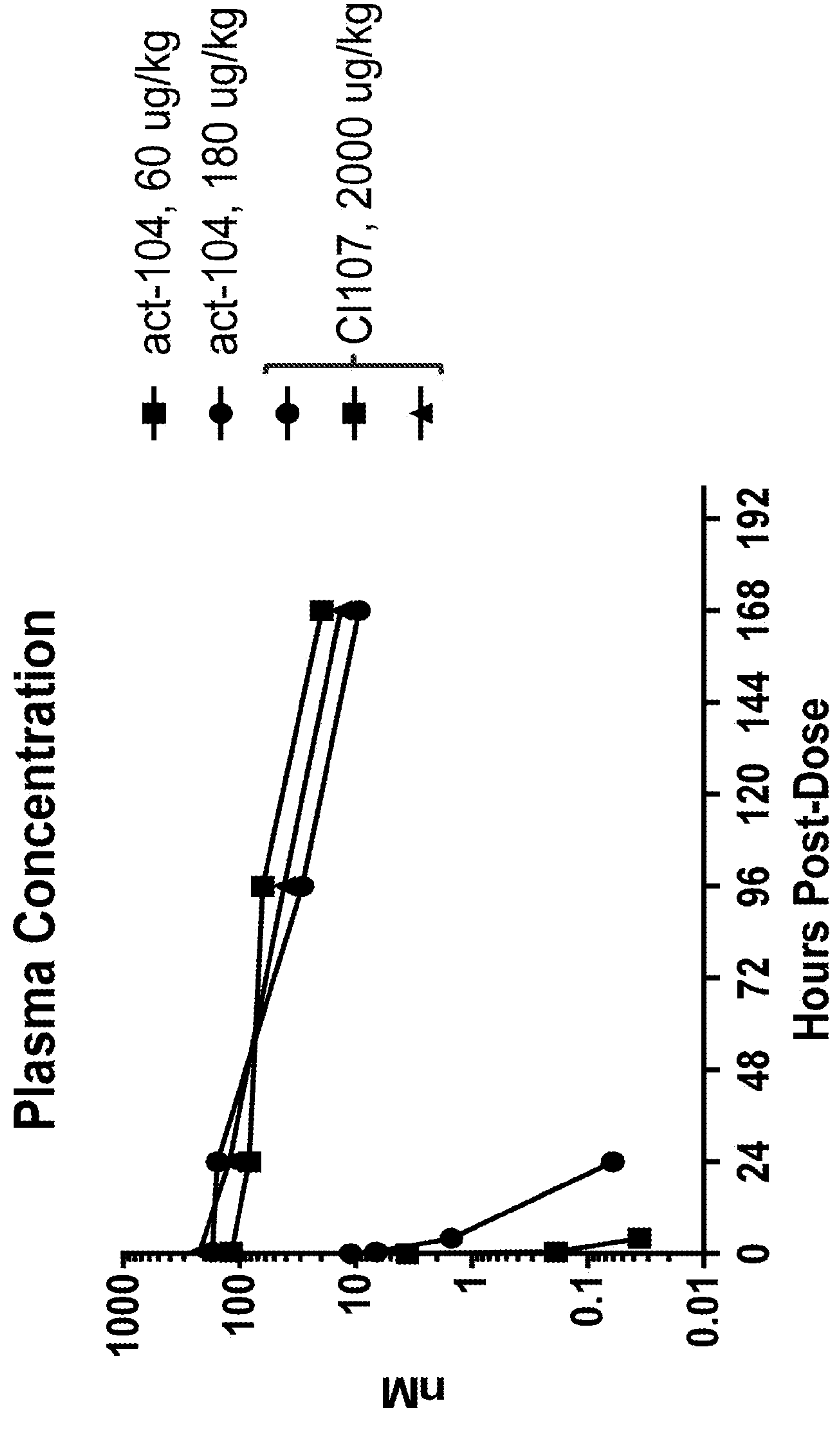
FIG. 13 depicts the extended PK of the dually masked antibody, CI107, relative to the protease activated bispecific antibody, act-104.

FIG. 13 depicts the extended PK of the dually masked molecule, CI107, relative to the protease activated molecule, act-104. Exposure (AUC) of CI107 was 448 day*nM and act-104 (60 μg/kg) was 0.04 day*nM representing a greater than 10,000 fold difference in plasma exposure.

Example 14. Sensitivity to Protease Cleavage of Dually Masked, Bispecific, AAs Correlates to Tumor Efficacy and Tumor T Cell Infiltration This example describes anti-tumor efficacy and tumor T cell infiltration in a HT29-luc2 xenograft model. The model was carried out as described in example 5. In the tumor T cell infiltration study, mice received a single dose of test article and tumors were harvested 7 days post dose. Formalin fixed paraffin embedded (FFPE) blocks were created to use for histology. Test articles used are CI011, CI020 (a dually masked bispecific antibody devoid of a cleavable substrate), CI040, and CI048. Protease sensitivity and substrate cleavability of the test articles is as follows: CI040>CI011>CI020. Mice were dosed according to Table 16.

TABLE 16

Groups and doses for HT29-luc2 xenograft study.

| Group | Count | Treatment | Dose (mg/kg) | Study |
|---|---|---|---|---|
| 1 | 8 | PBS | N/A | Efficacy |
| 2 | 8 | CI011 | 0.3 | Efficacy |
| 3 | 8 | CI020 | 0.3 | Efficacy |
| 4 | 8 | CI040 | 0.3 | Efficacy |
| 5 | 8 | CI048 | 0.3 | Efficacy |
| 6 | 5 | PBS | N/A | Infiltration |
| 7 | 5 | CI011 | 1.0 | Infiltration |
| 8 | 5 | CI020 | 1.0 | Infiltration |
| 9 | 5 | CI040 | 1.0 | Infiltration |
| 10 | 5 | CI048 | 1.0 | Infiltration |

Figures 14A, 14B:
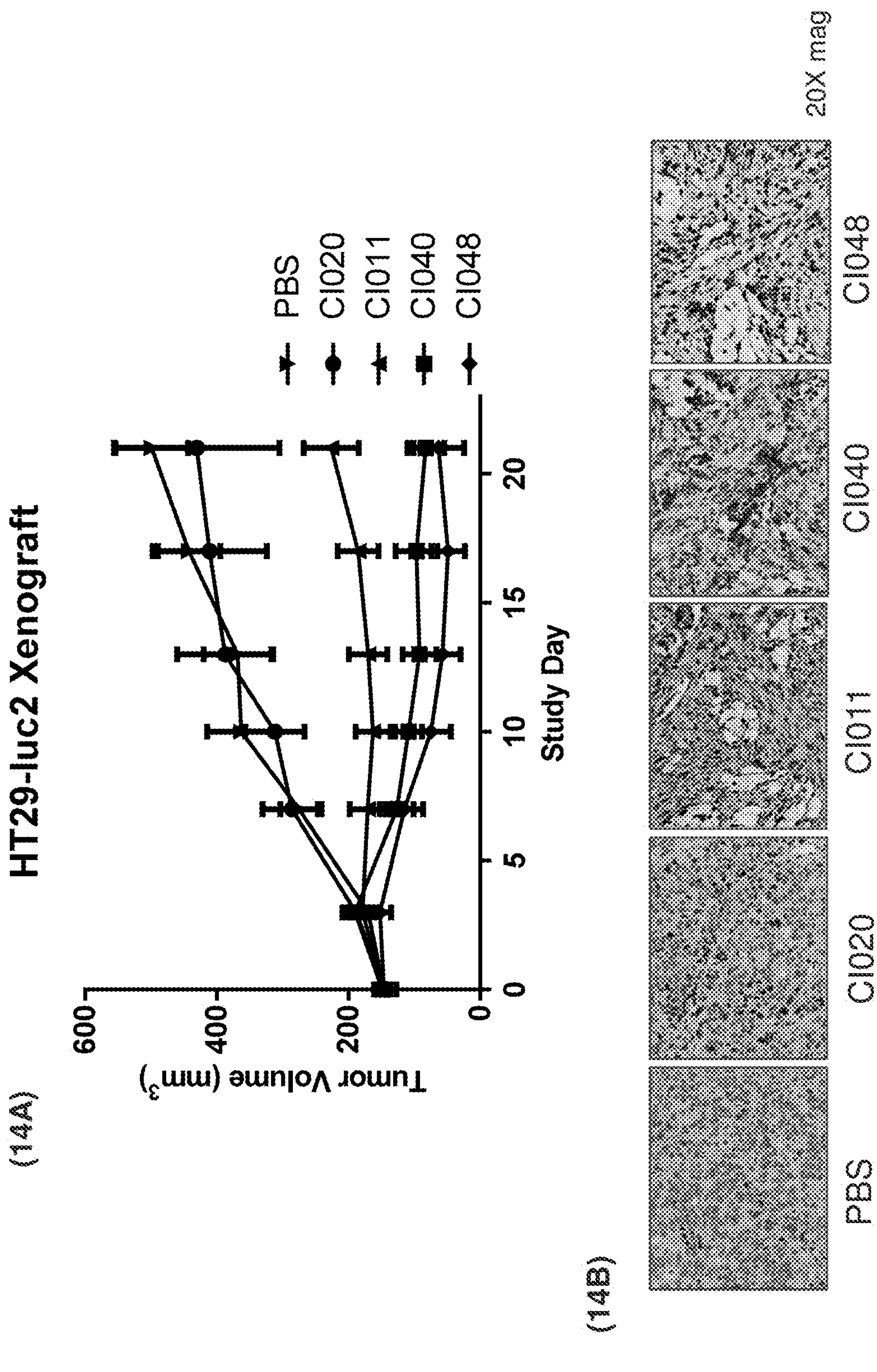
FIG. 14A depicts efficacy in a HT29-luc2 tumor intervention model in PBMC engrafted NSG mice. Anti-tumor potency in this example correlates to protease sensitivity and substrate cleavability of the test articles, with the most efficacious test article being the fully protease activated CI048.
FIG. 14B depicts staining of tumor sections for CD3 (dark staining) as a measure of the degree of T cell infiltration into tumors. Tumor T cell infiltration correlates with protease sensitivity and substrate cleavability of the test articles.

FIG. 14A depicts efficacy in a HT29-luc2 tumor intervention model in PBMC engrafted NSG mice. Anti-tumor potency in this example correlates to protease sensitivity and substrate cleavability of the test articles, with the most efficacious test article being the fully protease activated CI048.

FIG. 14B depicts staining of tumor sections for CD3 (dark staining) as a measure of the degree of T cell infiltration into tumors. Tumor T cell infiltration correlates with protease sensitivity and substrate cleavability of the test articles.

Example 15. Second Generation Dually Masked, Bispecific, AAs are Safer in Cynomolgus Monkeys than First Generation Molecules In this example, cynomolgus tolerability data was compared for CI011, CI040, CI048 (first generation molecules), act-104, CI106, and CI107 (second generation molecules). Data presented in this example was compiled from two cyno tolerability studies. Protease activated CI104 and CI048 were dosed in cynomolgus monkeys at 20 (CI048 only), 60 or 180 μg/kg (act-104 only). Dually masked CI011, CI040, CI106 and CI107 were dosed at 600, 2000, 4000 (CI107 only), or 6000 (CI107 only) μg/kg to compare the tolerability of dually masked and activated bispecific antibodies following a single IV bolus. Tolerability evaluation was as described in Example 8.

Table 17 summarizes the clinical observations following a single dose of test article. Second generation, protease activated bispecific antibody act-104 was tolerated at 2-fold higher dose than first generation protease activated bispecific antibody CI048. CI106 and CI107 were tolerated at 30-60-fold higher dose than first generation antibodies CI011 and CI040.

TABLE 17

| BAA | Dose (μg/kg) | Clinical Observations |
|---|---|---|
| CI048 | 20 (n = 2) | 1. Emesis and hunching in $1^{st}$ 24 hrs |
| | | 2. None |
| | 60 | Emesis at 4 hr; hunching lasting 4 days and inappetence lasting 2 days; 10% weight loss |
| CI011 | 600 (n = 3) | 1. None |
| | | 2. Emesis at 4 hrs, inappetence on day 4 |
| | | 3. Hunching and inappetence through day 5.5% weight loss |
| | 2000 | Emesis days 1-2, inappetence days 2-4 |
| CI040 | 600 (n = 2) | 1. Emesis at 4 hr |
| | | 2. Emesis within 12 hrs, inappetence on day 4 |
| | 2000 | Emesis days 1-2, moribund and euthanized day 2 |
| act-104 | 60 | Emesis and hunching in $1^{st}$ 24 hrs |
| CI104 | 180 | Severe emesis; hunching, paleness, inappetence lasting 3 days |
| CI106 | 600 | none |
| | 2000 | none |
| CI107 | 600 | None |
| | 2000 | Emesis, once in $1^{st}$ 24 hrs |
| | 4000 | Emesis, multiple incidences in $1^{st}$ 24 hrs |
| | 6000 | Severe emesis; bloody diarrhea |

Example 16. Evaluation of Masking Efficiencies of Activatable Anti-EGFR Antibodies Masking the ability of an antibody to bind to its antigen is an example of inhibition of binding and is enumerated herein as masking efficiency (ME). Masking efficiency can be calculated as the $K_D$ for binding of the AA divided by the $K_D$ for binding of the antibody measured under the same conditions. The extent of inhibition is dependent on the affinity of the antibody for its antigen, the affinity of the inhibitor (i.e., the masking moiety) for the antibody and the concentration of all reactants. Local concentrations of the tethered masking moiety peptide (inhibitor) is very high in the AA context, on the order of 10 mM, therefore moderate affinity peptides would effectively mask AA antigen binding.

The general outline for this assay is as follows: Nunc, Maxisorp™ plates are coated overnight at 4° C. with 100 μl/well of a 1 μg/mL solution of human EGFR (R and D Systems) in PBS, pH 7.4. Plates are washed 3×PBST (PBS, pH 7.4, 0.05% TWEEN®-20), and wells are blocked with 200 μl/well, 10 mg/mL BSA in PBST for 2 hours at RT.

Plates are washed 3×PBST (PBS, pH 7.4, 0.05% TWEEN®-20). Dilution curves can be prepared, in 10 mg/mL BSA in PBST, as illustrated below in Table 18. In this example the highest concentrations are 10 nM for the parental antibody and 400 nM for the AAs, however, the top concentrations can be increased or decreased to give full saturation binding curves for AAs with stronger or weaker masking.

TABLE 18

Plate layout for masking efficiency assay.

| | [Antibody] = nM Columns 1-3 | [AA 1] = nM Columns 4-6 | [AA 2] = nM Columns 7-9 | [AA 3] = nM Columns 10-12 |
|---|---|---|---|---|
| A | 10 | 400 | 400 | 400 |
| B | 2 | 100 | 100 | 100 |
| C | 0.625 | 25 | 25 | 25 |
| D | 0.156 | 6.25 | 6.25 | 6.25 |
| E | 0.039 | 1.56 | 1.56 | 1.56 |
| F | 0.0097 | 0.39 | 0.39 | 0.39 |
| G | 0.0024 | 0.098 | 0.098 | 0.098 |
| H | 0.0006 | 0.024 | 0.024 | 0.024 |

Figure 15:
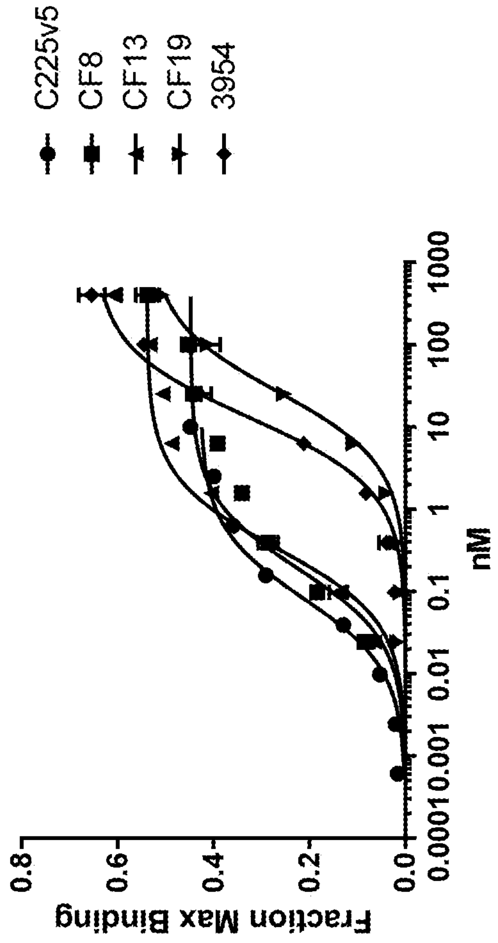
FIG. 15 and FIG. 16 are plots of binding isotherms for activatable anti-EGFR C225v5 antibodies of the disclosure, for activatable anti-EGFR antibody 3954-2001-C225v5 described herein, and for anti-EGFR antibody C225v5.
Figure 16:
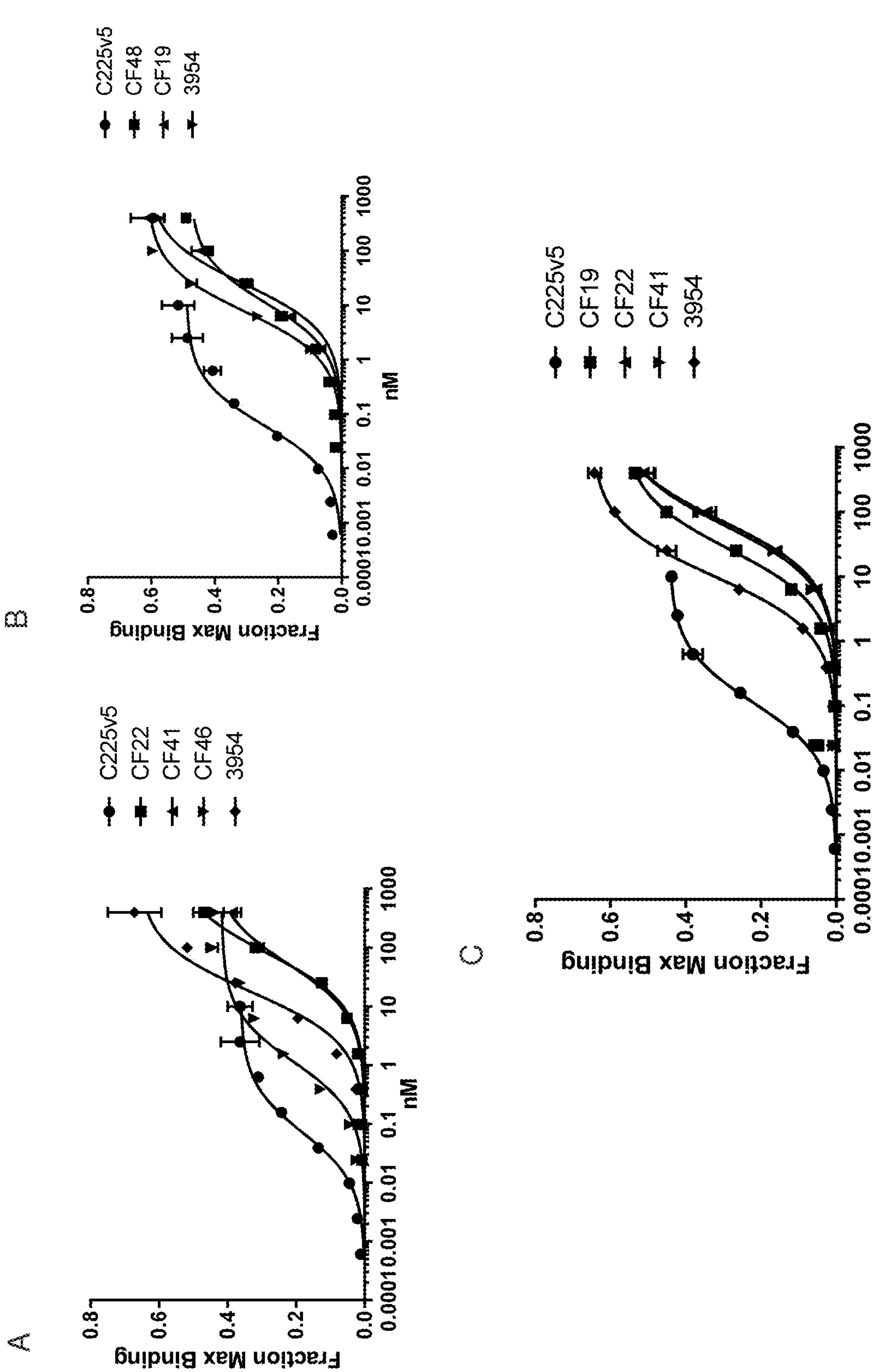

The binding solutions are added to the plates, which are then are incubated for 1 hour at room temperature, and then washed 3×PBST (PBS, pH 7.4, 0.05% TWEEN®-20). 100 µl/well 1:4000 dilution goat-anti-human IgG (Fab specific, Sigma cat #A0293) in 10 mg/mL BSA in PBST is added, and the plate is incubated for 1 hour at room temperature. The plate is developed with TMB and IN HCL. Shown in FIG. 15 and FIG. 16 are plots of binding isotherms for activatable anti-EGFR C225v5 antibodies of the disclosure, for activatable anti-EGFR antibody 3954-2001-C225v5 described above, and for anti-EGFR antibody C225v5. Plots are generated in GraphPad PRISM and the data are fit to a model of single site saturation and a $K_D$ is determined. The $K_D$ and ME values are provided in Table 19.

TABLE 19

$K_D$ and ME values calculated from the binding isotherms shown in FIG. 15 and FIG. 16.

| | $K_D$ (nM) | ME |
|---|---|---|
| 3954-2001-C225v5 | 13 | 130 |
| CF08-2001-C225v5 | 0.2 | 2 |
| CF13-2001-C225v5 | 0.3 | 3 |
| CF19-2001-C225v5 | 27 | 270 |
| CF22-2001-C225v5 | 78 | 780 |
| CF41-2001-C225v5 | 52 | 520 |
| CF46-2001-C225v5 | 1 | 10 |

Example 17. Pharmacokinetics of Dually Masked BAAs in Cynomolgus Monkeys

In this example, dually masked bispecific antibody CI107 was dosed at 600 µg/kg, 2000 µg/kg, or 4000 µg/kg in cynomolgus monkey. Plasma samples were collected at 30 min, 4 h (600 µg/kg only), 24 h, 48 h (600 and 4000 µg/kg only), 96 h, and 168 h. Plasma concentration was measured by ELISA as in example 13.

Figure 20:
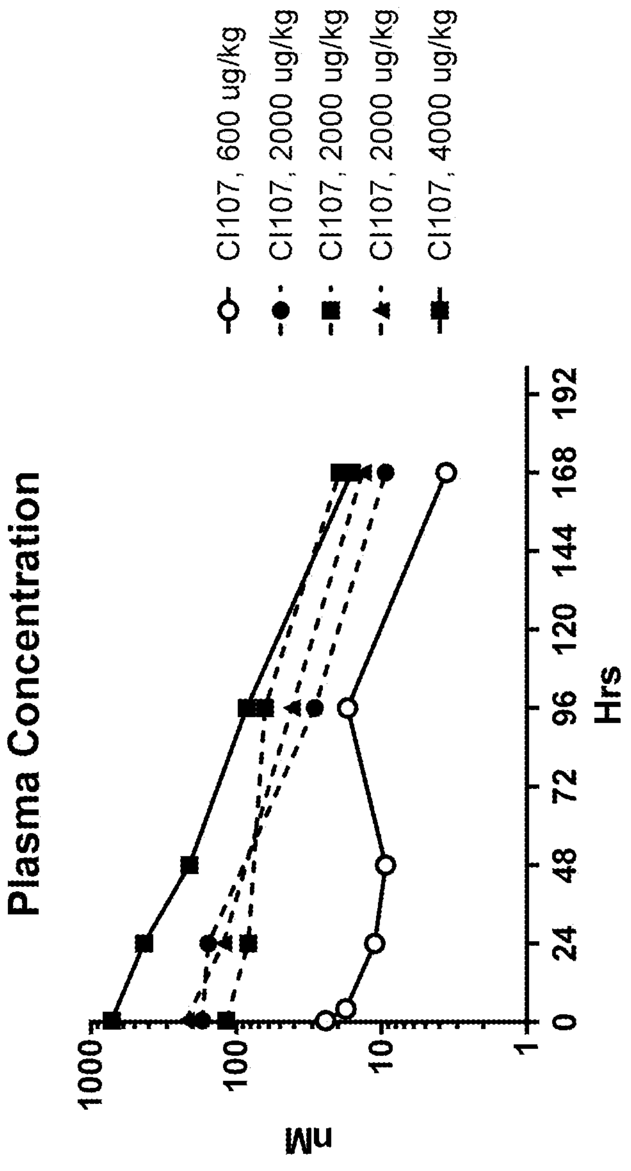
FIG. 20 depicts PK of the dually masked BAA CI107 following a single dose administration of 600, 2000, or 4000 ug/kg.

FIG. 20 depicts the PK of the dually masked BAA CI107 following a single i.v. dose of either 600, 2000, or 4000 µg/kg.

Example 18. EGFR-Dependent Cytotoxicity of Dually Masked, Bispecific, Activatable Antibodies To determine whether the anti-CD3ε, CD3 mask, and protease substrates in CI090 and CI091 could further attenuate cell killing relative to CI011, a cytotoxicity assay was performed using the method described in Example 3. Titrations of the following bispecific, activated antibodies and dually masked, bispecific, activatable antibodies were tested: CI011, CI090, CI091, activated CI090, and CI048. In addition, non-EGFR binding, bispecific, activatable antibody CI064 was used to demonstrate the EGFR dependence of cytotoxicity.

Figure 21:
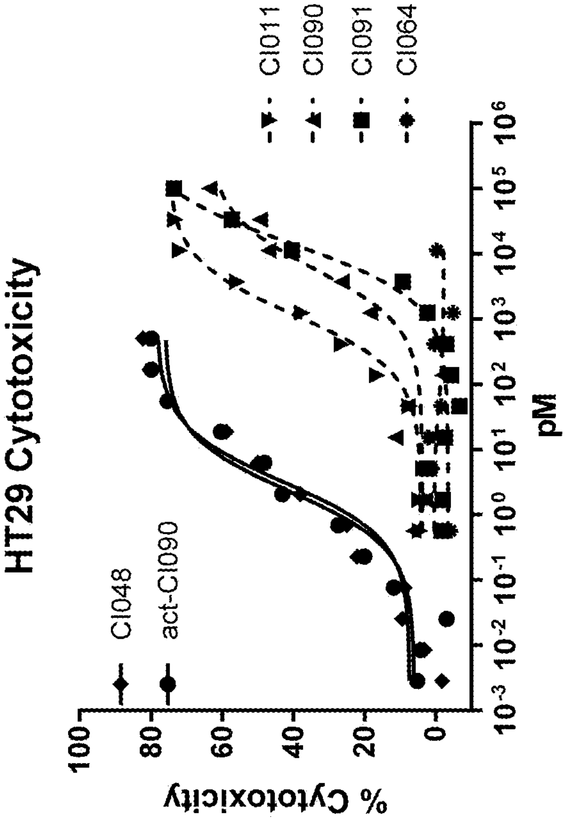
FIG. 21 demonstrates that the cytotoxicity of CI090 and CI091 was attenuated relative to CI011, on HT29-luc2 cells.

FIG. 21 demonstrates that killing of EGFR+HT29-luc2 cells was further attenuated by CI090 and CI091 relative to CI011, however the potency of the activated CI090 is equivalent to CI048. The EC50 shift of CI090 and CI091 relative to activated bispecific antibody is increased representing increased masking efficiency of these molecules relative to CI011. No cytotoxicity was observed when cells were treated with CI064, demonstrating the dependence of EGFR targeting for cell killing.

Example 19. Primary T Cell Activation by Dually Masked, Bispecific, Activatable Antibodies To determine if the anti-CD3ε, CD3 mask, and protease substrates in CI090 and CI091 could attenuate primary T cell activation relative to CI011, a flow cytometry assay was performed as described in Example 4.

Figure 22:
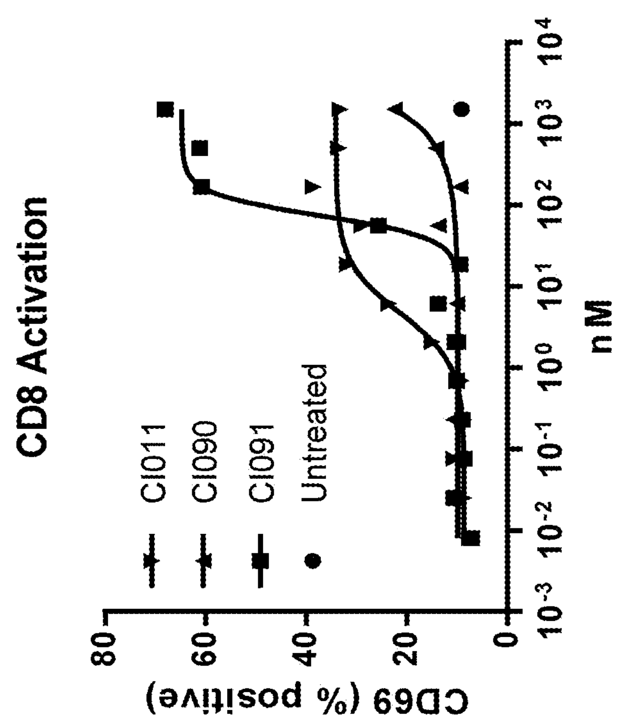
FIG. 22 demonstrates that activation of primary CD8+ T cells was attenuated by CI090 and CI091 relative to CI011.

FIG. 22 demonstrates that activation of primary CD8+ T cells was further attenuated by CI090 and CI091, relative to CI011.

Example 20. Dually Masked, Bispecific, Activatable Antibodies of the Embodiments Induced Regression of Established HT29-luc2 Tumors in Mice In this example, bispecific activatable antibodies CI011, CI090, and CI091 were analyzed for the ability to induce regression or reduce growth of established HT-29-Luc2 xenograft tumors in human PBMC engrafted NSG mice. The method is as described in Example 5.

TABLE 20

Groups and doses for HT-29-luc2 xenograft study.

| Group | Count | Treatment | Dose (mg/kg) |
|---|---|---|---|
| 1 | 7 | PBS | N/A |
| 2 | 7 | CI011 | 1.0 |
| 3 | 7 | CI090 | 1.0 |
| 4 | 7 | CI091 | 1.0 |

Figure 23:
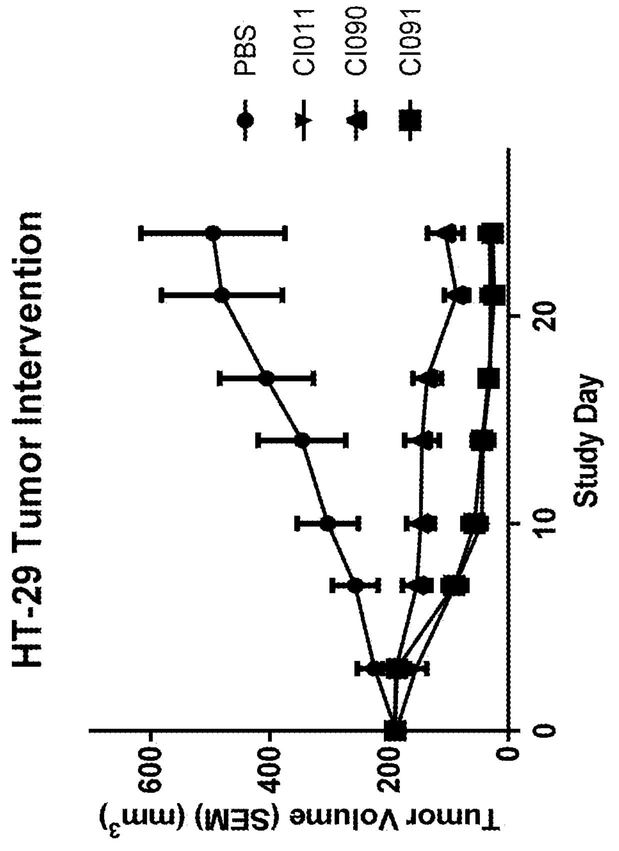
FIG. 23 depicts efficacy in a HT29-luc2 tumor intervention model in PBMC engrafted NSG mice. Showing anti-tumor potency of CI091, CI090 and CI011.

FIG. 23, which plots tumor volume versus days post initial treatment dose, demonstrates that a 1 mg/kg, weekly dose induced tumor regression for all bispecific activatable antibodies tested.

Example 21. Dually Masked, Bispecific, Activatable Antibodies Elicit Less Cytokine Release than Activated Bispecific Antibodies in Cynomolgus Monkey In this example, protease activated CI104, and dually masked CI011, CI090, and CI091 were dosed in cynomolgus monkeys (n=1) at 0.06, 0.18 (activated CI104), or 600 mg/kg (CI011, CI090, CI091). Blood was collected for cytokine analysis pre-dose and at 1 h, 4 h, 8 h, and 24 h post dose. Samples were analyzed using Life Technologies Monkey Magnetic 29-Plex Panel Kit (Product No. LCP0005M).

Data was acquired on a BioRad BioPlex 200 instrument. This analysis was conducted in compliance with standard operating procedures at SNBL USA, Ltd. (Everett, WA).

Figure 24:
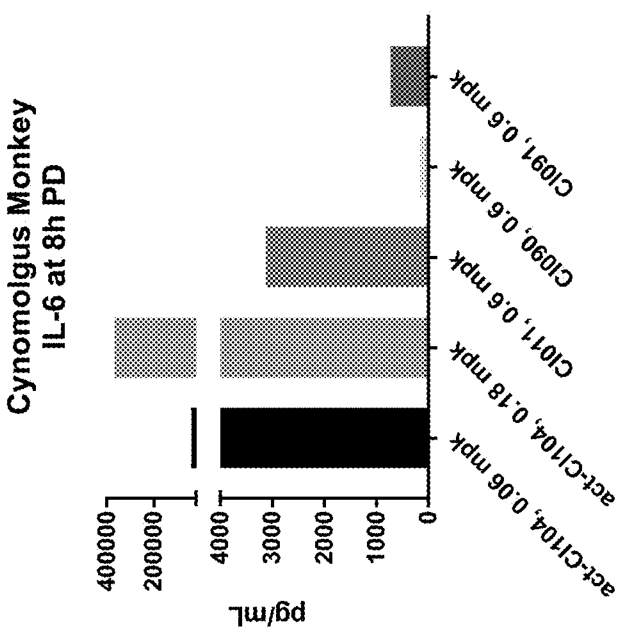
FIG. 24 plots IL-6 levels in cynomolgus monkeys in vivo study at 8 h post dose.

FIG. 24 plots IL-6 levels at 8 h post dose. The dually masked bispecific activatable antibody CI011 induces significantly less cytokine release than activated CI104 even when delivered at a higher dose, demonstrating the effect of masking on T cell activation. IL-6 is even further reduced in CI090 and CI091 treated animals reflecting the increased masking efficiency of these molecules relative to CI011.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following.

The invention claimed is:

1. An isolated polypeptide comprising the amino acid sequence of any one of SEQ ID NOs: 78-84 (MM).

2. The isolated polypeptide of claim 1, wherein the isolated polypeptide comprises the amino acid sequence of SEQ ID NO: 78.

3. The isolated polypeptide of claim 1, further comprising a cleavable moiety (CM).

4. The isolated polypeptide of claim 3, wherein the CM comprises a substrate cleavable by a serine protease or a matrix metalloproteinase (MMP).

5. The isolated polypeptide of claim 4, wherein the protease is an MMP.

6. The isolated polypeptide of claim 4, wherein the protease is a serine protease.

7. The isolated polypeptide of claim 6, wherein the serine protease is matriptase or uPA.

8. The isolated polypeptide of claim 3, comprising a linker between the MM and the CM.

9. The isolated polypeptide of claim 3, wherein the MM and the CM are not separated by a linker.

10. The isolated polypeptide of claim 3, wherein the isolated polypeptide comprises a linker at the carboxyl terminus of the CM.

11. The isolated polypeptide of claim 3, wherein the isolated polypeptide comprises a formula selected from the group consisting of:

i) (MM)-L1-(CM);

ii) (MM)-(CM)-L2;

iii) (MM)-L1-(CM)-L2; and iv) (MM)-(CM), wherein L1 and L2 are linkers.

12. The isolated polypeptide of claim 11, wherein L1 and L2 are the same.

13. The isolated polypeptide of claim 11, wherein L1 and L2 are different.

* * * * *

SEQUENCE LISTING

```
Sequence total quantity: 216
SEQ ID NO: 1            moltype = AA  length = 109
FEATURE                 Location/Qualifiers
REGION                  1..109
                        note = synthetic
source                  1..109
                        mol_type = protein
                        organism = synthetic construct
SEQUENCE: 1
QTVVTQEPSF SVSPGGTVTL TCRSSTGAVT TSNYANWVQQ TPGQAPRGLI GGTNKRAPGV  60
PDRFSGSILG NKAALTITGA QADDESDYYC ALWYSNLWVF GGGTKLTVL              109

SEQ ID NO: 2            moltype = AA  length = 125
FEATURE                 Location/Qualifiers
REGION                  1..125
                        note = synthetic
source                  1..125
                        mol_type = protein
                        organism = synthetic construct
SEQUENCE: 2
EVQLVESGGG LVQPGGSLRL SCAASGFTFS TYAMNWVRQA PGKGLEWVAR IRSKYNNYAT  60
YYADSVKDRF TISRDDSKNS LYLQMNSLKT EDTAVYYCVR HGNFGNSYVS WFAYWGQGTL  120
VTVSS                                                              125

SEQ ID NO: 3            moltype = AA  length = 125
FEATURE                 Location/Qualifiers
REGION                  1..125
                        note = synthetic
source                  1..125
                        mol_type = protein
                        organism = synthetic construct
SEQUENCE: 3
EVQLVESGGG LVQPGGSLKL SCAASGFTFS TYAMNWVRQA SGKGLEWVGR IRSKYNNYAT  60
YYADSVKDRF TISRDDSKNT AYLQMNSLKT EDTAVYYCTR HGNFGNSYVS WFAYWGQGTL  120
VTVSS                                                              125

SEQ ID NO: 4            moltype = AA  length = 109
FEATURE                 Location/Qualifiers
REGION                  1..109
                        note = synthetic
source                  1..109
                        mol_type = protein
                        organism = synthetic construct
SEQUENCE: 4
QAVVTQEPSL TVSPGGTVTL TCRSSTGAVT TSNYANWVQQ KPGQAPRGLI GGTNKRAPGT  60
PARFSGSLIG GKAALTLSGA QPEDEAEYYC ALWYSNLWVF GGGTKLTVL              109

SEQ ID NO: 5            moltype = AA  length = 7
FEATURE                 Location/Qualifiers
REGION                  1..7
                        note = synthetic
source                  1..7
                        mol_type = protein
                        organism = synthetic construct
SEQUENCE: 5
GTNKRAP                                                            7

SEQ ID NO: 6            moltype = AA  length = 9
FEATURE                 Location/Qualifiers
REGION                  1..9
                        note = synthetic
source                  1..9
                        mol_type = protein
                        organism = synthetic construct
```

```
SEQUENCE: 6
ALWYSNLWV                                                          9

SEQ ID NO: 7            moltype = AA  length = 5
FEATURE                 Location/Qualifiers
REGION                  1..5
                        note = synthetic
source                  1..5
                        mol_type = protein
                        organism = synthetic construct
SEQUENCE: 7
TYAMN                                                              5

SEQ ID NO: 8            moltype = AA  length = 19
FEATURE                 Location/Qualifiers
REGION                  1..19
                        note = synthetic
source                  1..19
                        mol_type = protein
                        organism = synthetic construct
SEQUENCE: 8
RIRSKYNNYA TYYADSVKD                                               19

SEQ ID NO: 9            moltype = AA  length = 14
FEATURE                 Location/Qualifiers
REGION                  1..14
                        note = synthetic
source                  1..14
                        mol_type = protein
                        organism = synthetic construct
SEQUENCE: 9
HGNFGNSYVS WFAY                                                    14

SEQ ID NO: 10           moltype = AA  length = 15
FEATURE                 Location/Qualifiers
REGION                  1..15
                        note = synthetic
source                  1..15
                        mol_type = protein
                        organism = synthetic construct
SEQUENCE: 10
MMYCGGNEVL CGPRV                                                   15

SEQ ID NO: 11           moltype = AA  length = 15
FEATURE                 Location/Qualifiers
REGION                  1..15
                        note = synthetic
source                  1..15
                        mol_type = protein
                        organism = synthetic construct
SEQUENCE: 11
GYRWGCEWNC GGITT                                                   15

SEQ ID NO: 12           moltype = AA  length = 15
FEATURE                 Location/Qualifiers
REGION                  1..15
                        note = synthetic
source                  1..15
                        mol_type = protein
                        organism = synthetic construct
SEQUENCE: 12
GYLWGCEWNC GGITT                                                   15

SEQ ID NO: 13           moltype = AA  length = 8
FEATURE                 Location/Qualifiers
REGION                  1..8
                        note = synthetic
source                  1..8
                        mol_type = protein
                        organism = synthetic construct
SEQUENCE: 13
LSGRSDNH                                                           8

SEQ ID NO: 14           moltype = AA  length = 8
FEATURE                 Location/Qualifiers
REGION                  1..8
                        note = synthetic
```

```
source                1..8
                      mol_type = protein
                      organism = synthetic construct
SEQUENCE: 14
LSGRSDDH                                                  8

SEQ ID NO: 15         moltype = AA  length = 13
FEATURE               Location/Qualifiers
REGION                1..13
                      note = synthetic
source                1..13
                      mol_type = protein
                      organism = synthetic construct
SEQUENCE: 15
ISSGLLSGRS DNH                                            13

SEQ ID NO: 16         moltype = AA  length = 13
FEATURE               Location/Qualifiers
REGION                1..13
                      note = synthetic
source                1..13
                      mol_type = protein
                      organism = synthetic construct
SEQUENCE: 16
ISSGLLSGRS DQH                                            13

SEQ ID NO: 17         moltype = AA  length = 13
FEATURE               Location/Qualifiers
REGION                1..13
                      note = synthetic
source                1..13
                      mol_type = protein
                      organism = synthetic construct
SEQUENCE: 17
ISSGLLSGRS DDH                                            13

SEQ ID NO: 18         moltype = AA  length = 8
FEATURE               Location/Qualifiers
REGION                1..8
                      note = synthetic
source                1..8
                      mol_type = protein
                      organism = synthetic construct
SEQUENCE: 18
LSGRSDNH                                                  8

SEQ ID NO: 19         moltype = AA  length = 8
FEATURE               Location/Qualifiers
REGION                1..8
                      note = synthetic
source                1..8
                      mol_type = protein
                      organism = synthetic construct
SEQUENCE: 19
LSGRSGNH                                                  8

SEQ ID NO: 20         moltype = AA  length = 12
FEATURE               Location/Qualifiers
REGION                1..12
                      note = synthetic
source                1..12
                      mol_type = protein
                      organism = synthetic construct
SEQUENCE: 20
TSTSGRSANP RG                                             12

SEQ ID NO: 21         moltype = AA  length = 8
FEATURE               Location/Qualifiers
REGION                1..8
                      note = synthetic
source                1..8
                      mol_type = protein
                      organism = synthetic construct
SEQUENCE: 21
ISSGLLSS                                                  8
```

```
SEQ ID NO: 22          moltype = AA  length = 8
FEATURE                Location/Qualifiers
REGION                 1..8
                       note = synthetic
source                 1..8
                       mol_type = protein
                       organism = synthetic construct
SEQUENCE: 22
QNQALRMA                                                     8

SEQ ID NO: 23          moltype = AA  length = 10
FEATURE                Location/Qualifiers
REGION                 1..10
                       note = synthetic
source                 1..10
                       mol_type = protein
                       organism = synthetic construct
SEQUENCE: 23
VHMPLGFLGP                                                   10

SEQ ID NO: 24          moltype = AA  length = 8
FEATURE                Location/Qualifiers
REGION                 1..8
                       note = synthetic
source                 1..8
                       mol_type = protein
                       organism = synthetic construct
SEQUENCE: 24
AVGLLAPP                                                     8

SEQ ID NO: 25          moltype = AA  length = 8
FEATURE                Location/Qualifiers
REGION                 1..8
                       note = synthetic
source                 1..8
                       mol_type = protein
                       organism = synthetic construct
SEQUENCE: 25
LSGRSDDH                                                     8

SEQ ID NO: 26          moltype = AA  length = 8
FEATURE                Location/Qualifiers
REGION                 1..8
                       note = synthetic
source                 1..8
                       mol_type = protein
                       organism = synthetic construct
SEQUENCE: 26
LSGRSDIH                                                     8

SEQ ID NO: 27          moltype = AA  length = 8
FEATURE                Location/Qualifiers
REGION                 1..8
                       note = synthetic
source                 1..8
                       mol_type = protein
                       organism = synthetic construct
SEQUENCE: 27
LSGRSDQH                                                     8

SEQ ID NO: 28          moltype = AA  length = 8
FEATURE                Location/Qualifiers
REGION                 1..8
                       note = synthetic
source                 1..8
                       mol_type = protein
                       organism = synthetic construct
SEQUENCE: 28
LSGRSDTH                                                     8

SEQ ID NO: 29          moltype = AA  length = 8
FEATURE                Location/Qualifiers
REGION                 1..8
                       note = synthetic
source                 1..8
                       mol_type = protein
                       organism = synthetic construct
```

-continued

```
SEQUENCE: 29
LSGRSDYH                                                                8

SEQ ID NO: 30           moltype = AA  length = 8
FEATURE                 Location/Qualifiers
REGION                  1..8
                        note = synthetic
source                  1..8
                        mol_type = protein
                        organism = synthetic construct
SEQUENCE: 30
LSGRSDNP                                                                8

SEQ ID NO: 31           moltype = AA  length = 8
FEATURE                 Location/Qualifiers
REGION                  1..8
                        note = synthetic
source                  1..8
                        mol_type = protein
                        organism = synthetic construct
SEQUENCE: 31
LSGRSANP                                                                8

SEQ ID NO: 32           moltype = AA  length = 8
FEATURE                 Location/Qualifiers
REGION                  1..8
                        note = synthetic
source                  1..8
                        mol_type = protein
                        organism = synthetic construct
SEQUENCE: 32
LSGRSANI                                                                8

SEQ ID NO: 33           moltype = AA  length = 8
FEATURE                 Location/Qualifiers
REGION                  1..8
                        note = synthetic
source                  1..8
                        mol_type = protein
                        organism = synthetic construct
SEQUENCE: 33
LSGRSDNI                                                                8

SEQ ID NO: 34           moltype = AA  length = 13
FEATURE                 Location/Qualifiers
REGION                  1..13
                        note = synthetic
source                  1..13
                        mol_type = protein
                        organism = synthetic construct
SEQUENCE: 34
ISSGLLSGRS DNH                                                          13

SEQ ID NO: 35           moltype = AA  length = 13
FEATURE                 Location/Qualifiers
REGION                  1..13
                        note = synthetic
source                  1..13
                        mol_type = protein
                        organism = synthetic construct
SEQUENCE: 35
ISSGLLSGRS GNH                                                          13

SEQ ID NO: 36           moltype = AA  length = 15
FEATURE                 Location/Qualifiers
REGION                  1..15
                        note = synthetic
source                  1..15
                        mol_type = protein
                        organism = synthetic construct
SEQUENCE: 36
ISSGLLSGRS ANPRG                                                        15

SEQ ID NO: 37           moltype = AA  length = 17
FEATURE                 Location/Qualifiers
REGION                  1..17
                        note = synthetic
```

-continued

```
source                 1..17
                       mol_type = protein
                       organism = synthetic construct
SEQUENCE: 37
AVGLLAPPSG RSANPRG                                                 17

SEQ ID NO: 38          moltype = AA  length = 13
FEATURE                Location/Qualifiers
REGION                 1..13
                       note = synthetic
source                 1..13
                       mol_type = protein
                       organism = synthetic construct
SEQUENCE: 38
ISSGLLSGRS DDH                                                     13

SEQ ID NO: 39          moltype = AA  length = 13
FEATURE                Location/Qualifiers
REGION                 1..13
                       note = synthetic
source                 1..13
                       mol_type = protein
                       organism = synthetic construct
SEQUENCE: 39
ISSGLLSGRS DIH                                                     13

SEQ ID NO: 40          moltype = AA  length = 13
FEATURE                Location/Qualifiers
REGION                 1..13
                       note = synthetic
source                 1..13
                       mol_type = protein
                       organism = synthetic construct
SEQUENCE: 40
ISSGLLSGRS DQH                                                     13

SEQ ID NO: 41          moltype = AA  length = 13
FEATURE                Location/Qualifiers
REGION                 1..13
                       note = synthetic
source                 1..13
                       mol_type = protein
                       organism = synthetic construct
SEQUENCE: 41
ISSGLLSGRS DTH                                                     13

SEQ ID NO: 42          moltype = AA  length = 13
FEATURE                Location/Qualifiers
REGION                 1..13
                       note = synthetic
source                 1..13
                       mol_type = protein
                       organism = synthetic construct
SEQUENCE: 42
ISSGLLSGRS DYH                                                     13

SEQ ID NO: 43          moltype = AA  length = 13
FEATURE                Location/Qualifiers
REGION                 1..13
                       note = synthetic
source                 1..13
                       mol_type = protein
                       organism = synthetic construct
SEQUENCE: 43
ISSGLLSGRS DNP                                                     13

SEQ ID NO: 44          moltype = AA  length = 13
FEATURE                Location/Qualifiers
REGION                 1..13
                       note = synthetic
source                 1..13
                       mol_type = protein
                       organism = synthetic construct
SEQUENCE: 44
ISSGLLSGRS ANP                                                     13
```

```
SEQ ID NO: 45          moltype = AA  length = 13
FEATURE                Location/Qualifiers
REGION                 1..13
                       note = synthetic
source                 1..13
                       mol_type = protein
                       organism = synthetic construct
SEQUENCE: 45
ISSGLLSGRS ANI                                              13

SEQ ID NO: 46          moltype = AA  length = 13
FEATURE                Location/Qualifiers
REGION                 1..13
                       note = synthetic
source                 1..13
                       mol_type = protein
                       organism = synthetic construct
SEQUENCE: 46
ISSGLLSGRS DNI                                              13

SEQ ID NO: 47          moltype = AA  length = 18
FEATURE                Location/Qualifiers
REGION                 1..18
                       note = synthetic
source                 1..18
                       mol_type = protein
                       organism = synthetic construct
SEQUENCE: 47
AVGLLAPPGG LSGRSDNH                                         18

SEQ ID NO: 48          moltype = AA  length = 18
FEATURE                Location/Qualifiers
REGION                 1..18
                       note = synthetic
source                 1..18
                       mol_type = protein
                       organism = synthetic construct
SEQUENCE: 48
AVGLLAPPGG LSGRSDDH                                         18

SEQ ID NO: 49          moltype = AA  length = 18
FEATURE                Location/Qualifiers
REGION                 1..18
                       note = synthetic
source                 1..18
                       mol_type = protein
                       organism = synthetic construct
SEQUENCE: 49
AVGLLAPPGG LSGRSDIH                                         18

SEQ ID NO: 50          moltype = AA  length = 18
FEATURE                Location/Qualifiers
REGION                 1..18
                       note = synthetic
source                 1..18
                       mol_type = protein
                       organism = synthetic construct
SEQUENCE: 50
AVGLLAPPGG LSGRSDQH                                         18

SEQ ID NO: 51          moltype = AA  length = 18
FEATURE                Location/Qualifiers
REGION                 1..18
                       note = synthetic
source                 1..18
                       mol_type = protein
                       organism = synthetic construct
SEQUENCE: 51
AVGLLAPPGG LSGRSDTH                                         18

SEQ ID NO: 52          moltype = AA  length = 18
FEATURE                Location/Qualifiers
REGION                 1..18
                       note = synthetic
source                 1..18
                       mol_type = protein
                       organism = synthetic construct
```

-continued

```
SEQUENCE: 52
AVGLLAPPGG LSGRSDYH                                                18

SEQ ID NO: 53           moltype = AA  length = 18
FEATURE                 Location/Qualifiers
REGION                  1..18
                        note = synthetic
source                  1..18
                        mol_type = protein
                        organism = synthetic construct
SEQUENCE: 53
AVGLLAPPGG LSGRSDNP                                                18

SEQ ID NO: 54           moltype = AA  length = 18
FEATURE                 Location/Qualifiers
REGION                  1..18
                        note = synthetic
source                  1..18
                        mol_type = protein
                        organism = synthetic construct
SEQUENCE: 54
AVGLLAPPGG LSGRSANP                                                18

SEQ ID NO: 55           moltype = AA  length = 18
FEATURE                 Location/Qualifiers
REGION                  1..18
                        note = synthetic
source                  1..18
                        mol_type = protein
                        organism = synthetic construct
SEQUENCE: 55
AVGLLAPPGG LSGRSANI                                                18

SEQ ID NO: 56           moltype = AA  length = 18
FEATURE                 Location/Qualifiers
REGION                  1..18
                        note = synthetic
source                  1..18
                        mol_type = protein
                        organism = synthetic construct
SEQUENCE: 56
AVGLLAPPGG LSGRSDNI                                                18

SEQ ID NO: 57           moltype = AA  length = 11
FEATURE                 Location/Qualifiers
REGION                  1..11
                        note = synthetic
source                  1..11
                        mol_type = protein
                        organism = synthetic construct
SEQUENCE: 57
RASQSIGTNI H                                                       11

SEQ ID NO: 58           moltype = AA  length = 7
FEATURE                 Location/Qualifiers
REGION                  1..7
                        note = synthetic
source                  1..7
                        mol_type = protein
                        organism = synthetic construct
SEQUENCE: 58
YASESIS                                                            7

SEQ ID NO: 59           moltype = AA  length = 9
FEATURE                 Location/Qualifiers
REGION                  1..9
                        note = synthetic
source                  1..9
                        mol_type = protein
                        organism = synthetic construct
SEQUENCE: 59
QQNNNWPTT                                                          9

SEQ ID NO: 60           moltype = AA  length = 5
FEATURE                 Location/Qualifiers
REGION                  1..5
                        note = synthetic
```

```
source                1..5
                      mol_type = protein
                      organism = synthetic construct
SEQUENCE: 60
NYGVH                                                                5

SEQ ID NO: 61         moltype = AA  length = 16
FEATURE               Location/Qualifiers
REGION                1..16
                      note = synthetic
source                1..16
                      mol_type = protein
                      organism = synthetic construct
SEQUENCE: 61
VIWSGGNTDY NTPFTS                                                    16

SEQ ID NO: 62         moltype = AA  length = 11
FEATURE               Location/Qualifiers
REGION                1..11
                      note = synthetic
source                1..11
                      mol_type = protein
                      organism = synthetic construct
SEQUENCE: 62
ALTYYDYEFA Y                                                         11

SEQ ID NO: 63         moltype = AA  length = 107
FEATURE               Location/Qualifiers
REGION                1..107
                      note = synthetic
source                1..107
                      mol_type = protein
                      organism = synthetic construct
SEQUENCE: 63
QILLTQSPVI LSVSPGERVS FSCRASQSIG TNIHWYQQRT NGSPRLLIKY ASESISGIPS  60
RFSGSGSGTD FTLSINSVES EDIADYYCQQ NNNWPTTFGA GTKLELK                107

SEQ ID NO: 64         moltype = AA  length = 119
FEATURE               Location/Qualifiers
REGION                1..119
                      note = synthetic
VARIANT               119
                      note = X may be Ser or Ala
source                1..119
                      mol_type = protein
                      organism = synthetic construct
SEQUENCE: 64
QVQLKQSGPG LVQPSQSLSI TCTVSGFSLT NYGVHWVRQS PGKGLEWLGV IWSGGNTDYN  60
TPFTSRLSIN KDNSKSQVFF KMNSLQSQDT AIYYCARALT YYDYEFAYWG QGTLVTVSX   119

SEQ ID NO: 65         moltype = AA  length = 214
FEATURE               Location/Qualifiers
REGION                1..214
                      note = synthetic
source                1..214
                      mol_type = protein
                      organism = synthetic construct
SEQUENCE: 65
QILLTQSPVI LSVSPGERVS FSCRASQSIG TNIHWYQQRT NGSPRLLIKY ASESISGIPS  60
RFSGSGSGTD FTLSINSVES EDIADYYCQQ NNNWPTTFGA GTKLELKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 66         moltype = AA  length = 449
FEATURE               Location/Qualifiers
REGION                1..449
                      note = synthetic
VARIANT               119
                      note = X may be Ser or Ala
source                1..449
                      mol_type = protein
                      organism = synthetic construct
SEQUENCE: 66
QVQLKQSGPG LVQPSQSLSI TCTVSGFSLT NYGVHWVRQS PGKGLEWLGV IWSGGNTDYN  60
TPFTSRLSIN KDNSKSQVFF KMNSLQSQDT AIYYCARALT YYDYEFAYWG QGTLVTVSXA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
```

-continued

```
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 67          moltype = AA  length = 449
FEATURE                Location/Qualifiers
REGION                 1..449
                       note = synthetic
VARIANT                119
                       note = X  may be Ser or Ala
VARIANT                299
                       note = X can be any amino acid
source                 1..449
                       mol_type = protein
                       organism = synthetic construct
SEQUENCE: 67
QVQLKQSGPG LVQPSQSLSI TCTVSGFSLT NYGVHWVRQS PGKGLEWLGV IWSGGNTDYN  60
TPFTSRLSIN KDNSKSQVFF KMNSLQSQDT AIYYCARALT YYDYEFAYWG QGTLVTVSXA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYXS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 68          moltype = AA  length = 449
FEATURE                Location/Qualifiers
REGION                 1..449
                       note = synthetic
VARIANT                119
                       note = X may be Ser or Ala
source                 1..449
                       mol_type = protein
                       organism = synthetic construct
SEQUENCE: 68
QVQLKQSGPG LVQPSQSLSI TCTVSGFSLT NYGVHWVRQS PGKGLEWLGV IWSGGNTDYN  60
TPFTSRLSIN KDNSKSQVFF KMNSLQSQDT AIYYCARALT YYDYEFAYWG QGTLVTVSXA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYQS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 69          moltype = AA  length = 449
FEATURE                Location/Qualifiers
REGION                 1..449
                       note = synthetic
VARIANT                119
                       note = X may be Ser or Ala
VARIANT                236
                       note = X can be any amino acid
source                 1..449
                       mol_type = protein
                       organism = synthetic construct
SEQUENCE: 69
QVQLKQSGPG LVQPSQSLSI TCTVSGFSLT NYGVHWVRQS PGKGLEWLGV IWSGGNTDYN  60
TPFTSRLSIN KDNSKSQVFF KMNSLQSQDT AIYYCARALT YYDYEFAYWG QGTLVTVSXA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEXLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 70          moltype = AA  length = 449
FEATURE                Location/Qualifiers
REGION                 1..449
                       note = synthetic
VARIANT                119
                       note = X may be Ser or Ala
source                 1..449
                       mol_type = protein
                       organism = synthetic construct
SEQUENCE: 70
QVQLKQSGPG LVQPSQSLSI TCTVSGFSLT NYGVHWVRQS PGKGLEWLGV IWSGGNTDYN  60
TPFTSRLSIN KDNSKSQVFF KMNSLQSQDT AIYYCARALT YYDYEFAYWG QGTLVTVSXA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEFLGGP  240
SVFLFPPKPK DTLMISRTPE VTCVVVDVSH EDPEVKFNWY VDGVEVHNAK TKPREEQYNS  300
```

-continued

```
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 71          moltype = AA  length = 449
FEATURE                Location/Qualifiers
REGION                 1..449
                       note = synthetic
VARIANT                119
                       note = X may be Ser or Ala
VARIANT                237
                       note = X can be any amino acid
source                 1..449
                       mol_type = protein
                       organism = synthetic construct
SEQUENCE: 71
QVQLKQSGPG LVQPSQSLSI TCTVSGFSLT NYGVHWVRQS PGKGLEWLGV IWSGGNTDYN  60
TPFTSRLSIN KDNSKSQVFF KMNSLQSQDT AIYYCARALT YYDYEFAYWG QGTLVTVSXA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELXGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 72          moltype = AA  length = 449
FEATURE                Location/Qualifiers
REGION                 1..449
                       note = synthetic
VARIANT                119
                       note = X may be Ser or Ala
source                 1..449
                       mol_type = protein
                       organism = synthetic construct
SEQUENCE: 72
QVQLKQSGPG LVQPSQSLSI TCTVSGFSLT NYGVHWVRQS PGKGLEWLGV IWSGGNTDYN  60
TPFTSRLSIN KDNSKSQVFF KMNSLQSQDT AIYYCARALT YYDYEFAYWG QGTLVTVSXA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELEGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 73          moltype = AA  length = 449
FEATURE                Location/Qualifiers
REGION                 1..449
                       note = synthetic
VARIANT                119
                       note = X may be Ser or Ala
VARIANT                333
                       note = X can be any amino acid
source                 1..449
                       mol_type = protein
                       organism = synthetic construct
SEQUENCE: 73
QVQLKQSGPG LVQPSQSLSI TCTVSGFSLT NYGVHWVRQS PGKGLEWLGV IWSGGNTDYN  60
TPFTSRLSIN KDNSKSQVFF KMNSLQSQDT AIYYCARALT YYDYEFAYWG QGTLVTVSXA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAXIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 74          moltype = AA  length = 449
FEATURE                Location/Qualifiers
REGION                 1..449
                       note = synthetic
VARIANT                119
                       note = X may be Ser or Ala
source                 1..449
                       mol_type = protein
                       organism = synthetic construct
SEQUENCE: 74
QVQLKQSGPG LVQPSQSLSI TCTVSGFSLT NYGVHWVRQS PGKGLEWLGV IWSGGNTDYN  60
TPFTSRLSIN KDNSKSQVFF KMNSLQSQDT AIYYCARALT YYDYEFAYWG QGTLVTVSXA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
```

```
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PASIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 75           moltype = AA  length = 449
FEATURE                 Location/Qualifiers
REGION                  1..449
                        note = synthetic
VARIANT                 119
                        note = X may be Ser or Ala
source                  1..449
                        mol_type = protein
                        organism = synthetic construct
SEQUENCE: 75
QVQLKQSGPG LVQPSQSLSI TCTVSGFSLT NYGVHWVRQS PGKGLEWLGV IWSGGNTDYN  60
TPFTSRLSIN KDNSKSQVFF KMNSLQSQDT AIYYCARALT YYDYEFAYWG QGTLVTVSXA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEFEGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PASIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 76           moltype = AA  length = 449
FEATURE                 Location/Qualifiers
REGION                  1..449
                        note = synthetic
VARIANT                 119
                        note = X may be Ser or Ala
source                  1..449
                        mol_type = protein
                        organism = synthetic construct
SEQUENCE: 76
QVQLKQSGPG LVQPSQSLSI TCTVSGFSLT NYGVHWVRQS PGKGLEWLGV IWSGGNTDYN  60
TPFTSRLSIN KDNSKSQVFF KMNSLQSQDT AIYYCARALT YYDYEFAYWG QGTLVTVSXA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEFEGGP  240
SVFLFPPKPK DTLMISRTPE VTCVVVDVSH EDPEVKFNWY VDGVEVHNAK TKPREEQYQS  300
TYRVVSVLTV LHQDWLNGKE YKCKVSNKAL PASIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 77           moltype = AA  length = 401
FEATURE                 Location/Qualifiers
REGION                  1..401
                        note = synthetic
VARIANT                 120
                        note = X may be Ser  or Ala
source                  1..401
                        mol_type = protein
                        organism = synthetic construct
SEQUENCE: 77
QVTLRESGPA LVKPTQTLTL TCTFSGFSLS TSGMSVGWIR QPPGKALEWL ADIWWDDKKD  60
YNPSLKSRLT ISKDTSKNQV VLKVTNMDPA DTATYYCARS MITNWYFDVW GAGTTVTVSX  120
VHTFPAVLQS SGLYSLSSVV TVPSSSLGTQ TYICNVNHKP SNTKVDKKVE PKSCDKTHTC  180
PPCPAPEFEG GPSVFLFPPK PKDTLMISRT PEVTCVVVDV SHEDPEVKFN WYVDGVEVHN  240
AKTKPREEQY QSTYRVVSVL TVLHQDWLNG KEYKCKVSNK ALPASIEKTI SKAKGQPREP  300
QVYTLPPSRE EMTKNQVSLT CLVKGFYPSD IAVEWESNGQ PENNYKTTPP VLDSDGSFFL  360
YSKLTVDKSR WQQGNVFSCS VMHEALHNHY TQKSLSLSPG K                     401

SEQ ID NO: 78           moltype = AA  length = 15
FEATURE                 Location/Qualifiers
REGION                  1..15
                        note = synthetic
source                  1..15
                        mol_type = protein
                        organism = synthetic construct
SEQUENCE: 78
LSCEGWAMNR EQCRA                                                  15

SEQ ID NO: 79           moltype = AA  length = 15
FEATURE                 Location/Qualifiers
REGION                  1..15
                        note = synthetic
source                  1..15
                        mol_type = protein
                        organism = synthetic construct
```

-continued

```
SEQUENCE: 79
PPLECNTKSM CSKHD                                                    15

SEQ ID NO: 80          moltype = AA  length = 15
FEATURE                Location/Qualifiers
REGION                 1..15
                       note = synthetic
source                 1..15
                       mol_type = protein
                       organism = synthetic construct
SEQUENCE: 80
DRDCRGRRAR CQQEG                                                    15

SEQ ID NO: 81          moltype = AA  length = 15
FEATURE                Location/Qualifiers
REGION                 1..15
                       note = synthetic
source                 1..15
                       mol_type = protein
                       organism = synthetic construct
SEQUENCE: 81
FTCEGWAMNR EQCRT                                                    15

SEQ ID NO: 82          moltype = AA  length = 15
FEATURE                Location/Qualifiers
REGION                 1..15
                       note = synthetic
source                 1..15
                       mol_type = protein
                       organism = synthetic construct
SEQUENCE: 82
GRCPPSRDIR FCTYM                                                    15

SEQ ID NO: 83          moltype = AA  length = 15
FEATURE                Location/Qualifiers
REGION                 1..15
                       note = synthetic
source                 1..15
                       mol_type = protein
                       organism = synthetic construct
SEQUENCE: 83
FSCEGWAMNR SQCRT                                                    15

SEQ ID NO: 84          moltype = AA  length = 15
FEATURE                Location/Qualifiers
REGION                 1..15
                       note = synthetic
source                 1..15
                       mol_type = protein
                       organism = synthetic construct
SEQUENCE: 84
FTCEGWAMNR DQCRT                                                    15

SEQ ID NO: 85          moltype = AA  length = 15
FEATURE                Location/Qualifiers
REGION                 1..15
                       note = synthetic
source                 1..15
                       mol_type = protein
                       organism = synthetic construct
SEQUENCE: 85
CISPRGCPDG PYVMY                                                    15

SEQ ID NO: 86          moltype = AA  length = 14
FEATURE                Location/Qualifiers
REGION                 1..14
                       note = synthetic
source                 1..14
                       mol_type = protein
                       organism = synthetic construct
SEQUENCE: 86
CISPRGCPDG PYVM                                                     14

SEQ ID NO: 87          moltype = AA  length = 7
FEATURE                Location/Qualifiers
REGION                 1..7
                       note = synthetic
```

-continued

```
source                1..7
                      mol_type = protein
                      organism = synthetic construct
SEQUENCE: 87
CISPRGC                                                                    7

SEQ ID NO: 88         moltype = AA  length = 5
FEATURE               Location/Qualifiers
REGION                1..5
                      note = synthetic
source                1..5
                      mol_type = protein
                      organism = synthetic construct
SEQUENCE: 88
GSGGS                                                                      5

SEQ ID NO: 89         moltype = AA  length = 4
FEATURE               Location/Qualifiers
REGION                1..4
                      note = synthetic
source                1..4
                      mol_type = protein
                      organism = synthetic construct
SEQUENCE: 89
GGGS                                                                       4

SEQ ID NO: 90         moltype = AA  length = 4
FEATURE               Location/Qualifiers
REGION                1..4
                      note = synthetic
source                1..4
                      mol_type = protein
                      organism = synthetic construct
SEQUENCE: 90
GGSG                                                                       4

SEQ ID NO: 91         moltype = AA  length = 5
FEATURE               Location/Qualifiers
REGION                1..5
                      note = synthetic
source                1..5
                      mol_type = protein
                      organism = synthetic construct
SEQUENCE: 91
GGSGG                                                                      5

SEQ ID NO: 92         moltype = AA  length = 5
FEATURE               Location/Qualifiers
REGION                1..5
                      note = synthetic
source                1..5
                      mol_type = protein
                      organism = synthetic construct
SEQUENCE: 92
GSGSG                                                                      5

SEQ ID NO: 93         moltype = AA  length = 5
FEATURE               Location/Qualifiers
REGION                1..5
                      note = synthetic
source                1..5
                      mol_type = protein
                      organism = synthetic construct
SEQUENCE: 93
GSGGG                                                                      5

SEQ ID NO: 94         moltype = AA  length = 5
FEATURE               Location/Qualifiers
REGION                1..5
                      note = synthetic
source                1..5
                      mol_type = protein
                      organism = synthetic construct
SEQUENCE: 94
GGGSG                                                                      5
```

-continued

```
SEQ ID NO: 95           moltype = AA  length = 5
FEATURE                 Location/Qualifiers
REGION                  1..5
                        note = synthetic
source                  1..5
                        mol_type = protein
                        organism = synthetic construct
SEQUENCE: 95
GSSSG                                                                5

SEQ ID NO: 96           moltype = AA  length = 11
FEATURE                 Location/Qualifiers
REGION                  1..11
                        note = synthetic
source                  1..11
                        mol_type = protein
                        organism = synthetic construct
SEQUENCE: 96
GSSGGSGGSG G                                                         11

SEQ ID NO: 97           moltype = AA  length = 4
FEATURE                 Location/Qualifiers
REGION                  1..4
                        note = synthetic
source                  1..4
                        mol_type = protein
                        organism = synthetic construct
SEQUENCE: 97
GGGS                                                                 4

SEQ ID NO: 98           moltype = AA  length = 15
FEATURE                 Location/Qualifiers
REGION                  1..15
                        note = synthetic
source                  1..15
                        mol_type = protein
                        organism = synthetic construct
SEQUENCE: 98
GGGGSGGGGS GGGGS                                                     15

SEQ ID NO: 99           moltype = AA  length = 5
FEATURE                 Location/Qualifiers
REGION                  1..5
                        note = synthetic
source                  1..5
                        mol_type = protein
                        organism = synthetic construct
SEQUENCE: 99
GGGGS                                                                5

SEQ ID NO: 100          moltype = AA  length = 13
FEATURE                 Location/Qualifiers
REGION                  1..13
                        note = synthetic
source                  1..13
                        mol_type = protein
                        organism = synthetic construct
SEQUENCE: 100
GSSGGSGGSG GSG                                                       13

SEQ ID NO: 101          moltype = AA  length = 23
FEATURE                 Location/Qualifiers
REGION                  1..23
                        note = synthetic
source                  1..23
                        mol_type = protein
                        organism = synthetic construct
SEQUENCE: 101
GSSGGSGGSG GGGGSGGGSG GGS                                            23

SEQ ID NO: 102          moltype = AA  length = 23
FEATURE                 Location/Qualifiers
REGION                  1..23
                        note = synthetic
source                  1..23
                        mol_type = protein
                        organism = synthetic construct
```

```
SEQUENCE: 102
GSSGGSGGSG GSGGGSGGGS GGS                                          23

SEQ ID NO: 103         moltype = AA  length = 5
FEATURE                Location/Qualifiers
REGION                 1..5
                       note = synthetic
source                 1..5
                       mol_type = protein
                       organism = synthetic construct
SEQUENCE: 103
GSSGT                                                              5

SEQ ID NO: 104         moltype = AA  length = 8
FEATURE                Location/Qualifiers
REGION                 1..8
                       note = synthetic
source                 1..8
                       mol_type = protein
                       organism = synthetic construct
SEQUENCE: 104
GGGSSGGS                                                           8

SEQ ID NO: 105         moltype = DNA  length = 2241
FEATURE                Location/Qualifiers
misc_feature           1..2241
                       note = synthetic
source                 1..2241
                       mol_type = other DNA
                       organism = synthetic construct
SEQUENCE: 105
caaggccagt ctggccaaat gatgtattgc ggtgggaatg aggtgttgtg cgggccgcgg  60
gttggctcga gcggtggcag cggtggctct ggtggtctga gcggccgttc cgataatcat  120
ggcggcggtt ctcagaccgt ggtcacacag gagccctcac tgacagtgag ccctggcggg  180
accgtcacac tgacttgtcg cagttcaact ggcgccgtga ctaccagcaa ttacgctaac  240
tgggtccagc agaaaccagg acaggcacca cgaggactga tcggaggaac taataagaga  300
gcaccaggaa cccctgcaag gttctccgga tctctgctgg ggggaaaagc cgctctgaca  360
ctgagcggcg tgcagcctga ggacgaagct gagtactatt gcgcactgtg gtactccaac  420
ctgtgggtgt ttggcggggg aactaagctg accgtcctgg gaggaggagg aagcggagga  480
ggagggagcg gaggaggagg atccgaagtg cagctggtcg agagcggagg aggactggtg  540
cagccaggag gatccctgaa gctgtcttgt gcagccagtg gcttcacctt caacacttac  600
gcaatgaact gggtgcggca ggcacctggg aagggactgg aatgggtcgc ccggatcaga  660
tctaaataca ataactatgc cacctactat gctgacagtg tgaaggatag gttcaccatt  720
tcacgcgacg atagcaaaaa cacagcttat ctgcagatga ataacctgaa gaccgaggat  780
acagcagtgt actattgcgt cagacacggc aatttcggga actcttacgt gagttggttt  840
gcctattggg gacaggggac actggtcacc gtctcctcag gaggtggtgg atcccaggtg  900
cagctgaaac agagcggccc gggcctggtg cagccgagcc agagcctgag cattacctgc  960
accgtgagcg gctttagcct gaccaactat ggcgtgcatt gggtgcgcca gagcccgggc  1020
aaaggcctgg aatggctggg cgtgatttgg agcggcggca acaccgatta taacaccccg  1080
tttaccagcc gcctgagcat taacaaagat aacagcaaaa gccaggtgtt ttttaaaatg  1140
aacagcctgc aaagccagga taccgcgatt tattattgcg cgcgcgcgct gacctattat  1200
gattatgaat ttgcgtattg gggccagggc accctggtga ccgtgagcgc ggctagcacc  1260
aagggcccat cggtcttccc cctggcaccc tcctccaaga gcacctctgg gggcacagcg  1320
gccctgggct gcctggtcaa ggactacttc cccgaaccgg tgacggtgtc gtggaactca  1380
ggcgccctga ccagcggcgt gcacaccttc ccggctgtcc tacagtcctc aggactctac  1440
tccctcagca gcgtggtgac cgtgccctcc agcagcttgg gcacccagac ctacatctgc  1500
aacgtgaatc acaagcccag caacaccaag gtggacaaga aagttgagcc caaatcttgt  1560
gacaaaactc acacatgccc accgtgccca gcacctgaac tcctgggggg accgtcagtc  1620
ttcctcttcc ccccaaaacc caaggacacc ctcatgatct cccggacccc tgaggtcaca  1680
tgcgtggtgg tggacgtgag ccacgaagac cctgaggtca agttcaactg gtacgtggac  1740
ggcgtggagg tgcataatgc caagacaaag ccgcgggagg agcagtacca gagcacgtac  1800
cgtgtggtca gcgtcctcac cgtcctgcac caggactggc tgaatggcaa ggagtacaag  1860
tgcaaggtct ccaacaaagc cctcccagcc cccatcgaga aaaccatctc caaagccaaa  1920
gggcagcccc gagaaccaca ggtgtacacc ctgcccccat cccgggagga gatgaccaag  1980
aaccaggtca gcctgacctg cctggtcaaa ggcttctatc ccagcgacat cgccgtggag  2040
tgggagagca atgggcagcc ggagaacaac tacaagacca cgcctcccgt gctggactcc  2100
gacggctcct tcttcctcta cagcaagctc accgtggaca agagcaggtg gcagcagggg  2160
aacgtcttct catgctccgt gatgcatgag gctctgcaca accactacac gcagaagagc  2220
ctctccctgt ctccgggtaa a                                            2241

SEQ ID NO: 106         moltype = AA  length = 747
FEATURE                Location/Qualifiers
REGION                 1..747
                       note = synthetic
source                 1..747
                       mol_type = protein
                       organism = synthetic construct
```

```
SEQUENCE: 106
QGQSGQMMYC GGNEVLCGPR VGSSGGSGGS GGLSGRSDNH GGGSQTVVTQ EPSLTVSPGG  60
TVTLTCRSST GAVTTSNYAN WVQQKPGQAP RGLIGGTNKR APGTPARFSG SLLGGKAALT  120
LSGVQPEDEA EYYCALWYSN LWVFGGGTKL TVLGGGGSGG GGSGGGGSEV QLVESGGGLV  180
QPGGSLKLSC AASGFTFNTY AMNWVRQAPG KGLEWVARIR SKYNNYATYY ADSVKDRFTI  240
SRDDSKNTAY LQMNNLKTED TAVYYCVRHG NFGNSYVSWF AYWGQGTLVT VSSGGGGSQV  300
QLKQSGPGLV QPSQSLSITC TVSGFSLTNY GVHWVRQSPG KGLEWLGVIW SGGNTDYNTP  360
FTSRLSINKD NSKSQVFFKM NSLQSQDTAI YYCARALTYY DYEFAYWGQG TLVTVSAAST  420
KGPSVFPLAP SSKSTSGGTA ALGCLVKDYF PEPVTVSWNS GALTSGVHTF PAVLQSSGLY  480
SLSSVVTVPS SSLGTQTYIC NVNHKPSNTK VDKKVEPKSC DKTHTCPPCP APELLGGPSV  540
FLFPPKPKDT LMISRTPEVT CVVVDVSHED PEVKFNWYVD GVEVHNAKTK PREEQYQSTY  600
RVVSVLTVLH QDWLNGKEYK CKVSNKALPA PIEKTISKAK GQPREPQVYT LPPSREEMTK  660
NQVSLTCLVK GFYPSDIAVE WESNGQPENN YKTTPPVLDS DGSFFLYSKL TVDKSRWQQG  720
NVFSCSVMHE ALHNHYTQKS LSLSPGK                                    747

SEQ ID NO: 107          moltype = DNA  length = 783
FEATURE                 Location/Qualifiers
misc_feature            1..783
                        note = synthetic
source                  1..783
                        mol_type = other DNA
                        organism = synthetic construct
SEQUENCE: 107
caaggccagt ctggccagtg catctcacct cgtggttgtc cggacggccc atacgtcatg  60
tacggctcga gcggtggcag cggtggctct ggtggatccg gtctgagcgg ccgttccgat  120
aatcatggca gtagcggtac ccagatcttg ctgacccaga gcccggtgat tctgagcgtg  180
agcccgggcg aacgtgtgag ctttagctgc cgcgcgagcc agagcattgg caccaacatt  240
cattggtatc agcagcgcac caacggcagc ccgcgcctgc tgattaaata tgcgagcgaa  300
agcattagcg gcattccgag ccgctttagc ggcagcggca gcggcaccga ttttaccctg  360
agcattaaca gcgtggaaag cgaagatatt gcggattatt attgccagca gaacaacaac  420
tggccgacca cctttggcgc gggcaccaaa ctggaactga aacgtacggt ggctgcacca  480
tctgtcttca tcttcccgcc atctgatgag cagttgaaat ctggaactgc ctctgttgtg  540
tgcctgctga ataacttcta tcccagagag gccaaagtac agtggaaggt ggataacgcc  600
ctccaatcgg gtaactccca ggagagtgtc acagagcagg acagcaagga cagcacctac  660
agcctcagca gcaccctgac gctgagcaaa gcagactacg agaaacacaa agtctacgcc  720
tgcgaagtca cccatcaggg cctgagctcg cccgtcacaa agagcttcaa caggggagag  780
tgt                                                              783

SEQ ID NO: 108          moltype = AA  length = 261
FEATURE                 Location/Qualifiers
REGION                  1..261
                        note = synthetic
source                  1..261
                        mol_type = protein
                        organism = synthetic construct
SEQUENCE: 108
QGQSGQCISP RGCPDGPYVM YGSSGGSGGS GGSGLSGRSD NHGSSGTQIL LTQSPVILSV  60
SPGERVSFSC RASQSIGTNI HWYQQRTNGS PRLLIKYASE SISGIPSRFS GSGSGTDFTL  120
SINSVESEDI ADYYCQQNNN WPTTFGAGTK LELKRTVAAP SVFIFPPSDE QLKSGTASVV  180
CLLNNFYPRE AKVQWKVDNA LQSGNSQESV TEQDSKDSTY SLSSTLTLSK ADYEKHKVYA  240
CEVTHQGLSS PVTKSFNRGE C                                          261

SEQ ID NO: 109          moltype = DNA  length = 2241
FEATURE                 Location/Qualifiers
misc_feature            1..2241
                        note = synthetic
source                  1..2241
                        mol_type = other DNA
                        organism = synthetic construct
SEQUENCE: 109
caaggccagt ctggccaaat gatgtattgc ggtgggaatg aggtgttgtg cgggccgcgg  60
gttggctcga gcggtggcag cggtggctct ggtggtggtg gaggctcggg cggtgggagc  120
ggcggcggtt ctcagaccgt ggtcacacag gagccctcac tgacagtgag ccctggcggg  180
accgtcacac tgacttgtcg cagttcaact ggcgccgtga ctaccagcaa ttacgctaac  240
tgggtccagc agaaaccagg acaggcacca cgaggactga tcggaggaac taataagaga  300
gcaccaggaa cccctgcaag gttctccgga tctctgctgg ggggaaaagc cgctctgaca  360
ctgagcggcg tgcagcctga ggacgaagct gagtactatt gcgcactgtg gtactccaac  420
ctgtgggtgt ttggcggggg aactaagctg accgtcctgg gaggaggagg aagcggagga  480
ggagggagcg gaggaggagg atccgaagtg cagctggtcg agagcggagg aggactggtg  540
cagccaggag gatccctgaa gctgtcttgt gcagccagtg gcttcacctt caacacttac  600
gcaatgaact gggtgcggca ggcacctggg aagggactgg aatgggtcgc ccggatcaga  660
tctaaataca ataactatgc cacctactat gctgacagtg tgaaggatag gttcaccatt  720
tcacgcgacg atagcaaaaa cacagcttat ctgcagatga ataacctgaa gaccgaggat  780
acagcagtgt actattgcgt cagacacggc aatttcggga actcttacgt gagttggttt  840
gcctattggg gacaggggac actggtcacc gtctcctcag gaggtggtgg atcccaggtg  900
cagctgaaac agagcggccc gggcctggtg cagccgagcc agagcctgag cattacctgc  960
accgtgagcg gctttagcct gaccaactat ggcgtgcatt gggtgcgcca gagcccgggc  1020
aaaggcctgg aatggctggg cgtgatttgg agcggcggca acaccgatta taacaccccg  1080
tttaccagcc gcctgagcat taacaaagat aacagcaaaa gccaggtgtt ttttaaaatg  1140
```

-continued

```
aacagcctgc aaagccagga taccgcgatt tattattgcg cgcgcgcgct gacctattat  1200
gattatgaat ttgcgtattg gggccagggc accctggtga ccgtgagcgc ggctagcacc  1260
aagggcccat cggtcttccc cctggcaccc tcctccaaga gcacctctgg gggcacagcg  1320
gccctgggct gcctggtcaa ggactacttc cccgaaccgg tgacggtgtc gtggaactca  1380
ggcgccctga ccagcggcgt gcacaccttc ccggctgtcc tacagtcctc aggactctac  1440
tccctcagca gcgtggtgac cgtgccctcc agcagcttgg gcacccagac ctacatctgc  1500
aacgtgaatc acaagcccag caacaccaag gtggacaaga aagttgagcc caaatcttgt  1560
gacaaaactc acacatgccc accgtgccca gcacctgaac tcctgggggg accgtcagtc  1620
ttcctcttcc ccccaaaacc caaggacacc ctcatgatct cccggacccc tgaggtcaca  1680
tgcgtggtgg tggacgtgag ccacgaagac cctgaggtca agttcaactg gtacgtggac  1740
ggcgtggagg tgcataatgc caagacaaag ccgcgggagg agcagtacca gagcacgtac  1800
cgtgtggtca gcgtcctcac cgtcctgcac caggactggc tgaatggcaa ggagtacaag  1860
tgcaaggtct ccaacaaagc cctcccagcc cccatcgaga aaaccatctc caaagccaaa  1920
gggcagcccc gagaaccaca ggtgtacacc ctgcccccat cccgggagga gatgaccaag  1980
aaccaggtca gcctgacctg cctggtcaaa ggcttctatc ccagcgacat cgccgtggag  2040
tgggagagca atgggcagcc ggagaacaac tacaagacca cgcctcccgt gctggactcc  2100
gacggctcct tcttcctcta cagcaagctc accgtggaca agagcaggtg gcagcagggg  2160
aacgtcttct catgctccgt gatgcatgag gctctgcaca accactacac gcagaagagc  2220
ctctccctgt ctccgggtaa a                                           2241

SEQ ID NO: 110          moltype = AA  length = 747
FEATURE                 Location/Qualifiers
REGION                  1..747
                        note = synthetic
source                  1..747
                        mol_type = protein
                        organism = synthetic construct
SEQUENCE: 110
QGQSGQMMYC GGNEVLCGPR VGSSGGSGGS GGGGGSGGGS GGGSQTVVTQ EPSLTVSPGG  60
TVTLTCRSST GAVTTSNYAN WVQQKPGQAP RGLIGGTNKR APGTPARFSG SLLGGKAALT  120
LSGVQPEDEA EYYCALWYSN LWVFGGGTKL TVLGGGGSGG GGSGGGGSEV QLVESGGGLV  180
QPGGSLKLSC AASGFTFNTY AMNWVRQAPG KGLEWVARIR SKYNNYATYY ADSVKDRFTI  240
SRDDSKNTAY LQMNNLKTED TAVYYCVRHG NFGNSYVSWF AYWGQGTLVT VSSGGGGSQV  300
QLKQSGPGLV QPSQSLSITC TVSGFSLTNY GVHWVRQSPG KGLEWLGVIW SGGNTDYNTP  360
FTSRLSINKD NSKSQVFFKM NSLQSQDTAI YYCARALTYY DYEFAYWGQG TLVTVSAAST  420
KGPSVFPLAP SSKSTSGGTA ALGCLVKDYF PEPVTVSWNS GALTSGVHTF PAVLQSSGLY  480
SLSSVVTVPS SSLGTQTYIC NVNHKPSNTK VDKKVEPKSC DKTHTCPPCP APELLGGPSV  540
FLFPPKPKDT LMISRTPEVT CVVVDVSHED PEVKFNWYVD GVEVHNAKTK PREEQYQSTY  600
RVVSVLTVLH QDWLNGKEYK CKVSNKALPA PIEKTISKAK GQPREPQVYT LPPSREEMTK  660
NQVSLTCLVK GFYPSDIAVE WESNGQPENN YKTTPPVLDS DGSFFLYSKL TVDKSRWQQG  720
NVFSCSVMHE ALHNHYTQKS LSLSPGK                                     747

SEQ ID NO: 111          moltype = DNA  length = 774
FEATURE                 Location/Qualifiers
misc_feature            1..774
                        note = synthetic
source                  1..774
                        mol_type = other DNA
                        organism = synthetic construct
SEQUENCE: 111
caaggccagt ctggccagtg catctcacct cgtggttgtc cggacggccc atacgtcatg  60
tacggctcga gcggtggcag cggtggctct ggtggctcag gtggaggctc gggcggtggg  120
agcggcggtt ctgatatctt gctgacccag agcccggtga ttctgagcgt gagcccgggc  180
gaacgtgtga gctttagctg ccgcgcgagc cagagcattg gcaccaacat tcattggtat  240
cagcagcgca ccaacggcag cccgcgcctg ctgattaaat atgcgagcga aagcattagc  300
ggcattccga gccgctttag cggcagcggc agcggcaccg attttaccct gagcattaac  360
agcgtggaaa gcgaagatat tgcggattat tattgccagc agaacaacaa ctggccgacc  420
acctttggcg cgggcaccaa actggaactg aaacgtacgg tggctgcacc atctgtcttc  480
atcttcccgc catctgatga gcagttgaaa tctggaactg cctctgttgt gtgcctgctg  540
aataacttct atcccagaga ggccaaagta cagtggaagg tggataacgc cctccaatcg  600
ggtaactccc aggagagtgt cacagagcag gacagcaagg acagcaccta cagcctcagc  660
agcaccctga cgctgagcaa agcagactac gagaaacaca aagtctacgc ctgcgaagtc  720
acccatcagg gcctgagctc gcccgtcaca aagagcttca acaggggaga gtgt        774

SEQ ID NO: 112          moltype = AA  length = 258
FEATURE                 Location/Qualifiers
REGION                  1..258
                        note = synthetic
source                  1..258
                        mol_type = protein
                        organism = synthetic construct
SEQUENCE: 112
QGQSGQCISP RGCPDGPYVM YGSSGGSGGS GGSGGGSGGG SGGSDILLTQ SPVILSVSPG  60
ERVSFSCRAS QSIGTNIHWY QQRTNGSPRL LIKYASESIS GIPSRFSGSG SGTDFTLSIN  120
SVESEDIADY YCQQNNNWPT TFGAGTKLEL KRTVAAPSVF IFPPSDEQLK SGTASVVCLL  180
NNFYPREAKV QWKVDNALQS GNSQESVTEQ DSKDSTYSLS STLTLSKADY EKHKVYACEV  240
THQGLSSPVT KSFNRGEC                                               258
```

```
SEQ ID NO: 113          moltype = DNA  length = 2256
FEATURE                 Location/Qualifiers
misc_feature            1..2256
                        note = synthetic
source                  1..2256
                        mol_type = other DNA
                        organism = synthetic construct
SEQUENCE: 113
caaggccagt ctggccaaat gatgtattgc ggtgggaatg aggtgttgtg cgggccgcgg  60
gttggctcga gcggtggcag cggtggctct ggtggtatct cttccggact gctgtccggc  120
agatccgaca atcacggcgg cggttctcag accgtggtca cacaggagcc ctcactgaca  180
gtgagccctg gcgggaccgt cacactgact tgtcgcagtt caactggcgc cgtgactacc  240
agcaattacg ctaactgggt ccagcagaaa ccaggacagg caccacgagg actgatcgga  300
ggaactaata agagagcacc aggaacccct gcaaggttct ccggatctct gctgggggga  360
aaagccgctc tgacactgag cggcgtgcag cctgaggacg aagctgagta ctattgcgca  420
ctgtggtact ccaacctgtg ggtgtttggc gggggaacta agctgaccgt cctgggagga  480
ggaggaagcg gaggaggagg gagcggagga ggaggatccg aagtgcagct ggtcgagagc  540
ggaggaggac tggtgcagcc aggaggatcc ctgaagctgt cttgtgcagc cagtggcttc  600
accttcaaca cttacgcaat gaactgggtg cggcaggcac ctgggaaggg actggaatgg  660
gtcgcccgga tcagatctaa atacaataac tatgccacct actatgctga cagtgtgaag  720
gataggttca ccatttcacg cgacgatagc aaaaacacag cttatctgca gatgaataac  780
ctgaagaccg aggatacagc agtgtactat tgcgtcagac acggcaattt cgggaactct  840
tacgtgagtt ggtttgccta ttggggacag gggacactgg tcaccgtctc ctcaggaggt  900
ggtggatccc aggtgcagct gaaacagagc ggcccgggcc tggtgcagcc gagccagagc  960
ctgagcatta cctgcaccgt gagcggcttt agcctgacca actatggcgt gcattgggtg  1020
cgccagagcc cgggcaaagg cctggaatgg ctgggcgtga tttggagcgg cggcaacacc  1080
gattataaca ccccgtttac cagccgcctg agcattaaca aagataacag caaaagccag  1140
gtgtttttta aaatgaacag cctgcaaagc caggataccg cgatttatta ttgcgcgcgc  1200
gcgctgacct attatgatta tgaatttgcg tattggggcc agggcaccct ggtgaccgtg  1260
agcgcggcta gcaccaaggg cccatcggtc ttccccctgg caccctcctc caagagcacc  1320
tctgggggca cagcggccct gggctgcctg gtcaaggact acttccccga accggtgacg  1380
gtgtcgtgga actcaggcgc cctgaccagc ggcgtgcaca ccttcccggc tgtcctacag  1440
tcctcaggac tctactccct cagcagcgtg gtgaccgtgc cctccagcag cttgggcacc  1500
cagacctaca tctgcaacgt gaatcacaag cccagcaaca ccaaggtgga caagaaagtt  1560
gagcccaaat cttgtgacaa aactcacaca tgcccaccgt gcccagcacc tgaactcctg  1620
gggggaccgt cagtcttcct cttcccccca aaacccaagg acaccctcat gatctcccgg  1680
acccctgagg tcacatgcgt ggtggtggac gtgagccacg aagaccctga ggtcaagttc  1740
aactggtacg tggacggcgt ggaggtgcat aatgccaaga caaagccgcg ggaggagcag  1800
taccagagca cgtaccgtgt ggtcagcgtc ctcaccgtcc tgcaccagga ctggctgaat  1860
ggcaaggagt acaagtgcaa ggtctccaac aaagccctcc cagcccccat cgagaaaacc  1920
atctccaaag ccaaagggca gccccgagaa ccacaggtgt acaccctgcc cccatcccgg  1980
gaggagatga ccaagaacca ggtcagcctg acctgcctgg tcaaaggctt ctatcccagc  2040
gacatcgccg tggagtggga gagcaatggg cagccggaga acaactacaa gaccacgcct  2100
cccgtgctgg actccgacgg ctccttcttc ctctacagca agctcaccgt ggacaagagc  2160
aggtggcagc aggggaacgt cttctcatgc tccgtgatgc atgaggctct gcacaaccac  2220
tacacgcaga agagcctctc cctgtctccg ggtaaa                            2256

SEQ ID NO: 114          moltype = AA  length = 752
FEATURE                 Location/Qualifiers
REGION                  1..752
                        note = synthetic
source                  1..752
                        mol_type = protein
                        organism = synthetic construct
SEQUENCE: 114
QGQSGQMMYC GGNEVLCGPR VGSSGGSGGS GGISSGLLSG RSDNHGGGSQ TVVTQEPSLT  60
VSPGGTVTLT CRSSTGAVTT SNYANWVQQK PGQAPRGLIG GTNKRAPGTP ARFSGSLLGG  120
KAALTLSGVQ PEDEAEYYCA LWYSNLWVFG GGTKLTVLGG GGSGGGGSGG GGSEVQLVES  180
GGGLVQPGGS LKLSCAASGF TFNTYAMNWV RQAPGKGLEW VARIRSKYNN YATYYADSVK  240
DRFTISRDDS KNTAYLQMNN LKTEDTAVYY CVRHGNFGNS YVSWFAYWGQ GTLVTVSSGG  300
GGSQVQLKQS GPGLVQPSQS LSITCTVSGF SLTNYGVHWV RQSPGKGLEW LGVIWSGGNT  360
DYNTPFTSRL SINKDNSKSQ VFFKMNSLQS QDTAIYYCAR ALTYYDYEFA YWGQGTLVTV  420
SAASTKGPSV FPLAPSSKST SGGTAALGCL VKDYFPEPVT VSWNSGALTS GVHTFPAVLQ  480
SSGLYSLSSV VTVPSSSLGT QTYICNVNHK PSNTKVDKKV EPKSCDKTHT CPPCPAPELL  540
GGPSVFLFPP KPKDTLMISR TPEVTCVVVD VSHEDPEVKF NWYVDGVEVH NAKTKPREEQ  600
YQSTYRVVSV LTVLHQDWLN GKEYKCKVSN KALPAPIEKT ISKAKGQPRE PQVYTLPPSR  660
EEMTKNQVSL TCLVKGFYPS DIAVEWESNG QPENNYKTTP PVLDSDGSFF LYSKLTVDKS  720
RWQQGNVFSC SVMHEALHNH YTQKSLSLSP GK                                752

SEQ ID NO: 115          moltype = DNA  length = 798
FEATURE                 Location/Qualifiers
misc_feature            1..798
                        note = synthetic
source                  1..798
                        mol_type = other DNA
                        organism = synthetic construct
```

-continued

```
SEQUENCE: 115
caaggccagt ctggccagtg catctcacct cgtggttgtc cggacggccc atacgtcatg  60
tacggctcga gcggtggcag cggtggctct ggtggatccg gtattagcag tggtctgtta  120
agcggtcgta gcgataatca tggcagtagc ggtacccaga tcttgctgac ccagagcccg  180
gtgattctga gcgtgagccc gggcgaacgt gtgagcttta gctgccgcgc gagccagagc  240
attggcacca acattcattg gtatcagcag cgcaccaacg gcagcccgcg cctgctgatt  300
aaatatgcga gcgaaagcat tagcggcatt ccgagccgct ttagcggcag cggcagcggc  360
accgatttta ccctgagcat taacagcgtg gaaagcgaag atattgcgga ttattattgc  420
cagcagaaca acaactggcc gaccaccttt ggcgcgggca ccaaactgga actgaaacgt  480
acggtggctg caccatctgt cttcatcttc ccgccatctg atgagcagtt gaaatctgga  540
actgcctctg ttgtgtgcct gctgaataac ttctatccca gagaggccaa agtacagtgg  600
aaggtggata acgccctcca atcgggtaac tcccaggaga gtgtcacaga gcaggacagc  660
aaggacagca cctacagcct cagcagcacc ctgacgctga gcaaagcaga ctacgagaaa  720
cacaaagtct acgcctgcga agtcacccat cagggcctga gctcgcccgt cacaaagagc  780
ttcaacaggg gagagtgt                                                 798

SEQ ID NO: 116         moltype = AA  length = 266
FEATURE                Location/Qualifiers
REGION                 1..266
                       note = synthetic
source                 1..266
                       mol_type = protein
                       organism = synthetic construct
SEQUENCE: 116
QGQSGQCISP RGCPDGPYVM YGSSGGSGGS GGSGISSGLL SGRSDNHGSS GTQILLTQSP  60
VILSVSPGER VSFSCRASQS IGTNIHWYQQ RTNGSPRLLI KYASESISGI PSRFSGSGSG  120
TDFTLSINSV ESEDIADYYC QQNNNWPTTF GAGTKLELKR TVAAPSVFIF PPSDEQLKSG  180
TASVVCLLNN FYPREAKVQW KVDNALQSGN SQESVTEQDS KDSTYSLSST LTLSKADYEK  240
HKVYACEVTH QGLSSPVTKS FNRGEC                                        266

SEQ ID NO: 117         moltype = DNA  length = 2133
FEATURE                Location/Qualifiers
misc_feature           1..2133
                       note = synthetic
source                 1..2133
                       mol_type = other DNA
                       organism = synthetic construct
SEQUENCE: 117
tccgataatc atggcggcgg ttctcagacc gtggtcacac aggagccctc actgacagtg  60
agccctggcg ggaccgtcac actgacttgt cgcagttcaa ctggcgccgt gactaccagc  120
aattacgcta actgggtcca gcagaaacca ggacaggcac cacgaggact gatcggagga  180
actaataaga gagcaccagg aacccctgca aggttctccg gatctctgct ggggggaaaa  240
gccgctctga cactgagcgg cgtgcagcct gaggacgaag ctgagtacta ttgcgcactg  300
tggtactcca acctgtgggt gtttggcggg ggaactaagc tgaccgtcct gggaggagga  360
ggaagcggag gaggagggag cggaggagga ggatccgaag tgcagctggt cgagagcgga  420
ggaggactgg tgcagccagg aggatccctg aagctgtctt gtgcagccag tggcttcacc  480
ttcaacactt acgcaatgaa ctgggtgcgg caggcacctg ggaagggact ggaatgggtc  540
gcccggatca gatctaaata caataactat gccacctact atgctgacag tgtgaaggat  600
aggttcacca tttcacgcga cgatagcaaa aacacagctt atctgcagat gaataacctg  660
aagaccgagg atacagcagt gtactattgc gtcagacacg gcaatttcgg gaactcttac  720
gtgagttggt ttgcctattg gggacagggg acactggtca ccgtctcctc aggaggtggt  780
ggatcccagg tgcagctgaa acagagcggc ccgggcctgg tgcagccgag ccagagcctg  840
agcattacct gcaccgtgag cggctttagc ctgaccaact atggcgtgca ttgggtgcgc  900
cagagcccgg gcaaaggcct ggaatggctg ggcgtgattt ggagcggcgg caacaccgat  960
tataacaccc cgtttaccag ccgcctgagc attaacaaag ataacagcaa aagccaggtg  1020
ttttttaaaa tgaacagcct gcaaagccag gataccgcga tttattattg cgcgcgcgcg  1080
ctgacctatt atgattatga atttgcgtat tggggccagg gcaccctggt gaccgtgagc  1140
gcggctagca ccaagggccc atcggtcttc cccctggcac cctcctccaa gagcacctct  1200
gggggcacag cggccctggg ctgcctggtc aaggactact tccccgaacc ggtgacggtg  1260
tcgtggaact caggcgccct gaccagcggc gtgcacacct tcccggctgt cctacagtcc  1320
tcaggactct actccctcag cagcgtggtg accgtgccct ccagcagctt gggcacccag  1380
acctacatct gcaacgtgaa tcacaagccc agcaacacca aggtggacaa gaaagttgag  1440
cccaaatctt gtgacaaaac tcacacatgc ccaccgtgcc cagcacctga actcctgggg  1500
ggaccgtcag tcttcctctt ccccccaaaa cccaaggaca ccctcatgat ctcccggacc  1560
cctgaggtca catgcgtggt ggtggacgtg agccacgaag accctgaggt caagttcaac  1620
tggtacgtgg acggcgtgga ggtgcataat gccaagacaa agccgcggga ggagcagtac  1680
cagagcacgt accgtgtggt cagcgtcctc accgtcctgc accaggactg gctgaatggc  1740
aaggagtaca agtgcaaggt ctccaacaaa gccctcccag cccccatcga gaaaaccatc  1800
tccaaagcca aagggcagcc ccgagaacca caggtgtaca ccctgccccc atcccgggag  1860
gagatgacca agaaccaggt cagcctgacc tgcctggtca aaggcttcta tcccagcgac  1920
atcgccgtgg agtgggagag caatgggcag ccggagaaca actacaagac cacgcctccc  1980
gtgctggact ccgacggctc cttcttcctc tacagcaagc tcaccgtgga caagagcagg  2040
tggcagcagg ggaacgtctt ctcatgctcc gtgatgcatg aggctctgca caaccactac  2100
acgcagaaga gcctctccct gtctccgggt aaa                                2133
```

```
SEQ ID NO: 118          moltype = AA  length = 711
FEATURE                 Location/Qualifiers
REGION                  1..711
                        note = synthetic
source                  1..711
                        mol_type = protein
                        organism = synthetic construct
SEQUENCE: 118
SDNHGGGSQT VVTQEPSLTV SPGGTVTLTC RSSTGAVTTS NYANWVQQKP GQAPRGLIGG  60
TNKRAPGTPA RFSGSLLGGK AALTLSGVQP EDEAEYYCAL WYSNLWVFGG GTKLTVLGGG  120
GSGGGGSGGG GSEVQLVESG GGLVQPGGSL KLSCAASGFT FNTYAMNWVR QAPGKGLEWV  180
ARIRSKYNNY ATYYADSVKD RFTISRDDSK NTAYLQMNNL KTEDTAVYYC VRHGNFGNSY  240
VSWFAYWGQG TLVTVSSGGG GSQVQLKQSG PGLVQPSQSL SITCTVSGFS LTNYGVHWVR  300
QSPGKGLEWL GVIWSGGNTD YNTPFTSRLS INKDNSKSQV FFKMNSLQSQ DTAIYYCARA  360
LTYYDYEFAY WGQGTLVTVS AASTKGPSVF PLAPSSKSTS GGTAALGCLV KDYFPEPVTV  420
SWNSGALTSG VHTFPAVLQS SGLYSLSSVV TVPSSSLGTQ TYICNVNHKP SNTKVDKKVE  480
PKSCDKTHTC PPCPAPELLG GPSVFLFPPK PKDTLMISRT PEVTCVVVDV SHEDPEVKFN  540
WYVDGVEVHN AKTKPREEQY QSTYRVVSVL TVLHQDWLNG KEYKCKVSNK ALPAPIEKTI  600
SKAKGQPREP QVYTLPPSRE EMTKNQVSLT CLVKGFYPSD IAVEWESNGQ PENNYKTTPP  660
VLDSDGSFFL YSKLTVDKSR WQQGNVFSCS VMHEALHNHY TQKSLSLSPG K           711

SEQ ID NO: 119          moltype = DNA  length = 669
FEATURE                 Location/Qualifiers
misc_feature            1..669
                        note = synthetic
source                  1..669
                        mol_type = other DNA
                        organism = synthetic construct
SEQUENCE: 119
tccgataatc atggcagtag cggtacccag atcttgctga cccagagccc ggtgattctg  60
agcgtgagcc cgggcgaacg tgtgagcttt agctgccgcg cgagccagag cattggcacc  120
aacattcatt ggtatcagca gcgcaccaac ggcagcccgc gcctgctgat taaatatgcg  180
agcgaaagca ttagcggcat tccgagccgc tttagcggca gcggcagcgg caccgatttt  240
accctgagca ttaacagcgt ggaaagcgaa gatattgcgg attattattg ccagcagaac  300
aacaactggc cgaccacctt tggcgcgggc accaaactgg aactgaaacg tacggtggct  360
gcaccatctg tcttcatctt cccgccatct gatgagcagt tgaaatctgg aactgcctct  420
gttgtgtgcc tgctgaataa cttctatccc agagaggcca aagtacagtg gaaggtggat  480
aacgccctcc aatcgggtaa ctcccaggag agtgtcacag agcaggacag caaggacagc  540
acctacagcc tcagcagcac cctgacgctg agcaaagcag actacgagaa acacaaagtc  600
tacgcctgcg aagtcaccca tcagggcctg agctcgcccg tcacaaagag cttcaacagg  660
ggagagtgt                                                          669

SEQ ID NO: 120          moltype = AA  length = 223
FEATURE                 Location/Qualifiers
REGION                  1..223
                        note = synthetic
source                  1..223
                        mol_type = protein
                        organism = synthetic construct
SEQUENCE: 120
SDNHGSSGTQ ILLTQSPVIL SVSPGERVSF SCRASQSIGT NIHWYQQRTN GSPRLLIKYA  60
SESISGIPSR FSGSGSGTDF TLSINSVESE DIADYYCQQN NNWPTTFGAG TKLELKRTVA  120
APSVFIFPPS DEQLKSGTAS VVCLLNNFYP REAKVQWKVD NALQSGNSQE SVTEQDSKDS  180
TYSLSSTLTL SKADYEKHKV YACEVTHQGL SSPVTKSFNR GEC                    223

SEQ ID NO: 121          moltype = DNA  length = 2244
FEATURE                 Location/Qualifiers
misc_feature            1..2244
                        note = synthetic
source                  1..2244
                        mol_type = other DNA
                        organism = synthetic construct
SEQUENCE: 121
caaggccagt ctggatccgg ttatctgtgg ggttgcgagt ggaattgcgg agggatcact  60
acaggctcga gcggtggcag cggtggctct ggtggtctga gcggccgttc cgataatcat  120
ggcggcggtt ctcaaactgt agtaactcaa gaaccaagct tctccgtctc ccctggggga  180
acagtcacac ttacctgccg aagtagtaca ggtgctgtta cgaccagtaa ctatgccaat  240
tgggtacaac aaacgcctgg tcaggctccg cgcggattga taggaggcac gaataaacgg  300
gcacccggtg tcccggacag attcagcgga agcatactcg gtaataaggc agctcttact  360
atcactgggg cccaagctga tgatgaaagt gattattatt gtgcgctctg gtacagcaac  420
ctctgggtgt ttgggggtgg cacgaaactt actgtcttgg gcggcggcgg atcaggggga  480
ggtggctctg gaggaggagg ctcagaagtc caactggtcg aatccggggg agggctcgta  540
cagccgggtg ggtccctcaa actctcttgt gcggcctcag ggtttacctt cagtacatac  600
gcgatgaatt gggtccggca ggccagtggg aaagggctcg aatgggtagg acgaatccga  660
tcaaaataca acaactacgc tacttattac gctgattccg tgaaggacag attcacaata  720
tcccgcgacg atagcaagaa tacggcatat cttcagatga attctcttaa aactgaggat  780
accgctgtgt attactgcac aagacatggt aattttggaa actcatatgt ctcttggttc  840
gcttattggg gacagggcac gttggttacc gtgtctagcg gaggtggtgg atcccaggtg  900
```

-continued

```
cagctgaaac agagcggccc gggcctggtg cagccgagcc agagcctgag cattacctgc  960
accgtgagcg gctttagcct gaccaactat ggcgtgcatt gggtgcgcca gagcccgggc  1020
aaaggcctgg aatggctggg cgtgatttgg agcggcggca acaccgatta taacaccccg  1080
tttaccagcc gcctgagcat taacaaagat aacagcaaaa gccaggtgtt ttttaaaatg  1140
aacagcctgc aaagccagga taccgcgatt tattattgcg cgcgcgcgct gacctattat  1200
gattatgaat ttgcgtattg gggccagggc accctggtga ccgtgagcgc ggctagcacc  1260
aagggcccat cggtcttccc cctggcaccc tcctccaaga gcacctctgg gggcacagcg  1320
gccctgggct gcctggtcaa ggactacttc cccgaaccgg tgacggtgtc gtggaactca  1380
ggcgccctga ccagcggcgt gcacaccttc ccggctgtcc tacagtcctc aggactctac  1440
tccctcagca gcgtggtgac cgtgccctcc agcagcttgg gcacccagac ctacatctgc  1500
aacgtgaatc acaagcccag caacaccaag gtggacaaga aagttgagcc caaatcttgt  1560
gacaaaactc acacatgccc accgtgccca gcacctgaat ttgaaggggg accgtcagtc  1620
ttcctcttcc ccccaaaacc caaggacacc ctcatgatct cccggacccc tgaggtcaca  1680
tgcgtggtgg tggacgtgag ccacgaagac cctgaggtca agttcaactg gtacgtggac  1740
ggcgtggagg tgcataatgc caagacaaag ccgcgggagg agcagtacaa tagcacgtac  1800
cgtgtggtca gcgtcctcac cgtcctgcac caggactggc tgaatggcaa ggagtacaag  1860
tgcaaggtct ccaacaaagc cctcccagcc tcaatcgaga aaaccatctc caaagccaaa  1920
gggcagcccc gagaaccaca ggtgtacacc ctgcccccat cccgggagga gatgaccaag  1980
aaccaggtca gcctgacctg cctggtcaaa ggcttctatc ccagcgacat cgccgtggag  2040
tgggagagca atgggcagcc ggagaacaac tacaagacca cgcctcccgt gctggactcc  2100
gacggctcct tcttcctcta cagcaagctc accgtggaca agagcaggtg gcagcagggg  2160
aacgtcttct catgctccgt gatgcatgag gctctgcaca accactacac gcagaagagc  2220
ctctccctgt ctccgggtaa atga                                        2244

SEQ ID NO: 122          moltype = AA  length = 747
FEATURE                 Location/Qualifiers
REGION                  1..747
                        note = synthetic
source                  1..747
                        mol_type = protein
                        organism = synthetic construct
SEQUENCE: 122
QGQSGSGYLW GCEWNCGGIT TGSSGGSGGS GGLSGRSDNH GGGSQTVVTQ EPSFSVSPGG  60
TVTLTCRSST GAVTTSNYAN WVQQTPGQAP RGLIGGTNKR APGVPDRFSG SILGNKAALT  120
ITGAQADDES DYYCALWYSN LWVFGGGTKL TVLGGGGSGG GGSGGGGSEV QLVESGGGLV  180
QPGGSLKLSC AASGFTFSTY AMNWVRQASG KGLEWVGRIR SKYNNYATYY ADSVKDRFTI  240
SRDDSKNTAY LQMNSLKTED TAVYYCTRHG NFGNSYVSWF AYWGQGTLVT VSSGGGGSQV  300
QLKQSGPGLV QPSQSLSITC TVSGFSLTNY GVHWVRQSPG KGLEWLGVIW SGGNTDYNTP  360
FTSRLSINKD NSKSQVFFKM NSLQSQDTAI YYCARALTYY DYEFAYWGQG TLVTVSAAST  420
KGPSVFPLAP SSKSTSGGTA ALGCLVKDYF PEPVTVSWNS GALTSGVHTF PAVLQSSGLY  480
SLSSVVTVPS SSLGTQTYIC NVNHKPSNTK VDKKVEPKSC DKTHTCPPCP APEFEGGPSV  540
FLFPPKPKDT LMISRTPEVT CVVVDVSHED PEVKFNWYVD GVEVHNAKTK PREEQYNSTY  600
RVVSVLTVLH QDWLNGKEYK CKVSNKALPA SIEKTISKAK GQPREPQVYT LPPSREEMTK  660
NQVSLTCLVK GFYPSDIAVE WESNGQPENN YKTTPPVLDS DGSFFLYSKL TVDKSRWQQG  720
NVFSCSVMHE ALHNHYTQKS LSLSPGK                                     747

SEQ ID NO: 123          moltype = DNA  length = 2244
FEATURE                 Location/Qualifiers
misc_feature            1..2244
                        note = synthetic
source                  1..2244
                        mol_type = other DNA
                        organism = synthetic construct
SEQUENCE: 123
caaggccagt ctggatccgg ttatctgtgg ggttgcgagt ggaattgcgg agggatcact  60
acaggctcga gcggtggcag cggtggctct ggtggtctga gcggccgttc cgataatcat  120
ggcggcggtt ctcaaactgt agtaactcaa gaaccaagct tctccgtctc ccctggggga  180
acagtcacac ttacctgccg aagtagtaca ggtgctgtta cgaccagtaa ctatgccaat  240
tgggtacaac aaacgcctgg tcaggctccg cgcggattga taggaggcac gaataaacgg  300
gcacccggtg tcccggacag attcagcgga agcatactcg gtaataaggc agctcttact  360
atcactgggg cccaagctga tgatgaaagt gattattatt gtgcgctctg gtacagcaac  420
ctctgggtgt ttgggggtgg cacgaaactt actgtcttgg gcggcggcgg atcaggggga  480
ggtggctctg gaggaggagg ctcagaagtc caactggtcg aatccggggg agggctcgta  540
cagccgggtg ggtccctcaa actctcttgt gcggcctcag ggtttacctt cagtacatac  600
gcgatgaatt gggtccggca ggccagtggg aaagggctcg aatgggtagg acgaatccga  660
tcaaaataca acaactacgc tacttattac gctgattccg tgaaggacag attcacaata  720
tcccgcgacg atagcaagaa tacggcatat cttcagatga attctcttaa aactgaggat  780
accgctgtgt attactgcac aagacatggt aattttggaa actcatatgt ctcttggttc  840
gcttattggg gacagggcac gttggttacc gtgtctagcg gaggtggtgg atcccaggtg  900
cagctgaaac agagcggccc gggcctggtg cagccgagcc agagcctgag cattacctgc  960
accgtgagcg gctttagcct gaccaactat ggcgtgcatt gggtgcgcca gagcccgggc  1020
aaaggcctgg aatggctggg cgtgatttgg agcggcggca acaccgatta taacaccccg  1080
tttaccagcc gcctgagcat taacaaagat aacagcaaaa gccaggtgtt ttttaaaatg  1140
aacagcctgc aaagccagga taccgcgatt tattattgcg cgcgcgcgct gacctattat  1200
gattatgaat ttgcgtattg gggccagggc accctggtga ccgtgagcgc ggctagcacc  1260
aagggcccat cggtcttccc cctggcaccc tcctccaaga gcacctctgg gggcacagcg  1320
gccctgggct gcctggtcaa ggactacttc cccgaaccgg tgacggtgtc gtggaactca  1380
ggcgccctga ccagcggcgt gcacaccttc ccggctgtcc tacagtcctc aggactctac  1440
tccctcagca gcgtggtgac cgtgccctcc agcagcttgg gcacccagac ctacatctgc  1500
```

-continued

```
aacgtgaatc acaagcccag caacaccaag gtggacaaga aagttgagcc caaatcttgt  1560
gacaaaactc acacatgccc accgtgccca gcacctgaat ttgaaggggg accgtcagtc  1620
ttcctcttcc ccccaaaacc caaggacacc ctcatgatct cccggacccc tgaggtcaca  1680
tgcgtggtgg tggacgtgag ccacgaagac cctgaggtca agttcaactg gtacgtggac  1740
ggcgtggagg tgcataatgc caagacaaag ccgcgggagg agcagtacca gagcacgtac  1800
cgtgtggtca gcgtcctcac cgtcctgcac caggactggc tgaatggcaa ggagtacaag  1860
tgcaaggtct ccaacaaagc cctcccagcc tcaatcgaga aaaccatctc caaagccaaa  1920
gggcagcccc gagaaccaca ggtgtacacc ctgcccccat cccgggagga gatgaccaag  1980
aaccaggtca gcctgacctg cctggtcaaa ggcttctatc ccagcgacat cgccgtggag  2040
tgggagagca atgggcagcc ggagaacaac tacaagacca cgcctcccgt gctggactcc  2100
gacggctcct tcttcctcta cagcaagctc accgtggaca agagcaggtg gcagcagggg  2160
aacgtcttct catgctccgt gatgcatgag gctctgcaca accactacac gcagaagagc  2220
ctctccctgt ctccgggtaa atga                                         2244

SEQ ID NO: 124          moltype = AA  length = 747
FEATURE                 Location/Qualifiers
REGION                  1..747
                        note = synthetic
source                  1..747
                        mol_type = protein
                        organism = synthetic construct
SEQUENCE: 124
QGQSGSGYLW GCEWNCGGIT TGSSGGSGGS GGLSGRSDNH GGGSQTVVTQ EPSFSVSPGG  60
TVTLTCRSST GAVTTSNYAN WVQQTPGQAP RGLIGGTNKR APGVPDRFSG SILGNKAALT  120
ITGAQADDES DYYCALWYSN LWVFGGGTKL TVLGGGGSGG GGSGGGGSEV QLVESGGGLV  180
QPGGSLKLSC AASGFTFSTY AMNWVRQASG KGLEWVGRIR SKYNNYATYY ADSVKDRFTI  240
SRDDSKNTAY LQMNSLKTED TAVYYCTRHG NFGNSYVSWF AYWGQGTLVT VSSGGGGSQV  300
QLKQSGPGLV QPSQSLSITC TVSGFSLTNY GVHWVRQSPG KGLEWLGVIW SGGNTDYNTP  360
FTSRLSINKD NSKSQVFFKM NSLQSQDTAI YYCARALTYY DYEFAYWGQG TLVTVSAAST  420
KGPSVFPLAP SSKSTSGGTA ALGCLVKDYF PEPVTVSWNS GALTSGVHTF PAVLQSSGLY  480
SLSSVVTVPS SSLGTQTYIC NVNHKPSNTK VDKKVEPKSC DKTHTCPPCP APEFEGGPSV  540
FLFPPKPKDT LMISRTPEVT CVVVDVSHED PEVKFNWYVD GVEVHNAKTK PREEQYQSTY  600
RVVSVLTVLH QDWLNGKEYK CKVSNKALPA SIEKTISKAK GQPREPQVYT LPPSREEMTK  660
NQVSLTCLVK GFYPSDIAVE WESNGQPENN YKTTPPVLDS DGSFFLYSKL TVDKSRWQQG  720
NVFSCSVMHE ALHNHYTQKS LSLSPGK                                      747

SEQ ID NO: 125          moltype = DNA  length = 2133
FEATURE                 Location/Qualifiers
misc_feature            1..2133
                        note = synthetic
source                  1..2133
                        mol_type = other DNA
                        organism = synthetic construct
SEQUENCE: 125
tccgatgatc atggcggcgg ttctcaaact gtagtaactc aagaaccaag cttctccgtc  60
tcccctgggg gaacagtcac acttacctgc cgaagtagta caggtgctgt tacgaccagt  120
aactatgcca attgggtaca acaaacgcct ggtcaggctc cgcgcggatt gataggaggc  180
acgaataaac gggcacccgg tgtcccggac agattcagcg gaagcatact cggtaataag  240
gcagctctta ctatcactgg ggcccaagct gatgatgaaa gtgattatta ttgtgcgctc  300
tggtacagca acctctgggt gtttgggggt ggcacgaaac ttactgtctt gggcggcggc  360
ggatcagggg gaggtggctc tggaggagga ggctcagaag tccaactggt cgaatccggg  420
ggagggctcg tacagccggg tggtccctc aaactctctt gtgcggcctc agggtttacc  480
ttcagtacat acgcgatgaa ttgggtccgg caggccagtg ggaaagggct cgaatgggta  540
ggacgaatcc gatcaaaata caacaactac gctacttatt acgctgattc cgtgaaggac  600
agattcacaa tatcccgcga cgatagcaag aatacggcat atcttcagat gaattctctt  660
aaaactgagg ataccgctgt gtattactgc acaagacatg gtaattttgg aaactcatat  720
gtctcttggt tcgcttattg gggacagggc acgttggtta ccgtgtctag cggaggtggt  780
ggatcccagg tgcagctgaa acagagcggc ccgggcctgg tgcagccgag ccagagcctg  840
agcattacct gcaccgtgag cggctttagc ctgaccaact atggcgtgca ttgggtgcgc  900
cagagcccgg gcaaaggcct ggaatggctg ggcgtgattt ggagcggcgg caacaccgat  960
tataacaccc cgtttaccag ccgcctgagc attaacaaag ataacagcaa aagccaggtg  1020
ttttttaaaa tgaacagcct gcaaagccag gataccgcga tttattattg cgcgcgcgcg  1080
ctgacctatt atgattatga atttgcgtat tggggccagg gcaccctggt gaccgtgagc  1140
gcggctagca ccaagggccc atcggtcttc cccctggcac cctcctccaa gagcacctct  1200
gggggcacag cggccctggg ctgcctggtc aaggactact tccccgaacc ggtgacggtg  1260
tcgtggaact caggcgccct gaccagcggc gtgcacacct tcccggctgt cctacagtcc  1320
tcaggactct actccctcag cagcgtggtg accgtgccct ccagcagctt gggcacccag  1380
acctacatct gcaacgtgaa tcacaagccc agcaacacca aggtggacaa gaaagttgag  1440
cccaaatctt gtgacaaaac tcacacatgc ccaccgtgcc cagcacctga atttgaaggg  1500
ggaccgtcag tcttcctctt ccccccaaaa cccaaggaca ccctcatgat ctcccggacc  1560
cctgaggtca catgcgtggt ggtggacgtg agccacgaag accctgaggt caagttcaac  1620
tggtacgtgg acggcgtgga ggtgcataat gccaagacaa agccgcggga ggagcagtac  1680
cagagcacgt accgtgtggt cagcgtcctc accgtcctgc accaggactg gctgaatggc  1740
aaggagtaca agtgcaaggt ctccaacaaa gccctcccag cctcaatcga gaaaaccatc  1800
tccaaagcca aagggcagcc ccgagaacca caggtgtaca ccctgccccc atcccgggag  1860
gagatgacca agaaccaggt cagcctgacc tgcctggtca aaggcttcta tcccagcgac  1920
atcgccgtgg agtgggagag caatgggcag ccggagaaca actacaagac cacgcctccc  1980
```

-continued

```
gtgctggact ccgacggctc cttcttcctc tacagcaagc tcaccgtgga caagagcagg  2040
tggcagcagg ggaacgtctt ctcatgctcc gtgatgcatg aggctctgca caaccactac  2100
acgcagaaga gcctctccct gtctccgggt aaa                               2133

SEQ ID NO: 126         moltype = AA  length = 711
FEATURE                Location/Qualifiers
REGION                 1..711
                       note = synthetic
source                 1..711
                       mol_type = protein
                       organism = synthetic construct
SEQUENCE: 126
SDDHGGGSQT VVTQEPSFSV SPGGTVTLTC RSSTGAVTTS NYANWVQQTP GQAPRGLIGG  60
TNKRAPGVPD RFSGSILGNK AALTITGAQA DDESDYYCAL WYSNLWVFGG GTKLTVLGGG  120
GSGGGGSGGG GSEVQLVESG GGLVQPGGSL KLSCAASGFT FSTYAMNWVR QASGKGLEWV  180
GRIRSKYNNY ATYYADSVKD RFTISRDDSK NTAYLQMNSL KTEDTAVYYC TRHGNFGNSY  240
VSWFAYWGQG TLVTVSSGGG GSQVQLKQSG PGLVQPSQSL SITCTVSGFS LTNYGVHWVR  300
QSPGKGLEWL GVIWSGGNTD YNTPFTSRLS INKDNSKSQV FFKMNSLQSQ DTAIYYCARA  360
LTYYDYEFAY WGQGTLVTVS AASTKGPSVF PLAPSSKSTS GGTAALGCLV KDYFPEPVTV  420
SWNSGALTSG VHTFPAVLQS SGLYSLSSVV TVPSSSLGTQ TYICNVNHKP SNTKVDKKVE  480
PKSCDKTHTC PPCPAPEFEG GPSVFLFPPK PKDTLMISRT PEVTCVVVDV SHEDPEVKFN  540
WYVDGVEVHN AKTKPREEQY QSTYRVVSVL TVLHQDWLNG KEYKCKVSNK ALPASIEKTI  600
SKAKGQPREP QVYTLPPSRE EMTKNQVSLT CLVKGFYPSD IAVEWESNGQ PENNYKTTPP  660
VLDSDGSFFL YSKLTVDKSR WQQGNVFSCS VMHEALHNHY TQKSLSLSPG K            711

SEQ ID NO: 127         moltype = DNA  length = 669
FEATURE                Location/Qualifiers
misc_feature           1..669
                       note = synthetic
source                 1..669
                       mol_type = other DNA
                       organism = synthetic construct
SEQUENCE: 127
tccgatgatc atggcagtag cggtacccag atcttgctga cccagagccc ggtgattctg  60
agcgtgagcc cgggcgaacg tgtgagcttt agctgccgcg cgagccagag cattggcacc  120
aacattcatt ggtatcagca gcgcaccaac ggcagcccgc gcctgctgat taaatatgcg  180
agcgaaagca ttagcggcat tccgagccgc tttagcggca gcggcagcgg caccgatttt  240
accctgagca ttaacagcgt ggaaagcgaa gatattgcgg attattattg ccagcagaac  300
aacaactggc cgaccacctt tggcgcgggc accaaactgg aactgaaacg tacggtggct  360
gcaccatctg tcttcatctt cccgccatct gatgagcagt tgaaatctgg aactgcctct  420
gttgtgtgcc tgctgaataa cttctatccc agagaggcca aagtacagtg gaaggtggat  480
aacgccctcc aatcgggtaa ctcccaggag agtgtcacag agcaggacag caaggacagc  540
acctacagcc tcagcagcac cctgacgctg agcaaagcag actacgagaa acacaaagtc  600
tacgcctgcg aagtcaccca tcagggcctg agctcgcccg tcacaaagag cttcaacagg  660
ggagagtgt                                                          669

SEQ ID NO: 128         moltype = AA  length = 223
FEATURE                Location/Qualifiers
REGION                 1..223
                       note = synthetic
source                 1..223
                       mol_type = protein
                       organism = synthetic construct
SEQUENCE: 128
SDDHGSSGTQ ILLTQSPVIL SVSPGERVSF SCRASQSIGT NIHWYQQRTN GSPRLLIKYA  60
SESISGIPSR FSGSGSGTDF TLSINSVESE DIADYYCQQN NNWPTTFGAG TKLELKRTVA  120
APSVFIFPPS DEQLKSGTAS VVCLLNNFYP REAKVQWKVD NALQSGNSQE SVTEQDSKDS  180
TYSLSSTLTL SKADYEKHKV YACEVTHQGL SSPVTKSFNR GEC                    223

SEQ ID NO: 129         moltype = DNA  length = 2241
FEATURE                Location/Qualifiers
misc_feature           1..2241
                       note = synthetic
source                 1..2241
                       mol_type = other DNA
                       organism = synthetic construct
SEQUENCE: 129
caaggccagt ctggatccgg ttatctgtgg ggttgcgagt ggaattgcgg agggatcact  60
acaggctcga gcggtggcag cggtggctct ggtggtctga gcggccgttc cgatgatcat  120
ggcggcggtt ctcaaactgt agtaactcaa gaaccaagct tctccgtctc ccctggggga  180
acagtcacac ttacctgccg aagtagtaca ggtgctgtta cgaccagtaa ctatgccaat  240
tgggtacaac aaacgcctgg tcaggctccg cgcggattga taggaggcac gaataaacgg  300
gcacccggtg tcccggacag attcagcgga agcatactcg gtaataaggc agctcttact  360
atcactgggg cccaagctga tgatgaaagt gattattatt gtgcgctctg gtacagcaac  420
ctctgggtgt ttgggggtgg cacgaaactt actgtcttgg gcggcggcgg atcaggggga  480
ggtggctctg gaggaggagg ctcagaagtc caactggtcg aatccggggg agggctcgta  540
cagccgggtg ggtccctcaa actctcttgt gcggcctcag ggtttacctt cagtacatac  600
gcgatgaatt gggtccggca ggccagtggg aaagggctcg aatgggtagg acgaatccga  660
tcaaaataca acaactacgc tacttattac gctgattccg tgaaggacag attcacaata  720
```

-continued

```
tcccgcgacg atagcaagaa tacggcatat cttcagatga attctcttaa aactgaggat  780
accgctgtgt attactgcac aagacatggt aattttggaa actcatatgt ctcttggttc  840
gcttattggg gacagggcac gttggttacc gtgtctagcg gaggtggtgg atcccaggtg  900
cagctgaaac agagcggccc gggcctggtg cagccgagcc agagcctgag cattacctgc  960
accgtgagcg gctttagcct gaccaactat ggcgtgcatt gggtgcgcca gagcccgggc  1020
aaaggcctgg aatggctggg cgtgatttgg agcggcggca acaccgatta taacaccccg  1080
tttaccagcc gcctgagcat taacaaagat aacagcaaaa gccaggtgtt ttttaaaatg  1140
aacagcctgc aaagccagga taccgcgatt tattattgcg cgcgcgcgct gacctattat  1200
gattatgaat ttgcgtattg gggccagggc accctggtga ccgtgagcgc ggctagcacc  1260
aagggcccat cggtcttccc cctggcaccc tcctccaaga gcacctctgg gggcacagcg  1320
gccctgggct gcctggtcaa ggactacttc cccgaaccgg tgacggtgtc gtggaactca  1380
ggcgccctga ccagcggcgt gcacaccttc ccggctgtcc tacagtcctc aggactctac  1440
tccctcagca gcgtggtgac cgtgccctcc agcagcttgg gcacccagac ctacatctgc  1500
aacgtgaatc acaagcccag caacaccaag gtggacaaga aagttgagcc caaatcttgt  1560
gacaaaactc acacatgccc accgtgccca gcacctgaat ttgaaggggg accgtcagtc  1620
ttcctcttcc ccccaaaacc caaggacacc ctcatgatct cccggacccc tgaggtcaca  1680
tgcgtggtgg tggacgtgag ccacgaagac cctgaggtca agttcaactg gtacgtggac  1740
ggcgtggagg tgcataatgc caagacaaag ccgcgggagg agcagtacca gagcacgtac  1800
cgtgtggtca gcgtcctcac cgtcctgcac caggactggc tgaatggcaa ggagtacaag  1860
tgcaaggtct ccaacaaagc cctcccagcc tcaatcgaga aaaccatctc caaagccaaa  1920
gggcagcccc gagaaccaca ggtgtacacc ctgcccccat cccgggagga gatgaccaag  1980
aaccaggtca gcctgacctg cctggtcaaa ggcttctatc ccagcgacat cgccgtggag  2040
tgggagagca atgggcagcc ggagaacaac tacaagacca cgcctcccgt gctggactcc  2100
gacggctcct tcttcctcta cagcaagctc accgtggaca agagcaggtg gcagcagggg  2160
aacgtcttct catgctccgt gatgcatgag gctctgcaca accactacac gcagaagagc  2220
ctctccctgt ctccgggtaa a                                          2241

SEQ ID NO: 130          moltype = AA  length = 747
FEATURE                 Location/Qualifiers
REGION                  1..747
                        note = synthetic
source                  1..747
                        mol_type = protein
                        organism = synthetic construct
SEQUENCE: 130
QGQSGSGYLW GCEWNCGGIT TGSSGGSGGS GGLSGRSDDH GGGSQTVVTQ EPSFSVSPGG  60
TVTLTCRSST GAVTTSNYAN WVQQTPGQAP RGLIGGTNKR APGVPDRFSG SILGNKAALT  120
ITGAQADDES DYYCALWYSN LWVFGGGTKL TVLGGGGSGG GGSGGGGSEV QLVESGGGLV  180
QPGGSLKLSC AASGFTFSTY AMNWVRQASG KGLEWVGRIR SKYNNYATYY ADSVKDRFTI  240
SRDDSKNTAY LQMNSLKTED TAVYYCTRHG NFGNSYVSWF AYWGQGTLVT VSSGGGGSQV  300
QLKQSGPGLV QPSQSLSITC TVSGFSLTNY GVHWVRQSPG KGLEWLGVIW SGGNTDYNTP  360
FTSRLSINKD NSKSQVFFKM NSLQSQDTAI YYCARALTYY DYEFAYWGQG TLVTVSAAST  420
KGPSVFPLAP SSKSTSGGTA ALGCLVKDYF PEPVTVSWNS GALTSGVHTF PAVLQSSGLY  480
SLSSVVTVPS SSLGTQTYIC NVNHKPSNTK VDKKVEPKSC DKTHTCPPCP APEFEGGPSV  540
FLFPPKPKDT LMISRTPEVT CVVVDVSHED PEVKFNWYVD GVEVHNAKTK PREEQYQSTY  600
RVVSVLTVLH QDWLNGKEYK CKVSNKALPA SIEKTISKAK GQPREPQVYT LPPSREEMTK  660
NQVSLTCLVK GFYPSDIAVE WESNGQPENN YKTTPPVLDS DGSFFLYSKL TVDKSRWQQG  720
NVFSCSVMHE ALHNHYTQKS LSLSPGK                                    747

SEQ ID NO: 131          moltype = DNA  length = 783
FEATURE                 Location/Qualifiers
misc_feature            1..783
                        note = synthetic
source                  1..783
                        mol_type = other DNA
                        organism = synthetic construct
SEQUENCE: 131
caaggccagt ctggccaagg tcttagttgt gaaggttggg cgatgaatag agaacaatgt  60
cgagccggag gtggctcgag cggcggctct atctcttccg gactgctgtc cggcagatcc  120
gaccagcacg gcggaggatc ccaaatcctg ctgacacagt ctcctgtcat actgagtgtc  180
tcccccggcg agagagtctc tttctcatgt cgggccagtc agtctattgg gactaacata  240
cactggtacc agcaacgcac caacggaagc ccgcgcctgc tgattaaata tgcgagcgaa  300
agcattagcg gcattccgag ccgctttagc ggcagcggca gcggcaccga ttttaccctg  360
agcattaaca gcgtggaaag cgaagatatt gcggattatt attgccagca gaacaacaac  420
tggccgacca cctttggcgc gggcaccaaa ctggaactga aacgtacggt ggctgcacca  480
tctgtcttca tcttcccgcc atctgatgag cagttgaaat ctggaactgc ctctgttgtg  540
tgcctgctga ataacttcta tcccagagag gccaaagtac agtggaaggt ggataacgcc  600
ctccaatcgg gtaactccca ggagagtgtc acagagcagg acagcaagga cagcacctac  660
agcctcagca gcaccctgac gctgagcaaa gcagactacg agaaacacaa agtctacgcc  720
tgcgaagtca cccatcaggg cctgagctcg cccgtcacaa agagcttcaa caggggagag  780
tgt                                                              783

SEQ ID NO: 132          moltype = AA  length = 261
FEATURE                 Location/Qualifiers
REGION                  1..261
                        note = synthetic
```

-continued

```
source                  1..261
                        mol_type = protein
                        organism = synthetic construct
SEQUENCE: 132
QGQSGQGLSC EGWAMNREQC RAGGGSSGGS ISSGLLSGRS DQHGGGSQIL LTQSPVILSV  60
SPGERVSFSC RASQSIGTNI HWYQQRTNGS PRLLIKYASE SISGIPSRFS GSGSGTDFTL  120
SINSVESEDI ADYYCQQNNN WPTTFGAGTK LELKRTVAAP SVFIFPPSDE QLKSGTASVV  180
CLLNNFYPRE AKVQWKVDNA LQSGNSQESV TEQDSKDSTY SLSSTLTLSK ADYEKHKVYA  240
CEVTHQGLSS PVTKSFNRGE C                                           261

SEQ ID NO: 133          moltype = DNA  length = 2256
FEATURE                 Location/Qualifiers
misc_feature            1..2256
                        note = synthetic
source                  1..2256
                        mol_type = other DNA
                        organism = synthetic construct
SEQUENCE: 133
caaggccagt ctggatccgg ttatctgtgg ggttgcgagt ggaattgcgg agggatcact  60
acaggctcga gcggtggcag cggtggctct ggtggtatat cgagtggatt gctgtctggc  120
agatctgacg atcacggcgg cggttctcaa actgtagtaa ctcaagaacc aagcttctcc  180
gtctcccctg ggggaacagt cacacttacc tgccgaagta gtacaggtgc tgttacgacc  240
agtaactatg ccaattgggt acaacaaacg cctggtcagg ctccgcgcgg attgatagga  300
ggcacgaata aacgggcacc cggtgtcccg gacagattca gcggaagcat actcggtaat  360
aaggcagctc ttactatcac tggggcccaa gctgatgatg aaagtgatta ttattgtgcg  420
ctctggtaca gcaacctctg ggtgtttggg ggtggcacga aacttactgt cttgggcggc  480
ggcggatcag gggaggtgg ctctggagga ggaggctcag aagtccaact ggtcgaatcc  540
gggggagggc tcgtacagcc gggtgggtcc ctcaaactct cttgtgcggc ctcagggttt  600
accttcagta catacgcgat gaattgggtc cggcaggcca gtgggaaagg gctcgaatgg  660
gtaggacgaa tccgatcaaa atacaacaac tacgctactt attacgctga ttccgtgaag  720
gacagattca caatatcccg cgacgatagc aagaatacgg catatcttca gatgaattct  780
cttaaaactg aggataccgc tgtgtattac tgcacaagac atggtaattt tggaaactca  840
tatgtctctt ggttcgctta ttggggacag ggcacgttgg ttaccgtgtc tagcggaggt  900
ggtggatccc aggtgcagct gaaacagagc ggcccgggcc tggtgcagcc gagccagagc  960
ctgagcatta cctgcaccgt gagcggcttt agcctgacca actatggcgt gcattgggtg  1020
cgccagagcc cgggcaaagg cctggaatgg ctgggcgtga tttggagcgg cggcaacacc  1080
gattataaca ccccgtttac cagccgcctg agcattaaca aagataacag caaaagccag  1140
gtgtttttta aaatgaacag cctgcaaagc caggataccg cgatttatta ttgcgcgcgc  1200
gcgctgacct attatgatta tgaatttgcg tattggggcc agggcaccct ggtgaccgtg  1260
agcgcggcta gcaccaaggg cccatcggtc ttccccctgg caccctcctc caagagcacc  1320
tctgggggca cagcggccct gggctgcctg gtcaaggact acttccccga accggtgacg  1380
gtgtcgtgga actcaggcgc cctgaccagc ggcgtgcaca ccttcccggc tgtcctacag  1440
tcctcaggac tctactccct cagcagcgtg gtgaccgtgc cctccagcag cttgggcacc  1500
cagacctaca tctgcaacgt gaatcacaag cccagcaaca ccaaggtgga caagaaagtt  1560
gagcccaaat cttgtgacaa aactcacaca tgcccaccgt gcccagcacc tgaatttgaa  1620
gggggaccgt cagtcttcct cttcccccca aaacccaagg acaccctcat gatctcccgg  1680
acccctgagg tcacatgcgt ggtggtggac gtgagccacg aagaccctga ggtcaagttc  1740
aactggtacg tggacggcgt ggaggtgcat aatgccaaga caaagccgcg ggaggagcag  1800
taccagagca cgtaccgtgt ggtcagcgtc ctcaccgtcc tgcaccagga ctggctgaat  1860
ggcaaggagt acaagtgcaa ggtctccaac aaagccctcc cagcctcaat cgagaaaacc  1920
atctccaaag ccaaagggca gccccgagaa ccacaggtgt acaccctgcc cccatcccgg  1980
gaggagatga ccaagaacca ggtcagcctg acctgcctgg tcaaaggctt ctatcccagc  2040
gacatcgccg tggagtggga gagcaatggg cagccggaga acaactacaa gaccacgcct  2100
cccgtgctgg actccgacgg ctccttcttc ctctacagca agctcaccgt ggacaagagc  2160
aggtggcagc aggggaacgt cttctcatgc tccgtgatgc atgaggctct gcacaaccac  2220
tacacgcaga agagcctctc cctgtctccg ggtaaa                          2256

SEQ ID NO: 134          moltype = AA  length = 752
FEATURE                 Location/Qualifiers
REGION                  1..752
                        note = synthetic
source                  1..752
                        mol_type = protein
                        organism = synthetic construct
SEQUENCE: 134
QGQSGSGYLW GCEWNCGGIT TGSSGGSGGS GGISSGLLSG RSDDHGGGSQ TVVTQEPSFS  60
VSPGGTVTLT CRSSTGAVTT SNYANWVQQT PGQAPRGLIG GTNKRAPGVP DRFSGSILGN  120
KAALTITGAQ ADDESDYYCA LWYSNLWVFG GGTKLTVLGG GGSGGGGSGG GGSEVQLVES  180
GGGLVQPGGS LKLSCAASGF TFSTYAMNWV RQASGKGLEW VGRIRSKYNN YATYYADSVK  240
DRFTISRDDS KNTAYLQMNS LKTEDTAVYY CTRHGNFGNS YVSWFAYWGQ GTLVTVSSGG  300
GGSQVQLKQS GPGLVQPSQS LSITCTVSGF SLTNYGVHWV RQSPGKGLEW LGVIWSGGNT  360
DYNTPFTSRL SINKDNSKSQ VFFKMNSLQS QDTAIYYCAR ALTYYDYEFA YWGQGTLVTV  420
SAASTKGPSV FPLAPSSKST SGGTAALGCL VKDYFPEPVT VSWNSGALTS GVHTFPAVLQ  480
SSGLYSLSSV VTVPSSSLGT QTYICNVNHK PSNTKVDKKV EPKSCDKTHT CPPCPAPEFE  540
GGPSVFLFPP KPKDTLMISR TPEVTCVVVD VSHEDPEVKF NWYVDGVEVH NAKTKPREEQ  600
YQSTYRVVSV LTVLHQDWLN GKEYKCKVSN KALPASIEKT ISKAKGQPRE PQVYTLPPSR  660
EEMTKNQVSL TCLVKGFYPS DIAVEWESNG QPENNYKTTP PVLDSDGSFF LYSKLTVDKS  720
RWQQGNVFSC SVMHEALHNH YTQKSLSLSP GK                               752
```

```
SEQ ID NO: 135         moltype = DNA  length = 783
FEATURE                Location/Qualifiers
misc_feature           1..783
                       note = synthetic
source                 1..783
                       mol_type = other DNA
                       organism = synthetic construct
SEQUENCE: 135
caaggccagt ctggccagtg catctcacct cgtggttgtc cggacggccc atacgtcatg  60
tacggctcga gcggtggcag cggtggctct ggtggatccg gtctgagcgg ccgttccgat  120
gatcatggca gtagcggtac ccagatcttg ctgacccaga gcccggtgat tctgagcgtg  180
agcccgggcg aacgtgtgag ctttagctgc cgcgcgagcc agagcattgg caccaacatt  240
cattggtatc agcagcgcac caacggcagc ccgcgcctgc tgattaaata tgcgagcgaa  300
agcattagcg gcattccgag ccgctttagc ggcagcggca gcggcaccga ttttaccctg  360
agcattaaca gcgtggaaag cgaagatatt gcggattatt attgccagca gaacaacaac  420
tggccgacca cctttggcgc gggcaccaaa ctggaactga aacgtacggt ggctgcacca  480
tctgtcttca tcttcccgcc atctgatgag cagttgaaat ctggaactgc ctctgttgtg  540
tgcctgctga ataacttcta tcccagagag gccaaagtac agtggaaggt ggataacgcc  600
ctccaatcgg gtaactccca ggagagtgtc acagagcagg acagcaagga cagcacctac  660
agcctcagca gcaccctgac gctgagcaaa gcagactacg agaaacacaa agtctacgcc  720
tgcgaagtca cccatcaggg cctgagctcg cccgtcacaa agagcttcaa caggggagag  780
tgt                                                                783

SEQ ID NO: 136         moltype = AA  length = 261
FEATURE                Location/Qualifiers
REGION                 1..261
                       note = synthetic
source                 1..261
                       mol_type = protein
                       organism = synthetic construct
SEQUENCE: 136
QGQSGQCISP RGCPDGPYVM YGSSGGSGGS GGSGLSGRSD DHGSSGTQIL LTQSPVILSV  60
SPGERVSFSC RASQSIGTNI HWYQQRTNGS PRLLIKYASE SISGIPSRFS GSGSGTDFTL  120
SINSVESEDI ADYYCQQNNN WPTTFGAGTK LELKRTVAAP SVFIFPPSDE QLKSGTASVV  180
CLLNNFYPRE AKVQWKVDNA LQSGNSQESV TEQDSKDSTY SLSSTLTLSK ADYEKHKVYA  240
CEVTHQGLSS PVTKSFNRGE C                                            261

SEQ ID NO: 137         moltype = DNA  length = 2244
FEATURE                Location/Qualifiers
misc_feature           1..2244
                       note = synthetic
source                 1..2244
                       mol_type = other DNA
                       organism = synthetic construct
SEQUENCE: 137
caaggccagt ctggatccgg ttatctgtgg ggttgcgagt ggaattgcgg agggatcact  60
acaggctcga gcggtggcag cggtggctct ggtggtctga gcggccgttc cgatgatcat  120
ggcggcggtt ctcaaactgt agtaactcaa gaaccaagct tctccgtctc ccctggggga  180
acagtcacac ttacctgccg aagtagtaca ggtgctgtta cgaccagtaa ctatgccaat  240
tgggtacaac aaacgcctgg tcaggctccg cgcggattga taggaggcac gaataaacgg  300
gcacccggtg tcccggacag attcagcgga agcatactcg gtaataaggc agctcttact  360
atcactgggg cccaagctga tgatgaaagt gattattatt gtgcgctctg gtacagcaac  420
ctctgggtgt ttgggggtgg cacgaaactt actgtcttgg gcggcggcgg atcaggggga  480
ggtggctctg gaggaggagg ctcagaagtc caactggtcg aatccggggg agggctcgta  540
cagccgggtg ggtccctcaa actctcttgt gcggcctcag ggtttacctt cagtacatac  600
gcgatgaatt gggtccggca ggccagtggg aaagggctcg aatgggtagg acgaatccga  660
tcaaaataca acaactacgc tacttattac gctgattccg tgaaggacag attcacaata  720
tcccgcgacg atagcaagaa tacggcatat cttcagatga attctcttaa aactgaggat  780
accgctgtgt attactgcac aagacatggt aattttggaa actcatatgt ctcttggttc  840
gcttattggg gacagggcac gttggttacc gtgtctagcg gaggtggtgg atcccaagtg  900
accctgagag agtctggccc tgccctcgtg aagcctaccc agaccctgac actgacctgc  960
accttcagcg gcttcagcct gagcaccagc ggcatgtctg tgggctggat cagacagcct  1020
cctggcaagg ccctggaatg gctggccgac atttggtggg acgacaagaa ggactacaac  1080
cccagcctga agtcccggct gaccatcagc aaggacacca gcaagaacca ggtggtgctg  1140
aaagtgacca acatggaccc cgccgacacc gccacctact actgcgccag atccatgatc  1200
accaactggt acttcgacgt gtggggagcc ggcaccaccg tgacagtgtc atctgctagc  1260
accaagggcc catcggtctt ccccctggca ccctcctcca agagcacctc tgggggcaca  1320
gcggccctgg gctgcctggt caaggactac ttccccgaac cggtgacggt gtcgtggaac  1380
tcaggcgccc tgaccagcgg cgtgcacacc ttcccggctg tcctacagtc ctcaggactc  1440
tactccctca gcagcgtggt gaccgtgccc tccagcagct tgggcaccca gacctacatc  1500
tgcaacgtga atcacaagcc cagcaacacc aaggtggaca agaaagttga gcccaaatct  1560
tgtgacaaaa ctcacacatg cccaccgtgc ccagcacctg aatttgaagg gggaccgtca  1620
gtcttcctct tccccccaaa acccaaggac accctcatga tctcccggac ccctgaggtc  1680
acatgcgtgg tggtggacgt gagccacgaa gaccctgagg tcaagttcaa ctggtacgtg  1740
gacggcgtgg aggtgcataa tgccaagaca aagccgcggg aggagcagta ccagagcacg  1800
taccgtgtgg tcagcgtcct caccgtcctg caccaggact ggctgaatgg caaggagtac  1860
aagtgcaagg tctccaacaa agccctccca gcctcaatcg agaaaaccat ctccaaagcc  1920
aaagggcagc cccgagaacc acaggtgtac accctgcccc catcccggga ggagatgacc  1980
aagaaccagg tcagcctgac ctgcctggtc aaaggcttct atcccagcga catcgccgtg  2040
```

-continued

```
gagtgggaga gcaatgggca gccggagaac aactacaaga ccacgcctcc cgtgctggac  2100
tccgacggct ccttcttcct ctacagcaag ctcaccgtgg acaagagcag gtggcagcag  2160
gggaacgtct tctcatgctc cgtgatgcat gaggctctgc acaaccacta cacgcagaag  2220
agcctctccc tgtctccggg taaa                                         2244

SEQ ID NO: 138          moltype = AA  length = 748
FEATURE                 Location/Qualifiers
REGION                  1..748
                        note = synthetic
source                  1..748
                        mol_type = protein
                        organism = synthetic construct
SEQUENCE: 138
QGQSGSGYLW GCEWNCGGIT TGSSGGSGGS GGLSGRSDDH GGGSQTVVTQ EPSFSVSPGG  60
TVTLTCRSST GAVTTSNYAN WVQQTPGQAP RGLIGGTNKR APGVPDRFSG SILGNKAALT  120
ITGAQADDES DYYCALWYSN LWVFGGGTKL TVLGGGGSGG GGSGGGGSEV QLVESGGGLV  180
QPGGSLKLSC AASGFTFSTY AMNWVRQASG KGLEWVGRIR SKYNNYATYY ADSVKDRFTI  240
SRDDSKNTAY LQMNSLKTED TAVYYCTRHG NFGNSYVSWF AYWGQGTLVT VSSGGGGSQV  300
TLRESGPALV KPTQTLTLTC TFSGFSLSTS GMSVGWIRQP PGKALEWLAD IWWDDKKDYN  360
PSLKSRLTIS KDTSKNQVVL KVTNMDPADT ATYYCARSMI TNWYFDVWGA GTTVTVSSAS  420
TKGPSVFPLA PSSKSTSGGT AALGCLVKDY FPEPVTVSWN SGALTSGVHT FPAVLQSSGL  480
YSLSSVVTVP SSSLGTQTYI CNVNHKPSNT KVDKKVEPKS CDKTHTCPPC PAPEFEGGPS  540
VFLFPPKPKD TLMISRTPEV TCVVVDVSHE DPEVKFNWYV DGVEVHNAKT KPREEQYQST  600
YRVVSVLTVL HQDWLNGKEY KCKVSNKALP ASIEKTISKA KGQPREPQVY TLPPSREEMT  660
KNQVSLTCLV KGFYPSDIAV EWESNGQPEN NYKTTPPVLD SDGSFFLYSK LTVDKSRWQQ  720
GNVFSCSVMH EALHNHYTQK SLSLSPGK                                     748

SEQ ID NO: 139          moltype = DNA  length = 639
FEATURE                 Location/Qualifiers
misc_feature            1..639
                        note = synthetic
source                  1..639
                        mol_type = other DNA
                        organism = synthetic construct
SEQUENCE: 139
gacatccaga tgacccagag ccccagcaca ctgagcgcca gcgtgggcga cagagtgacc  60
atcacatgca agtgccagct gagcgtgggc tacatgcact ggtatcagca gaagcccggc  120
aaggccccca agctgctgat ctacgacacc agcaagctgg cctccggcgt gcccagcaga  180
ttttctggca gcggctccgg caccgagttc accctgacaa tcagcagcct gcagcccgac  240
gacttcgcca cctactactg ttttcaaggc tccggctacc ccttcacctt cggcggaggc  300
accaagctgg aaatcaagcg gacggtggct gcaccatctg tcttcatctt cccgccatct  360
gatgagcagt tgaaatctgg aactgcctct gttgtgtgcc tgctgaataa cttctatccc  420
agagaggcca aagtacagtg gaaggtggat aacgccctcc aatcgggtaa ctcccaggag  480
agtgtcacag agcaggacag caaggacagc acctacagcc tcagcagcac cctgacgctg  540
agcaaagcag actacgagaa acacaaagtc tacgcctgcg aagtcaccca tcagggcctg  600
agctcgcccg tcacaaagag cttcaacagg ggagagtgt                         639

SEQ ID NO: 140          moltype = AA  length = 213
FEATURE                 Location/Qualifiers
REGION                  1..213
                        note = synthetic
source                  1..213
                        mol_type = protein
                        organism = synthetic construct
SEQUENCE: 140
DIQMTQSPST LSASVGDRVT ITCKCQLSVG YMHWYQQKPG KAPKLLIYDT SKLASGVPSR  60
FSGSGSGTEF TLTISSLQPD DFATYYCFQG SGYPFTFGGG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 141          moltype = DNA  length = 2259
FEATURE                 Location/Qualifiers
misc_feature            1..2259
                        note = synthetic
source                  1..2259
                        mol_type = other DNA
                        organism = synthetic construct
SEQUENCE: 141
caaggccagt ctggatccgg ttatctgtgg ggttgcgagt ggaattgcgg agggatcact  60
acaggctcga gcggtggcag cggtggctct ggtggtatat cgagtggatt gctgtctggc  120
agatctgacg atcacggcgg cggttctcaa actgtagtaa ctcaagaacc aagcttctcc  180
gtctcccctg gggggaacagt cacacttacc tgccgaagta gtacaggtgc tgttacgacc  240
agtaactatg ccaattgggt acaacaaacg cctggtcagg ctccgcgcgg attgatagga  300
ggcacgaata aacgggcacc cggtgtcccg gacagattca gcggaagcat actcggtaat  360
aaggcagctc ttactatcac tggggcccaa gctgatgatg aaagtgatta ttattgtgcg  420
ctctggtaca gcaacctctg ggtgtttggg ggtggcacga aacttactgt cttgggcggc  480
ggcggatcag ggggaggtgg ctctggagga ggaggctcag aagtccaact ggtcgaatcc  540
gggggagggc tcgtacagcc gggtgggtcc ctcaaactct cttgtgcggc ctcagggttt  600
accttcagta catacgcgat gaattgggtc cggcaggcca gtgggaaagg gctcgaatgg  660
```

-continued

```
gtaggacgaa tccgatcaaa atacaacaac tacgctactt attacgctga ttccgtgaag  720
gacagattca caatatcccg cgacgatagc aagaatacgg catatcttca gatgaattct  780
cttaaaactg aggataccgc tgtgtattac tgcacaagac atggtaattt tggaaactca  840
tatgtctctt ggttcgctta ttggggacag ggcacgttgg ttaccgtgtc tagcggaggt  900
ggtggatccc aagtgaccct gagagagtct ggccctgccc tcgtgaagcc tacccagacc  960
ctgacactga cctgcacctt cagcggcttc agcctgagca ccagcggcat gtctgtgggc  1020
tggatcagac agcctcctgg caaggccctg gaatggctgg ccgacatttg gtgggacgac  1080
aagaaggact acaaccccag cctgaagtcc cggctgacca tcagcaagga caccagcaag  1140
aaccaggtgg tgctgaaagt gaccaacatg gaccccgccg acaccgccac ctactactgc  1200
gccagatcca tgatcaccaa ctggtacttc gacgtgtggg gagccggcac caccgtgaca  1260
gtgtcatctg ctagcaccaa gggcccatcg gtcttccccc tggcaccctc ctccaagagc  1320
acctctgggg gcacagcggc cctgggctgc ctggtcaagg actacttccc cgaaccggtg  1380
acggtgtcgt ggaactcagg cgccctgacc agcggcgtgc acaccttccc ggctgtccta  1440
cagtcctcag gactctactc cctcagcagc gtggtgaccg tgccctccag cagcttgggc  1500
acccagacct acatctgcaa cgtgaatcac aagcccagca acaccaaggt ggacaagaaa  1560
gttgagccca aatcttgtga caaaactcac acatgcccac cgtgcccagc acctgaattt  1620
gaagggggac cgtcagtctt cctcttcccc ccaaaaccca aggacaccct catgatctcc  1680
cggacccctg aggtcacatg cgtggtggtg gacgtgagcc acgaagaccc tgaggtcaag  1740
ttcaactggt acgtggacgg cgtggaggtg cataatgcca agacaaagcc gcgggaggag  1800
cagtaccaga gcacgtaccg tgtggtcagc gtcctcaccg tcctgcacca ggactggctg  1860
aatggcaagg agtacaagtg caaggtctcc aacaaagccc tcccagcctc aatcgagaaa  1920
accatctcca aagccaaagg gcagccccga gaaccacagg tgtacaccct gcccccatcc  1980
cgggaggaga tgaccaagaa ccaggtcagc ctgacctgcc tggtcaaagg cttctatccc  2040
agcgacatcg ccgtggagtg ggagagcaat gggcagccgg agaacaacta caagaccacg  2100
cctcccgtgc tggactccga cggctccttc ttcctctaca gcaagctcac cgtggacaag  2160
agcaggtggc agcaggggaa cgtcttctca tgctccgtga tgcatgaggc tctgcacaac  2220
cactacacgc agaagagcct ctccctgtct ccgggtaaa                        2259
```

```
SEQ ID NO: 142          moltype = AA  length = 753
FEATURE                 Location/Qualifiers
REGION                  1..753
                        note = synthetic
source                  1..753
                        mol_type = protein
                        organism = synthetic construct
SEQUENCE: 142
QGQSGSGYLW GCEWNCGGIT TGSSGGSGGS GGISSGLLSG RSDDHGGGSQ TVVTQEPSFS  60
VSPGGTVTLT CRSSTGAVTT SNYANWVQQT PGQAPRGLIG GTNKRAPGVP DRFSGSILGN  120
KAALTITGAQ ADDESDYYCA LWYSNLWVFG GGTKLTVLGG GGSGGGGSGG GGSEVQLVES  180
GGGLVQPGGS LKLSCAASGF TFSTYAMNWV RQASGKGLEW VGRIRSKYNN YATYYADSVK  240
DRFTISRDDS KNTAYLQMNS LKTEDTAVYY CTRHGNFGNS YVSWFAYWGQ GTLVTVSSGG  300
GGSQVTLRES GPALVKPTQT LTLTCTFSGF SLSTSGMSVG WIRQPPGKAL EWLADIWWDD  360
KKDYNPSLKS RLTISKDTSK NQVVLKVTNM DPADTATYYC ARSMITNWYF DVWGAGTTVT  420
VSSASTKGPS VFPLAPSSKS TSGGTAALGC LVKDYFPEPV TVSWNSGALT SGVHTFPAVL  480
QSSGLYSLSS VVTVPSSSLG TQTYICNVNH KPSNTKVDKK VEPKSCDKTH TCPPCPAPEF  540
EGGPSVFLFP PKPKDTLMIS RTPEVTCVVV DVSHEDPEVK FNWYVDGVEV HNAKTKPREE  600
QYQSTYRVVS VLTVLHQDWL NGKEYKCKVS NKALPASIEK TISKAKGQPR EPQVYTLPPS  660
REEMTKNQVS LTCLVKGFYP SDIAVEWESN GQPENNYKTT PPVLDSDGSF FLYSKLTVDK  720
SRWQQGNVFS CSVMHEALHN HYTQKSLSLS PGK                               753
```

```
SEQ ID NO: 143          moltype = AA  length = 249
FEATURE                 Location/Qualifiers
REGION                  1..249
                        note = synthetic
source                  1..249
                        mol_type = protein
                        organism = synthetic construct
SEQUENCE: 143
QTVVTQEPSF SVSPGGTVTL TCRSSTGAVT TSNYANWVQQ TPGQAPRGLI GGTNKRAPGV  60
PDRFSGSILG NKAALTITGA QADDESDYYC ALWYSNLWVF GGGTKLTVLG GGGSGGGGSG  120
GGGSEVQLVE SGGGLVQPGG SLRLSCAASG FTFSTYAMNW VRQAPGKGLE WVARIRSKYN  180
NYATYYADSV KDRFTISRDD SKNSLYLQMN SLKTEDTAVY YCVRHGNFGN SYVSWFAYWG  240
QGTLVTVSS                                                          249
```

```
SEQ ID NO: 144          moltype = AA  length = 249
FEATURE                 Location/Qualifiers
REGION                  1..249
                        note = synthetic
source                  1..249
                        mol_type = protein
                        organism = synthetic construct
SEQUENCE: 144
QTVVTQEPSF SVSPGGTVTL TCRSSTGAVT TSNYANWVQQ TPGQAPRGLI GGTNKRAPGV  60
PDRFSGSILG NKAALTITGA QADDESDYYC ALWYSNLWVF GGGTKLTVLG GGGSGGGGSG  120
GGGSEVQLVE SGGGLVQPGG SLKLSCAASG FTFSTYAMNW VRQASGKGLE WVGRIRSKYN  180
NYATYYADSV KDRFTISRDD SKNTAYLQMN SLKTEDTAVY YCTRHGNFGN SYVSWFAYWG  240
QGTLVTVSS                                                          249
```

```
SEQ ID NO: 145          moltype = AA  length = 249
FEATURE                 Location/Qualifiers
REGION                  1..249
                        note = synthetic
source                  1..249
                        mol_type = protein
                        organism = synthetic construct
SEQUENCE: 145
QAVVTQEPSL TVSPGGTVTL TCRSSTGAVT TSNYANWVQQ KPGQAPRGLI GGTNKRAPGT  60
PARFSGSLIG GKAALTLSGA QPEDEAEYYC ALWYSNLWVF GGGTKLTVLG GGGSGGGGSG  120
GGGSEVQLVE SGGGLVQPGG SLKLSCAASG FTFSTYAMNW VRQASGKGLE WVGRIRSKYN  180
NYATYYADSV KDRFTISRDD SKNTAYLQMN SLKTEDTAVY YCTRHGNFGN SYVSWFAYWG  240
QGTLVTVSS                                                          249

SEQ ID NO: 146          moltype = AA  length = 747
FEATURE                 Location/Qualifiers
REGION                  1..747
                        note = synthetic
source                  1..747
                        mol_type = protein
                        organism = synthetic construct
SEQUENCE: 146
QGQSGSGYLW GCEWNCGGIT TGSSGGSGGS GGLSGRSDDH GGGSQTVVTQ EPSFSVSPGG  60
TVTLTCRSST GAVTTSNYAN WVQQTPGQAP RGLIGGTNKR APGVPDRFSG SILGNKAALT  120
ITGAQADDES DYYCALWYSN LWVFGGGTKL TVLGGGGSGG GGSGGGGSEV QLVESGGGLV  180
QPGGSLRLSC AASGFTFSTY AMNWVRQAPG KGLEWVARIR SKYNNYATYY ADSVKDRFTI  240
SRDDSKNSLY LQMNSLKTED TAVYYCVRHG NFGNSYVSWF AYWGQGTLVT VSSGGGGSQV  300
QLKQSGPGLV QPSQSLSITC TVSGFSLTNY GVHWVRQSPG KGLEWLGVIW SGGNTDYNTP  360
FTSRLSINKD NSKSQVFFKM NSLQSQDTAI YYCARALTYY DYEFAYWGQG TLVTVSAAST  420
KGPSVFPLAP SSKSTSGGTA ALGCLVKDYF PEPVTVSWNS GALTSGVHTF PAVLQSSGLY  480
SLSSVVTVPS SSLGTQTYIC NVNHKPSNTK VDKKVEPKSC DKTHTCPPCP APEFEGGPSV  540
FLFPPKPKDT LMISRTPEVT CVVVDVSHED PEVKFNWYVD GVEVHNAKTK PREEQYQSTY  600
RVVSVLTVLH QDWLNGKEYK CKVSNKALPA SIEKTISKAK GQPREPQVYT LPPSREEMTK  660
NQVSLTCLVK GFYPSDIAVE WESNGQPENN YKTTPPVLDS DGSFFLYSKL TVDKSRWQQG  720
NVFSCSVMHE ALHNHYTQKS LSLSPGK                                      747

SEQ ID NO: 147          moltype = DNA  length = 2244
FEATURE                 Location/Qualifiers
misc_feature            1..2244
                        note = synthetic
source                  1..2244
                        mol_type = other DNA
                        organism = synthetic construct
SEQUENCE: 147
caaggccagt ctggccaaat gatgtattgc ggtgggaatg aggtgttgtg cgggccgcgg  60
gttggctcga gcggtggcag cggtggctct ggtggtctga gcggccgttc cgataatcat  120
ggcggcggtt ctcagaccgt ggtcacacag gagccctcac tgacagtgag ccctggcggg  180
accgtcacac tgacttgtcg cagttcaact ggcgccgtga ctaccagcaa ttacgctaac  240
tgggtccagc agaaaccagg acaggcacca cgaggactga tcggaggaac taataagaga  300
gcaccaggaa cccctgcaag gttctccgga tctctgctgg ggggaaaagc cgctctgaca  360
ctgagcggcg tgcagcctga ggacgaagct gagtactatt gcgcactgtg gtactccaac  420
ctgtgggtgt ttggcggggg aactaagctg accgtcctgg gaggaggagg aagcggagga  480
ggagggagcg gaggaggagg atccgaagtg cagctggtcg agagcggagg aggactggtg  540
cagccaggag gatccctgaa gctgtcttgt gcagccagtg gcttcacctt caacacttac  600
gcaatgaact gggtgcggca ggcacctggg aagggactgg aatgggtcgc ccggatcaga  660
tctaaataca ataactatgc cacctactat gctgacagtg tgaaggatag gttcaccatt  720
tcacgcgacg atagcaaaaa cacagcttat ctgcagatga ataacctgaa gaccgaggat  780
acagcagtgt actattgcgt cagacacggc aatttcggga actcttacgt gagttggttt  840
gcctattggg gacaggggac actggtcacc gtctcctcag gaggtggtgg atcccaagtg  900
accctgagag agtctggccc tgccctcgtg aagcctaccc agaccctgac actgacctgc  960
accttcagcg gcttcagcct gagcaccagc ggcatgtctg tgggctggat cagacagcct  1020
cctggcaagg ccctggaatg gctggccgac atttggtggg acgacaagaa ggactacaac  1080
cccagcctga agtcccggct gaccatcagc aaggacacca gcaagaacca ggtggtgctg  1140
aaagtgacca acatggaccc cgccgacacc gccacctact actgcgccag atccatgatc  1200
accaactggt acttcgacgt gtggggagcc ggcaccaccg tgacagtgtc atctgctagc  1260
accaagggcc catcggtctt ccccctggca ccctcctcca agagcacctc tgggggcaca  1320
gcggccctgg gctgcctggt caaggactac ttccccgaac cggtgacggt gtcgtggaac  1380
tcaggcgccc tgaccagcgg cgtgcacacc ttcccggctg tcctacagtc ctcaggactc  1440
tactccctca gcagcgtggt gaccgtgccc tccagcagct tgggcaccca gacctacatc  1500
tgcaacgtga atcacaagcc cagcaacacc aaggtggaca agaaagttga gcccaaatct  1560
tgtgacaaaa ctcacacatg cccaccgtgc ccagcacctg aactcctggg gggaccgtca  1620
gtcttcctct tccccccaaa acccaaggac accctcatga tctcccggac ccctgaggtc  1680
acatgcgtgg tggtggacgt gagccacgaa gaccctgagg tcaagttcaa ctggtacgtg  1740
gacggcgtgg aggtgcataa tgccaagaca aagccgcggg aggagcagta ccagagcacg  1800
taccgtgtgg tcagcgtcct caccgtcctg caccaggact ggctgaatgg caaggagtac  1860
aagtgcaagg tctccaacaa agccctccca gcccccatcg agaaaaccat ctccaaagcc  1920
aaagggcagc cccgagaacc acaggtgtac accctgcccc catcccggga ggagatgacc  1980
aagaaccagg tcagcctgac ctgcctggtc aaaggcttct atcccagcga catcgccgtg  2040
```

-continued

```
gagtgggaga gcaatgggca gccggagaac aactacaaga ccacgcctcc cgtgctggac  2100
tccgacggct ccttcttcct ctacagcaag ctcaccgtgg acaagagcag gtggcagcag  2160
gggaacgtct tctcatgctc cgtgatgcat gaggctctgc acaaccacta cacgcagaag  2220
agcctctccc tgtctccggg taaa                                         2244

SEQ ID NO: 148         moltype = AA  length = 747
FEATURE                Location/Qualifiers
REGION                 1..747
                       note = synthetic
source                 1..747
                       mol_type = protein
                       organism = synthetic construct
SEQUENCE: 148
QGQSGSGYLW GCEWNCGGIT TGSSGGSGGS GGLSGRSDDH GGGSQAVVTQ EPSLTVSPGG  60
TVTLTCRSST GAVTTSNYAN WVQQKPGQAP RGLIGGTNKR APGTPARFSG SLIGGKAALT  120
LSGAQPEDEA EYYCALWYSN LWVFGGGTKL TVLGGGGSGG GGSGGGGSEV QLVESGGGLV  180
QPGGSLKLSC AASGFTFSTY AMNWVRQASG KGLEWVGRIR SKYNNYATYY ADSVKDRFTI  240
SRDDSKNTAY LQMNSLKTED TAVYYCTRHG NFGNSYVSWF AYWGQGTLVT VSSGGGGSQV  300
QLKQSGPGLV QPSQSLSITC TVSGFSLTNY GVHWVRQSPG KGLEWLGVIW SGGNTDYNTP  360
FTSRLSINKD NSKSQVFFKM NSLQSQDTAI YYCARALTYY DYEFAYWGQG TLVTVSAAST  420
KGPSVFPLAP SSKSTSGGTA ALGCLVKDYF PEPVTVSWNS GALTSGVHTF PAVLQSSGLY  480
SLSSVVTVPS SSLGTQTYIC NVNHKPSNTK VDKKVEPKSC DKTHTCPPCP APEFEGGPSV  540
FLFPPKPKDT LMISRTPEVT CVVVDVSHED PEVKFNWYVD GVEVHNAKTK PREEQYQSTY  600
RVVSVLTVLH QDWLNGKEYK CKVSNKALPA SIEKTISKAK GQPREPQVYT LPPSREEMTK  660
NQVSLTCLVK GFYPSDIAVE WESNGQPENN YKTTPPVLDS DGSFFLYSKL TVDKSRWQQG  720
NVFSCSVMHE ALHNHYTQKS LSLSPGK                                      747

SEQ ID NO: 149         moltype = AA  length = 14
FEATURE                Location/Qualifiers
REGION                 1..14
                       note = synthetic
source                 1..14
                       mol_type = protein
                       organism = synthetic construct
SEQUENCE: 149
RSSTGAVTTS NYAN                                                    14

SEQ ID NO: 150         moltype = AA  length = 249
FEATURE                Location/Qualifiers
REGION                 1..249
                       note = synthetic
source                 1..249
                       mol_type = protein
                       organism = synthetic construct
SEQUENCE: 150
QAVVTQEPSL TVSPGGTVTL TCRSSTGAVT TSNYANWVQQ KPGQAPRGLI GGTNKRAPGT  60
PARFSGSLIG GKAALTLSGA QPEDEAEYYC ALWYSNLWVF GGGTKLTVLG GGGSGGGGSG  120
GGGSEVQLVE SGGGLVQPGG SLRLSCAASG FTFSTYAMNW VRQAPGKGLE WVARIRSKYN  180
NYATYYADSV KDRFTISRDD SKNSLYLQMN SLKTEDTAVY YCVRHGNFGN SYVSWFAYWG  240
QGTLVTVSS                                                          249

SEQ ID NO: 151         moltype = DNA  length = 2241
FEATURE                Location/Qualifiers
misc_feature           1..2241
                       note = synthetic
source                 1..2241
                       mol_type = other DNA
                       organism = synthetic construct
SEQUENCE: 151
caaggccagt ctggttctgg ttatctgtgg ggttgcgagt ggaattgcgg agggatcact  60
acaggctcga gcggtggcag cggtggctct ggtggtctga gcggccgttc cgatgatcat  120
ggcggcggat cccagacggt agtgactcag gagccatcat tttctgtctc tcctggaggt  180
actgtgacac tcacatgtag aagctcaact ggtgcagtca ccacttcaaa ttacgcgaat  240
tgggtccagc agacccctgg gcaggctccg agagggttga ttggaggtac taacaaacgg  300
gcaccgggag tgcctgatag gttttccggt tctattctcg gaaacaaggc ggctctcacg  360
atcacgggtg cgcaggccga cgatgaatca gactattact gcgctttgtg gtactcaaac  420
ctgtgggtat tcggaggggg caccaagctg acggtgttgg gtgggggggg ctctgggggga  480
gggggaagcg gaggtggggg cagcgaggtt cagcttgttg aaagtggtgg cggactcgta  540
caaccgggtg gaagtcttag actctcatgt gcagcatctg gatttacttt ttctacttat  600
gctatgaact gggtaagaca ggcaccgggg aaagggctgg aatgggttgc acgcattcga  660
tctaaataca ataactatgc tacatactac gccgatagtg ttaaggatcg attcactata  720
tctcgggacg acagtaagaa ctcactttac ctgcagatga attccttgaa aactgaggac  780
acggccgttt attattgtgt acggcacggg aatttcggca attcttacgt ttcctggttc  840
gcctattggg ggcaaggtac gctggtcacg gtgtctagcg gaggtggtgg atcccaggtg  900
cagctgaaac agagcggccc gggcctggtg cagccgagcc agagcctgag cattacctgc  960
accgtgagcg gctttagcct gaccaactat ggcgtgcatt gggtgcgcca gagcccgggc  1020
aaaggcctgg aatggctggg cgtgatttgg agcggcggca acaccgatta taacaccccg  1080
tttaccagcc gcctgagcat taacaaagat aacagcaaaa gccaggtgtt ttttaaaatg  1140
aacagcctgc aaagccagga taccgcgatt tattattgcg cgcgcgcgct gacctattat  1200
```

```
gattatgaat ttgcgtattg gggccagggc accctggtga ccgtgagcgc ggctagcacc  1260
aagggcccat cggtcttccc cctggcaccc tcctccaaga gcacctctgg gggcacagcg  1320
gccctgggct gcctggtcaa ggactacttc cccgaaccgg tgacggtgtc gtggaactca  1380
ggcgccctga ccagcggcgt gcacaccttc ccggctgtcc tacagtcctc aggactctac  1440
tccctcagca gcgtggtgac cgtgccctcc agcagcttgg gcacccagac ctacatctgc  1500
aacgtgaatc acaagcccag caacaccaag gtggacaaga aagttgagcc caaatcttgt  1560
gacaaaactc acacatgccc accgtgccca gcacctgaat ttgaaggggg accgtcagtc  1620
ttcctcttcc ccccaaaacc caaggacacc ctcatgatct cccggacccc tgaggtcaca  1680
tgcgtggtgg tggacgtgag ccacgaagac cctgaggtca agttcaactg gtacgtggac  1740
ggcgtggagg tgcataatgc caagacaaag ccgcgggagg agcagtacca gagcacgtac  1800
cgtgtggtca gcgtcctcac cgtcctgcac caggactggc tgaatggcaa ggagtacaag  1860
tgcaaggtct ccaacaaagc cctcccagcc tcaatcgaga aaaccatctc caaagccaaa  1920
gggcagcccc gagaaccaca ggtgtacacc ctgcccccat cccgggagga gatgaccaag  1980
aaccaggtca gcctgacctg cctggtcaaa ggcttctatc ccagcgacat cgccgtggag  2040
tgggagagca atgggcagcc ggagaacaac tacaagacca cgcctcccgt gctggactcc  2100
gacggctcct tcttcctcta cagcaagctc accgtggaca agagcaggtg gcagcagggg  2160
aacgtcttct catgctccgt gatgcatgag gctctgcaca accactacac gcagaagagc  2220
ctctccctgt ctccgggtaa a                                            2241

SEQ ID NO: 152          moltype = DNA  length = 2241
FEATURE                 Location/Qualifiers
misc_feature            1..2241
                        note = synthetic
source                  1..2241
                        mol_type = other DNA
                        organism = synthetic construct
SEQUENCE: 152
caaggccagt ctggatccgg ttatctgtgg ggttgcgagt ggaattgcgg agggatcact  60
acaggctcga gcggtggcag cggtggctct ggtggtctga gcggccgttc cgatgatcat  120
ggcggcggtt ctcaggccgt tgttacacaa gagccttcac ttactgtgtc tccaggaggc  180
actgtgacac ttacgtgccg atcctctacg ggtgccgtga ccacaagcaa ctatgccaac  240
tgggtccagc agaagccagg tcaagcgcct cgaggtctga tcgggggcac gaataaacga  300
gctcctggaa ctccggccag atttctgggg agtcttattg gtggcaaggc ggcgttgacc  360
ctgagtggag cccaaccgga agacgaggcc gagtactact gcgccttgtg gtattccaat  420
ttgtgggtct tcggaggcgg aacaaagctc acagtactgg gaggtggagg tagcgggggc  480
ggaggctccg gggaggtgg ttccgaagtc cagcttgttg aatcaggtgg gggcttggta  540
caaccaggtg gttcactgaa gttgtcctgt gcagcgtccg gatttacatt tagtacgtat  600
gctatgaact gggtcaggca ggccagtggt aaaggtctcg aatgggttgg ccggataagg  660
tcaaagtaca ataattacgc aacctactac gcggattccg tgaaagacag gttcactatt  720
tcacgagatg atagcaaaaa tactgcgtat ctccaaatga atagtcttaa aactgaagac  780
actgccgtat attattgcac taggcacggc aactttggta actcttatgt ttcttggttc  840
gcatactggg gacaaggaac tttggtcact gtctcatctg gaggtggtgg atcccaggtg  900
cagctgaaac agagcggccc gggcctggtg cagccgagcc agagcctgag cattacctgc  960
accgtgagcg gctttagcct gaccaactat ggcgtgcatt gggtgcgcca gagcccgggc  1020
aaaggcctgg aatggctggg cgtgatttgg agcggcggca acaccgatta taacaccccg  1080
tttaccagcc gcctgagcat taacaaagat aacagcaaaa gccaggtgtt ttttaaaatg  1140
aacagcctgc aaagccagga taccgcgatt tattattgcg cgcgcgcgct gacctattat  1200
gattatgaat ttgcgtattg gggccagggc accctggtga ccgtgagcgc ggctagcacc  1260
aagggcccat cggtcttccc cctggcaccc tcctccaaga gcacctctgg gggcacagcg  1320
gccctgggct gcctggtcaa ggactacttc cccgaaccgg tgacggtgtc gtggaactca  1380
ggcgccctga ccagcggcgt gcacaccttc ccggctgtcc tacagtcctc aggactctac  1440
tccctcagca gcgtggtgac cgtgccctcc agcagcttgg gcacccagac ctacatctgc  1500
aacgtgaatc acaagcccag caacaccaag gtggacaaga aagttgagcc caaatcttgt  1560
gacaaaactc acacatgccc accgtgccca gcacctgaat ttgaaggggg accgtcagtc  1620
ttcctcttcc ccccaaaacc caaggacacc ctcatgatct cccggacccc tgaggtcaca  1680
tgcgtggtgg tggacgtgag ccacgaagac cctgaggtca agttcaactg gtacgtggac  1740
ggcgtggagg tgcataatgc caagacaaag ccgcgggagg agcagtacca gagcacgtac  1800
cgtgtggtca gcgtcctcac cgtcctgcac caggactggc tgaatggcaa ggagtacaag  1860
tgcaaggtct ccaacaaagc cctcccagcc tcaatcgaga aaaccatctc caaagccaaa  1920
gggcagcccc gagaaccaca ggtgtacacc ctgcccccat cccgggagga gatgaccaag  1980
aaccaggtca gcctgacctg cctggtcaaa ggcttctatc ccagcgacat cgccgtggag  2040
tgggagagca atgggcagcc ggagaacaac tacaagacca cgcctcccgt gctggactcc  2100
gacggctcct tcttcctcta cagcaagctc accgtggaca agagcaggtg gcagcagggg  2160
aacgtcttct catgctccgt gatgcatgag gctctgcaca accactacac gcagaagagc  2220
ctctccctgt ctccgggtaa a                                            2241

SEQ ID NO: 153          moltype = AA  length = 742
FEATURE                 Location/Qualifiers
REGION                  1..742
                        note = synthetic
source                  1..742
                        mol_type = protein
                        organism = synthetic construct
SEQUENCE: 153
MMYCGGNEVL CGPRVGSSGG SGGSGGLSGR SDNHGGGSQT VVTQEPSLTV SPGGTVTLTC  60
RSSTGAVTTS NYANWVQQKP GQAPRGLIGG TNKRAPGTPA RFSGSLLGGK AALTLSGVQP  120
EDEAEYYCAL WYSNLWVFGG GTKLTVLGGG GSGGGGSGGG GSEVQLVESG GGLVQPGGSL  180
KLSCAASGFT FNTYAMNWVR QAPGKGLEWV ARIRSKYNNY ATYYADSVKD RFTISRDDSK  240
NTAYLQMNNL KTEDTAVYYC VRHGNFGNSY VSWFAYWGQG TLVTVSSGGG GSQVTLRESG  300
```

-continued

```
PALVKPTQTL TLTCTFSGFS LSTSGMSVGW IRQPPGKALE WLADIWWDDK KDYNPSLKSR  360
LTISKDTSKN QVVLKVTNMD PADTATYYCA RSMITNWYFD VWGAGTTVTV SSASTKGPSV  420
FPLAPSSKST SGGTAALGCL VKDYFPEPVT VSWNSGALTS GVHTFPAVLQ SSGLYSLSSV  480
VTVPSSSLGT QTYICNVNHK PSNTKVDKKV EPKSCDKTHT CPPCPAPELL GGPSVFLFPP  540
KPKDTLMISR TPEVTCVVVD VSHEDPEVKF NWYVDGVEVH NAKTKPREEQ YQSTYRVVSV  600
LTVLHQDWLN GKEYKCKVSN KALPAPIEKT ISKAKGQPRE PQVYTLPPSR EEMTKNQVSL  660
TCLVKGFYPS DIAVEWESNG QPENNYKTTP PVLDSDGSFF LYSKLTVDKS RWQQGNVFSC  720
SVMHEALHNH YTQKSLSLSP GK                                          742

SEQ ID NO: 154         moltype = AA  length = 330
FEATURE                Location/Qualifiers
REGION                 1..330
                       note = synthetic
VARIANT                180
                       note = X may be any amino acid
source                 1..330
                       mol_type = protein
                       organism = synthetic construct
SEQUENCE: 154
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYX  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 155         moltype = AA  length = 330
FEATURE                Location/Qualifiers
REGION                 1..330
                       note = synthetic
source                 1..330
                       mol_type = protein
                       organism = synthetic construct
SEQUENCE: 155
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYQ  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 156         moltype = AA  length = 330
FEATURE                Location/Qualifiers
REGION                 1..330
                       note = synthetic
VARIANT                117
                       note = X can be any amino acid
source                 1..330
                       mol_type = protein
                       organism = synthetic construct
SEQUENCE: 156
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEXLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 157         moltype = AA  length = 449
FEATURE                Location/Qualifiers
REGION                 1..449
                       note = synthetic
VARIANT                119
                       note = X may be Ser or Ala
source                 1..449
                       mol_type = protein
                       organism = synthetic construct
SEQUENCE: 157
QVQLKQSGPG LVQPSQSLSI TCTVSGFSLT NYGVHWVRQS PGKGLEWLGV IWSGGNTDYN  60
TPFTSRLSIN KDNSKSQVFF KMNSLQSQDT AIYYCARALT YYDYEFAYWG QGTLVTVSXA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEFLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449
```

```
SEQ ID NO: 158          moltype = AA  length = 449
FEATURE                 Location/Qualifiers
REGION                  1..449
                        note = synthetic
VARIANT                 119
                        note = X may be Ser or Ala
VARIANT                 237
                        note = X may be any amino acid
source                  1..449
                        mol_type = protein
                        organism = synthetic construct
SEQUENCE: 158
QVQLKQSGPG LVQPSQSLSI TCTVSGFSLT NYGVHWVRQS PGKGLEWLGV IWSGGNTDYN  60
TPFTSRLSIN KDNSKSQVFF KMNSLQSQDT AIYYCARALT YYDYEFAYWG QGTLVTVSXA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELXGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                  449

SEQ ID NO: 159          moltype = AA  length = 330
FEATURE                 Location/Qualifiers
REGION                  1..330
                        note = synthetic
source                  1..330
                        mol_type = protein
                        organism = synthetic construct
SEQUENCE: 159
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELEGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                 330

SEQ ID NO: 160          moltype = AA  length = 330
FEATURE                 Location/Qualifiers
REGION                  1..330
                        note = synthetic
VARIANT                 214
                        note = X can be any amino acid
source                  1..330
                        mol_type = protein
                        organism = synthetic construct
SEQUENCE: 160
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAXIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                 330

SEQ ID NO: 161          moltype = AA  length = 330
FEATURE                 Location/Qualifiers
REGION                  1..330
                        note = synthetic
source                  1..330
                        mol_type = protein
                        organism = synthetic construct
SEQUENCE: 161
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPASIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                 330

SEQ ID NO: 162          moltype = AA  length = 330
FEATURE                 Location/Qualifiers
REGION                  1..330
                        note = synthetic
source                  1..330
                        mol_type = protein
                        organism = synthetic construct
SEQUENCE: 162
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEFEGG  120
```

```
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPASIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 163          moltype = AA  length = 330
FEATURE                 Location/Qualifiers
REGION                  1..330
                        note = synthetic
source                  1..330
                        mol_type = protein
                        organism = synthetic construct
SEQUENCE: 163
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEFEGG  120
PSVFLFPPKP KDTLMISRTP EVTCVVVDVS HEDPEVKFNW YVDGVEVHNA KTKPREEQYQ  180
STYRVVSVLT VLHQDWLNGK EYKCKVSNKA LPASIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 164          moltype = DNA  length = 2133
FEATURE                 Location/Qualifiers
misc_feature            1..2133
                        note = synthetic
source                  1..2133
                        mol_type = other DNA
                        organism = synthetic construct
SEQUENCE: 164
tccgataatc atggcggcgg ttctcaaact gtagtaactc aagaaccaag cttctccgtc  60
tcccctgggg gaacagtcac acttacctgc cgaagtagta caggtgctgt tacgaccagt  120
aactatgcca attgggtaca acaaacgcct ggtcaggctc cgcgcggatt gataggaggc  180
acgaataaac gggcacccgg tgtcccggac agattcagcg gaagcatact cggtaataag  240
gcagctctta ctatcactgg ggcccaagct gatgatgaaa gtgattatta ttgtgcgctc  300
tggtacagca acctctgggt gtttgggggt ggcacgaaac ttactgtctt gggcggcggc  360
ggatcagggg gaggtggctc tggaggagga ggctcagaag tccaactggt cgaatccggg  420
ggagggctcg tacagccggg tgggtccctc aaactctctt gtgcggcctc agggtttacc  480
ttcagtacat acgcgatgaa ttgggtccgg caggccagtg ggaaagggct cgaatgggta  540
ggacgaatcc gatcaaaata caacaactac gctacttatt acgctgattc cgtgaaggac  600
agattcacaa tatcccgcga cgatagcaag aatacggcat atcttcagat gaattctctt  660
aaaactgagg ataccgctgt gtattactgc acaagacatg gtaattttgg aaactcatat  720
gtctcttggt tcgcttattg gggacagggc acgttggtta ccgtgtctag cggaggtggt  780
ggatcccagg tgcagctgaa acagagcggc ccgggcctgg tgcagccgag ccagagcctg  840
agcattacct gcaccgtgag cggctttagc ctgaccaact atggcgtgca ttgggtgcgc  900
cagagcccgg gcaaaggcct ggaatggctg ggcgtgattt ggagcggcgg caacaccgat  960
tataacaccc cgtttaccag ccgcctgagc attaacaaag ataacagcaa aagccaggtg  1020
ttttttaaaa tgaacagcct gcaaagccag gataccgcga tttattattg cgcgcgcgcg  1080
ctgacctatt atgattatga atttgcgtat tggggccagg gcaccctggt gaccgtgagc  1140
gcggctagca ccaagggccc atcggtcttc cccctggcac cctcctccaa gagcacctct  1200
gggggcacag cggccctggg ctgcctggtc aaggactact tccccgaacc ggtgacggtg  1260
tcgtggaact caggcgccct gaccagcggc gtgcacacct tcccggctgt cctacagtcc  1320
tcaggactct actccctcag cagcgtggtg accgtgccct ccagcagctt gggcacccag  1380
acctacatct gcaacgtgaa tcacaagccc agcaacacca aggtggacaa gaaagttgag  1440
cccaaatctt gtgacaaaac tcacacatgc ccaccgtgcc cagcacctga atttgaaggg  1500
ggaccgtcag tcttcctctt ccccccaaaa cccaaggaca ccctcatgat ctcccggacc  1560
cctgaggtca catgcgtggt ggtggacgtg agccacgaag accctgaggt caagttcaac  1620
tggtacgtgg acggcgtgga ggtgcataat gccaagacaa agccgcggga ggagcagtac  1680
cagagcacgt accgtgtggt cagcgtcctc accgtcctgc accaggactg gctgaatggc  1740
aaggagtaca agtgcaaggt ctccaacaaa gccctcccag cctcaatcga gaaaaccatc  1800
tccaaagcca aagggcagcc ccgagaacca caggtgtaca ccctgccccc atcccgggag  1860
gagatgacca agaaccaggt cagcctgacc tgcctggtca aaggcttcta tcccagcgac  1920
atcgccgtgg agtgggagag caatgggcag ccggagaaca actacaagac cacgcctccc  1980
gtgctggact ccgacggctc cttcttcctc tacagcaagc tcaccgtgga caagagcagg  2040
tggcagcagg ggaacgtctt ctcatgctcc gtgatgcatg aggctctgca caaccactac  2100
acgcagaaga gcctctccct gtctccgggt aaa                               2133

SEQ ID NO: 165          moltype = AA  length = 711
FEATURE                 Location/Qualifiers
REGION                  1..711
                        note = synthetic
source                  1..711
                        mol_type = protein
                        organism = synthetic construct
SEQUENCE: 165
SDNHGGGSQT VVTQEPSFSV SPGGTVTLTC RSSTGAVTTS NYANWVQQTP GQAPRGLIGG  60
TNKRAPGVPD RFSGSILGNK AALTITGAQA DDESDYYCAL WYSNLWVFGG GTKLTVLGGG  120
GSGGGGSGGG GSEVQLVESG GGLVQPGGSL KLSCAASGFT FSTYAMNWVR QASGKGLEWV  180
GRIRSKYNNY ATYYADSVKD RFTISRDDSK NTAYLQMNSL KTEDTAVYYC TRHGNFGNSY  240
VSWFAYWGQG TLVTVSSGGG GSQVQLKQSG PGLVQPSQSL SITCTVSGFS LTNYGVHWVR  300
QSPGKGLEWL GVIWSGGNTD YNTPFTSRLS INKDNSKSQV FFKMNSLQSQ DTAIYYCARA  360
```

-continued

```
LTYYDYEFAY WGQGTLVTVS AASTKGPSVF PLAPSSKSTS GGTAALGCLV KDYFPEPVTV  420
SWNSGALTSG VHTFPAVLQS SGLYSLSSVV TVPSSSLGTQ TYICNVNHKP SNTKVDKKVE  480
PKSCDKTHTC PPCPAPEFEG GPSVFLFPPK PKDTLMISRT PEVTCVVVDV SHEDPEVKFN  540
WYVDGVEVHN AKTKPREEQY QSTYRVVSVL TVLHQDWLNG KEYKCKVSNK ALPASIEKTI  600
SKAKGQPREP QVYTLPPSRE EMTKNQVSLT CLVKGFYPSD IAVEWESNGQ PENNYKTTPP  660
VLDSDGSFFL YSKLTVDKSR WQQGNVFSCS VMHEALHNHY TQKSLSLSPG K           711

SEQ ID NO: 166         moltype = DNA  length = 669
FEATURE                Location/Qualifiers
misc_feature           1..669
                       note = synthetic
source                 1..669
                       mol_type = other DNA
                       organism = synthetic construct
SEQUENCE: 166
tccgataatc atggcagtag cggtacccag atcttgctga cccagagccc ggtgattctg  60
agcgtgagcc cgggcgaacg tgtgagcttt agctgccgcg cgagccagag cattggcacc  120
aacattcatt ggtatcagca gcgcaccaac ggcagcccgc gcctgctgat taaatatgcg  180
agcgaaagca ttagcggcat tccgagccgc tttagcggca gcggcagcgg caccgatttt  240
accctgagca ttaacagcgt ggaaagcgaa gatattgcgg attattattg ccagcagaac  300
aacaactggc cgaccacctt tggcgcgggc accaaactgg aactgaaacg tacggtggct  360
gcaccatctg tcttcatctt cccgccatct gatgagcagt tgaaatctgg aactgcctct  420
gttgtgtgcc tgctgaataa cttctatccc agagaggcca aagtacagtg gaaggtggat  480
aacgccctcc aatcgggtaa ctcccaggag agtgtcacag agcaggacag caaggacagc  540
acctacagcc tcagcagcac cctgacgctg agcaaagcag actacgagaa acacaaagtc  600
tacgcctgcg aagtcaccca tcagggcctg agctcgcccg tcacaaagag cttcaacagg  660
ggagagtgt                                                          669

SEQ ID NO: 167         moltype = AA  length = 223
FEATURE                Location/Qualifiers
REGION                 1..223
                       note = synthetic
source                 1..223
                       mol_type = protein
                       organism = synthetic construct
SEQUENCE: 167
SDNHGSSGTQ ILLTQSPVIL SVSPGERVSF SCRASQSIGT NIHWYQQRTN GSPRLLIKYA  60
SESISGIPSR FSGSGSGTDF TLSINSVESE DIADYYCQQN NNWPTTFGAG TKLELKRTVA  120
APSVFIFPPS DEQLKSGTAS VVCLLNNFYP REAKVQWKVD NALQSGNSQE SVTEQDSKDS  180
TYSLSSTLTL SKADYEKHKV YACEVTHQGL SSPVTKSFNR GEC                    223

SEQ ID NO: 168         moltype = DNA  length = 2256
FEATURE                Location/Qualifiers
misc_feature           1..2256
                       note = synthetic
source                 1..2256
                       mol_type = other DNA
                       organism = synthetic construct
SEQUENCE: 168
caaggccagt ctggatccgg ttatctgtgg ggttgcgagt ggaattgcgg agggatcact  60
acaggctcga gcggtggcag cggtggctct ggtggtatat cgagtggatt gctgtctggc  120
agatctgacc aacacggcgg cggttctcaa actgtagtaa ctcaagaacc aagcttctcc  180
gtctcccctg ggggaacagt cacacttacc tgccgaagta gtacaggtgc tgttacgacc  240
agtaactatg ccaattgggt acaacaaacg cctggtcagg ctccgcgcgg attgatagga  300
ggcacgaata aacgggcacc cggtgtcccg gacagattca gcggaagcat actcggtaat  360
aaggcagctc ttactatcac tggggcccaa gctgatgatg aaagtgatta ttattgtgcg  420
ctctggtaca gcaacctctg ggtgtttggg ggtggcacga aacttactgt cttgggcggc  480
ggcggatcag gggaggtgg ctctggagga ggaggctcag aagtccaact ggtcgaatcc  540
gggggagggc tcgtacagcc gggtgggtcc ctcaaactct cttgtgcggc ctcagggttt  600
accttcagta catacgcgat gaattgggtc cggcaggcca gtgggaaagg gctcgaatgg  660
gtaggacgaa tccgatcaaa atacaacaac tacgctactt attacgctga ttccgtgaag  720
gacagattca caatatcccg cgacgatagc aagaatacgg catatcttca gatgaattct  780
cttaaaactg aggataccgc tgtgtattac tgcacaagac atggtaattt tggaaactca  840
tatgtctctt ggttcgctta ttggggacag ggcacgttgg ttaccgtgtc tagcggaggt  900
ggtggatccc aggtgcagct gaaacagagc ggcccgggcc tggtgcagcc gagccagagc  960
ctgagcatta cctgcaccgt gagcggcttt agcctgacca actatggcgt gcattgggtg  1020
cgccagagcc cgggcaaagg cctggaatgg ctgggcgtga tttggagcgg cggcaacacc  1080
gattataaca ccccgtttac cagccgcctg agcattaaca aagataacag caaaagccag  1140
gtgtttttta aaatgaacag cctgcaaagc caggataccg cgatttatta ttgcgcgcgc  1200
gcgctgacct attatgatta tgaatttgcg tattggggcc agggcaccct ggtgaccgtg  1260
agcgcggcta gcaccaaggg cccatcggtc ttccccctgg caccctcctc caagagcacc  1320
tctgggggca cagcggccct gggctgcctg gtcaaggact acttccccga accggtgacg  1380
gtgtcgtgga actcaggcgc cctgaccagc ggcgtgcaca ccttcccggc tgtcctacag  1440
tcctcaggac tctactccct cagcagcgtg gtgaccgtgc cctccagcag cttgggcacc  1500
cagacctaca tctgcaacgt gaatcacaag cccagcaaca ccaaggtgga caagaaagtt  1560
gagcccaaat cttgtgacaa aactcacaca tgcccaccgt gcccagcacc tgaatttgaa  1620
gggggaccgt cagtcttcct cttcccccca aaacccaagg acaccctcat gatctcccgg  1680
acccctgagg tcacatgcgt ggtggtggac gtgagccacg aagaccctga ggtcaagttc  1740
aactggtacg tggacggcgt ggaggtgcat aatgccaaga caaagccgcg ggaggagcag  1800
```

```
taccagagca cgtaccgtgt ggtcagcgtc ctcaccgtcc tgcaccagga ctggctgaat  1860
ggcaaggagt acaagtgcaa ggtctccaac aaagccctcc cagcctcaat cgagaaaacc  1920
atctccaaag ccaaagggca gccccgagaa ccacaggtgt acaccctgcc cccatcccgg  1980
gaggagatga ccaagaacca ggtcagcctg acctgcctgg tcaaaggctt ctatcccagc  2040
gacatcgccg tggagtggga gagcaatggg cagccggaga acaactacaa gaccacgcct  2100
cccgtgctgg actccgacgg ctccttcttc ctctacagca agctcaccgt ggacaagagc  2160
aggtggcagc aggggaacgt cttctcatgc tccgtgatgc atgaggctct gcacaaccac  2220
tacacgcaga agagcctctc cctgtctccg ggtaaa                           2256

SEQ ID NO: 169          moltype = AA  length = 752
FEATURE                 Location/Qualifiers
REGION                  1..752
                        note = synthetic
source                  1..752
                        mol_type = protein
                        organism = synthetic construct
SEQUENCE: 169
QGQSGSGYLW GCEWNCGGIT TGSSGGSGGS GGISSGLLSG RSDQHGGGSQ TVVTQEPSFS  60
VSPGGTVTLT CRSSTGAVTT SNYANWVQQT PGQAPRGLIG GTNKRAPGVP DRFSGSILGN  120
KAALTITGAQ ADDESDYYCA LWYSNLWVFG GGTKLTVLGG GGSGGGGSGG GGSEVQLVES  180
GGGLVQPGGS LKLSCAASGF TFSTYAMNWV RQASGKGLEW VGRIRSKYNN YATYYADSVK  240
DRFTISRDDS KNTAYLQMNS LKTEDTAVYY CTRHGNFGNS YVSWFAYWGQ GTLVTVSSGG  300
GGSQVQLKQS GPGLVQPSQS LSITCTVSGF SLTNYGVHWV RQSPGKGLEW LGVIWSGGNT  360
DYNTPFTSRL SINKDNSKSQ VFFKMNSLQS QDTAIYYCAR ALTYYDYEFA YWGQGTLVTV  420
SAASTKGPSV FPLAPSSKST SGGTAALGCL VKDYFPEPVT VSWNSGALTS GVHTFPAVLQ  480
SSGLYSLSSV VTVPSSSLGT QTYICNVNHK PSNTKVDKKV EPKSCDKTHT CPPCPAPEFE  540
GGPSVFLFPP KPKDTLMISR TPEVTCVVVD VSHEDPEVKF NWYVDGVEVH NAKTKPREEQ  600
YQSTYRVVSV LTVLHQDWLN GKEYKCKVSN KALPASIEKT ISKAKGQPRE PQVYTLPPSR  660
EEMTKNQVSL TCLVKGFYPS DIAVEWESNG QPENNYKTTP PVLDSDGSFF LYSKLTVDKS  720
RWQQGNVFSC SVMHEALHNH YTQKSLSLSP GK                                752

SEQ ID NO: 170          moltype = DNA  length = 798
FEATURE                 Location/Qualifiers
misc_feature            1..798
                        note = synthetic
source                  1..798
                        mol_type = other DNA
                        organism = synthetic construct
SEQUENCE: 170
caaggccagt ctggccagtg catctcacct cgtggttgtc cggacggccc atacgtcatg  60
tacggctcga gcggtggcag cggtggctct ggtggatccg gtatatcgag tggattgctg  120
tctggcagat ctgaccaaca cggcagtagc ggtacccaga tcttgctgac ccagagcccg  180
gtgattctga gcgtgagccc gggcgaacgt gtgagcttta gctgccgcgc gagccagagc  240
attggcacca acattcattg gtatcagcag cgcaccaacg gcagcccgcg cctgctgatt  300
aaatatgcga gcgaaagcat tagcggcatt ccgagccgct ttagcggcag cggcagcggc  360
accgatttta ccctgagcat taacagcgtg gaaagcgaag atattgcgga ttattattgc  420
cagcagaaca acaactggcc gaccaccttt ggcgcgggca ccaaactgga actgaaacgt  480
acggtggctg caccatctgt cttcatcttc ccgccatctg atgagcagtt gaaatctgga  540
actgcctctg ttgtgtgcct gctgaataac ttctatccca gagaggccaa agtacagtgg  600
aaggtggata acgccctcca atcgggtaac tcccaggaga gtgtcacaga gcaggacagc  660
aaggacagca cctacagcct cagcagcacc ctgacgctga gcaaagcaga ctacgagaaa  720
cacaaagtct acgcctgcga agtcacccat cagggcctga gctcgcccgt cacaaagagc  780
ttcaacaggg gagagtgt                                                798

SEQ ID NO: 171          moltype = AA  length = 266
FEATURE                 Location/Qualifiers
REGION                  1..266
                        note = synthetic
source                  1..266
                        mol_type = protein
                        organism = synthetic construct
SEQUENCE: 171
QGQSGQCISP RGCPDGPYVM YGSSGGSGGS GGSGISSGLL SGRSDQHGSS GTQILLTQSP  60
VILSVSPGER VSFSCRASQS IGTNIHWYQQ RTNGSPRLLI KYASESISGI PSRFSGSGSG  120
TDFTLSINSV ESEDIADYYC QQNNNWPTTF GAGTKLELKR TVAAPSVFIF PPSDEQLKSG  180
TASVVCLLNN FYPREAKVQW KVDNALQSGN SQESVTEQDS KDSTYSLSST LTLSKADYEK  240
HKVYACEVTH QGLSSPVTKS FNRGEC                                       266

SEQ ID NO: 172          moltype = DNA  length = 2244
FEATURE                 Location/Qualifiers
misc_feature            1..2244
                        note = synthetic
source                  1..2244
                        mol_type = other DNA
                        organism = synthetic construct
SEQUENCE: 172
caaggccagt ctggccaaat gatgtattgc ggtgggaatg aggtgttgtg cgggccgcgg  60
gttggctcga gcggtggcag cggtggctct ggtggtctga gcggccgttc cgataatcat  120
ggcggcggtt ctcagaccgt ggtcacacag gagccctcac tgacagtgag ccctggcggg  180
```

```
accgtcacac tgacttgtcg cagttcaact ggcgccgtga ctaccagcaa ttacgctaac  240
tgggtccagc agaaaccagg acaggcacca cgaggactga tcggaggaac taataagaga  300
gcaccaggaa cccctgcaag gttctccgga tctctgctgg ggggaaaagc cgctctgaca  360
ctgagcggcg tgcagcctga ggacgaagct gagtactatt gcgcactgtg gtactccaac  420
ctgtgggtgt ttggcggggg aactaagctg accgtcctgg gaggaggagg aagcggagga  480
ggagggagcg gaggaggagg atccgaagtg cagctggtcg agagcggagg aggactggtg  540
cagccaggag gatccctgaa gctgtcttgt gcagcccagtg gcttcacctt caacacttac  600
gcaatgaact gggtgcggca ggcacctggg aagggactgg aatgggtcgc ccggatcaga  660
tctaaataca ataactatgc cacctactat gctgacagtg tgaaggatag gttcaccatt  720
tcacgcgacg atagcaaaaa cacagcttat ctgcagatga ataacctgaa gaccgaggat  780
acagcagtgt actattgcgt cagacacggc aatttcggga actcttacgt gagttggttt  840
gcctattggg gacaggggac actggtcacc gtctcctcag gaggtggtgg atcccaagtg  900
accctgagag agtctggccc tgccctcgtg aagcctaccc agaccctgac actgacctgc  960
accttcagcg gcttcagcct gagcaccagc ggcatgtctg tgggctggat cagacagcct  1020
cctggcaagg ccctggaatg gctggccgac atttggtggg acgacaagaa ggactacaac  1080
cccagcctga agtcccggct gaccatcagc aaggacacca gcaagaacca ggtggtgctg  1140
aaagtgacca acatggaccc cgccgacacc gccacctact actgcgccag atccatgatc  1200
accaactggt acttcgacgt gtggggagcc ggcaccaccg tgacagtgtc atctgctagc  1260
accaagggcc catcggtctt ccccctggca ccctcctcca agagcacctc tgggggcaca  1320
gcggccctgg gctgcctggt caaggactac ttccccgaac cggtgacggt gtcgtggaac  1380
tcaggcgccc tgaccagcgg cgtgcacacc ttcccggctg tcctacagtc ctcaggactc  1440
tactccctca gcagcgtggt gaccgtgccc tccagcagct tgggcaccca gacctacatc  1500
tgcaacgtga atcacaagcc cagcaacacc aaggtggaca agaaagttga gcccaaatct  1560
tgtgacaaaa ctcacacatg cccaccgtgc ccagcacctg aactcctggg gggaccgtca  1620
gtcttcctct tccccccaaa acccaaggac accctcatga tctcccggac ccctgaggtc  1680
acatgcgtgg tggtggacgt gagccacgaa gaccctgagg tcaagttcaa ctggtacgtg  1740
gacggcgtgg aggtgcataa tgccaagaca aagccgcggg aggagcagta ccagagcacg  1800
taccgtgtgg tcagcgtcct caccgtcctg caccaggact ggctgaatgg caaggagtac  1860
aagtgcaagg tctccaacaa agccctccca gcccccatcg agaaaaccat ctccaaagcc  1920
aaagggcagc cccgagaacc acaggtgtac accctgcccc catcccggga ggagatgacc  1980
aagaaccagg tcagcctgac ctgcctggtc aaaggcttct atcccagcga catcgccgtg  2040
gagtgggaga gcaatgggca gccggagaac aactacaaga ccacgcctcc cgtgctggac  2100
tccgacggct ccttcttcct ctacagcaag ctcaccgtgg acaagagcag gtggcagcag  2160
gggaacgtct tctcatgctc cgtgatgcat gaggctctgc acaaccacta cacgcagaag  2220
agcctctccc tgtctccggg taaa                                         2244
```

```
SEQ ID NO: 173         moltype = AA  length = 748
FEATURE                Location/Qualifiers
REGION                 1..748
                       note = synthetic
source                 1..748
                       mol_type = protein
                       organism = synthetic construct
SEQUENCE: 173
QGQSGQMMYC GGNEVLCGPR VGSSGGSGGS GGLSGRSDNH GGGSQTVVTQ EPSLTVSPGG  60
TVTLTCRSST GAVTTSNYAN WVQQKPGQAP RGLIGGTNKR APGTPARFSG SLLGGKAALT  120
LSGVQPEDEA EYYCALWYSN LWVFGGGTKL TVLGGGGSGG GGSGGGGSEV QLVESGGGLV  180
QPGGSLKLSC AASGFTFNTY AMNWVRQAPG KGLEWVARIR SKYNNYATYY ADSVKDRFTI  240
SRDDSKNTAY LQMNNLKTED TAVYYCVRHG NFGNSYVSWF AYWGQGTLVT VSSGGGGSQV  300
TLRESGPALV KPTQTLTLTC TFSGFSLSTS GMSVGWIRQP PGKALEWLAD IWWDDKKDYN  360
PSLKSRLTIS KDTSKNQVVL KVTNMDPADT ATYYCARSMI TNWYFDVWGA GTTVTVSSAS  420
TKGPSVFPLA PSSKSTSGGT AALGCLVKDY FPEPVTVSWN SGALTSGVHT FPAVLQSSGL  480
YSLSSVVTVP SSSLGTQTYI CNVNHKPSNT KVDKKVEPKS CDKTHTCPPC PAPELLGGPS  540
VFLFPPKPKD TLMISRTPEV TCVVVDVSHE DPEVKFNWYV DGVEVHNAKT KPREEQYQST  600
YRVVSVLTVL HQDWLNGKEY KCKVSNKALP APIEKTISKA KGQPREPQVY TLPPSREEMT  660
KNQVSLTCLV KGFYPSDIAV EWESNGQPEN NYKTTPPVLD SDGSFFLYSK LTVDKSRWQQ  720
GNVFSCSVMH EALHNHYTQK SLSLSPGK                                     748
```

```
SEQ ID NO: 174         moltype = DNA  length = 639
FEATURE                Location/Qualifiers
misc_feature           1..639
                       note = synthetic
source                 1..639
                       mol_type = other DNA
                       organism = synthetic construct
SEQUENCE: 174
gacatccaga tgacccagag ccccagcaca ctgagcgcca gcgtgggcga cagagtgacc  60
atcacatgca agtgccagct gagcgtgggc tacatgcact ggtatcagca gaagcccggc  120
aaggccccca agctgctgat ctacgacacc agcaagctgg cctccggcgt gcccagcaga  180
ttttctggca gcggctccgg caccgagttc accctgacaa tcagcagcct gcagcccgac  240
gacttcgcca cctactactg ttttcaaggc tccggctacc ccttcacctt cggcggaggc  300
accaagctgg aaatcaagcg gacggtggct gcaccatctg tcttcatctt cccgccatct  360
gatgagcagt tgaaatctgg aactgcctct gttgtgtgcc tgctgaataa cttctatccc  420
agagaggcca aagtacagtg gaaggtggat aacgccctcc aatcgggtaa ctcccaggag  480
agtgtcacag agcaggacag caaggacagc acctacagcc tcagcagcac cctgacgctg  540
agcaaagcag actacgagaa acacaaagtc tacgcctgcg aagtcaccca tcagggcctg  600
agctcgcccg tcacaaagag cttcaacagg ggagagtgt                         639
```

```
SEQ ID NO: 175          moltype = AA  length = 213
FEATURE                 Location/Qualifiers
REGION                  1..213
                        note = synthetic
source                  1..213
                        mol_type = protein
                        organism = synthetic construct
SEQUENCE: 175
DIQMTQSPST LSASVGDRVT ITCKCQLSVG YMHWYQQKPG KAPKLLIYDT SKLASGVPSR  60
FSGSGSGTEF TLTISSLQPD DFATYYCFQG SGYPFTFGGG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                              213

SEQ ID NO: 176          moltype = DNA  length = 18
FEATURE                 Location/Qualifiers
misc_feature            1..18
                        note = synthetic
source                  1..18
                        mol_type = other DNA
                        organism = synthetic construct
SEQUENCE: 176
caaggccagt ctggccaa                                               18

SEQ ID NO: 177          moltype = DNA  length = 2223
FEATURE                 Location/Qualifiers
misc_feature            1..2223
                        note = synthetic
source                  1..2223
                        mol_type = other DNA
                        organism = synthetic construct
SEQUENCE: 177
atgatgtatt gcggtgggaa tgaggtgttg tgcgggccgc gggttggctc gagcggtggc  60
agcggtggct ctggtggtct gagcggccgt tccgataatc atggcggcgg ttctcagacc  120
gtggtcacac aggagccctc actgacagtg agccctggcg ggaccgtcac actgacttgt  180
cgcagttcaa ctggcgccgt gactaccagc aattacgcta actgggtcca gcagaaacca  240
ggacaggcac cacgaggact gatcggagga actaataaga gagcaccagg aacccctgca  300
aggttctccg gatctctgct ggggggaaaa gccgctctga cactgagcgg cgtgcagcct  360
gaggacgaag ctgagtacta ttgcgcactg tggtactcca acctgtgggt gtttggcggg  420
ggaactaagc tgaccgtcct gggaggagga ggaagcggag gaggagggag cggaggagga  480
ggatccgaag tgcagctggt cgagagcgga ggaggactgg tgcagccagg aggatccctg  540
aagctgtctt gtgcagccag tggcttcacc ttcaacactt acgcaatgaa ctgggtgcgg  600
caggcacctg ggaagggact ggaatgggtc gcccggatca gatctaaata caataactat  660
gccacctact atgctgacag tgtgaaggat aggttcacca tttcacgcga cgatagcaaa  720
aacacagctt atctgcagat gaataacctg aagaccgagg atacagcagt gtactattgc  780
gtcagacacg gcaatttcgg gaactcttac gtgagttggt ttgcctattg gggacagggg  840
acactggtca ccgtctcctc aggaggtggt ggatcccagg tgcagctgaa acagagcggc  900
ccgggcctgg tgcagccgag ccagagcctg agcattacct gcaccgtgag cggctttagc  960
ctgaccaact atggcgtgca ttgggtgcgc cagagcccgg gcaaaggcct ggaatggctg  1020
ggcgtgattt ggagcggcgg caacaccgat tataacaccc cgtttaccag ccgcctgagc  1080
attaacaaag ataacagcaa aagccaggtg ttttttaaaa tgaacagcct gcaaagccag  1140
gataccgcga tttattattg cgcgcgcgcg ctgacctatt atgattatga atttgcgtat  1200
tggggccagg gcaccctggt gaccgtgagc gcggctagca ccaagggccc atcggtcttc  1260
cccctggcac cctcctccaa gagcacctct gggggcacag cggccctggg ctgcctggtc  1320
aaggactact tccccgaacc ggtgacggtg tcgtggaact caggcgccct gaccagcggc  1380
gtgcacacct tcccggctgt cctacagtcc tcaggactct actccctcag cagcgtggtg  1440
accgtgccct ccagcagctt gggcacccag acctacatct gcaacgtgaa tcacaagccc  1500
agcaacacca aggtggacaa gaaagttgag cccaaatctt gtgacaaaac tcacacatgc  1560
ccaccgtgcc cagcacctga actcctgggg ggaccgtcag tcttcctctt ccccccaaaa  1620
cccaaggaca ccctcatgat ctcccggacc cctgaggtca catgcgtggt ggtggacgtg  1680
agccacgaag accctgaggt caagttcaac tggtacgtgg acggcgtgga ggtgcataat  1740
gccaagacaa agccgcggga ggagcagtac cagagcacgt accgtgtggt cagcgtcctc  1800
accgtcctgc accaggactg gctgaatggc aaggagtaca agtgcaaggt ctccaacaaa  1860
gccctcccag cccccatcga gaaaaccatc tccaaagcca aagggcagcc ccgagaacca  1920
caggtgtaca ccctgccccc atcccgggag gagatgacca agaaccaggt cagcctgacc  1980
tgcctggtca aaggcttcta tcccagcgac atcgccgtgg agtgggagag caatgggcag  2040
ccggagaaca actacaagac cacgcctccc gtgctggact ccgacggctc cttcttcctc  2100
tacagcaagc tcaccgtgga caagagcagg tggcagcagg ggaacgtctt ctcatgctcc  2160
gtgatgcatg aggctctgca caaccactac acgcagaaga gcctctccct gtctccgggt  2220
aaa                                                               2223

SEQ ID NO: 178          moltype = AA  length = 6
FEATURE                 Location/Qualifiers
REGION                  1..6
                        note = synthetic
source                  1..6
                        mol_type = protein
                        organism = synthetic construct
```

```
SEQUENCE: 178
QGQSGQ                                                          6

SEQ ID NO: 179          moltype = AA  length = 741
FEATURE                 Location/Qualifiers
REGION                  1..741
                        note = synthetic
source                  1..741
                        mol_type = protein
                        organism = synthetic construct
SEQUENCE: 179
MMYCGGNEVL CGPRVGSSGG SGGSGGLSGR SDNHGGGSQT VVTQEPSLTV SPGGTVTLTC  60
RSSTGAVTTS NYANWVQQKP GQAPRGLIGG TNKRAPGTPA RFSGSLLGGK AALTLSGVQP  120
EDEAEYYCAL WYSNLWVFGG GTKLTVLGGG GSGGGGSGGG GSEVQLVESG GGLVQPGGSL  180
KLSCAASGFT FNTYAMNWVR QAPGKGLEWV ARIRSKYNNY ATYYADSVKD RFTISRDDSK  240
NTAYLQMNNL KTEDTAVYYC VRHGNFGNSY VSWFAYWGQG TLVTVSSGGG GSQVQLKQSG  300
PGLVQPSQSL SITCTVSGFS LTNYGVHWVR QSPGKGLEWL GVIWSGGNTD YNTPFTSRLS  360
INKDNSKSQV FFKMNSLQSQ DTAIYYCARA LTYYDYEFAY WGQGTLVTVS AASTKGPSVF  420
PLAPSSKSTS GGTAALGCLV KDYFPEPVTV SWNSGALTSG VHTFPAVLQS SGLYSLSSVV  480
TVPSSSLGTQ TYICNVNHKP SNTKVDKKVE PKSCDKTHTC PPCPAPELLG GPSVFLFPPK  540
PKDTLMISRT PEVTCVVVDV SHEDPEVKFN WYVDGVEVHN AKTKPREEQY QSTYRVVSVL  600
TVLHQDWLNG KEYKCKVSNK ALPAPIEKTI SKAKGQPREP QVYTLPPSRE EMTKNQVSLT  660
CLVKGFYPSD IAVEWESNGQ PENNYKTTPP VLDSDGSFFL YSKLTVDKSR WQQGNVFSCS  720
VMHEALHNHY TQKSLSLSPG K                                          741

SEQ ID NO: 180          moltype = DNA  length = 18
FEATURE                 Location/Qualifiers
misc_feature            1..18
                        note = synthetic
source                  1..18
                        mol_type = other DNA
                        organism = synthetic construct
SEQUENCE: 180
caaggccagt ctggccag                                             18

SEQ ID NO: 181          moltype = DNA  length = 765
FEATURE                 Location/Qualifiers
misc_feature            1..765
                        note = synthetic
source                  1..765
                        mol_type = other DNA
                        organism = synthetic construct
SEQUENCE: 181
tgcatctcac ctcgtggttg tccggacggc ccatacgtca tgtacggctc gagcggtggc  60
agcggtggct ctggtggatc cggtctgagc ggccgttccg ataatcatgg cagtagcggt  120
acccagatct tgctgaccca gagcccggtg attctgagcg tgagcccggg cgaacgtgtg  180
agctttagct gccgcgcgag ccagagcatt ggcaccaaca ttcattggta tcagcagcgc  240
accaacggca gcccgcgcct gctgattaaa tatgcgagcg aaagcattag cggcattccg  300
agccgcttta gcggcagcgg cagcggcacc gattttaccc tgagcattaa cagcgtggaa  360
agcgaagata ttgcggatta ttattgccag cagaacaaca actggccgac cacctttggc  420
gcgggcacca aactggaact gaaacgtacg gtggctgcac catctgtctt catcttcccg  480
ccatctgatg agcagttgaa atctggaact gcctctgttg tgtgcctgct gaataacttc  540
tatcccagag aggccaaagt acagtggaag gtggataacg ccctccaatc gggtaactcc  600
caggagagtg tcacagagca ggacagcaag gacagcacct acagcctcag cagcaccctg  660
acgctgagca aagcagacta cgagaaacac aaagtctacg cctgcgaagt cacccatcag  720
ggcctgagct cgcccgtcac aaagagcttc aacaggggag agtgt                765

SEQ ID NO: 182          moltype = AA  length = 255
FEATURE                 Location/Qualifiers
REGION                  1..255
                        note = synthetic
source                  1..255
                        mol_type = protein
                        organism = synthetic construct
SEQUENCE: 182
CISPRGCPDG PYVMYGSSGG SGGSGGSGLS GRSDNHGSSG TQILLTQSPV ILSVSPGERV  60
SFSCRASQSI GTNIHWYQQR TNGSPRLLIK YASESISGIP SRFSGSGSGT DFTLSINSVE  120
SEDIADYYCQ QNNNWPTTFG AGTKLELKRT VAAPSVFIFP PSDEQLKSGT ASVVCLLNNF  180
YPREAKVQWK VDNALQSGNS QESVTEQDSK DSTYSLSSTL TLSKADYEKH KVYACEVTHQ  240
GLSSPVTKSF NRGEC                                                255

SEQ ID NO: 183          moltype = DNA  length = 2223
FEATURE                 Location/Qualifiers
misc_feature            1..2223
                        note = synthetic
source                  1..2223
                        mol_type = other DNA
                        organism = synthetic construct
```

SEQUENCE: 183
atgatgtatt gcggtgggaa tgaggtgttg tgcgggccgc gggttggctc gagcggtggc 60
agcggtggct ctggtggtgg tggaggctcg ggcggtggga gcggcggcgg ttctcagacc 120
gtggtcacac aggagccctc actgacagtg agccctggcg ggaccgtcac actgacttgt 180
cgcagttcaa ctggcgccgt gactaccagc aattacgcta actgggtcca gcagaaacca 240
ggacaggcac cacgaggact gatcggagga actaataaga gagcaccagg aacccctgca 300
aggttctccg gatctctgct ggggggaaaa gccgctctga cactgagcgg cgtgcagcct 360
gaggacgaag ctgagtacta ttgcgcactg tggtactcca acctgtgggt gtttggcggg 420
ggaactaagc tgaccgtcct gggaggagga ggaagcggag gaggagggag cggaggagga 480
ggatccgaag tgcagctggt cgagagcgga ggaggactgg tgcagccagg aggatccctg 540
aagctgtctt gtgcagccag tggcttcacc ttcaacactt acgcaatgaa ctgggtgcgg 600
caggcacctg ggaagggact ggaatgggtc gcccggatca gatctaaata caataactat 660
gccacctact atgctgacag tgtgaaggat aggttcacca tttcacgcga cgatagcaaa 720
aacacagctt atctgcagat gaataacctg aagaccgagg atacagcagt gtactattgc 780
gtcagacacg gcaatttcgg gaactcttac gtgagttggt ttgcctattg gggacagggg 840
acactggtca ccgtctcctc aggaggtggt ggatcccagg tgcagctgaa acagagcggc 900
ccgggcctgg tgcagccgag ccagagcctg agcattacct gcaccgtgag cggctttagc 960
ctgaccaact atggcgtgca ttgggtgcgc cagagcccgg gcaaaggcct ggaatggctg 1020
ggcgtgattt ggagcggcgg caacaccgat tataacaccc cgtttaccag ccgcctgagc 1080
attaacaaag ataacagcaa aagccaggtg ttttttaaaa tgaacagcct gcaaagccag 1140
gataccgcga tttattattg cgcgcgcgcg ctgacctatt atgattatga atttgcgtat 1200
tggggccagg gcaccctggt gaccgtgagc gcggctagca ccaagggccc atcggtcttc 1260
cccctggcac cctcctccaa gagcacctct gggggcacag cggccctggg ctgcctggtc 1320
aaggactact tccccgaacc ggtgacggtg tcgtggaact caggcgccct gaccagcggc 1380
gtgcacacct tcccggctgt cctacagtcc tcaggactct actccctcag cagcgtggtg 1440
accgtgccct ccagcagctt gggcacccag acctacatct gcaacgtgaa tcacaagccc 1500
agcaacacca aggtggacaa gaaagttgag cccaaatctt gtgacaaaac tcacacatgc 1560
ccaccgtgcc cagcacctga actcctgggg ggaccgtcag tcttcctctt ccccccaaaa 1620
cccaaggaca ccctcatgat ctcccggacc cctgaggtca catgcgtggt ggtggacgtg 1680
agccacgaag accctgaggt caagttcaac tggtacgtgg acggcgtgga ggtgcataat 1740
gccaagacaa agccgcggga ggagcagtac cagagcacgt accgtgtggt cagcgtcctc 1800
accgtcctgc accaggactg gctgaatggc aaggagtaca agtgcaaggt ctccaacaaa 1860
gccctcccag cccccatcga gaaaaccatc tccaaagcca aagggcagcc ccgagaacca 1920
caggtgtaca ccctgccccc atcccgggag gagatgacca agaaccaggt cagcctgacc 1980
tgcctggtca aaggcttcta tcccagcgac atcgccgtgg agtgggagag caatgggcag 2040
ccggagaaca actacaagac cacgcctccc gtgctggact ccgacggctc cttcttcctc 2100
tacagcaagc tcaccgtgga caagagcagg tggcagcagg ggaacgtctt ctcatgctcc 2160
gtgatgcatg aggctctgca caaccactac acgcagaaga gcctctccct gtctccgggt 2220
aaa 2223

SEQ ID NO: 184 moltype = AA length = 741
FEATURE Location/Qualifiers
REGION 1..741
note = synthetic
source 1..741
mol_type = protein
organism = synthetic construct
SEQUENCE: 184
MMYCGGNEVL CGPRVGSSGG SGGSGGGGS GGGSGGGSQT VVTQEPSLTV SPGGTVTLTC 60
RSSTGAVTTS NYANWVQQKP GQAPRGLIGG TNKRAPGTPA RFSGSLLGGK AALTLSGVQP 120
EDEAEYYCAL WYSNLWVFGG GTKLTVLGGG GSGGGGSGGG GSEVQLVESG GGLVQPGGSL 180
KLSCAASGFT FNTYAMNWVR QAPGKGLEWV ARIRSKYNNY ATYYADSVKD RFTISRDDSK 240
NTAYLQMNNL KTEDTAVYYC VRHGNFGNSY VSWFAYWGQG TLVTVSSGGG GSQVQLKQSG 300
PGLVQPSQSL SITCTVSGFS LTNYGVHWVR QSPGKGLEWL GVIWSGGNTD YNTPFTSRLS 360
INKDNSKSQV FFKMNSLQSQ DTAIYYCARA LTYYDYEFAY WGQGTLVTVS AASTKGPSVF 420
PLAPSSKSTS GGTAALGCLV KDYFPEPVTV SWNSGALTSG VHTFPAVLQS SGLYSLSSVV 480
TVPSSSLGTQ TYICNVNHKP SNTKVDKKVE PKSCDKTHTC PPCPAPELLG GPSVFLFPPK 540
PKDTLMISRT PEVTCVVVDV SHEDPEVKFN WYVDGVEVHN AKTKPREEQY QSTYRVVSVL 600
TVLHQDWLNG KEYKCKVSNK ALPAPIEKTI SKAKGQPREP QVYTLPPSRE EMTKNQVSLT 660
CLVKGFYPSD IAVEWESNGQ PENNYKTTPP VLDSDGSFFL YSKLTVDKSR WQQGNVFSCS 720
VMHEALHNHY TQKSLSLSPG K 741

SEQ ID NO: 185 moltype = DNA length = 756
FEATURE Location/Qualifiers
misc_feature 1..756
note = synthetic
source 1..756
mol_type = other DNA
organism = synthetic construct
SEQUENCE: 185
tgcatctcac ctcgtggttg tccggacggc ccatacgtca tgtacggctc gagcggtggc 60
agcggtggct ctggtggctc aggtggaggc tcgggcggtg ggagcggcgg ttctgatatc 120
ttgctgaccc agagcccggt gattctgagc gtgagcccgg gcgaacgtgt gagctttagc 180
tgccgcgcga gccagagcat tggcaccaac attcattggt atcagcagcg caccaacggc 240
agcccgcgcc tgctgattaa atatgcgagc gaaagcatta gcggcattcc gagccgcttt 300
agcggcagcg gcagcggcac cgattttacc ctgagcatta acagcgtgga aagcgaagat 360
attgcggatt attattgcca gcagaacaac aactggccga ccacctttgg cgcgggcacc 420
aaactggaac tgaaacgtac ggtggctgca ccatctgtct tcatcttccc gccatctgat 480
gagcagttga aatctggaac tgcctctgtt gtgtgcctgc tgaataactt ctatcccaga 540

-continued

```
gaggccaaag tacagtggaa ggtggataac gccctccaat cgggtaactc ccaggagagt  600
gtcacagagc aggacagcaa ggacagcacc tacagcctca gcagcaccct gacgctgagc  660
aaagcagact acgagaaaca caaagtctac gcctgcgaag tcacccatca gggcctgagc  720
tcgcccgtca caaagagctt caacagggga gagtgt                            756

SEQ ID NO: 186          moltype = AA  length = 252
FEATURE                 Location/Qualifiers
REGION                  1..252
                        note = synthetic
source                  1..252
                        mol_type = protein
                        organism = synthetic construct
SEQUENCE: 186
CISPRGCPDG PYVMYGSSGG SGGSGGSGGG SGGGSGGSDI LLTQSPVILS VSPGERVSFS  60
CRASQSIGTN IHWYQQRTNG SPRLLIKYAS ESISGIPSRF SGSGSGTDFT LSINSVESED  120
IADYYCQQNN NWPTTFGAGT KLELKRTVAA PSVFIFPPSD EQLKSGTASV VCLLNNFYPR  180
EAKVQWKVDN ALQSGNSQES VTEQDSKDST YSLSSTLTLS KADYEKHKVY ACEVTHQGLS  240
SPVTKSFNRG EC                                                      252

SEQ ID NO: 187          moltype = DNA  length = 2238
FEATURE                 Location/Qualifiers
misc_feature            1..2238
                        note = synthetic
source                  1..2238
                        mol_type = other DNA
                        organism = synthetic construct
SEQUENCE: 187
atgatgtatt gcggtgggaa tgaggtgttg tgcgggccgc gggttggctc gagcggtggc  60
agcggtggct ctggtggtat ctcttccgga ctgctgtccg gcagatccga caatcacggc  120
ggcggttctc agaccgtggt cacacaggag ccctcactga cagtgagccc tggcgggacc  180
gtcacactga cttgtcgcag ttcaactggc gccgtgacta ccagcaatta cgctaactgg  240
gtccagcaga aaccaggaca ggcaccacga ggactgatcg gaggaactaa taagagagca  300
ccaggaaccc ctgcaaggtt ctccggatct ctgctggggg gaaaagccgc tctgacactg  360
agcggcgtgc agcctgagga cgaagctgag tactattgcg cactgtggta ctccaacctg  420
tgggtgtttg gcgggggaac taagctgacc gtcctgggag gaggaggaag cggaggagga  480
gggagcggag gaggaggatc cgaagtgcag ctggtcgaga gcggaggagg actggtgcag  540
ccaggaggat ccctgaagct gtcttgtgca gccagtggct tcaccttcaa cacttacgca  600
atgaactggg tgcggcaggc acctgggaag ggactggaat gggtcgcccg gatcagatct  660
aaatacaata actatgccac ctactatgct gacagtgtga aggataggtt caccatttca  720
cgcgacgata gcaaaaacac agcttatctg cagatgaata acctgaagac cgaggataca  780
gcagtgtact attgcgtcag acacggcaat ttcgggaact cttacgtgag ttggtttgcc  840
tattggggac aggggacact ggtcaccgtc tcctcaggag gtggtggatc ccaggtgcag  900
ctgaaacaga gcggcccggg cctggtgcag ccgagccaga gcctgagcat tacctgcacc  960
gtgagcggct ttagcctgac caactatggc gtgcattggg tgcgccagag cccgggcaaa  1020
ggcctggaat ggctgggcgt gatttggagc ggcggcaaca ccgattataa caccccgttt  1080
accagccgcc tgagcattaa caaagataac agcaaaagcc aggtgttttt taaaatgaac  1140
agcctgcaaa gccaggatac cgcgatttat tattgcgcgc gcgcgctgac ctattatgat  1200
tatgaatttg cgtattgggg ccagggcacc ctggtgaccg tgagcgcggc tagcaccaag  1260
ggcccatcgg tcttccccct ggcaccctcc tccaagagca cctctggggg cacagcggcc  1320
ctgggctgcc tggtcaagga ctacttcccc gaaccggtga cggtgtcgtg gaactcaggc  1380
gccctgacca gcggcgtgca caccttcccg gctgtcctac agtcctcagg actctactcc  1440
ctcagcagcg tggtgaccgt gccctccagc agcttgggca cccagaccta catctgcaac  1500
gtgaatcaca agcccagcaa caccaaggtg gacaagaaag ttgagcccaa atcttgtgac  1560
aaaactcaca catgcccacc gtgcccagca cctgaactcc tggggggacc gtcagtcttc  1620
ctcttccccc caaaacccaa ggacaccctc atgatctccc ggacccctga ggtcacatgc  1680
gtggtggtgg acgtgagcca cgaagaccct gaggtcaagt tcaactggta cgtggacggc  1740
gtggaggtgc ataatgccaa gacaaagccg cgggaggagc agtaccagag cacgtaccgt  1800
gtggtcagcg tcctcaccgt cctgcaccag gactggctga atggcaagga gtacaagtgc  1860
aaggtctcca acaaagccct cccagccccc atcgagaaaa ccatctccaa agccaaaggg  1920
cagccccgag aaccacaggt gtacaccctg cccccatccc gggaggagat gaccaagaac  1980
caggtcagcc tgacctgcct ggtcaaaggc ttctatccca gcgacatcgc cgtggagtgg  2040
gagagcaatg ggcagccgga gaacaactac aagaccacgc ctcccgtgct ggactccgac  2100
ggctccttct tcctctacag caagctcacc gtggacaaga gcaggtggca gcaggggaac  2160
gtcttctcat gctccgtgat gcatgaggct ctgcacaacc actacacgca gaagagcctc  2220
tccctgtctc cgggtaaa                                                2238

SEQ ID NO: 188          moltype = AA  length = 746
FEATURE                 Location/Qualifiers
REGION                  1..746
                        note = synthetic
source                  1..746
                        mol_type = protein
                        organism = synthetic construct
SEQUENCE: 188
MMYCGGNEVL CGPRVGSSGG SGGSGGISSG LLSGRSDNHG GGSQTVVTQE PSLTVSPGGT  60
VTLTCRSSTG AVTTSNYANW VQQKPGQAPR GLIGGTNKRA PGTPARFSGS LLGGKAALTL  120
SGVQPEDEAE YYCALWYSNL WVFGGGTKLT VLGGGGSGGG GSGGGGSEVQ LVESGGGLVQ  180
PGGSLKLSCA ASGFTFNTYA MNWVRQAPGK GLEWVARIRS KYNNYATYYA DSVKDRFTIS  240
RDDSKNTAYL QMNNLKTEDT AVYYCVRHGN FGNSYVSWFA YWGQGTLVTV SSGGGGSQVQ  300
```

-continued

```
LKQSGPGLVQ PSQSLSITCT VSGFSLTNYG VHWVRQSPGK GLEWLGVIWS GGNTDYNTPF  360
TSRLSINKDN SKSQVFFKMN SLQSQDTAIY YCARALTYYD YEFAYWGQGT LVTVSAASTK  420
GPSVFPLAPS SKSTSGGTAA LGCLVKDYFP EPVTVSWNSG ALTSGVHTFP AVLQSSGLYS  480
LSSVVTVPSS SLGTQTYICN VNHKPSNTKV DKKVEPKSCD KTHTCPPCPA PELLGGPSVF  540
LFPPKPKDTL MISRTPEVTC VVVDVSHEDP EVKFNWYVDG VEVHNAKTKP REEQYQSTYR  600
VVSVLTVLHQ DWLNGKEYKC KVSNKALPAP IEKTISKAKG QPREPQVYTL PPSREEMTKN  660
QVSLTCLVKG FYPSDIAVEW ESNGQPENNY KTTPPVLDSD GSFFLYSKLT VDKSRWQQGN  720
VFSCSVMHEA LHNHYTQKSL SLSPGK                                      746

SEQ ID NO: 189          moltype = DNA  length = 780
FEATURE                 Location/Qualifiers
misc_feature            1..780
                        note = synthetic
source                  1..780
                        mol_type = other DNA
                        organism = synthetic construct
SEQUENCE: 189
tgcatctcac ctcgtggttg tccggacggc ccatacgtca tgtacggctc gagcggtggc  60
agcggtggct ctggtggatc cggtattagc agtggtctgt taagcggtcg tagcgataat  120
catggcagta gcggtaccca gatcttgctg acccagagcc cggtgattct gagcgtgagc  180
ccgggcgaac gtgtgagctt tagctgccgc gcgagccaga gcattggcac caacattcat  240
tggtatcagc agcgcaccaa cggcagcccg cgcctgctga ttaaatatgc gagcgaaagc  300
attagcggca ttccgagccg ctttagcggc agcggcagcg gcaccgattt taccctgagc  360
attaacagcg tggaaagcga agatattgcg gattattatt gccagcagaa caacaactgg  420
ccgaccacct ttggcgcggg caccaaactg gaactgaaac gtacggtggc tgcaccatct  480
gtcttcatct tcccgccatc tgatgagcag ttgaaatctg gaactgcctc tgttgtgtgc  540
ctgctgaata acttctatcc cagagaggcc aaagtacagt ggaaggtgga taacgccctc  600
caatcgggta actcccagga gagtgtcaca gagcaggaca gcaaggacag cacctacagc  660
ctcagcagca ccctgacgct gagcaaagca gactacgaga aacacaaagt ctacgcctgc  720
gaagtcaccc atcagggcct gagctcgccc gtcacaaaga gcttcaacag gggagagtgt  780

SEQ ID NO: 190          moltype = AA  length = 260
FEATURE                 Location/Qualifiers
REGION                  1..260
                        note = synthetic
source                  1..260
                        mol_type = protein
                        organism = synthetic construct
SEQUENCE: 190
CISPRGCPDG PYVMYGSSGG SGGSGGSGIS SGLLSGRSDN HGSSGTQILL TQSPVILSVS  60
PGERVSFSCR ASQSIGTNIH WYQQRTNGSP RLLIKYASES ISGIPSRFSG SGSGTDFTLS  120
INSVESEDIA DYYCQQNNNW PTTFGAGTKL ELKRTVAAPS VFIFPPSDEQ LKSGTASVVC  180
LLNNFYPREA KVQWKVDNAL QSGNSQESVT EQDSKDSTYS LSSTLTLSKA DYEKHKVYAC  240
EVTHQGLSSP VTKSFNRGEC                                             260

SEQ ID NO: 191          moltype = DNA  length = 18
FEATURE                 Location/Qualifiers
misc_feature            1..18
                        note = synthetic
source                  1..18
                        mol_type = other DNA
                        organism = synthetic construct
SEQUENCE: 191
caaggccagt ctggatcc                                               18

SEQ ID NO: 192          moltype = DNA  length = 2226
FEATURE                 Location/Qualifiers
misc_feature            1..2226
                        note = synthetic
source                  1..2226
                        mol_type = other DNA
                        organism = synthetic construct
SEQUENCE: 192
ggttatctgt ggggttgcga gtggaattgc ggagggatca ctacaggctc gagcggtggc  60
agcggtggct ctggtggtct gagcggccgt tccgataatc atggcggcgg ttctcaaact  120
gtagtaactc aagaaccaag cttctccgtc tcccctgggg gaacagtcac acttacctgc  180
cgaagtagta caggtgctgt tacgaccagt aactatgcca attgggtaca acaaacgcct  240
ggtcaggctc cgcgcggatt gataggaggc acgaataaac gggcacccgg tgtcccggac  300
agattcagcg gaagcatact cggtaataag gcagctctta ctatcactgg ggcccaagct  360
gatgatgaaa gtgattatta ttgtgcgctc tggtacagca acctctgggt gtttgggggt  420
ggcacgaaac ttactgtctt gggcggcggc ggatcagggg gaggtggctc tggaggagga  480
ggctcagaag tccaactggt cgaatccggg ggagggctcg tacagccggg tgggtccctc  540
aaactctctt gtgcggcctc agggtttacc ttcagtacat acgcgatgaa ttgggtccgg  600
caggccagtg ggaaagggct cgaatgggta ggacgaatcc gatcaaaata caacaactac  660
gctacttatt acgctgattc cgtgaaggac agattcacaa tatcccgcga cgatagcaag  720
aatacggcat atcttcagat gaattctctt aaaactgagg ataccgctgt gtattactgc  780
acaagacatg gtaattttgg aaactcatat gtctcttggt tcgcttattg gggacagggc  840
acgttggtta ccgtgtctag cggaggtggt ggatcccagg tgcagctgaa acagagcggc  900
ccgggcctgg tgcagccgag ccagagcctg agcattacct gcaccgtgag cggctttagc  960
```

-continued

```
ctgaccaact atggcgtgca ttgggtgcgc cagagcccgg gcaaaggcct ggaatggctg  1020
ggcgtgattt ggagcggcgg caacaccgat tataacaccc cgtttaccag ccgcctgagc  1080
attaacaaag ataacagcaa aagccaggtg ttttttaaaa tgaacagcct gcaaagccag  1140
gataccgcga tttattattg cgcgcgcgcg ctgacctatt atgattatga atttgcgtat  1200
tggggccagg gcaccctggt gaccgtgagc gcggctagca ccaagggccc atcggtcttc  1260
cccctggcac cctcctccaa gagcacctct gggggcacag cggccctggg ctgcctggtc  1320
aaggactact tccccgaacc ggtgacggtg tcgtggaact caggcgccct gaccagcggc  1380
gtgcacacct tcccggctgt cctacagtcc tcaggactct actccctcag cagcgtggtg  1440
accgtgccct ccagcagctt gggcacccag acctacatct gcaacgtgaa tcacaagccc  1500
agcaacacca aggtggacaa gaaagttgag cccaaatctt gtgacaaaac tcacacatgc  1560
ccaccgtgcc cagcacctga atttgaaggg ggaccgtcag tcttcctctt ccccccaaaa  1620
cccaaggaca ccctcatgat ctcccggacc cctgaggtca catgcgtggt ggtggacgtg  1680
agccacgaag accctgaggt caagttcaac tggtacgtgg acggcgtgga ggtgcataat  1740
gccaagacaa agccgcggga ggagcagtac aatagcacgt accgtgtggt cagcgtcctc  1800
accgtcctgc accaggactg gctgaatggc aaggagtaca agtgcaaggt ctccaacaaa  1860
gccctcccag cctcaatcga gaaaaccatc tccaaagcca aagggcagcc ccgagaacca  1920
caggtgtaca ccctgccccc atcccgggag gagatgacca agaaccaggt cagcctgacc  1980
tgcctggtca aaggcttcta tcccagcgac atcgccgtgg agtgggagag caatgggcag  2040
ccggagaaca actacaagac cacgcctccc gtgctggact ccgacggctc cttcttcctc  2100
tacagcaagc tcaccgtgga caagagcagg tggcagcagg ggaacgtctt ctcatgctcc  2160
gtgatgcatg aggctctgca caaccactac acgcagaaga gcctctccct gtctccgggt  2220
aaatga                                                             2226

SEQ ID NO: 193          moltype = AA  length = 741
FEATURE                 Location/Qualifiers
REGION                  1..741
                        note = synthetic
source                  1..741
                        mol_type = protein
                        organism = synthetic construct
SEQUENCE: 193
GYLWGCEWNC GGITTGSSGG SGGSGGLSGR SDNHGGGSQT VVTQEPSFSV SPGGTVTLTC  60
RSSTGAVTTS NYANWVQQTP GQAPRGLIGG TNKRAPGVPD RFSGSILGNK AALTITGAQA  120
DDESDYYCAL WYSNLWVFGG GTKLTVLGGG GSGGGGSGGG GSEVQLVESG GGLVQPGGSL  180
KLSCAASGFT FSTYAMNWVR QASGKGLEWV GRIRSKYNNY ATYYADSVKD RFTISRDDSK  240
NTAYLQMNSL KTEDTAVYYC TRHGNFGNSY VSWFAYWGQG TLVTVSSGGG GSQVQLKQSG  300
PGLVQPSQSL SITCTVSGFS LTNYGVHWVR QSPGKGLEWL GVIWSGGNTD YNTPFTSRLS  360
INKDNSKSQV FFKMNSLQSQ DTAIYYCARA LTYYDYEFAY WGQGTLVTVS AASTKGPSVF  420
PLAPSSKSTS GGTAALGCLV KDYFPEPVTV SWNSGALTSG VHTFPAVLQS SGLYSLSSVV  480
TVPSSSLGTQ TYICNVNHKP SNTKVDKKVE PKSCDKTHTC PPCPAPEFEG GPSVFLFPPK  540
PKDTLMISRT PEVTCVVVDV SHEDPEVKFN WYVDGVEVHN AKTKPREEQY NSTYRVVSVL  600
TVLHQDWLNG KEYKCKVSNK ALPASIEKTI SKAKGQPREP QVYTLPPSRE EMTKNQVSLT  660
CLVKGFYPSD IAVEWESNGQ PENNYKTTPP VLDSDGSFFL YSKLTVDKSR WQQGNVFSCS  720
VMHEALHNHY TQKSLSLSPG K                                            741

SEQ ID NO: 194          moltype = DNA  length = 2226
FEATURE                 Location/Qualifiers
misc_feature            1..2226
                        note = synthetic
source                  1..2226
                        mol_type = other DNA
                        organism = synthetic construct
SEQUENCE: 194
ggttatctgt ggggttgcga gtggaattgc ggagggatca ctacaggctc gagcggtggc  60
agcggtggct ctggtggtct gagcggccgt tccgataatc atggcggcgg ttctcaaact  120
gtagtaactc aagaaccaag cttctccgtc tcccctgggg gaacagtcac acttacctgc  180
cgaagtagta caggtgctgt tacgaccagt aactatgcca attgggtaca acaaacgcct  240
ggtcaggctc cgcgcggatt gataggaggc acgaataaac gggcacccgg tgtcccggac  300
agattcagcg gaagcatact cggtaataag gcagctctta ctatcactgg ggcccaagct  360
gatgatgaaa gtgattatta ttgtgcgctc tggtacagca acctctgggt gtttgggggt  420
ggcacgaaac ttactgtctt gggcggcggc ggatcagggg gaggtggctc tggaggagga  480
ggctcagaag tccaactggt cgaatccggg ggagggctcg tacagccggg tgggtccctc  540
aaactctctt gtgcggcctc agggtttacc ttcagtacat acgcgatgaa ttgggtccgg  600
caggccagtg ggaaagggct cgaatgggta ggacgaatcc gatcaaaata caacaactac  660
gctacttatt acgctgattc cgtgaaggac agattcacaa tatcccgcga cgatagcaag  720
aatacggcat atcttcagat gaattctctt aaaactgagg ataccgctgt gtattactgc  780
acaagacatg gtaattttgg aaactcatat gtctcttggt tcgcttattg gggacagggc  840
acgttggtta ccgtgtctag cggaggtggt ggatcccagg tgcagctgaa acagagcggc  900
ccgggcctgg tgcagccgag ccagagcctg agcattacct gcaccgtgag cggctttagc  960
ctgaccaact atggcgtgca ttgggtgcgc cagagcccgg gcaaaggcct ggaatggctg  1020
ggcgtgattt ggagcggcgg caacaccgat tataacaccc cgtttaccag ccgcctgagc  1080
attaacaaag ataacagcaa aagccaggtg ttttttaaaa tgaacagcct gcaaagccag  1140
gataccgcga tttattattg cgcgcgcgcg ctgacctatt atgattatga atttgcgtat  1200
tggggccagg gcaccctggt gaccgtgagc gcggctagca ccaagggccc atcggtcttc  1260
cccctggcac cctcctccaa gagcacctct gggggcacag cggccctggg ctgcctggtc  1320
aaggactact tccccgaacc ggtgacggtg tcgtggaact caggcgccct gaccagcggc  1380
gtgcacacct tcccggctgt cctacagtcc tcaggactct actccctcag cagcgtggtg  1440
accgtgccct ccagcagctt gggcacccag acctacatct gcaacgtgaa tcacaagccc  1500
agcaacacca aggtggacaa gaaagttgag cccaaatctt gtgacaaaac tcacacatgc  1560
```

-continued

```
ccaccgtgcc cagcacctga atttgaaggg ggaccgtcag tcttcctctt ccccccaaaa  1620
cccaaggaca ccctcatgat ctcccggacc cctgaggtca catgcgtggt ggtggacgtg  1680
agccacgaag accctgaggt caagttcaac tggtacgtgg acggcgtgga ggtgcataat  1740
gccaagacaa agccgcggga ggagcagtac cagagcacgt accgtgtggt cagcgtcctc  1800
accgtcctgc accaggactg gctgaatggc aaggagtaca agtgcaaggt ctccaacaaa  1860
gccctcccag cctcaatcga gaaaaccatc tccaaagcca aagggcagcc ccgagaacca  1920
caggtgtaca ccctgccccc atcccgggag gagatgacca agaaccaggt cagcctgacc  1980
tgcctggtca aaggcttcta tcccagcgac atcgccgtgg agtgggagag caatgggcag  2040
ccggagaaca actacaagac cacgcctccc gtgctggact ccgacggctc cttcttcctc  2100
tacagcaagc tcaccgtgga caagagcagg tggcagcagg ggaacgtctt ctcatgctcc  2160
gtgatgcatg aggctctgca caaccactac acgcagaaga gcctctccct gtctccgggt  2220
aaatga                                                            2226

SEQ ID NO: 195          moltype = AA  length = 741
FEATURE                 Location/Qualifiers
REGION                  1..741
                        note = synthetic
source                  1..741
                        mol_type = protein
                        organism = synthetic construct
SEQUENCE: 195
GYLWGCEWNC GGITTGSSGG SGGSGGLSGR SDNHGGGSQT VVTQEPSFSV SPGGTVTLTC  60
RSSTGAVTTS NYANWVQQTP GQAPRGLIGG TNKRAPGVPD RFSGSILGNK AALTITGAQA  120
DDESDYYCAL WYSNLWVFGG GTKLTVLGGG GSGGGGSGGG GSEVQLVESG GGLVQPGGSL  180
KLSCAASGFT FSTYAMNWVR QASGKGLEWV GRIRSKYNNY ATYYADSVKD RFTISRDDSK  240
NTAYLQMNSL KTEDTAVYYC TRHGNFGNSY VSWFAYWGQG TLVTVSSGGG GSQVQLKQSG  300
PGLVQPSQSL SITCTVSGFS LTNYGVHWVR QSPGKGLEWL GVIWSGGNTD YNTPFTSRLS  360
INKDNSKSQV FFKMNSLQSQ DTAIYYCARA LTYYDYEFAY WGQGTLVTVS AASTKGPSVF  420
PLAPSSKSTS GGTAALGCLV KDYFPEPVTV SWNSGALTSG VHTFPAVLQS SGLYSLSSVV  480
TVPSSSLGTQ TYICNVNHKP SNTKVDKKVE PKSCDKTHTC PPCPAPEFEG GPSVFLFPPK  540
PKDTLMISRT PEVTCVVVDV SHEDPEVKFN WYVDGVEVHN AKTKPREEQY QSTYRVVSVL  600
TVLHQDWLNG KEYKCKVSNK ALPASIEKTI SKAKGQPREP QVYTLPPSRE EMTKNQVSLT  660
CLVKGFYPSD IAVEWESNGQ PENNYKTTPP VLDSDGSFFL YSKLTVDKSR WQQGNVFSCS  720
VMHEALHNHY TQKSLSLSPG K                                          741

SEQ ID NO: 196          moltype = DNA  length = 2223
FEATURE                 Location/Qualifiers
misc_feature            1..2223
                        note = synthetic
source                  1..2223
                        mol_type = other DNA
                        organism = synthetic construct
SEQUENCE: 196
ggttatctgt ggggttgcga gtggaattgc ggagggatca ctacaggctc gagcggtggc  60
agcggtggct ctggtggtct gagcggccgt tccgatggtc atggcggcgg ttctcaaact  120
gtagtaactc aagaaccaag cttctccgtc tcccctgggg gaacagtcac acttacctgc  180
cgaagtagta caggtgctgt tacgaccagt aactatgcca attgggtaca acaaacgcct  240
ggtcaggctc cgcgcggatt gataggaggc acgaataaac gggcacccgg tgtcccggac  300
agattcagcg gaagcatact cggtaataag gcagctctta ctatcactgg ggcccaagct  360
gatgatgaaa gtgattatta ttgtgcgctc tggtacagca acctctgggt gtttgggggt  420
ggcacgaaac ttactgtctt gggcggcggc ggatcagggg gaggtggctc tggaggagga  480
ggctcagaag tccaactggt cgaatccggg ggagggctcg tacagccggg tgggtccctc  540
aaactctctt gtgcggcctc agggtttacc ttcagtacat acgcgatgaa ttgggtccgg  600
caggccagtg ggaaagggct cgaatgggta ggacgaatcc gatcaaaata caacaactac  660
gctacttatt acgctgattc cgtgaaggac agattcacaa tatcccgcga cgatagcaag  720
aatacggcat atcttcagat gaattctctt aaaactgagg ataccgctgt gtattactgc  780
acaagacatg gtaattttgg aaactcatat gtctcttggt tcgcttattg gggacagggc  840
acgttggtta ccgtgtctag cggaggtggt ggatcccagg tgcagctgaa acagagcggc  900
ccgggcctgg tgcagccgag ccagagcctg agcattacct gcaccgtgag cggctttagc  960
ctgaccaact atggcgtgca ttgggtgcgc cagagcccgg gcaaaggcct ggaatggctg  1020
ggcgtgattt ggagcggcgg caacaccgat tataacaccc cgtttaccag ccgcctgagc  1080
attaacaaag ataacagcaa aagccaggtg ttttttaaaa tgaacagcct gcaaagccag  1140
gataccgcga tttattattg cgcgcgcgcg ctgacctatt atgattatga atttgcgtat  1200
tggggccagg gcaccctggt gaccgtgagc gcggctagca ccaagggccc atcggtcttc  1260
cccctggcac cctcctccaa gagcacctct gggggcacag cggccctggg ctgcctggtc  1320
aaggactact tccccgaacc ggtgacggtg tcgtggaact caggcgccct gaccagcggc  1380
gtgcacacct tcccggctgt cctacagtcc tcaggactct actccctcag cagcgtggtg  1440
accgtgccct ccagcagctt gggcacccag acctacatct gcaacgtgaa tcacaagccc  1500
agcaacacca aggtggacaa gaaagttgag cccaaatctt gtgacaaaac tcacacatgc  1560
ccaccgtgcc cagcacctga atttgaaggg ggaccgtcag tcttcctctt ccccccaaaa  1620
cccaaggaca ccctcatgat ctcccggacc cctgaggtca catgcgtggt ggtggacgtg  1680
agccacgaag accctgaggt caagttcaac tggtacgtgg acggcgtgga ggtgcataat  1740
gccaagacaa agccgcggga ggagcagtac cagagcacgt accgtgtggt cagcgtcctc  1800
accgtcctgc accaggactg gctgaatggc aaggagtaca agtgcaaggt ctccaacaaa  1860
gccctcccag cctcaatcga gaaaaccatc tccaaagcca aagggcagcc ccgagaacca  1920
caggtgtaca ccctgccccc atcccgggag gagatgacca agaaccaggt cagcctgacc  1980
tgcctggtca aaggcttcta tcccagcgac atcgccgtgg agtgggagag caatgggcag  2040
ccggagaaca actacaagac cacgcctccc gtgctggact ccgacggctc cttcttcctc  2100
tacagcaagc tcaccgtgga caagagcagg tggcagcagg ggaacgtctt ctcatgctcc  2160
```

-continued

```
gtgatgcatg aggctctgca caaccactac acgcagaaga gcctctccct gtctccgggt  2220
aaa                                                                2223

SEQ ID NO: 197         moltype = AA  length = 741
FEATURE                Location/Qualifiers
REGION                 1..741
                       note = synthetic
source                 1..741
                       mol_type = protein
                       organism = synthetic construct
SEQUENCE: 197
GYLWGCEWNC GGITTGSSGG SGGSGGLSGR SDDHGGGSQT VVTQEPSFSV SPGGTVTLTC  60
RSSTGAVTTS NYANWVQQTP GQAPRGLIGG TNKRAPGVPD RFSGSILGNK AALTITGAQA  120
DDESDYYCAL WYSNLWVFGG GTKLTVLGGG GSGGGGSGGG GSEVQLVESG GGLVQPGGSL  180
KLSCAASGFT FSTYAMNWVR QASGKGLEWV GRIRSKYNNY ATYYADSVKD RFTISRDDSK  240
NTAYLQMNSL KTEDTAVYYC TRHGNFGNSY VSWFAYWGQG TLVTVSSGGG GSQVQLKQSG  300
PGLVQPSQSL SITCTVSGFS LTNYGVHWVR QSPGKGLEWL GVIWSGGNTD YNTPFTSRLS  360
INKDNSKSQV FFKMNSLQSQ DTAIYYCARA LTYYDYEFAY WGQGTLVTVS AASTKGPSVF  420
PLAPSSKSTS GGTAALGCLV KDYFPEPVTV SWNSGALTSG VHTFPAVLQS SGLYSLSSVV  480
TVPSSSLGTQ TYICNVNHKP SNTKVDKKVE PKSCDKTHTC PPCPAPEFEG GPSVFLFPPK  540
PKDTLMISRT PEVTCVVVDV SHEDPEVKFN WYVDGVEVHN AKTKPREEQY QSTYRVVSVL  600
TVLHQDWLNG KEYKCKVSNK ALPASIEKTI SKAKGQPREP QVYTLPPSRE EMTKNQVSLT  660
CLVKGFYPSD IAVEWESNGQ PENNYKTTPP VLDSDGSFFL YSKLTVDKSR WQQGNVFSCS  720
VMHEALHNHY TQKSLSLSPG K                                            741

SEQ ID NO: 198         moltype = DNA  length = 768
FEATURE                Location/Qualifiers
misc_feature           1..768
                       note = Synthetic
source                 1..768
                       mol_type = other DNA
                       organism = synthetic construct
SEQUENCE: 198
caaggtctta gttgtgaagg ttgggcgatg aatagagaac aatgtcgagc cggaggtggc  60
tcgagcggcg gctctatctc ttccggactg ctgtccggca gatccgacca gcacggcgga  120
ggatcccaaa tcctgctgac acagtctcct gtcatactga gtgtctcccc cggcgagaga  180
gtctctttct catgtcgggc cagtcagtct attgggacta acatacactg gtaccagcaa  240
cgcaccaacg gaagcccgcg cctgctgatt aaatatgcga gcgaaagcat tagcggcatt  300
ccgagccgct ttagcggcag cggcagcggc accgatttta ccctgagcat taacagcgtg  360
gaaagcgaag atattgcgga ttattattgc cagcagaaca acaactggcc gaccaccttt  420
ggcgcgggca ccaaactgga actgaaacgt acggtggctg caccatctgt cttcatcttc  480
ccgccatctg atgagcagtt gaaatctgga actgcctctg ttgtgtgcct gctgaataac  540
ttctatccca gagaggccaa agtacagtgg aaggtggata acgccctcca atcgggtaac  600
tcccaggaga gtgtcacaga gcaggacagc aaggacagca cctacagcct cagcagcacc  660
ctgacgctga gcaaagcaga ctacgagaaa cacaaagtct acgcctgcga agtcacccat  720
cagggcctga gctcgcccgt cacaaagagc ttcaacaggg gagagtgt             768

SEQ ID NO: 199         moltype = AA  length = 254
FEATURE                Location/Qualifiers
REGION                 1..254
                       note = synthetic
source                 1..254
                       mol_type = protein
                       organism = synthetic construct
SEQUENCE: 199
LSCEGWAMNR EQCRAGGGSS GGSISSGLLS GRSDQHGGGS QILLTQSPVI LSVSPGERVS  60
FSCRASQSIG TNIHWYQQRT NGSPRLLIKY ASESISGIPS RFSGSGSGTD FTLSINSVES  120
EDIADYYCQQ NNNWPTTFGA GTKLELKRTV AAPSVFIFPP SDEQLKSGTA SVVCLLNNFY  180
PREAKVQWKV DNALQSGNSQ ESVTEQDSKD STYSLSSTLT LSKADYEKHK VYACEVTHQG  240
LSSPVTKSFN RGEC                                                    254

SEQ ID NO: 200         moltype = DNA  length = 2238
FEATURE                Location/Qualifiers
misc_feature           1..2238
                       note = synthetic
source                 1..2238
                       mol_type = other DNA
                       organism = synthetic construct
SEQUENCE: 200
ggttatctgt ggggttgcga gtggaattgc ggagggatca ctacaggctc gagcggtggc  60
agcggtggct ctggtggtat atcgagtgga ttgctgtctg gcagatctga cgatcacggc  120
ggcggttctc aaactgtagt aactcaagaa ccaagcttct ccgtctcccc tgggggaaca  180
gtcacactta cctgccgaag tagtacaggt gctgttacga ccagtaacta tgccaattgg  240
gtacaacaaa cgcctggtca ggctccgcgc ggattgatag gaggcacgaa taaacgggca  300
cccggtgtcc cggacagatt cagcggaagc atactcggta ataaggcagc tcttactatc  360
actggggccc aagctgatga tgaaagtgat tattattgtg cgctctggta cagcaacctc  420
tgggtgtttg ggggtggcac gaaacttact gtcttgggcg gcggcggatc agggggaggt  480
ggctctggag gaggaggctc agaagtccaa ctggtcgaat ccgggggagg gctcgtacag  540
ccgggtgggt ccctcaaact ctcttgtgcg gcctcagggt ttaccttcag tacatacgcg  600
```

-continued

```
atgaattggg tccggcaggc cagtgggaaa gggctcgaat gggtaggacg aatccgatca  660
aaatacaaca actacgctac ttattacgct gattccgtga aggacagatt cacaatatcc  720
cgcgacgata gcaagaatac ggcatatctt cagatgaatt ctcttaaaac tgaggatacc  780
gctgtgtatt actgcacaag acatggtaat tttggaaact catatgtctc ttggttcgct  840
tattggggac agggcacgtt ggttaccgtg tctagcggag gtggtggatc ccaggtgcag  900
ctgaaacaga gcggcccggg cctggtgcag ccgagccaga gcctgagcat tacctgcacc  960
gtgagcggct ttagcctgac caactatggc gtgcattggg tgcgccagag cccgggcaaa  1020
ggcctggaat ggctgggcgt gatttggagc ggcggcaaca ccgattataa caccccgttt  1080
accagccgcc tgagcattaa caaagataac agcaaaagcc aggtgttttt taaaatgaac  1140
agcctgcaaa gccaggatac cgcgatttat tattgcgcgc gcgcgctgac ctattatgat  1200
tatgaatttg cgtattgggg ccagggcacc ctggtgaccg tgagcgcggc tagcaccaag  1260
ggcccatcgg tcttccccct ggcaccctcc tccaagagca cctctggggg cacagcggcc  1320
ctgggctgcc tggtcaagga ctacttcccc gaaccggtga cggtgtcgtg gaactcaggc  1380
gccctgacca gcggcgtgca caccttcccg gctgtcctac agtcctcagg actctactcc  1440
ctcagcagcg tggtgaccgt gccctccagc agcttgggca cccagaccta catctgcaac  1500
gtgaatcaca agcccagcaa caccaaggtg gacaagaaag ttgagcccaa atcttgtgac  1560
aaaactcaca catgcccacc gtgcccagca cctgaatttg aaggggggacc gtcagtcttc  1620
ctcttccccc caaaacccaa ggacaccctc atgatctccc ggacccctga ggtcacatgc  1680
gtggtggtgg acgtgagcca cgaagaccct gaggtcaagt tcaactggta cgtggacggc  1740
gtggaggtgc ataatgccaa gacaaagccg cgggaggagc agtaccagag cacgtaccgt  1800
gtggtcagcg tcctcaccgt cctgcaccag gactggctga atggcaagga gtacaagtgc  1860
aaggtctcca acaaagccct cccagcctca atcgagaaaa ccatctccaa agccaaaggg  1920
cagccccgag aaccacaggt gtacaccctg cccccatccc gggaggagat gaccaagaac  1980
caggtcagcc tgacctgcct ggtcaaaggc ttctatccca gcgacatcgc cgtggagtgg  2040
gagagcaatg ggcagccgga gaacaactac aagaccacgc ctcccgtgct ggactccgac  2100
ggctccttct tcctctacag caagctcacc gtggacaaga gcaggtggca gcaggggaac  2160
gtcttctcat gctccgtgat gcatgaggct ctgcacaacc actacacgca gaagagcctc  2220
tccctgtctc cgggtaaa                                               2238

SEQ ID NO: 201          moltype = AA  length = 746
FEATURE                 Location/Qualifiers
REGION                  1..746
                        note = synthetic
source                  1..746
                        mol_type = protein
                        organism = synthetic construct
SEQUENCE: 201
GYLWGCEWNC GGITTGSSGG SGGSGGISSG LLSGRSDDHG GGSQTVVTQE PSFSVSPGGT  60
VTLTCRSSTG AVTTSNYANW VQQTPGQAPR GLIGGTNKRA PGVPDRFSGS ILGNKAALTI  120
TGAQADDESD YYCALWYSNL WVFGGGTKLT VLGGGGSGGG GSGGGGSEVQ LVESGGGLVQ  180
PGGSLKLSCA ASGFTFSTYA MNWVRQASGK GLEWVGRIRS KYNNYATYYA DSVKDRFTIS  240
RDDSKNTAYL QMNSLKTEDT AVYYCTRHGN FGNSYVSWFA YWGQGTLVTV SSGGGGSQVQ  300
LKQSGPGLVQ PSQSLSITCT VSGFSLTNYG VHWVRQSPGK GLEWLGVIWS GGNTDYNTPF  360
TSRLSINKDN SKSQVFFKMN SLQSQDTAIY YCARALTYYD YEFAYWGQGT LVTVSAASTK  420
GPSVFPLAPS SKSTSGGTAA LGCLVKDYFP EPVTVSWNSG ALTSGVHTFP AVLQSSGLYS  480
LSSVVTVPSS SLGTQTYICN VNHKPSNTKV DKKVEPKSCD KTHTCPPCPA PEFEGGPSVF  540
LFPPKPKDTL MISRTPEVTC VVVDVSHEDP EVKFNWYVDG VEVHNAKTKP REEQYQSTYR  600
VVSVLTVLHQ DWLNGKEYKC KVSNKALPAS IEKTISKAKG QPREPQVYTL PPSREEMTKN  660
QVSLTCLVKG FYPSDIAVEW ESNGQPENNY KTTPPVLDSD GSFFLYSKLT VDKSRWQQGN  720
VFSCSVMHEA LHNHYTQKSL SLSPGK                                      746

SEQ ID NO: 202          moltype = DNA  length = 765
FEATURE                 Location/Qualifiers
misc_feature            1..765
                        note = synthetic
source                  1..765
                        mol_type = other DNA
                        organism = synthetic construct
SEQUENCE: 202
tgcatctcac ctcgtggttg tccggacggc ccatacgtca tgtacggctc gagcggtggc  60
agcggtggct ctggtggatc cggtctgagc ggccgttccg atgatcatgg cagtagcggt  120
acccagatct tgctgaccca gagcccggtg attctgagcg tgagcccggg cgaacgtgtg  180
agctttagct gccgcgcgag ccagagcatt ggcaccaaca ttcattggta tcagcagcgc  240
accaacggca gcccgcgcct gctgattaaa tatgcgagcg aaagcattag cggcattccg  300
agccgcttta gcggcagcgg cagcggcacc gattttaccc tgagcattaa cagcgtggaa  360
agcgaagata ttgcggatta ttattgccag cagaacaaca actggccgac cacctttggc  420
gcgggcacca aactggaact gaaacgtacg gtggctgcac catctgtctt catcttcccg  480
ccatctgatg agcagttgaa atctggaact gcctctgttg tgtgcctgct gaataacttc  540
tatcccagag aggccaaagt acagtggaag gtggataacg ccctccaatc gggtaactcc  600
caggagagtg tcacagagca ggacagcaag gacagcacct acagcctcag cagcaccctg  660
acgctgagca aagcagacta cgagaaacac aaagtctacg cctgcgaagt cacccatcag  720
ggcctgagct cgcccgtcac aaagagcttc aacaggggag agtgt                 765

SEQ ID NO: 203          moltype = AA  length = 255
FEATURE                 Location/Qualifiers
REGION                  1..255
                        note = synthetic
```

```
source                  1..255
                        mol_type = protein
                        organism = synthetic construct
SEQUENCE: 203
CISPRGCPDG PYVMYGSSGG SGGSGGSGLS GRSDDHGSSG TQILLTQSPV ILSVSPGERV  60
SFSCRASQSI GTNIHWYQQR TNGSPRLLIK YASESISGIP SRFSGSGSGT DFTLSINSVE  120
SEDIADYYCQ QNNNWPTTFG AGTKLELKRT VAAPSVFIFP PSDEQLKSGT ASVVCLLNNF  180
YPREAKVQWK VDNALQSGNS QESVTEQDSK DSTYSLSSTL TLSKADYEKH KVYACEVTHQ  240
GLSSPVTKSF NRGEC                                                  255

SEQ ID NO: 204          moltype = DNA  length = 2226
FEATURE                 Location/Qualifiers
misc_feature            1..2226
                        note = synthetic
source                  1..2226
                        mol_type = other DNA
                        organism = synthetic construct
SEQUENCE: 204
ggttatctgt ggggttgcga gtggaattgc ggagggatca ctacaggctc gagcggtggc  60
agcggtggct ctggtggtct gagcggccgt tccgatgatc atggcggcgg ttctcaaact  120
gtagtaactc aagaaccaag cttctccgtc tcccctgggg gaacagtcac acttacctgc  180
cgaagtagta caggtgctgt tacgaccagt aactatgcca attgggtaca acaaacgcct  240
ggtcaggctc cgcgcggatt gataggaggc acgaataaac gggcacccgg tgtcccggac  300
agattcagcg gaagcatact cggtaataag gcagctctta ctatcactgg ggcccaagct  360
gatgatgaaa gtgattatta ttgtgcgctc tggtacagca acctctgggt gtttgggggt  420
ggcacgaaac ttactgtctt gggcggcggc ggatcagggg gaggtggctc tggaggagga  480
ggctcagaag tccaactggt cgaatccggg ggagggctcg tacagccggg tgggtccctc  540
aaactctctt gtgcggcctc aggtttacc ttcagtacat acgcgatgaa ttgggtccgg  600
caggccagtg ggaaagggct cgaatgggta ggacgaatcc gatcaaaata caacaactac  660
gctacttatt acgctgattc cgtgaaggac agattcacaa tatcccgcga cgatagcaag  720
aatacggcat atcttcagat gaattctctt aaaactgagg ataccgctgt gtattactgc  780
acaagacatg gtaattttgg aaactcatat gtctcttggt tcgcttattg gggacagggc  840
acgttggtta ccgtgtctag cggaggtggt ggatcccaag tgaccctgag agagtctggc  900
cctgccctcg tgaagcctac ccagaccctg acactgacct gcaccttcag cggcttcagc  960
ctgagcacca gcggcatgtc tgtgggctgg atcagacagc ctcctggcaa ggccctggaa  1020
tggctggccg acatttggtg ggacgacaag aaggactaca accccagcct gaagtcccgg  1080
ctgaccatca gcaaggacac cagcaagaac caggtggtgc tgaaagtgac caacatggac  1140
cccgccgaca ccgccaccta ctactgcgcc agatccatga tcaccaactg gtacttcgac  1200
gtgtggggag ccggcaccac cgtgacagtg tcatctgcta gcaccaaggg cccatcggtc  1260
ttccccctgg caccctcctc caagagcacc tctgggggca cagcggccct gggctgcctg  1320
gtcaaggact acttccccga accggtgacg gtgtcgtgga actcaggcgc cctgaccagc  1380
ggcgtgcaca ccttcccggc tgtcctacag tcctcaggac tctactccct cagcagcgtg  1440
gtgaccgtgc cctccagcag cttgggcacc cagacctaca tctgcaacgt gaatcacaag  1500
cccagcaaca ccaaggtgga caagaaagtt gagcccaaat cttgtgacaa aactcacaca  1560
tgcccaccgt gcccagcacc tgaatttgaa gggggaccgt cagtcttcct cttcccccca  1620
aaacccaagg acaccctcat gatctcccgg acccctgagg tcacatgcgt ggtggtggac  1680
gtgagccacg aagaccctga ggtcaagttc aactggtacg tggacggcgt ggaggtgcat  1740
aatgccaaga caaagccgcg ggaggagcag taccagagca cgtaccgtgt ggtcagcgtc  1800
ctcaccgtcc tgcaccagga ctggctgaat ggcaaggagt acaagtgcaa ggtctccaac  1860
aaagccctcc cagcctcaat cgagaaaacc atctccaaag ccaaagggca gccccgagaa  1920
ccacaggtgt acaccctgcc cccatcccgg gaggagatga ccaagaacca ggtcagcctg  1980
acctgcctgg tcaaaggctt ctatcccagc gacatcgccg tggagtggga gagcaatggg  2040
cagccggaga acaactacaa gaccacgcct cccgtgctgg actccgacgg ctccttcttc  2100
ctctacagca agctcaccgt ggacaagagc aggtggcagc aggggaacgt cttctcatgc  2160
tccgtgatgc atgaggctct gcacaaccac tacacgcaga agagcctctc cctgtctccg  2220
ggtaaa                                                            2226

SEQ ID NO: 205          moltype = AA  length = 742
FEATURE                 Location/Qualifiers
REGION                  1..742
                        note = synthetic
source                  1..742
                        mol_type = protein
                        organism = synthetic construct
SEQUENCE: 205
GYLWGCEWNC GGITTGSSGG SGGSGGLSGR SDDHGGGSQT VVTQEPSFSV SPGGTVTLTC  60
RSSTGAVTTS NYANWVQQTP GQAPRGLIGG TNKRAPGVPD RFSGSILGNK AALTITGAQA  120
DDESDYYCAL WYSNLWVFGG GTKLTVLGGG GSGGGGSGGG GSEVQLVESG GGLVQPGGSL  180
KLSCAASGFT FSTYAMNWVR QASGKGLEWV GRIRSKYNNY ATYYADSVKD RFTISRDDSK  240
NTAYLQMNSL KTEDTAVYYC TRHGNFGNSY VSWFAYWGQG TLVTVSSGGG GSQVTLRESG  300
PALVKPTQTL TLTCTFSGFS LSTSGMSVGW IRQPPGKALE WLADIWWDDK KDYNPSLKSR  360
LTISKDTSKN QVVLKVTNMD PADTATYYCA RSMITNWYFD VWGAGTTVTV SSASTKGPSV  420
FPLAPSSKST SGGTAALGCL VKDYFPEPVT VSWNSGALTS GVHTFPAVLQ SSGLYSLSSV  480
VTVPSSSLGT QTYICNVNHK PSNTKVDKKV EPKSCDKTHT CPPCPAPEFE GGPSVFLFPP  540
KPKDTLMISR TPEVTCVVVD VSHEDPEVKF NWYVDGVEVH NAKTKPREEQ YQSTYRVVSV  600
LTVLHQDWLN GKEYKCKVSN KALPASIEKT ISKAKGQPRE PQVYTLPPSR EEMTKNQVSL  660
TCLVKGFYPS DIAVEWESNG QPENNYKTTP PVLDSDGSFF LYSKLTVDKS RWQQGNVFSC  720
SVMHEALHNH YTQKSLSLSP GK                                          742
```

-continued

```
SEQ ID NO: 206         moltype = DNA  length = 2241
FEATURE                Location/Qualifiers
misc_feature           1..2241
                       note = synthetic
source                 1..2241
                       mol_type = other DNA
                       organism = synthetic construct
SEQUENCE: 206
ggttatctgt ggggttgcga gtggaattgc ggagggatca ctacaggctc gagcggtggc  60
agcggtggct ctggtggtat atcgagtgga ttgctgtctg gcagatctga cgatcacggc  120
ggcggttctc aaactgtagt aactcaagaa ccaagcttct ccgtctcccc tgggggaaca  180
gtcacactta cctgccgaag tagtacaggt gctgttacga ccagtaacta tgccaattgg  240
gtacaacaaa cgcctggtca ggctccgcgc ggattgatag gaggcacgaa taaacgggca  300
cccggtgtcc cggacagatt cagcggaagc atactcggta ataaggcagc tcttactatc  360
actggggccc aagctgatga tgaaagtgat tattattgtg cgctctggta cagcaacctc  420
tgggtgtttg gggggtggcac gaaacttact gtcttgggcg gcggcggatc agggggaggt  480
ggctctggag gaggaggctc agaagtccaa ctggtcgaat ccgggggagg gctcgtacag  540
ccgggtgggt ccctcaaact ctcttgtgcg gcctcagggt ttaccttcag tacatacgcg  600
atgaattggg tccggcaggc cagtgggaaa gggctcgaat gggtaggacg aatccgatca  660
aaatacaaca actacgctac ttattacgct gattccgtga aggacagatt cacaatatcc  720
cgcgacgata gcaagaatac ggcatatctt cagatgaatt ctcttaaaac tgaggatacc  780
gctgtgtatt actgcacaag acatggtaat tttggaaact catatgtctc ttggttcgct  840
tattggggac agggcacgtt ggttaccgtg tctagcggag gtggtggatc ccaagtgacc  900
ctgagagagt ctggccctgc cctcgtgaag cctacccaga ccctgacact gacctgcacc  960
ttcagcggct tcagcctgag caccagcggc atgtctgtgg gctggatcag acagcctcct  1020
ggcaaggccc tggaatggct ggccgacatt tggtgggacg acaagaagga ctacaacccc  1080
agcctgaagt cccggctgac catcagcaag gacaccagca agaaccaggt ggtgctgaaa  1140
gtgaccaaca tggaccccgc cgacaccgcc acctactact gcgccagatc catgatcacc  1200
aactggtact tcgacgtgtg gggagccggc accaccgtga cagtgtcatc tgctagcacc  1260
aagggcccat cggtcttccc cctggcaccc tcctccaaga gcacctctgg gggcacagcg  1320
gccctgggct gcctggtcaa ggactacttc cccgaaccgg tgacggtgtc gtggaactca  1380
ggcgccctga ccagcggcgt gcacaccttc ccggctgtcc tacagtcctc aggactctac  1440
tccctcagca gcgtggtgac cgtgccctcc agcagcttgg gcacccagac ctacatctgc  1500
aacgtgaatc acaagcccag caacaccaag gtggacaaga aagttgagcc caaatcttgt  1560
gacaaaactc acacatgccc accgtgccca gcacctgaat ttgaaggggg accgtcagtc  1620
ttcctcttcc ccccaaaacc caaggacacc ctcatgatct cccggacccc tgaggtcaca  1680
tgcgtggtgg tggacgtgag ccacgaagac cctgaggtca agttcaactg gtacgtggac  1740
ggcgtggagg tgcataatgc caagacaaag ccgcgggagg agcagtacca gagcacgtac  1800
cgtgtggtca gcgtcctcac cgtcctgcac caggactggc tgaatggcaa ggagtacaag  1860
tgcaaggtct ccaacaaagc cctcccagcc tcaatcgaga aaaccatctc caaagccaaa  1920
gggcagcccc gagaaccaca ggtgtacacc ctgcccccat cccgggagga gatgaccaag  1980
aaccaggtca gcctgacctg cctggtcaaa ggcttctatc ccagcgacat cgccgtggag  2040
tgggagagca atgggcagcc ggagaacaac tacaagacca cgcctcccgt gctggactcc  2100
gacggctcct tcttcctcta cagcaagctc accgtggaca agagcaggtg gcagcagggg  2160
aacgtcttct catgctccgt gatgcatgag gctctgcaca accactacac gcagaagagc  2220
ctctccctgt ctccgggtaa a                                            2241

SEQ ID NO: 207         moltype = AA  length = 747
FEATURE                Location/Qualifiers
REGION                 1..747
                       note = synthetic
source                 1..747
                       mol_type = protein
                       organism = synthetic construct
SEQUENCE: 207
GYLWGCEWNC GGITTGSSGG SGGSGGISSG LLSGRSDDHG GGSQTVVTQE PSFSVSPGGT  60
VTLTCRSSTG AVTTSNYANW VQQTPGQAPR GLIGGTNKRA PGVPDRFSGS ILGNKAALTI  120
TGAQADDESD YYCALWYSNL WVFGGGTKLT VLGGGGSGGG GSGGGGSEVQ LVESGGGLVQ  180
PGGSLKLSCA ASGFTFSTYA MNWVRQASGK GLEWVGRIRS KYNNYATYYA DSVKDRFTIS  240
RDDSKNTAYL QMNSLKTEDT AVYYCTRHGN FGNSYVSWFA YWGQGTLVTV SSGGGGSQVT  300
LRESGPALVK PTQTLTLTCT FSGFSLSTSG MSVGWIRQPP GKALEWLADI WWDDKKDYNP  360
SLKSRLTISK DTSKNQVVLK VTNMDPADTA TYYCARSMIT NWYFDVWGAG TTVTVSSAST  420
KGPSVFPLAP SSKSTSGGTA ALGCLVKDYF PEPVTVSWNS GALTSGVHTF PAVLQSSGLY  480
SLSSVVTVPS SSLGTQTYIC NVNHKPSNTK VDKKVEPKSC DKTHTCPPCP APEFEGGPSV  540
FLFPPKPKDT LMISRTPEVT CVVVDVSHED PEVKFNWYVD GVEVHNAKTK PREEQYQSTY  600
RVVSVLTVLH QDWLNGKEYK CKVSNKALPA SIEKTISKAK GQPREPQVYT LPPSREEMTK  660
NQVSLTCLVK GFYPSDIAVE WESNGQPENN YKTTPPVLDS DGSFFLYSKL TVDKSRWQQG  720
NVFSCSVMHE ALHNHYTQKS LSLSPGK                                     747

SEQ ID NO: 208         moltype = DNA  length = 18
FEATURE                Location/Qualifiers
misc_feature           1..18
                       note = synthetic
source                 1..18
                       mol_type = other DNA
                       organism = synthetic construct
SEQUENCE: 208
caaggccagt ctggttct                                                18
```

```
SEQ ID NO: 209         moltype = DNA  length = 2223
FEATURE                Location/Qualifiers
misc_feature           1..2223
                       note = synthetic
source                 1..2223
                       mol_type = other DNA
                       organism = synthetic construct
SEQUENCE: 209
ggttatctgt ggggttgcga gtggaattgc ggagggatca ctacaggctc gagcggtggc  60
agcggtggct ctggtggtct gagcggccgt tccgatgatc atggcggcgg atcccagacg  120
gtagtgactc aggagccatc attttctgtc tctcctggag gtactgtgac actcacatgt  180
agaagctcaa ctggtgcagt caccacttca aattacgcga attgggtcca gcagacccct  240
gggcaggctc cgagagggtt gattggaggt actaacaaac gggcaccggg agtgcctgat  300
aggttttccg gttctattct cggaaacaag gcggctctca cgatcacggg tgcgcaggcc  360
gacgatgaat cagactatta ctgcgctttg tggtactcaa acctgtgggt attcggaggg  420
ggcaccaagc tgacggtgtt gggtgggggg ggctctgggg gagggggaag cggaggtggg  480
ggcagcgagg ttcagcttgt tgaaagtggt ggcggactcg tacaaccggg tggaagtctt  540
agactctcat gtgcagcatc tggatttact ttttctactt atgctatgaa ctgggtaaga  600
caggcaccgg ggaaagggct ggaatgggtt gcacgcattc gatctaaata caataactat  660
gctacatact acgccgatag tgttaaggat cgattcacta tatctcggga cgacagtaag  720
aactcacttt acctgcagat gaattccttg aaaactgagg acacggccgt ttattattgt  780
gtacggcacg ggaatttcgg caattcttac gtttcctggt tcgcctattg gggcaaggt  840
acgctggtca cggtgtctag cggaggtggt ggatcccagg tgcagctgaa acagagcggc  900
ccgggcctgg tgcagccgag ccagagcctg agcattacct gcaccgtgag cggctttagc  960
ctgaccaact atggcgtgca ttgggtgcgc cagagcccgg gcaaaggcct ggaatggctg  1020
ggcgtgattt ggagcggcgg caacaccgat tataacaccc cgtttaccag ccgcctgagc  1080
attaacaaag ataacagcaa aagccaggtg ttttttaaaa tgaacagcct gcaaagccag  1140
gataccgcga tttattattg cgcgcgcgcg ctgacctatt atgattatga atttgcgtat  1200
tggggccagg gcaccctggt gaccgtgagc gcggctagca ccaagggccc atcggtcttc  1260
cccctggcac cctcctccaa gagcacctct gggggcacag cggccctggg ctgcctggtc  1320
aaggactact tccccgaacc ggtgacggtg tcgtggaact caggcgccct gaccagcggc  1380
gtgcacacct tcccggctgt cctacagtcc tcaggactct actccctcag cagcgtggtg  1440
accgtgccct ccagcagctt gggcacccag acctacatct gcaacgtgaa tcacaagccc  1500
agcaacacca aggtggacaa gaaagttgag cccaaatctt gtgacaaaac tcacacatgc  1560
ccaccgtgcc cagcacctga atttgaaggg ggaccgtcag tcttcctctt cccccccaaaa  1620
cccaaggaca ccctcatgat ctcccggacc cctgaggtca catgcgtggt ggtggacgtg  1680
agccacgaag accctgaggt caagttcaac tggtacgtgg acggcgtgga ggtgcataat  1740
gccaagacaa agccgcggga ggagcagtac cagagcacgt accgtgtggt cagcgtcctc  1800
accgtcctgc accaggactg gctgaatggc aaggagtaca agtgcaaggt ctccaacaaa  1860
gccctcccag cctcaatcga gaaaaccatc tccaaagcca aagggcagcc ccgagaacca  1920
caggtgtaca ccctgccccc atcccgggag gagatgacca agaaccaggt cagcctgacc  1980
tgcctggtca aaggcttcta tcccagcgac atcgccgtgg agtgggagag caatgggcag  2040
ccggagaaca actacaagac cacgcctccc gtgctggact ccgacggctc cttcttcctc  2100
tacagcaagc tcaccgtgga caagagcagg tggcagcagg ggaacgtctt ctcatgctcc  2160
gtgatgcatg aggctctgca caaccactac acgcagaaga gcctctccct gtctccgggt  2220
aaa                                                                2223

SEQ ID NO: 210         moltype = AA  length = 741
FEATURE                Location/Qualifiers
REGION                 1..741
                       note = synthetic
source                 1..741
                       mol_type = protein
                       organism = synthetic construct
SEQUENCE: 210
GYLWGCEWNC GGITTGSSGG SGGSGGLSGR SDDHGGGSQT VVTQEPSFSV SPGGTVTLTC  60
RSSTGAVTTS NYANWVQQTP GQAPRGLIGG TNKRAPGVPD RFSGSILGNK AALTITGAQA  120
DDESDYYCAL WYSNLWVFGG GTKLTVLGGG GSGGGGSGGG GSEVQLVESG GGLVQPGGSL  180
RLSCAASGFT FSTYAMNWVR QAPGKGLEWV ARIRSKYNNY ATYYADSVKD RFTISRDDSK  240
NSLYLQMNSL KTEDTAVYYC VRHGNFGNSY VSWFAYWGQG TLVTVSSGGG GSQVQLKQSG  300
PGLVQPSQSL SITCTVSGFS LTNYGVHWVR QSPGKGLEWL GVIWSGGNTD YNTPFTSRLS  360
INKDNSKSQV FFKMNSLQSQ DTAIYYCARA LTYYDYEFAY WGQGTLVTVS AASTKGPSVF  420
PLAPSSKSTS GGTAALGCLV KDYFPEPVTV SWNSGALTSG VHTFPAVLQS SGLYSLSSVV  480
TVPSSSLGTQ TYICNVNHKP SNTKVDKKVE PKSCDKTHTC PPCPAPEFEG GPSVFLFPPK  540
PKDTLMISRT PEVTCVVVDV SHEDPEVKFN WYVDGVEVHN AKTKPREEQY QSTYRVVSVL  600
TVLHQDWLNG KEYKCKVSNK ALPASIEKTI SKAKGQPREP QVYTLPPSRE EMTKNQVSLT  660
CLVKGFYPSD IAVEWESNGQ PENNYKTTPP VLDSDGSFFL YSKLTVDKSR WQQGNVFSCS  720
VMHEALHNHY TQKSLSLSPG K                                           741

SEQ ID NO: 211         moltype = DNA  length = 2223
FEATURE                Location/Qualifiers
misc_feature           1..2223
                       note = synthetic
source                 1..2223
                       mol_type = other DNA
                       organism = synthetic construct
SEQUENCE: 211
ggttatctgt ggggttgcga gtggaattgc ggagggatca ctacaggctc gagcggtggc  60
agcggtggct ctggtggtct gagcggccgt tccgatgatc atggcggcgg ttctcaggcc  120
```

-continued

```
gttgttacac aagagccttc acttactgtg tctccaggag gcactgtgac acttacgtgc  180
cgatcctcta cgggtgccgt gaccacaagc aactatgcca actgggtcca gcagaagcca  240
ggtcaagcgc ctcgaggtct gatcgggggc acgaataaac gagctcctgg aactccggcc  300
agattttctg ggagtcttat tggtggcaag gcggcgttga ccctgagtgg agcccaaccg  360
gaagacgagg ccgagtacta ctgcgccttg tggtattcca atttgtgggt cttcggaggc  420
ggaacaaagc tcacagtact gggaggtgga ggtagcgggg gcggaggctc cgggggaggt  480
ggttccgaag tccagcttgt tgaatcaggt gggggcttgg tacaaccagg tggttcactg  540
aagttgtcct gtgcagcgtc cggatttaca tttagtacgt atgctatgaa ctgggtcagg  600
caggccagtg gtaaaggtct cgaatgggtt ggccggataa ggtcaaagta caataattac  660
gcaacctact acgcggattc cgtgaaagac aggttcacta tttcacgaga tgatagcaaa  720
aatactgcgt atctccaaat gaatagtctt aaaactgaag acactgccgt atattattgc  780
actaggcacg gcaactttgg taactcttat gtttcttggt tcgcatactg gggacaagga  840
actttggtca ctgtctcatc tggaggtggt ggatcccagg tgcagctgaa acagagcggc  900
ccgggcctgg tgcagccgag ccagagcctg agcattacct gcaccgtgag cggctttagc  960
ctgaccaact atggcgtgca ttgggtgcgc cagagcccgg gcaaaggcct ggaatggctg  1020
ggcgtgattt ggagcggcgg caacaccgat tataacaccc cgtttaccag ccgcctgagc  1080
attaacaaag ataacagcaa aagccaggtg ttttttaaaa tgaacagcct gcaaagccag  1140
gataccgcga tttattattg cgcgcgcgcg ctgacctatt atgattatga atttgcgtat  1200
tggggccagg gcaccctggt gaccgtgagc gcggctagca ccaagggccc atcggtcttc  1260
cccctggcac cctcctccaa gagcacctct gggggcacag cggccctggg ctgcctggtc  1320
aaggactact tccccgaacc ggtgacggtg tcgtggaact caggcgccct gaccagcggc  1380
gtgcacacct tcccggctgt cctacagtcc tcaggactct actccctcag cagcgtggtg  1440
accgtgccct ccagcagctt gggcacccag acctacatct gcaacgtgaa tcacaagccc  1500
agcaacacca aggtggacaa gaaagttgag cccaaatctt gtgacaaaac tcacacatgc  1560
ccaccgtgcc cagcacctga atttgaaggg ggaccgtcag tcttcctctt ccccccaaaa  1620
cccaaggaca ccctcatgat ctcccggacc cctgaggtca catgcgtggt ggtggacgtg  1680
agccacgaag accctgaggt caagttcaac tggtacgtgg acggcgtgga ggtgcataat  1740
gccaagacaa agccgcggga ggagcagtac cagagcacgt accgtgtggt cagcgtcctc  1800
accgtcctgc accaggactg gctgaatggc aaggagtaca agtgcaaggt ctccaacaaa  1860
gccctcccag cctcaatcga gaaaaccatc tccaaagcca aagggcagcc ccgagaacca  1920
caggtgtaca ccctgccccc atcccgggag gagatgacca agaaccaggt cagcctgacc  1980
tgcctggtca aaggcttcta tcccagcgac atcgccgtgg agtgggagag caatgggcag  2040
ccggagaaca actacaagac cacgcctccc gtgctggact ccgacggctc cttcttcctc  2100
tacagcaagc tcaccgtgga caagagcagg tggcagcagg ggaacgtctt ctcatgctcc  2160
gtgatgcatg aggctctgca caaccactac acgcagaaga gcctctccct gtctccgggt  2220
aaa                                                                2223

SEQ ID NO: 212          moltype = AA  length = 741
FEATURE                 Location/Qualifiers
REGION                  1..741
                        note = synthetic
source                  1..741
                        mol_type = protein
                        organism = synthetic construct
SEQUENCE: 212
GYLWGCEWNC GGITTGSSGG SGGSGGLSGR SDDHGGGSQA VVTQEPSLTV SPGGTVTLTC  60
RSSTGAVTTS NYANWVQQKP GQAPRGLIGG TNKRAPGTPA RFSGSLIGGK AALTLSGAQP  120
EDEAEYYCAL WYSNLWVFGG GTKLTVLGGG GSGGGGSGGG GSEVQLVESG GGLVQPGGSL  180
KLSCAASGFT FSTYAMNWVR QASGKGLEWV GRIRSKYNNY ATYYADSVKD RFTISRDDSK  240
NTAYLQMNSL KTEDTAVYYC TRHGNFGNSY VSWFAYWGQG TLVTVSSGGG GSQVQLKQSG  300
PGLVQPSQSL SITCTVSGFS LTNYGVHWVR QSPGKGLEWL GVIWSGGNTD YNTPFTSRLS  360
INKDNSKSQV FFKMNSLQSQ DTAIYYCARA LTYYDYEFAY WGQGTLVTVS AASTKGPSVF  420
PLAPSSKSTS GGTAALGCLV KDYFPEPVTV SWNSGALTSG VHTFPAVLQS SGLYSLSSVV  480
TVPSSSLGTQ TYICNVNHKP SNTKVDKKVE PKSCDKTHTC PPCPAPEFEG GPSVFLFPPK  540
PKDTLMISRT PEVTCVVVDV SHEDPEVKFN WYVDGVEVHN AKTKPREEQY QSTYRVVSVL  600
TVLHQDWLNG KEYKCKVSNK ALPASIEKTI SKAKGQPREP QVYTLPPSRE EMTKNQVSLT  660
CLVKGFYPSD IAVEWESNGQ PENNYKTTPP VLDSDGSFFL YSKLTVDKSR WQQGNVFSCS  720
VMHEALHNHY TQKSLSLSPG K                                            741

SEQ ID NO: 213          moltype = DNA  length = 2256
FEATURE                 Location/Qualifiers
misc_feature            1..2256
                        note = synthetic
source                  1..2256
                        mol_type = other DNA
                        organism = synthetic construct
SEQUENCE: 213
caaggccagt ctggatccgg ttatctgtgg ggttgcgagt ggaattgcgg agggatcact  60
acaggctcga gcggtggcag cggtggctct ggtggtatat cgagtggatt gctgtctggc  120
agatctgacc aacacggcgg cggttctcaa actgtagtaa ctcaagaacc aagcttctcc  180
gtctcccctg ggggaacagt cacacttacc tgccgaagta gtacaggtgc tgttacgacc  240
agtaactatg ccaattgggt acaacaaacg cctggtcagg ctccgcgcgg attgatagga  300
ggcacgaata aacgggcacc cggtgtcccg gacagattca gcggaagcat actcggtaat  360
aaggcagctc ttactatcac tggggcccaa gctgatgatg aaagtgatta ttattgtgcg  420
ctctggtaca gcaacctctg ggtgtttggg ggtggcacga aacttactgt cttgggcggc  480
ggcggatcag gggaggtgg ctctggagga ggaggctcag aagtccaact ggtcgaatcc  540
gggggagggc tcgtacagcc gggtgggtcc ctcaaactct cttgtgcggc ctcagggttt  600
accttcagta catacgcgat gaattgggtc cggcaggcca gtgggaaagg gctcgaatgg  660
gtaggacgaa tccgatcaaa atacaacaac tacgctactt attacgctga ttccgtgaag  720
```

-continued

```
gacagattca caatatcccg cgacgatagc aagaatacgg catatcttca gatgaattct  780
cttaaaactg aggataccgc tgtgtattac tgcacaagac atggtaattt tggaaactca  840
tatgtctctt ggttcgctta ttggggacag ggcacgttgg ttaccgtgtc tagcggaggt  900
ggtggatccc aggtgcagct gaaacagagc ggcccgggcc tggtgcagcc gagccagagc  960
ctgagcatta cctgcaccgt gagcggcttt agcctgacca actatggcgt gcattgggtg  1020
cgccagagcc cgggcaaagg cctggaatgg ctgggcgtga tttggagcgg cggcaacacc  1080
gattataaca ccccgtttac cagccgcctg agcattaaca aagataacag caaaagccag  1140
gtgtttttta aaatgaacag cctgcaaagc caggataccg cgatttatta ttgcgcgcgc  1200
gcgctgacct attatgatta tgaatttgcg tattggggcc agggcaccct ggtgaccgtg  1260
agcgcggcta gcaccaaggg cccatcggtc ttccccctgg caccctcctc caagagcacc  1320
tctgggggca cagcggccct gggctgcctg gtcaaggact acttccccga accggtgacg  1380
gtgtcgtgga actcaggcgc cctgaccagc ggcgtgcaca ccttcccggc tgtcctacag  1440
tcctcaggac tctactccct cagcagcgtg gtgaccgtgc cctccagcag cttgggcacc  1500
cagacctaca tctgcaacgt gaatcacaag cccagcaaca ccaaggtgga caagaaagtt  1560
gagcccaaat cttgtgacaa aactcacaca tgcccaccgt gcccagcacc tgaatttgaa  1620
gggggaccgt cagtcttcct cttcccccca aaacccaagg acaccctcat gatctcccgg  1680
acccctgagg tcacatgcgt ggtggtggac gtgagccacg aagaccctga ggtcaagttc  1740
aactggtacg tggacggcgt ggaggtgcat aatgccaaga caaagccgcg ggaggagcag  1800
taccagagca cgtaccgtgt ggtcagcgtc ctcaccgtcc tgcaccagga ctggctgaat  1860
ggcaaggagt acaagtgcaa ggtctccaac aaagccctcc cagcctcaat cgagaaaacc  1920
atctccaaag ccaaagggca gccccgagaa ccacaggtgt acaccctgcc cccatcccgg  1980
gaggagatga ccaagaacca ggtcagcctg acctgcctgg tcaaaggctt ctatcccagc  2040
gacatcgccg tggagtggga gagcaatggg cagccggaga acaactacaa gaccacgcct  2100
cccgtgctgg actccgacgg ctccttcttc ctctacagca agctcaccgt ggacaagagc  2160
aggtggcagc aggggaacgt cttctcatgc tccgtgatgc atgaggctct gcacaaccac  2220
tacacgcaga agagcctctc cctgtctccg ggtaaa                          2256

SEQ ID NO: 214          moltype = AA  length = 746
FEATURE                 Location/Qualifiers
REGION                  1..746
                        note = synthetic
source                  1..746
                        mol_type = protein
                        organism = synthetic construct
SEQUENCE: 214
GYLWGCEWNC GGITTGSSGG SGGSGGISSG LLSGRSDQHG GGSQTVVTQE PSFSVSPGGT  60
VTLTCRSSTG AVTTSNYANW VQQTPGQAPR GLIGGTNKRA PGVPDRFSGS ILGNKAALTI  120
TGAQADDESD YYCALWYSNL WVFGGGTKLT VLGGGGSGGG GSGGGGSEVQ LVESGGGLVQ  180
PGGSLKLSCA ASGFTFSTYA MNWVRQASGK GLEWVGRIRS KYNNYATYYA DSVKDRFTIS  240
RDDSKNTAYL QMNSLKTEDT AVYYCTRHGN FGNSYVSWFA YWGQGTLVTV SSGGGGSQVQ  300
LKQSGPGLVQ PSQSLSITCT VSGFSLTNYG VHWVRQSPGK GLEWLGVIWS GGNTDYNTPF  360
TSRLSINKDN SKSQVFFKMN SLQSQDTAIY YCARALTYYD YEFAYWGQGT LVTVSAASTK  420
GPSVFPLAPS SKSTSGGTAA LGCLVKDYFP EPVTVSWNSG ALTSGVHTFP AVLQSSGLYS  480
LSSVVTVPSS SLGTQTYICN VNHKPSNTKV DKKVEPKSCD KTHTCPPCPA PEFEGGPSVF  540
LFPPKPKDTL MISRTPEVTC VVVDVSHEDP EVKFNWYVDG VEVHNAKTKP REEQYQSTYR  600
VVSVLTVLHQ DWLNGKEYKC KVSNKALPAS IEKTISKAKG QPREPQVYTL PPSREEMTKN  660
QVSLTCLVKG FYPSDIAVEW ESNGQPENNY KTTPPVLDSD GSFFLYSKLT VDKSRWQQGN  720
VFSCSVMHEA LHNHYTQKSL SLSPGK                                      746

SEQ ID NO: 215          moltype = DNA  length = 780
FEATURE                 Location/Qualifiers
misc_feature            1..780
                        note = synthetic
source                  1..780
                        mol_type = other DNA
                        organism = synthetic construct
SEQUENCE: 215
tgcatctcac ctcgtggttg tccggacggc ccatacgtca tgtacggctc gagcggtggc  60
agcggtggct ctggtggatc cggtatatcg agtggattgc tgtctggcag atctgaccaa  120
cacggcagta gcggtaccca gatcttgctg acccagagcc cggtgattct gagcgtgagc  180
ccgggcgaac gtgtgagctt tagctgccgc gcgagccaga gcattggcac caacattcat  240
tggtatcagc agcgcaccaa cggcagcccg cgcctgctga ttaaatatgc gagcgaaagc  300
attagcggca ttccgagccg ctttagcggc agcggcagcg gcaccgattt taccctgagc  360
attaacagcg tggaaagcga agatattgcg gattattatt gccagcagaa caacaactgg  420
ccgaccacct ttggcgcggg caccaaactg gaactgaaac gtacggtggc tgcaccatct  480
gtcttcatct tcccgccatc tgatgagcag ttgaaatctg gaactgcctc tgttgtgtgc  540
ctgctgaata acttctatcc cagagaggcc aaagtacagt ggaaggtgga taacgccctc  600
caatcgggta actcccagga gagtgtcaca gagcaggaca gcaaggacag cacctacagc  660
ctcagcagca ccctgacgct gagcaaagca gactacgaga aacacaaagt ctacgcctgc  720
gaagtcaccc atcagggcct gagctcgccc gtcacaaaga gcttcaacag gggagagtgt  780

SEQ ID NO: 216          moltype = AA  length = 260
FEATURE                 Location/Qualifiers
REGION                  1..260
                        note = synthetic
source                  1..260
                        mol_type = protein
                        organism = synthetic construct
```

-continued

```
SEQUENCE: 216
CISPRGCPDG PYVMYGSSGG SGGSGGSGIS SGLLSGRSDQ HGSSGTQILL TQSPVILSVS  60
PGERVSFSCR ASQSIGTNIH WYQQRTNGSP RLLIKYASES ISGIPSRFSG SGSGTDFTLS  120
INSVESEDIA DYYCQQNNNW PTTFGAGTKL ELKRTVAAPS VFIFPPSDEQ LKSGTASVVC  180
LLNNFYPREA KVQWKVDNAL QSGNSQESVT EQDSKDSTYS LSSTLTLSKA DYEKHKVYAC  240
EVTHQGLSSP VTKSFNRGEC                                              260
```